(12) United States Patent
Hanna et al.

(10) Patent No.: US 9,498,514 B2
(45) Date of Patent: Nov. 22, 2016

(54) SYSTEMS, COMPOSITIONS, AND METHODS FOR TRANSPLANTATION AND TREATING CONDITIONS

(71) Applicant: CYTONICS CORPORATION, Jupiter, FL (US)

(72) Inventors: Lewis Hanna, Naples, FL (US); John David Laughlin, Jupiter, FL (US); Shawn Robert Browning, Jupiter, FL (US)

(73) Assignee: Cytonics Corporation, Jupiter, FL (US)

( * ) Notice: Subject to any disclaimer, the term of this patent is extended or adjusted under 35 U.S.C. 154(b) by 0 days.

(21) Appl. No.: 15/081,408

(22) Filed: Mar. 25, 2016

(65) Prior Publication Data

US 2016/0271215 A1 Sep. 22, 2016

Related U.S. Application Data

(62) Division of application No. 14/471,663, filed on Aug. 28, 2014, now Pat. No. 9,352,021.

(60) Provisional application No. 61/871,009, filed on Aug. 28, 2013, provisional application No. 61/990,522, filed on May 8, 2014, provisional application No. 61/990,524, filed on May 8, 2014.

(51) Int. Cl.

| | |
|---|---|
| *C07K 14/81* | (2006.01) |
| *A61K 38/17* | (2006.01) |
| *A61K 9/00* | (2006.01) |
| *A61L 15/44* | (2006.01) |
| *A61L 15/32* | (2006.01) |
| *B01D 61/18* | (2006.01) |
| *B01D 69/08* | (2006.01) |
| *B01D 69/02* | (2006.01) |
| *A61M 1/34* | (2006.01) |

(52) U.S. Cl.
CPC ......... *A61K 38/1722* (2013.01); *A61K 9/0014* (2013.01); *A61L 15/32* (2013.01); *A61L 15/44* (2013.01); *A61M 1/34* (2013.01); *B01D 61/18* (2013.01); *B01D 69/02* (2013.01); *B01D 69/08* (2013.01); *A61L 2300/252* (2013.01); *A61L 2300/434* (2013.01); *B01D 2313/10* (2013.01); *B01D 2313/24* (2013.01); *B01D 2317/02* (2013.01); *B01D 2317/08* (2013.01); *B01D 2325/02* (2013.01)

(58) Field of Classification Search
CPC ............ A61K 38/1722; C07K 14/811; C07K 14/4717

See application file for complete search history.

(56) References Cited

U.S. PATENT DOCUMENTS

| | | |
|---|---|---|
| 4,518,584 A | 5/1985 | Mark et al. |
| 4,683,195 A | 7/1987 | Mullis et al. |
| 4,683,202 A | 7/1987 | Mullis |
| 4,800,159 A | 1/1989 | Mullis et al. |
| 5,143,854 A | 9/1992 | Pirrung et al. |
| 5,242,974 A | 9/1993 | Holmes |
| 5,384,261 A | 1/1995 | Winkler et al. |
| 5,405,783 A | 4/1995 | Pirrung et al. |
| 5,409,818 A | 4/1995 | Davey et al. |
| 5,412,087 A | 5/1995 | McGall et al. |
| 5,424,186 A | 6/1995 | Fodor et al. |
| 5,429,807 A | 7/1995 | Matson et al. |
| 5,436,327 A | 7/1995 | Southern et al. |
| 5,445,934 A | 8/1995 | Fodor et al. |
| 5,472,672 A | 12/1995 | Brennan |
| 5,527,681 A | 6/1996 | Holmes |
| 5,529,756 A | 6/1996 | Brennan |
| 5,532,128 A | 7/1996 | Eggers et al. |
| 5,545,531 A | 8/1996 | Rava et al. |
| 5,554,293 A | 9/1996 | Uhoch |
| 5,554,501 A | 9/1996 | Coassin et al. |
| 5,554,527 A | 9/1996 | Fickenscher |
| 5,556,752 A | 9/1996 | Lockhart et al. |
| 5,561,071 A | 10/1996 | Hollenberg et al. |
| 5,563,120 A | 10/1996 | Kuznetsov |
| 5,571,639 A | 11/1996 | Hubbell et al. |
| 5,593,839 A | 1/1997 | Hubbell et al. |
| 5,599,695 A | 2/1997 | Pease et al. |
| 5,624,711 A | 4/1997 | Sundberg et al. |
| 5,658,734 A | 8/1997 | Brock et al. |

(Continued)

FOREIGN PATENT DOCUMENTS

| | | |
|---|---|---|
| EP | 1320308 A1 | 6/2003 |
| JP | 2004256436 A | 9/2004 |

(Continued)

OTHER PUBLICATIONS

A2M and Chronic Wounds. 7 pages. Feb. 18, 2014.
A2M Peptide Biomarkers. 8 pgs.
Abrams, et al. Hip Synovial Fluid Cytokine Profiling In Patients with and without Arthritis. Poster No. 1801. ORS 2012 Annual Meeting.
Barilla, et al. Fibronectin fragments and their role in inflammatory arthritis. Semin Arthritis Rheum. Feb. 2000;29(4):252-65.
Bedi, et al. The effect of matrix metalloproteinase inhibition on tendon-to-bone healing in a rotator cuff repair model. J Shoulder Elbow Surg. Apr. 2010; 19(3):384-91. Epub Oct. 2, 2009.
Bhattacharjee, et al. The conformation-dependent interaction of alpha 2-macroglobulin with vascular endothelial growth factor. A novel mechanism of alpha 2-macroglobulin/growth factor binding. J Biol Chem. Sep. 1, 2000;275(35):26806-11.

(Continued)

*Primary Examiner* — Karen Cochrane Carlson
(74) *Attorney, Agent, or Firm* — Wilson Sonsini Goodrich & Rosati

(57) ABSTRACT

Systems and methods for purification and concentration of autologous alpha-2 macroglobulin (A2M) from whole blood and or recombinant A2M are provided. Also provided are methods of treating wounds with A2M. Methods for utilizing A2M in combination with other treatments (e.g., platelets and other growth factors) are provided in addition to combinations with exogenous drugs or carriers. Also provided is a method of producing recombinant A2M wild type or variants thereof where the bait region was modified to enhance the inhibition characteristics of A2M and/or to prolong the half-life of the protein for treating wounds.

19 Claims, 47 Drawing Sheets

(56) References Cited

U.S. PATENT DOCUMENTS

| | | |
|---|---|---|
| 5,700,637 A | 12/1997 | Southern |
| 5,728,554 A | 3/1998 | Bayer et al. |
| 5,747,251 A | 5/1998 | Carson et al. |
| 5,807,522 A | 9/1998 | Brown et al. |
| 5,837,832 A | 11/1998 | Chee et al. |
| 5,876,980 A | 3/1999 | Defrees et al. |
| 5,922,577 A | 7/1999 | Defrees et al. |
| 6,004,755 A | 12/1999 | Wang |
| 6,010,627 A | 1/2000 | Hood, III |
| 6,030,815 A | 2/2000 | Defrees et al. |
| 6,040,138 A | 3/2000 | Lockhart et al. |
| 6,040,166 A | 3/2000 | Erlich et al. |
| 6,045,996 A | 4/2000 | Cronin et al. |
| 6,218,114 B1 | 4/2001 | Peck et al. |
| 6,218,122 B1 | 4/2001 | Friend et al. |
| 6,271,002 B1 | 8/2001 | Linsley et al. |
| 6,284,460 B1 | 9/2001 | Fodor et al. |
| 6,342,157 B1 | 1/2002 | Hood, III |
| 6,607,885 B1 | 8/2003 | Larossa et al. |
| 6,683,155 B1 | 1/2004 | Silbiger et al. |
| 6,806,254 B2 | 10/2004 | Godbole et al. |
| 6,903,201 B2 | 6/2005 | Padigaru |
| 7,011,852 B2 | 3/2006 | Sukavaneshvar et al. |
| 7,186,695 B2 | 3/2007 | Hogg |
| 7,291,450 B2 | 11/2007 | Sowemimo-Coker et al. |
| 7,709,215 B2 | 5/2010 | Scuderi |
| 7,806,845 B2 | 10/2010 | Arm et al. |
| 7,858,296 B2 | 12/2010 | Sowemimo-Coker et al. |
| 7,888,313 B2 | 2/2011 | Greenspan et al. |
| 7,923,203 B2 | 4/2011 | Sowemimo-Coker et al. |
| 7,927,344 B2 | 4/2011 | Burba et al. |
| 8,101,077 B2 | 1/2012 | Sukavaneshvar et al. |
| 9,352,021 B2 | 5/2016 | Hanna et al. |
| 2003/0180835 A1 | 9/2003 | Bayer |
| 2006/0165710 A1 | 7/2006 | Srivastava et al. |
| 2007/0259030 A1 | 11/2007 | Drapeau |
| 2008/0040153 A1 | 2/2008 | Davis |
| 2009/0123452 A1 | 5/2009 | Madison |
| 2010/0085606 A1 | 4/2010 | Daos |
| 2010/0098684 A1 | 4/2010 | Scuderi et al. |
| 2013/0059371 A1 | 3/2013 | Shevitz |

FOREIGN PATENT DOCUMENTS

| | | |
|---|---|---|
| WO | WO-9831826 A1 | 7/1998 |
| WO | WO-03031464 A2 | 4/2003 |
| WO | WO-03068822 A2 | 8/2003 |
| WO | WO-03090686 A2 | 11/2003 |
| WO | WO-03099846 A3 | 5/2005 |
| WO | WO-2006003388 A2 | 1/2006 |
| WO | WO-2006023911 A2 | 3/2006 |
| WO | WO-2008074029 A2 | 6/2008 |
| WO | WO-2009137074 A1 | 11/2009 |
| WO | WO-2010045024 A1 | 4/2010 |
| WO | WO-2010075249 A2 | 7/2010 |
| WO | WO-2010085606 A1 | 7/2010 |
| WO | WO-2013126587 A1 | 8/2013 |

OTHER PUBLICATIONS

Binder, R. Purification of alpha2-macroglobulin and the construction of immunogenic alpha2-macroglobulin-peptide complexes for use as cancer vaccines. Methods. Jan. 2004; 34(1):29-31.

Borth, W. Alpha 2-macroglobulin. A multifunctional binding and targeting protein with possible roles in immunity and autoimmunity. Ann N Y Acad Sci. Sep. 10, 1994;737:267-72.

Bowen, et al. Bait region involvement in the dimer-dimer interface of human alpha 2-macroglobulin and in mediating gross conformational change. Evidence from cysteine variants that form interdimer disulfides. J Biol Chem. Jan. 16, 1998;273(3):1825-31.

Braun, et al. The effect of local anaesthetics on synoviocytes: a possible indirect mechanism of chondrolysis. Knee Surg Sports Traumatol Arthrosc. Jun. 21, 2012. 1468-74.

Browning, et al. Platelet-rich plasma increases matrix metalloproteinases in cultures of human synovial fibroblasts. J Bone Joint Surg Am. Dec. 5, 2012;94(23):e1721-7. doi: 10.2106/JBJS.K.01501.

Burton-Wurster, et al. Fibronectin and water content of articular cartilage explants after partial depletion of proteoglycans. J Orthop Res. 1986;4(4):437-45.

Castillo, et al. Comparison of growth factor and platelet concentration from commercial platelet-rich plasma separation systems. Am J Sports Med. 2011;39(2):266-271.

Chellan et al. 2010; Spectrum and prevalence of fungi infecting deep tissues of lower-limb wounds in patients with type 3 diabetes. Journal of Clinical Microbiology. 48(6): 2097-2102.

Cote, et al. Generation of human monoclonal antibodies reactive with cellular antigens. Proc Natl Aced Sci U S A. Apr. 1983;80(7):2026-30.

Cuellar, et al. Can Intra-articular cytokine profiling predict the development of knee pain? Four-year follow-up of asymptomatic controls. Poster No. 1793. ORS 2012 Annual Meeting.

Cuellar, et al. Cytokine Expression in the Epidural Space: A Model of Non-compressive Disc Herniation-induced Inflammation. Spine (Phila Pa 1976). May 29, 2012. 38(1):17-23.

Cuellar, et al. Cytokine profiling in acute anterior cruciate ligament injury. Arthroscopy. Oct. 2010;26(10):1296-301.

Cuellar, et al. Does a fibronectin and aggrecan complex play a role in painful vertebral disks? PM R. Apr. 2013;5(4):297-302; quiz 302. doi: 10.1016/j.pmrj.2013.01.002. Epub Mar. 13, 2013.

Cytonics Publication Summary. 2 pages.

Demirag, et al. Enhancement of tendon-bone healing of anterior cruciate ligament grafts by blockage of matrix metalloproteinases. J Bone Joint Surg Am. Nov. 2005;87(11):2401-10.

Dissemond, et al. EPA made easy. Wounds International. 2013; 4(2):1-6.

Dumfarth, et al. Prophylactic low-energy shock wave therapy improves wound healing after vein harvesting for coronary artery bypass graft surgery: a prospective, randomized trial. Ann Thorac Surg. Dec. 2008;86(6):1909-13. doi: 10.1016/j.athoracsur.2008.07.117.

Edsberg, et al. Analysis of the proteomic profile of chronic pressure ulcers. Wound Repair Regen. May-Jun. 2012;20(3):378-401. doi: 10.1111/j.1524-475X.2012.00791.x.

Eming, et al. The inhibition of matrix metalloproteinase activity in chronic wounds by a polyacrylate superabsorber. Biomaterials. Jul. 2008;29(19):2932-40. doi: 10.1016/j.biomaterials.2008.03.029. Epub Apr. 9, 2008.

Frechette, et al. Platelet-rich plasmas: growth factor content and roles in wound healing. J. Dent. Res. 2005;84(5):434-439.

Gibson, et al. MMPs made easy. Wounds International. 2009; 1:1-6.

Golish, et al. Functional outcome after lumbar epidural steroid injection is predicted by a complex of fibronectin and aggrecan.

Greenwald. Thirty-six years in the clinic without an MMP inhibitor. What hath collagenase wrought? Ann N Y Acad Sci. Jun. 30, 1999;878:413-9.

Grinnell, et al. Fibronectin degradation in chronic wounds depends on the relative levels of elastase, alpha1-proteinase inhibitor, and alpha2-macroglobulin. J Invest Dermatol. Feb. 1996;106(2):335-41.

Hashimoto, et al. ADAMTS4 (aggrecanase-1) interaction with the C-terminal domain of fibronectin inhibits proteolysis of aggrecan. J Biol Chem. Jul. 30, 2004;279(31):32483-91. Epub May 25, 2004.

Henikoff, et al. Amino acid substitution matrices from protein blocks. Proc Natl Acad Sci U S A. Nov. 15, 1992;89(22):10915-9.

Hermanson, Bioconjugate Techniques 1996, Academic Press, Inc., San Diego.

Hofheinz, E. Eureka! Rush Researchers Find Breakthrough in OA. Jan. 3, 2013. Available at http://ryortho.com/breaking/eureka-rush-researchers-find-breakthrough-in-oa/. Accessed Jul. 11, 2013.

Holland, et al. Detection of specific polymerase chain reaction product by utilizing the 5'—3' exonuclease activity of Thermus aquaticus DNA polymerase. Proc Natl Acad Sci U S A. Aug. 15, 1991;88(16):7276-80.

Huse, et al. Generation of a large combinatorial library of the immunoglobulin repertoire in phage lambda. Science. Dec. 8, 1989;246(4935):1275-81.

(56) References Cited

OTHER PUBLICATIONS

Ikai, et al. A recombinant bait region mutant of human alpha2-macroglobulin exhibiting an altered proteinase-inhibiting spectrum. Cytotechnology. Sep. 1999;31(1-2):53-60. doi: 10.1023/A:1008011919876.
Inman, E. Researchers create "truth serum" to explain knee pain. http://www.stanforddaily.com/2011/02/17/researchers-create-%E2%80%9Ctruth-serum%E2%80%9D-to-explain-knee-pain/ Accessed Dec. 3, 2014.
Innis, et al., eds. PCR protocols: a guide to methods and applications. Academic press, New York. 1990.
International search report and written opinion dated Jan. 21, 2015 for PCT/US2014/053223.
Jackson. Cytokine Biomarkers in Orthopedics Offer An Enormous Diagnosis and Prognosis Potential. Orthopedics Today. Jan. 2010. 3 pgs.
Kimmel, et al. Preparation of cDNA and the generation of cDNA libraries: overview. Methods Enzymol. 1987;152:307-16.
Kohler, et al. Continuous cultures of fused cells secreting antibody of predefined specificity. Nature. Aug. 7, 1975;256(5517):495-7.
Kozbor, et al. Specific immunoglobulin production and enhanced tumorigenicity following ascites growth of human hybridomas. J Immunol Methods. Jul. 16, 1985;81(1):31-42.
Liang, et al. Distribution and cloning of eukaryotic mRNAs by means of differential display: refinements and optimization. Nucleic Acids Res. Jul. 11, 1993;21(14):3269-75.
Lobmann, et al. Expression of matrix-metalloproteinases and their inhibitors in the wounds of diabetic and non-diabetic patients. Diabetologia. Jul. 2002;45(7):1011-6. Epub May 25, 2002.
Lobmann, et al. Proteases and the diabetic foot syndrome: mechanisms and therapeutic implications. Diabetes Care. Feb. 2005;28(2):461-71.
Maniatis, et al. Molecular Cloning: A Laboratory Manual, Cold Spring Harbor Laboratory Press, Cold Spring Harbor, N.Y., USA 1982.
Masters, et al. Effects of nitric oxide releasing poly(vinyl alcohol) hydrogel dressings on dermal wound healing in diabetic mice. Wound Repair Regen. Sep.-Oct. 2002;10(5):286-94.
McCafferty, et al. Phage antibodies: filamentous phage displaying antibody variable domains. Nature. Dec. 6, 1990;348(6301):552-4.
Miyoshi et al. 1989; Inhibitory effect of alpha 2 macroglobulin on Vibrio vulnificus protease. J. Biochem. 106: 299-303.
Morrison et al. Chimeric human antibody molecules: mouse antigen-binding domains with human constant region domains. Proc Natl Acad Sci U S A. Nov. 1984;81(21):6851-5.
Nakayama, et al. Removal of trypsin complexed alpha-2 macroglobulin by plasma fractionation. ASAIO Journal. 1993; M297-M300.
Needleman, et al. A general method applicable to the search for similarities in the amino acid sequence of two proteins. J Mol Biol. Mar. 1970;48(3):443-53.
Neuberger et al. Recombinant antibodies possessing novel effector functions. Nature. Dec. 13-19, 1984;312(5995):604-8.
Nguyen, et al. Applications of platelet-rich plasma in musculoskeletal and sports medicine: An evidence-based approach. PM R. 2011;3(3):226-250.
Notice of allowance dated Feb. 24, 2016 for U.S. Appl. No. 14/471,663.
Office action dated Jul. 23, 2015 for U.S. Appl. No. 14/471,663.
Ohara, et al. One-sided polymerase chain reaction: the amplification of cDNA. Proc Natl Acad Sci U S A. Aug. 1989;86(15):5673-7.
Organs, et al. A2M Prior Art. Technical and clinical aspects of cascade filtration plasma exchange (CFPE). 3pages.
Poller, et al. Cloning of the human alpha 2-macroglobulin gene and detection of mutations in two functional domains: the bait region and the thiolester site. Hum Genet. Jan. 1992;88(3):313-9.
Quaranta, et al. Technical and clinical aspects of cascade filtration plasma exchange (CFPE). Int J Artif Organs. Nov. 1983;6(6):309-14.
Rayment, et al. Attenuation of protease activity in chronic wound fluid with bisphosphonate-functionalised hydrogels. Biomaterials. Apr. 2008;29(12):1785-95. doi: 10.1016/j.biomaterials.2007.12.043. Epub Jan. 31, 2008.
Re: Cytonics Patent Status and Strategy Summary letter. McHale & Slavin, P.A. Dated Mar. 23, 2011. 37 pages.
Rompaey, et al. Design of a new protease inhibitor by the manipulation of the bait region of alpha 2-macroglobulin: inhibition of the tobacco etch virus protease by mutant alpha 2-macroglobulin. Biochem J. Nov. 15, 1995;312 ( Pt 1):191-5.
Sambrook, et al. Molecular cloning: a laboratory manual. Cold Spring Harbor Laboratory Press, Cold Spring Harbor, NY 11: 18. 2nd Ed. 1989.
San Giovanni, et al. Correlation of intra-articular ankle pathology with cytokine biomarkers and matrix degradation products. Foot Ankle Int. Aug. 2012;33(8):627-31.
Sanchez, et al. Intra-articular injection of an autologous preparation rich in growth factors for the treatment of knee OA: a retrospective cohort study. Clin Exp Rheumatol. Sep.-Oct. 2008;26(5):910-3.
Sato, et al. Relationship of calcitonin gene-related peptide in synovial tissues and temporomandibular joint pain in humans. Oral Surg Oral Med Oral Pathol Oral Radiol Endod. Nov. 2004;98(5):533-40.
Scopes. Protein purification: Principles and Practice, Springer-Verlag (1994).
Scuderi, et al. Cytokine assay of the epidural space lavage in patients with lumbar intervertebral disk herniation and radiculopathy. J Spinal Disord Tech. Jun. 2006;19(4):266-9.
Scuderi, et al. Epidural interferon gamma-immunoreactivity: a biomarker for lumbar nerve root irritation. Spine (Phila Pa 1976). Oct. 1, 2009;34(21):2311-7.
Shena, et al. Parallel human genome analysis: microarray-based expression monitoring of 1000 genes. Proc Natl Acad Sci U S A. Oct. 1, 1996;93(20):10614-9.
Shena, et al. Quantitative monitoring of gene expression patterns with a complementary DNA microarray. Science. Oct. 20, 1995;270(5235):467-70.
Struglics, et al. Human osteoarthritis synovial fluid and joint cartilage contain both aggrecanase- and matrix metalloproteinase-generated aggrecan fragments. Osteoarthritis Cartilage. Feb. 2006;14(2):101-13. Epub Sep. 26, 2005.
Sundman, et al. Growth Factor and Catabolic Cytokine Concentrations Are Influenced by the Cellular Composition of Platelet-Rich Plasma. Am J Sports Med. Oct. 2011;39(10):2135-40. Epub Aug. 16, 2011.
Swenson, et al. Structural characterization of human alpha2-macroglobulin subunits. J Biol Chem. Jun. 10, 1979;254(11):4452-6.
Takeda, et al. Construction of chimaeric processed immunoglobulin genes containing mouse variable and human constant region sequences. Nature. Apr. 4-10, 1985;314(6010):452-4.
Trengove, et al. Analysis of the acute and chronic wound environments: the role of proteases and their inhibitors. Wound Repair Regen. Nov.-Dec. 1999;7(6):442-52.
Twining, SS. Fluorescein isothiocyanate-labeled casein assay for proteolytic enzymes. Anal Biochem. Nov. 15, 1984;143(1):30-4.
U.S. Appl. No. 14/471,663, filed Aug. 28, 2014.
Van Den Dolder, et al. Platelet-rich plasma: quantification of growth factor levels and the effect on growth and differentiation of rat bone marrow cells. Tissue Eng. 2006;12(11):3067-3073.
Ventura, et al. A pseudobiospecific hollow fiber cartridge for in vitro adsorbtion of autoantibodies from pathological serum. Braz. J. Chem. Eng. vol. 17 n.4-7 São Paulo Dec. 2000.
Wang, et al. Identification of α2-macroglobulin as a master inhibitor of cartilage-degrading factors that attenuates the progression of posttraumatic osteoarthritis. Arthritis Rheumatol. Jul. 2014;66(7):1843-53. doi: 10.1002/art.38576.
Weibrich, et al. Curasan PRP kit vs. PCCS PRP system. Collection efficiency and platelet counts of two different methods for the preparation of platelet-rich plasma. Clin Oral Implants Res. Aug. 2002;13(4):437-43.

(56) References Cited

OTHER PUBLICATIONS

Weibrich, et al. Growth factor levels in platelet-rich plasma and correlations with donor age, sex, and platelet count. J Craniomaxillofac Surg. 2002;30(2):97-102.
Wild. Biomarkers Predict Response to Steroid Injections In Radiculopathy Patients. Jan. 2011; vol. 37:1. http://www.anesthesiologynews.com/default.aspx. Accessed on Dec. 5, 2014. 2 pages.
Wildeboer, et al. Specific protease activity indicates the degree of Pseudomonas aeruginosa infection in chronic infected wounds. Eur J Clin Microbiol Infect Dis. Sep. 2012;31(9):2183-9. doi: 10.1007/s10096-012-1553-6. Epub Jan. 26, 2012.
Yager, et al. Ability of chronic wound fluids to degrade peptide growth factors is associated with increased levels of elastase activity and diminished levels of proteinase inhibitors. Wound Repair and Regeneration. 1997; 5:23-32.
Zack, et al. Identification of fibronectin neoepitopes present in human osteoarthritic cartilage. Arthritis Rheum. Sep. 2006;54(9):2912-22.
Zhang, et al. Inhibition of bone morphogenetic protein 1 by native and altered forms of alpha2-macroglobulin. J Biol Chem. Dec. 22, 2006;281(51):39096-104. Epub Oct. 27, 2006.
Zhang, et al. Phosphoprotein analysis using antibodies broadly reactive against phosphorylated motifs. J Biol Chem. Oct. 18, 2002;277(42):39379-87. Epub Jul. 31, 2002.
Zhang, et al. Poster 108: Characterization of fibronectin fragments in human surgical intervertebral disk specimens. Archives of Phyisical medicine and rehabilitation. 2007; 88(9):e40.

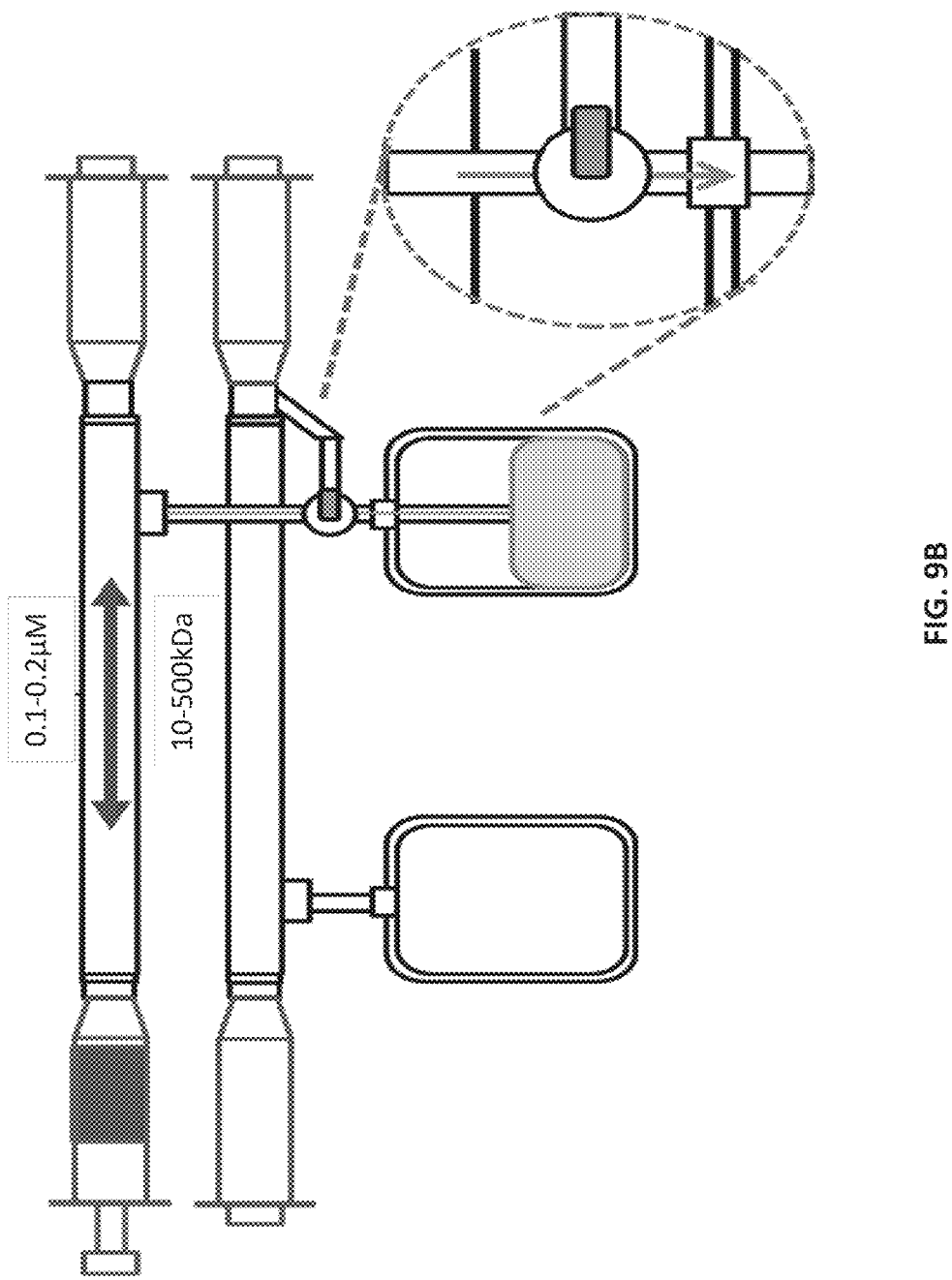

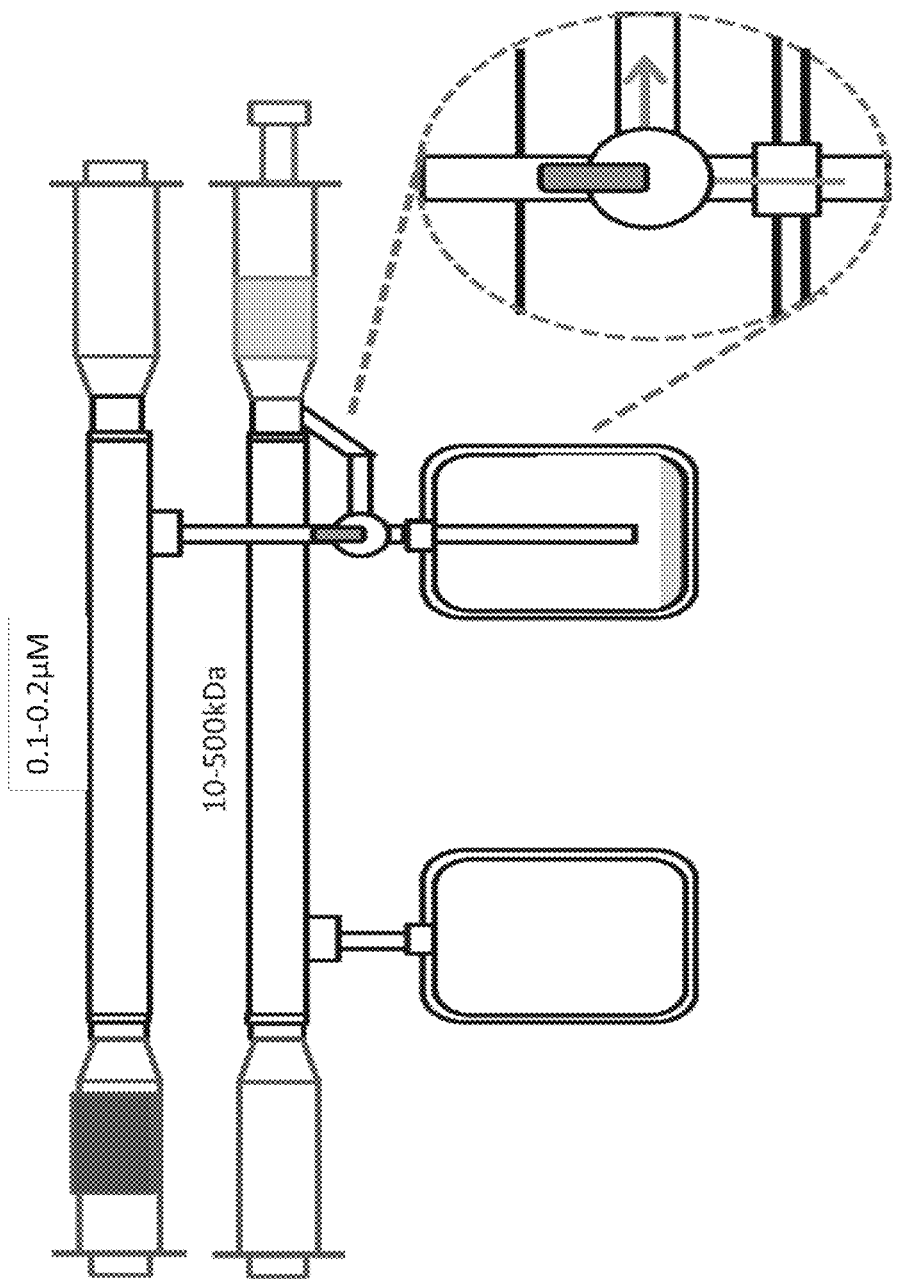

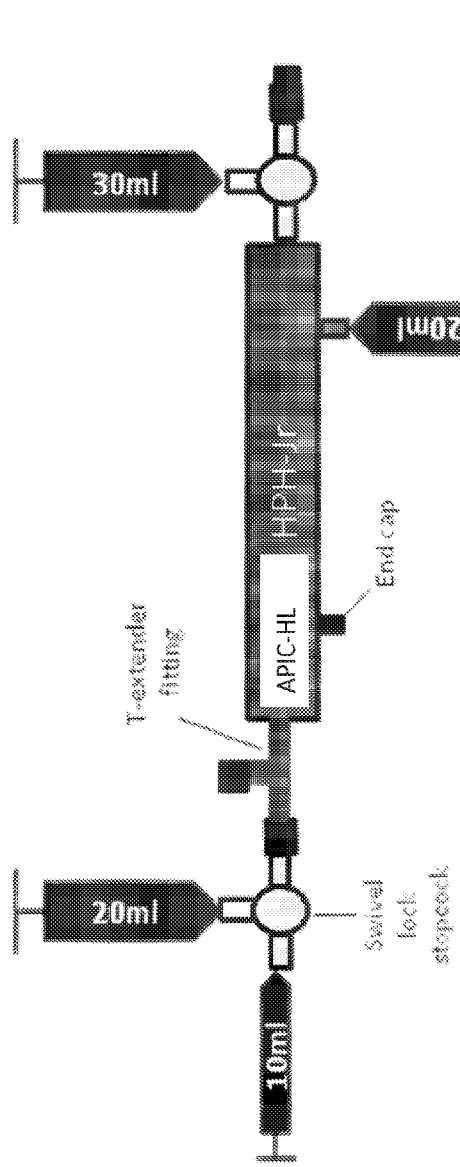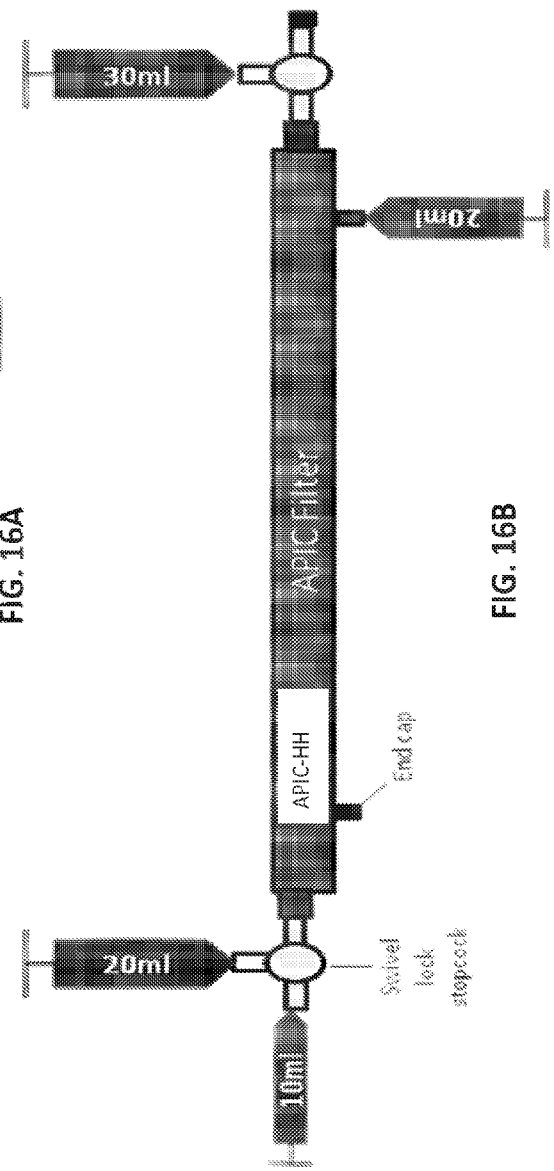
FIG. 16A
FIG. 16B

| Sample | | Adj. rato to MMP-13 | Collagenase activity (ug/ml MMP-13) |
|---|---|---|---|
| 140731NL | Wound Fluid | 19.18 | 15.34 |
| 140731AW | Deb. Tissue | 40.72 | 3.26 |
| 140731DMB | Deb. Tissue | 5.47 | 0.44 |

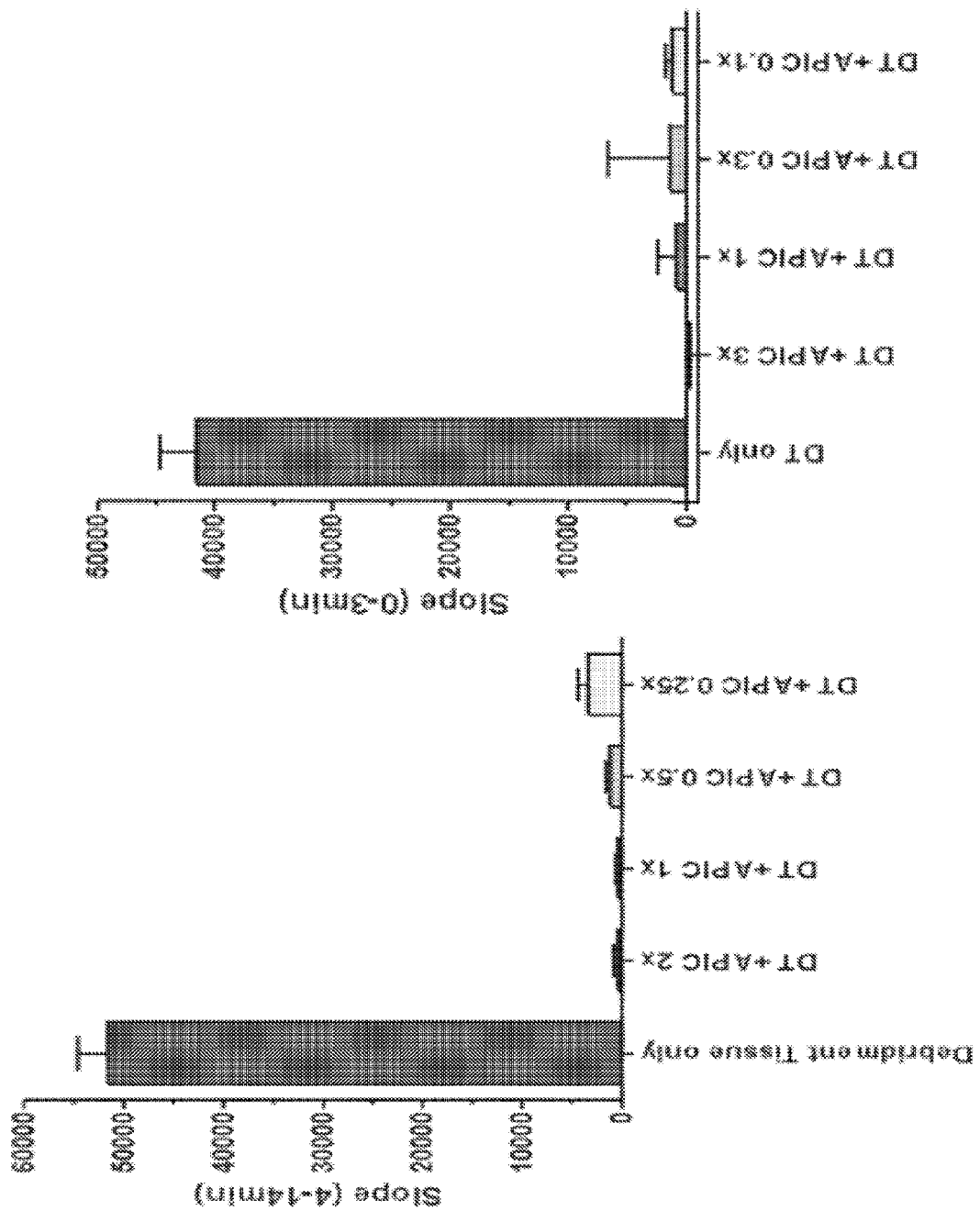

SYSTEMS, COMPOSITIONS, AND METHODS FOR TRANSPLANTATION AND TREATING CONDITIONS

CROSS-REFERENCE

This application is a divisional application of U.S. Nonprovisional application Ser. No. 14/471,663, filed Aug. 28, 2014, which claims the benefit of U.S. Provisional Application No. 61/871,009, filed on Aug. 28, 2013, U.S. Provisional Application No. 61/990,522, filed on May 8, 2014, and U.S. Provisional Application No. 61/990,524, filed on May 8, 2014, all of which are incorporated herein by reference in their entirety.

REFERENCE TO A SEQUENCE LISTING

The instant application contains a Sequence Listing which has been submitted in ASCII format via EFS-Web and is hereby incorporated by reference in its entirety. Said ASCII copy, created on Mar. 25, 2016, is named 37151_703_401_SL.txt and is 85,687 bytes in size. The aforementioned file is hereby incorporated by reference in its entirety.

BACKGROUND

The physiological cellular response to tissue injury in the skin progresses through a sequence of structured phases and normally results in a nearly complete recovery the injured area. Wounds can be either acute or chronic with respect to healing. In chronic wounds, the duration of the wound healing processes is either much slower or static. Wound healing depends on several factors, including the patient's age and physical condition, the location of the wound, the cause of the injury, and accompanying diseases such as diabetes or renal insufficiency, which all have a negative effect on wound healing processes.

Wound healing involve several populations of cells (thrombocytes or platelets, neutrophile granulocytes, macrophages, fibroblasts, and keratinocytes), soluble factors (cytokines and growth factors), and proteases (e.g., matrix metalloproteinases [MMPs], plasmin, and elastase). Healing initially involves hemostasis initiated by the activation of the clotting cascade. Fibrin clots forming the provisional wound matrix entrap erythrocytes and platelets and block blood flow. Numerous growth factors (e.g., platelet-derived growth factor (PDGF), platelet-derived angiogenic factor (PDAF), transforming growth factor and epidermal growth factor (EGF)) are released from platelet granules and chemotactically attract neutrophils, fibroblasts, endothelial cells, and keratinocytes into the wound. The initial release of growth factors from platelets is important in initiating the phases of wound healing.

Inflammation is the initial response to tissue injury. Within 6 h after tissue injury, inflammation begins. The main goal of the inflammatory phase is to provide rapid hemostasis and begin the sequence of events that leads to regeneration of tissue. Neutrophil granulocytes typically appear in wounds first and control bacterial contamination and cleanse the wound from cell detritus. After 48 h, the concentration of neutrophil granulocytes is maximized. Monocytes begin infiltrating the wound site 24 h after injury, attracted by chemotactic factors including complement factor 5, fibrin degradation products, and TGF-β. In response to wound cytokines, monocytes differentiate into wound macrophages to aid wound repair.

During the proliferative phase, the damaged, necrotic tissue that is being removed via phagocytosis starts to be replaced with living tissue that is specific to the local tissue environment. Proliferation is primarily characterized by granulation tissue. MMPs take part in the structured development of granulation tissue by removing damaged matrix proteins, helping cells migrate into the wound, and developing new blood vessels.

About 2 days after injury, macrophages from monocytes begin expressing growth factors. Macrophages continue to release PDGF, macrophage angiogenesis factor, and TGF-β. PDGF, macrophage angiogenesis factor, and angiotensin stimulate new blood vessel formation, generating granulation tissue in the wound. EGF, keratinocyte growth factor, and PDGF stimulate epidermal cells to migrate, divide, and differentiate (keratinize), covering the granulation tissue with a cellular barrier to desiccation and infection.

During remodeling, newly generated tissue reshapes and reorganizes to more closely resemble the original tissue. Remodeling begins about the $7^{th}$ day of wound healing and can continue for 6 months to a year. Early in the remodeling, the provisional wound matrix, predominately fibrin and fibronectin, is replaced with proteoglycan molecules and collagen molecules (type III, type I) that become cross-linked by enzymatic action, which greatly increases the tensile strength of the scar matrix. In addition, some fibroblasts are stimulated to transform into myofibroblasts that contract the wound matrix. The high density of new blood vessels and myofibroblasts in the scar then decrease as vascular endothelial cells and fibroblasts undergo apoptosis, and the hypertrophic epidermal layer becomes thinner. At the end of the wound healing process, the wound is closed. However, the repaired tissue does not completely regenerate the original tissue structure, and some level of functionality of the scar tissue is usually lost.

Platelets play a prominent role as one of the first responders during the acute inflammatory phase. In response to tissue damage, platelets are activated resulting in the formation of a platelet plug and blood clot for hemostasis. The alpha granules of activated platelets contain numerous proteins that influence wound healing. Thrombin production ultimately occurs and converts fibrinogen to fibrin which binds to platelet surface receptors. Proteins from platelet degranulation are partly responsible for cellular chemotaxis, proliferation, and differentiation. This includes removal of tissue debris, angiogenesis, establishing the extracellular matrix, and regeneration of the appropriate type of tissue.

Platelet rich plasma (PRP) contains clotting factors and higher concentration of platelets than baseline. The portion of plasma that remains deficient in platelets is known as platelet poor plasma (PPP). PPP has clinical roles as fibrin sealant for hemostasis.

A common characteristic of chronic wounds is elevated protease activities. Thus, local (or systemic) treatment of chronic wounds with protease inhibitor(s) could promote healing. However, high levels of protease activity in chronic wounds of widely differing aetiology have been shown and may be related to a problem with the healing process itself rather than with the aetiology of the wound.

MMPs play vital roles in initial wound debridement as well as in the phases of angiogenesis, epithelialization, and scar remodeling. A balance between proteases and their inhibitors is necessary for a correct wound healing, and elevated levels of proteases and reduced levels of inhibitors have been found in chronic wounds. Increased levels of MMP-2 and MMP-9 have been demonstrated in various chronic wound liquids. Increased levels of MMP-1 and MMP-8 have been found in decubital ulcers, and MMP-13 in venous ulcer lesions. Reduced levels of TIMPs have been found in chronic wound fluid. The MMP-9 to TIMP-1 ratio may be a predictor for chronic wound healing, as an inverse correlation with the healing tendency of chronic pressure ulcers has been shown. (Ladewig et al).

Similar processes may occur in non-healing or poorly healing diabetic foot lesions. Loots et al., Dahn et al., Mansbridge et al.). Higher concentrations of MMPs and reduced concentrations of MMP inhibitors have been found in diabetic wounds compared with trauma lesions of a control group. Unlike normal wound healing, an overexpression of these proteases seems to support a delayed wound healing and lead to a failure of wounds to heal. Additionally, an imbalance between MMPs and TIMPs that contributes to the pathogenesis of nonhealing chronic lesions may exist. Chronic diabetic foot ulcers have been treated with the antibiotic doxycycline, which is also a competitive inhibitor of certain metalloproteases. Dressings that contain high concentrations of gelatin, which is a substrate for MMPs, have also been used. Elastase and plasmin activities in wound fluids have been found at significantly reduced by a local therapy with Promogran, which may improve healing by reducing the activities of MMPs in the molecular environment of the wound. Cullen et al. A dressing consisting of metal ions and citric acid has also been used and reduced reactive oxygen species and MMP-2 production in vitro.

Use of recombinant PDGF (Regranex) for diabetic foot syndrome showed improvements in the probability of healing and reduction of healing time. Smiell et al. It was also determined that the wound bed needed to be properly debrided for the growth factor to have maximum benefit. Thus, wound bed preparation is important, and emphasizes the removal of barriers to healing and the integration of advanced technologies in wound care.

Alpha-2-macroglobulin (A2M) is a highly conserved protease inhibitor present in plasma at relatively high concentrations (0.1-6 mg/ml). It is unique in its ability to inhibit all the major classes of proteases (Bhattacharjee et al., J. Biol. Chem. 275, 26806-11 (2000)). A2M can be produced by several cell types, such as hepatocytes, lung fibroblasts, macrophages, astrocytes and tumor cells (Borth W, Ann N.Y. Acad. Sci. 737:267-72 (1994)). A2M often exists as a tetramer of four identical 180 kDa subunits that forms a hollow cylinder-like structure. It can present multiple target peptide bonds to attacking proteases in its central "bait" domain. A2M can be the major protease inhibitor acting on foreign proteases, such as snake venoms. However, there are many other protease inhibitors in the circulation and it has been proposed that A2M can have other functions including binding to and regulation of cytokine and growth factor activity, promotion of tumoricidal capabilities of macrophages, and enhancement of antigen presentation. A2M can also be a targeting carrier for cytokines or growth factors.

Despite advances in the understanding of the principles underlying the wound healing process, there remains a significant unmet need for suitable therapeutic options for wound care and tissue repair and improving and/or promoting wound healing, including wounds that do not heal at expected rates, such as delayed-healing wounds, incompletely healing wounds, and compromised wound healing such as is seen in chronic wounds, scarring and abnormal or excessive scarring, including keloid and hypertrophic scarring, atropic scarring, widespread scarring, and scar contractures, as well as adhesions including surgical adhesions. There is a need in the art for improved methods and compositions for treating conditions such as those caused by acute and chronic wounds, inflammation, fibrosis, scarring, and adhesions.

Therefore, it is an object of the invention to provide compositions, systems, methods, and kits for the detection, diagnosis, and treatment of inflammation, degradation of extracellular matrix, and wounds. It is another object of the invention to provide systems and methods to produce compositions for the treatment of inflammation, degradation of extracellular matrix, and chronic wounds. It is another object of the invention to provide biomarkers and methods for identifying sites of chronic wounds. It is another object of the invention to provide methods for diagnosing or assisting in the diagnosis of the presence of pathologies that are causative of chronic wounds. Yet another object of the invention is to provide biomarkers and methods to determine an appropriate therapy for a subject experiencing chronic wounds. Another object of the invention is to provide biomarkers and methods to monitor and assess the efficacy of a treatment for chronic wounds. Another object of the invention is to provide compositions and methods for treating chronic wounds and for selecting treatment sites and methods for treatment of chronic wounds.

It is another object of the invention to provide variant polypeptides for treating chronic wounds. It is another object of the invention to provide variant A2M polypeptides with a higher protease inhibitory activity than a wild-type A2M polypeptide. It is another object of the invention to provide methods of making variant polypeptides for the treatment of chronic wounds.

SUMMARY OF THE INVENTION

One aspect provided is a method for the treatment or prophylaxis of a wound in a subject, comprising administering to the wound an effective amount of a composition comprising alpha-2-macroglobulin (A2M) isolated from a biological sample from a subject, wherein the A2M is present at a concentration of at least 1.1 times higher than the concentration of A2M present in the biological sample from the subject; and plasma, bone marrow aspirate (BMA), or another body fluid from the biological sample.

One aspect provided is a method for the treatment or prophylaxis of a wound in a subject, comprising administering to the wound an effective amount of a composition comprising a variant A2M polypeptide or portion thereof.

One aspect provided is a method for the treatment or prophylaxis of a wound in a subject, comprising administering to the wound an effective amount of a composition comprising an agent that inhibits one or more proteins or cells associated with formation of the FAC.

In some embodiments, the administering comprises topically applying. In some embodiments, the administering comprises systemically administering. In some embodiments, matrix metalloproteinases are inhibited in the wound. In some embodiments, FAC formation is inhibited or FAC dissociation is promoted. In some embodiments, the wound is a chronic wound. In some embodiments, the wound is a slow healing wound. In some embodiments, the wound is an incomplete healing wound. In some embodiments, the wound is an open wound. In some embodiments, the wound is closed wound. In some embodiments, the wound is characterized at least in part by one or more of a prolonged inflammatory phase, a slow forming extracellular matrix, and a stalled or decreased rate of epithelialization. In some embodiments, the chronic wound is characterized at least in part by one or more of a chronic self-perpetuating state of wound inflammation, a deficient and defective wound extracellular matrix (ECM), poorly responding wound cells, limited ECM production, and failure of re-epithelialization due in part to lack of the necessary ECM orchestration and lack of scaffold for migration. In some embodiments, the chronic wound is characterized at least in part by one or more of prolonged inflammation and proteolytic activity, leading to ulcerative lesions prolonged fibrosis in the wound leading to scarring, progressive deposition of matrix in the affected area, longer repair times, less wound contraction, slower re-epithelialization, and increased thickness of granulation tissue. In some embodiments, the chronic wound is a chronic skin wound. In some embodiments, the chronic wound has not healed within one month. In some embodiments, chronic wound is selected from the group consisting of sores and ulcers. In some embodiments, the ulcers are selected from the group consisting of venous ulcers, diabetic pressure ulcers, stasis ulcers, venous stasis ulcers, diabetic foot ulcers, arterial insufficiency ulcers, burn ulcers, traumatic ulcers, or any combination thereof. In some embodiments, the sores are selected from the group consisting of pressure sores. In some embodiments, the subject has undergone a cosmetic procedure. In some embodiments, the cosmetic procedure comprises a cosmetic surgery, plastic surgery, breast augmentation, hair replacement, laser skin resurfacing, tummy tuck, ear surgery, microderm-abrasion treatment, nose surgery, spider vein treatment, eyelid surgery, thigh lift, chemical peel, arm lift, treatment with a dermal filler, chin surgery, liposuction, brow lift, facelift, treatment with Botulinum Toxin, skin rejuvenation procedure, implantation, tattooing, or any combination thereof. In some embodiments, the subject is an animal. In some embodiments, the subject is a mammal. In some embodiments, the subject is a human pig, mouse, rat, rabbit, cat, dog, monkey, frog, horse or goat. In some embodiments, the subject is a human. In some embodiments, the composition is autologous. In some embodiments, the composition is not immunogenic to the subject. In some embodiments, the composition is a liquid. In some embodiments, the composition comprises platelets. In some embodiments, the composition is on a wound dressing. In some embodiments, the biological sample is a blood, BMA, or a body fluid. In some embodiments, the composition comprises one or more additional non-blood derived components. In some embodiments, the one or more additional non-blood derived components comprise an anti-coagulant, wherein the anti-coagulant comprises EDTA, tri-sodium citrate, water for injection (WFI), or saline. In some embodiments, the composition comprises one or more additional blood-derived components. In some embodiments, the one or more additional blood-derived components comprise platelets. In some embodiments, the composition is substantially free of cells and particles with a diameter of at least about 0.1 μm, 0.2 μm, 0.6 μm or 1 μm or more. In some embodiments, the composition is substantially free of red blood cells. In some embodiments, the composition is substantially free of white blood cells. In some embodiments, the composition is substantially free of platelets. In some embodiments, the composition comprises a first plurality of non-A2M proteins and molecules. In some embodiments, the composition comprises a second plurality of non-A2M proteins and molecules. In some embodiments, the first plurality of non-A2M proteins and molecules are characterized as having a molecular weight more than about 10 kDa, and are present at a concentration of at least 1.1 times higher than found in the biological sample from the mammal. In some embodiments, the first plurality of non-A2M proteins and molecules are characterized as having a molecular weight less than about 500 kDa, and are present at a concentration of less than about 90%, 70%, 50%, 30%, or 10% of a concentration of those proteins in the biological sample from the mammal. In some embodiments, the second plurality of non-A2M proteins and molecules are characterized as having a molecular weight more than about 10 kDa, and are present at a concentration of at least 1.1 times higher than found in the biological sample from the mammal. In some embodiments, the first plurality of non-A2M proteins and molecules comprise cytokines; chemokines; immunomodulatory mediators, peptides, proteins, DNA, RNA, carbohydrates, small molecules; proteases; degradative proteins; or any combination thereof. In some embodiments, the cytokines comprise interleukins, tumor necrosis factors (TNFs), monocyte chemoattractant proteins (MCPs), macrophage inflammatory proteins (MIPs), tumor growth factors (TGFs), matrix metalloproteases (MMPs), or any combination thereof. In some embodiments, the first plurality of non-A2M proteins and molecules are characterized as having a molecular weight of less than about 100 kDa. In some embodiments, the first plurality of non-A2M proteins and molecules are characterized as having a molecular weight of less than about 50 kDa. In some embodiments, the first plurality of non-A2M proteins and molecules are characterized as having a molecular weight of less than about 10 kDa. In some embodiments, the second plurality of non-A2M proteins and molecules are characterized as having a molecular weight more than about 50 kDa. In some embodiments, the second plurality of non-A2M proteins and molecules are characterized as having a molecular weight of more than about 100 kDa. In some embodiments, the second plurality of non-A2M proteins and molecules are characterized as having a molecular weight of more than about 500 kDa. In some embodiments, the first plurality of non-A2M proteins and molecules are characterized as having a molecular weight more than about 50 kDa. In some embodiments, the first plurality of non-A2M proteins and molecules are characterized as having a molecular weight of more than about 100 kDa. In some embodiments, the first plurality of non-A2M proteins and molecules are characterized as having a molecular weight of more than about 500 kDa. In some embodiments, the A2M is present at a concentration of at least 1.1, 1.2, 1.3, 1.4, 1.5, 2, 3, 5, 10, or 20 times higher than the concentration of A2M present in the biological sample from the mammal. In some embodiments, protease activity is inhibited at a site of administration. In some embodiments, the subject has been previously diagnosed as having a wound. In some embodiments, the rate of wound healing is increased in the subject. In some embodiments, the treating results in a reduction in severity, size, infection, or bleeding, or an increase in a rate of progression, of the wound. In some embodiments, the method further comprises administering one or more additional carriers or drugs. In some embodiments, the one or more additional carriers or drugs steroidal or non-steroidal anti-inflammatory agents, ibuprofen, aspirin, paracetamol, glucocorticoids, acetaminophen, hydrocortisone, betamethosone, local anesthetics, antimicrobial agents, growth factors, protease inhibitors. an antiseptic, an antibiotic, cephalosporins, penicillins, tetracyclines, aminoglycosides, antifungals, sulphadiazine, chloramphenicol, erythromycin, vancomycin, trimethoprim, silver, chlorhexidine, povidone iodine, triclosan, sucralfate, quarternary ammonium salts, or any combination thereof. In some embodiments, the composition further comprises one or more pharmaceutical acceptable excipients.

In some embodiments, the variant A2M polypeptide comprising a bait region, the bait region of the variant A2M polypeptide comprising a plurality of protease recognition sites arranged in series. In some embodiments, the variant A2M polypeptide protein is a recombinant protein. In some embodiments, the variant A2M polypeptide protein is produced in a host comprising bacteria, yeast, fungi, insect, or mammalian cells, or a cell free system. In some embodiments, the variant A2M polypeptide protein is characterized by an enhanced nonspecific inhibition of serine proteases, threonine proteases, cysteine proteases, aspartate proteases, metalloproteases, glutamic acid proteases, or any combination thereof. In some embodiments, the variant A2M polypeptide protein further comprises PEG with abnormal glycosylation sites. In some embodiments, the variant A2M polypeptide protein has a longer half-life than the half-life of a wild type A2M protein when disposed within a chronic wound of a subject. In some embodiments, the plurality of protease recognition sites comprise one or more protease substrate bait regions from one or more proteins other than A2M, one or more additional protease bait regions from A2M, one or more non-natural protein sequences, or any combination thereof, wherein the modified A2M protein is characterized by at least a 10% increase in protease inhibitory effectiveness compared to the protease inhibitory effectiveness of a wild type A2M protein. In some embodiments, the non-natural protein sequences comprise one or more protease recognition sites that can function as bait for proteases. In some embodiments, the one or more protease substrate bait regions comprise consensus sequences for serine proteases, threonine proteases, cysteine proteases, aspartate proteases, metalloproteinases, glutamic acid proteases, or any combination thereof. In some embodiments, the protease substrate bait regions comprise one or more consensus sequences for one or more proteases from one or more organisms. In some embodiments, the one or more organisms comprise, animals, plants, bacteria, yeast, fish, reptiles, amphibians, or fungi. In some embodiments, one or more of the one or more protease substrate bait regions from the one or more proteins other than A2M are the same. In some embodiments, one or more of the one or more protease substrate bait regions from A2M are the same. In some embodiments, one or more of the one or more protease substrate bait regions from the one or more non-natural protein sequences are the same. In some embodiments, one or more of the one or more protease substrate bait regions from the one or more proteins other than A2M or from the one or more non-natural protein sequences comprise a suicide inhibitor; wherein the suicide inhibitor is operable to covalently attach a protease to A2M. In some embodiments, one or more of the one or more protease substrate bait regions are from different species. In some embodiments, the variant A2M polypeptide comprises one or more non-natural bait regions, wherein the one or more non-natural bait regions comprise one or more protease recognition sites not present in a wild-type A2M polypeptide. In some embodiments, the variant A2M polypeptide is characterized by at least a 10% enhanced inhibition of one or more proteases compared to a wild-type A2M inhibition of the one or more proteases. In some embodiments, the enhanced inhibition comprises enhanced nonspecific inhibition. In some embodiments, the enhanced inhibition comprises enhanced specific inhibition. In some embodiments, the protease comprises a serine protease, threonine protease, cysteine protease, aspartate protease, metalloprotease, glutamic acid protease, or any combination thereof. In some embodiments, the protease comprises MMP1 (Interstitial collagenase), MMP2 (Gelatinase-A), MMP3 (Stromelysin 1), MMP7 (Matrilysin, PUMP 1), MMP8 (Neutrophil collagenase), MMP9 (Gelatinase-B), MMP10 (Stromelysin 2), MMP11), Stromelysin 3), MMP12 (Macrophage metalloelastase), MMP13 (Collagenase 3), MMP14 (MT1-MMP), MMP15 (MT2-MMP), MMP16 (MT3-MMP), MMP17 (MT4-MMP), MMP18 (Collagenase 4, xcol4, xenopus collagenase), MMP19 (RASI-1, stromelysin-4), MMP20 (Enamelysin), MMP21 (X-MMP), MMP23A (CA-MMP), MMP23B MMP24 (MT5-MMP), MMP25 (MT6-MMP), MMP26 (Matrilysin-2, endometase), MMP27 (MMP-22, C-MMP), MMP28 (Epilysin); A Disintegrin and Metalloproteinase with Thrombospondin Motifs protease, such as ADAMTS1, ADAMTS2, ADAMTS3, ADAMTS4, ADAMTS5 (ADAMTS11), ADAMTS6, ADAMTS7, ADAMTS8 (METH-2), ADAMTS9, ADAMTS10, ADAMTS12, ADAMTS13, ADAMTS14, ADAMTS15, ADAMTS16, ADAMTS17, ADAMTS18, ADAMTS19, ADAMTS20; chymotrypsin; trypsin; elastase; compliment factors; clotting factors; thrombin; plasmin; subtilisin; Neprilysin; Procollagen peptidase; Thermolysin; Pregnancy-associated plasma protein A; Bone morphogenetic protein 1; Lysostaphin; Insulin degrading enzyme; ZMP-STE2; acetylcholinesterase; or a combination thereof. In some embodiments, the protease comprises ADAMTS4, ADAMTS 5, MMP13, or a combination thereof. In some embodiments, the modified A2M polypeptide is characterized by at least a 10% enhanced inhibition of FAC formation compared to a wild-type A2M inhibition of FAC formation. In some embodiments, the one or more non-natural bait regions are derived from one or more proteins other than A2M. In some embodiments, the one or more proteins other than A2M are from a non-human organism. In some embodiments, the non-human organism comprises an animal, plant, bacterium, yeast, fish, reptile, amphibian, or fungi. In some embodiments, the one or more non-natural bait regions comprise SEQ ID NOs 5-66. In some embodiments, the variant A2M polypeptide comprises SEQ ID NO 4, or a fragment thereof. In some embodiments, the one or more non-natural bait regions comprise SEQ ID NOs 5-66, or fragments thereof. In some embodiments, the wild-type A2M polypeptide comprises SEQ ID NO 3, or a fragment thereof. In some embodiments, one or more of the one or more non-natural bait regions comprise a suicide inhibitor; wherein the suicide inhibitor is operable to covalently attach a protease to the variant A2M polypeptide. In some embodiments, the one or more protease recognition sites comprise 2 or more copies of the one or more protease recognition sequences. In some embodiments, the one or more non-natural bait regions comprise 2 or more copies of the one or more non-natural bait regions. In some embodiments, the variant A2M polypeptide comprises a wild-type A2M bait region sequence. In some embodiments, the variant A2M polypeptide is a recombinant polypeptide. In some embodiments, the one or more protease recognition sites comprise a consensus sequence for a protease. In some embodiments, the variant A2M polypeptide comprises one or more modified glycosylation sites. In some embodiments, the one or more modified glycosylation sites are functionalized with PEG. In some embodiments, the variant A2M polypeptide has at least a 10% longer half-life than the half-life of a wild type A2M polypeptide when disposed within the subject.

In some embodiments, the agent comprises an antibody, polypeptide, nucleotide, or small molecule. In some embodiments, the agent binds to the FAC but not to the individual components of the complex separately. In some embodiments, the agent comprises a recombinant aggrecan G3 domain, wherein the domain contains the aggrecan G3 Lectin domain and competitively binds to fibronectin; and wherein the newly formed complex lacks the binding site to PAMP receptor and the binding site DAMP receptor. In some embodiments, the agent comprises a recombinant fibronectin fragment, wherein the fragment comprises a G3 binding domain and competitively binds to aggrecan, and wherein the newly formed fibronectin fragment aggrecan G3 complex lacks the binding site to PAMP receptor, and the DAMP receptor. In some embodiments, the agent comprises an aggrecan antibody. In some embodiments, the agent comprises a fibronectin antibody. In some embodiments, the agent comprises an antibody that binds to the PAMP receptor recognition domain of aggrecan, the DAMP receptor recognition domain of aggrecan, or both, thereby inhibiting activation of monocytes and other cells. In some embodiments, the agent comprises an antibody that binds to the PAMP receptor recognition domain of fibronectin, the DAMP receptor recognition domain of fibronectin, or both, thereby inhibiting activation of monocytes and other cells. In some embodiments, the agent comprises a PAMP receptor or DAMP receptor that binds to the PAMP domain of aggrecan G3, the DAMP domain of aggrecan G3, or both, thereby inhibiting activation of monocytes and other cells. In some embodiments, the agent comprises a soluble form of the PAMP receptor or DAMP receptor that binds to the PAMP domain of fibronectin, the DAMP domain of fibronectin, or both, thereby inhibiting activation of monocytes and other cells. In some embodiments, the agent inhibits production of proinflammatory cytokines, chemokines, proteases, or any combination thereof. In some embodiments, the agent inhibits fibroblast cells, thereby inhibiting production of fibronectin, recruitment of other fibroblast cells, or a combination thereof. In some embodiments, the agent is identified using one or more high-throughput screening methods. In some embodiments, the small molecule or polypeptide inhibits FAC formation, inhibits activation of monocytes, inhibits increased production of fibronectin, inhibits recruitment of fibroblast cells, binds to the DAMP domain of fibronectin, binds to the DAMP domain of aggrecan G3, binds to the PAMP domain of fibronectin, or binds to the PAMP domain of aggrecan G3. In some embodiments, the small molecule or polypeptide inhibits FAC formation by competitively binding to fibronectin or aggrecan. In some embodiments, the small molecule or polypeptide binds to the FAC complex resulting in dissociation or degradation of the FAC complex. In some embodiments, inhibiting the formation of the FAC comprises inhibiting of one or more steps in FAC formation. In some embodiments, the one or more steps in FAC formation comprise production of fibronectin in the ECM, production of proteases and metalloproteases, production of inflammatory cytokines and chemokines, degradation of aggrecan in cartilage, and production of aggrecan G3 domain fragment.

In one aspect, provided herein is a system for enrichment of A2M from a fluid sample comprising: a centrifuge; a flow filtration module comprising one or more filters; and an A2M enriched retentate from the fluid sample.

In some embodiments, the system further comprises a pump adapted to be fluidly coupled to the flow filtration module, and produce a flow of the fluid sample that passes through an inlet and an outlet of the flow filtration module. In some embodiments, the pump is fluidly coupled to the flow filtration module upstream of the inlet. In some embodiments, the pump is fluidly coupled to the flow filtration module downstream of the outlet. In some embodiments, the centrifuge comprises a supernatant of the fluid sample. In some embodiments, the flow filtration module comprises a supernatant of the fluid sample. In some embodiments, a pellet of the centrifuged fluid sample is not in the flow filtration module. In some embodiments, the supernatant of the fluid sample is from the centrifuge. In some embodiments, red blood cells have been substantially removed from the supernatant. In some embodiments, white blood cells have been substantially removed from the supernatant. In some embodiments, a filter of the one or more filters has a pore size of at least about 0.1 µm, 0.2 µm, 0.6 µm, or 1 µm. In some embodiments, a filter of the one or more filters has a pore size of at most about 10, 50, 100, 200, 300, 400, or 500 kDa. In some embodiments, a filter of the one or more filters comprise a cross flow filter. In some embodiments, the flow filtration module further comprises a permeate collection reservoir. In some embodiments, the permeate collection reservoir stores a permeate from the one or more filters. In some embodiments, a retentate of the one or more filters comprises the A2M enriched retentate. In some embodiments, the A2M enriched retentate remains in the permeate collection reservoir. In some embodiments, a retentate of the one or more filters comprises cells and particles from the fluid sample comprising a diameter of at least about 0.1 µm, 0.2 µm, 0.6 µm, or 1 µm. In some embodiments, a retentate of the one or more filters comprises a concentration of proteins with a molecular weight of at least about 10, 50, 100, 200, 300, 400, or 500 kDa, of at least about 1.1 times their concentration in the sample. In some embodiments, a permeate from the one or more filters has a concentration of proteins having a molecular weight less than about 10, 50, 100, 200, 300, 400, or 500 kDa of less than about 90%, 80%, 60%, 30%, or 10% of the concentration of those proteins in the sample. In some embodiments, the one or more filters comprise two or more filters.

In one aspect, provided herein is a system for concentrating A2M from a fluid sample comprising: a flow filtration module comprising an inlet, an outlet, and two or more filters fluidly connected in series between the inlet and outlet; and an A2M enriched retentate from the fluid sample.

In some embodiments, the system further comprises a pump adapted to be fluidly coupled to the flow filtration module, and produce a flow of the fluid sample that passes through the filter unit from the inlet to the outlet. In some embodiments, the pump is fluidly coupled to the flow filtration module upstream of the inlet. In some embodiments, the pump is fluidly coupled to the flow filtration module downstream of the outlet. In some embodiments, the system further comprises a centrifuge. In some embodiments, the two or more filters are fluidly connected in series between an inlet and an outlet of the flow filtration module. In some embodiments, a first of the two or more filters has a pore size of at least about 0.1 µm, 0.2 µm, 0.6 µm, or 1 µm, and a second of the two or more filters has a pore size of at most about 10, 50, 100, 200, 300, 400, or 500 kDa. In some embodiments, the fluid sample passes through the two or more filters to produce the A2M enriched retentate. In some embodiments, the two or more filters comprise a first and a second filter, wherein the second filter is downstream of the first filter. In some embodiments, the first and the second of the two or more filters comprise a first and a second cross flow filter. In some embodiments, a retentate of the second filter comprises the A2M enriched retentate. In some embodiments, a retentate of the first filter comprises cells and particles from the fluid sample comprising a diameter of at least about 0.1 µm, 0.2 µm, 0.6 µm, or 1 µm. In some embodiments, a retentate of the second filter comprises proteins with a molecular weight of at least about 10, 50, 100, 200, 300, 400, or 500 kDa, wherein the concentration of those proteins is at least about 1.1 times their concentration in the fluid sample. In some embodiments, the permeate from the second filter has a concentration of proteins having a molecular weight less than about 10, 50, 100, 200, 300, 400, or 500 kDa of less than about 90%, 80%, 60%, 30%, or 10% of the concentration of those proteins in the sample. In some embodiments, a first permeate from the first filter flows through the second filter. In some embodiments, the flow filtration module further comprises a first and a second permeate collection reservoir. In some embodiments, the first permeate collection reservoir stores a permeate from the first filter and a retentate of the second filter. In some embodiments, the second permeate collection reservoir stores a permeate from the second filter. In some embodiments, the A2M enriched retentate remains in the first permeate collection reservoir. In some embodiments, the flow filtration module is a dead end and/or tangential flow filtration module. In some embodiments, the fluid sample comprises a biological sample. In some embodiments, the biological sample is from an animal. In some embodiments, the biological sample is from a mammal. In some embodiments, the biological sample is from a human. In some embodiments, the system further comprises one or more waste modules in fluid connection with the flow filtration module. In some embodiments, the one or more waste modules are downstream of the flow filtration module. In some embodiments, the one or more waste modules comprise particles, and other molecules with a diameter of at least about 0.1 μm, 0.2 μm, 0.6 μm, or 1 μm from the fluid sample. In some embodiments, the one or more waste modules comprise proteins with a molecular weight of less than about 10, 50, 100, 200, 300, 400, or 500 kDa from the fluid sample. In some embodiments, the fluid sample is flowing through the one or more filters in sequence using the centrifuge, a pump, or a combination thereof. In some embodiments, the fluid sample is flowing through the two or more filters in sequence using the centrifuge, a pump, or a combination thereof. In some embodiments, the system further comprises a collection module in fluid connection with the flow filtration module. In some embodiments, the collection module is downstream of the centrifuge. In some embodiments, the collection module comprises the A2M enriched retentate. In some embodiments, the system further comprises a sample loading module operable to introduce the fluid sample into the system. In some embodiments, the sample loading module is directly or indirectly attached to the blood stream of a subject. In some embodiments, the A2M enriched retentate comprises A2M at a concentration of at least 1.1 times higher than found in the fluid sample. In some embodiments, the A2M enriched retentate comprises a first plurality of non-A2M proteins and molecules. In some embodiments, the A2M enriched retentate comprises a second plurality of non-A2M proteins and molecules. In some embodiments, the first plurality of non-A2M proteins and molecules are characterized as having a molecular weight more than about 10, 50, 100, 300, or 500 kDa, and are present at a concentration of at least 1.1 times higher than found in the fluid sample. In some embodiments, the first plurality of non-A2M proteins and molecules are characterized as having a molecular weight less than about 500 kDa, and are present at a concentration of less than about 90%, 70%, 50%, 30%, or 10% of a concentration of those proteins in the fluid sample. In some embodiments, the second plurality of non-A2M proteins and molecules are characterized as having a molecular weight more than about 10 kDa, and are present at a concentration of at least 1.1 times higher than found in the fluid sample. In some embodiments, the first plurality of non-A2M proteins and molecules comprise cytokines; chemokines; immunomodulatory mediators, peptides, proteins, DNA, RNA, carbohydrates, small molecules; proteases; degradative proteins; or any combination thereof. In some embodiments, the cytokines comprise interleukins, tumor necrosis factors (TNFs), monocyte chemoattractant proteins (MCPs), macrophage inflammatory proteins (MIPs), tumor growth factors (TGFs), matrix metalloproteases (MMPs), or any combination thereof. In some embodiments, red blood cells have been substantially removed from the fluid sample. In some embodiments, white blood cells have been substantially removed from the fluid sample. In some embodiments, platelets have been substantially removed from the fluid sample. In some embodiments, red blood cells have been substantially removed from the A2M enriched retentate. In some embodiments, white blood cells have been substantially removed from the A2M enriched retentate. In some embodiments, platelets have been substantially removed from the A2M enriched retentate. In some embodiments, the A2M enriched retentate comprises platelets. In some embodiments, the A2M enriched retentate is obtained in less than about 15 minutes, 30 minutes, 45 minutes, 1 hour, or 3 hours.

In one aspect, provided herein is a method for enrichment of A2M from a biological sample obtained from an animal comprising: flowing the biological sample through one or more filters of a flow filtration module, thereby separating the sample into a permeate and a retentate; and collecting the retentate; wherein the collected retentate is an A2M enriched retentate, wherein the concentration of A2M in the A2M enriched retentate is at least 1.1, 1.2, 1.3, 1.4, 1.5, 2, 3, 4, 5, 10, or 20 times higher than the concentration of A2M in the sample, and wherein the concentration in the A2M enriched retentate of proteins having a molecular weight less than about 10, 50, 100, 200, 300, 400, or 500 kDa is less than 90%, 80%, 60%, 30%, or 10% of the concentration of those proteins in the sample.

In some embodiments, the method further comprises removing cells and particles with a diameter of at least about 0.1 μm, 0.2 μm, 0.6 μm, or 1 μm from the sample before (a). In some embodiments, the removing comprises centrifuging the biological sample, and obtaining a supernatant of the fluid sample. In some embodiments, the removing comprises flowing the biological sample through a filter. In some embodiments, the flowing comprises flowing the biological sample through a first filter of the one or more filters, thereby separating the biological sample into a first permeate and a first retentate, and flowing the first permeate through a second filter of the one or more filters, thereby separating the biological sample into a second permeate and a second retentate; wherein the second retentate is the A2M enriched retentate.

In one aspect, provided herein is a method of enriching A2M from a biological sample from an animal comprising: removing cells and particles with a diameter of at least about 0.1 μm, 0.2 μm, 0.6 μm, or 1 μm from a biological sample to produce a fluid sample, and flowing the fluid sample through one or more filters of a flow filtration module, thereby producing a an A2M enriched retentate.

In some embodiments, the removing comprises centrifuging the biological sample, and obtaining a supernatant of the fluid sample. In some embodiments, the removing comprises flowing the biological sample through a filter. In some embodiments, the method further comprises discarding or retaining a pellet of the fluid sample. In some embodiments, the flowing comprises flowing the fluid sample through a first filter of the one or more filters, thereby separating the fluid sample into a first permeate and a first retentate, and flowing the first permeate through a second filter of the one or more filters, thereby separating the fluid sample into a second permeate and a second retentate; wherein the second retentate is the A2M enriched retentate. In some embodiments, a first filter of the one or more filters has a pore size of at least about 0.1 µm, 0.2 µm, 0.6 µm, or 1 µm. In some embodiments, a first filter of the one or more filters has a pore size of at least about 10, 50, 100, 200, 300, 400, or 500 kDa. In some embodiments, a retentate from the one or more filters has a concentration of proteins having a molecular weight less than about 10, 50, 100, 200, 300, 400, or 500 kDa of less than about 99%, 95%, 90%, 80%, 60%, 30%, or 10% of the concentration of those proteins in the biological sample. In some embodiments, a permeate from the one or more filters has a concentration of proteins having a molecular weight less than about 10, 50, 100, 200, 300, 400, or 500 kDa of more than about 99%, 95%, 90%, 80%, 60%, 30%, or 10% of the concentration of those proteins in the biological sample. In some embodiments, the one or more filters comprise two or more filters.

In one aspect, provided herein is a method for enriching A2M from a biological sample obtained from an animal comprising: flowing the biological sample through two or more filters of a flow filtration module, thereby separating the biological sample into two or more permeates and two or more retentates; and collecting at least one of the two or more retentates; wherein the collected retentate is an A2M enriched retentate.

In some embodiments, the flowing comprises flowing the biological sample through a first filter of the two or more filters, thereby separating the sample into a first permeate and a first retentate, and flowing the first permeate through a second filter of the two or more filters, thereby separating the sample into a second permeate and a second retentate; wherein the second retentate is the collected retentate. In some embodiments, a first filter of the two or more filters has a pore size of at least about 0.1 µm, 0.2 µm, 0.6 µm, or 1 µm. In some embodiments, a first filter of the two or more filters has a pore size of at least about 10, 50, 100, 200, 300, 400, or 500 kDa. In some embodiments, a second filter of the two or more filters has a pore size of at least about 10, 50, 100, 200, 300, 400, or 500 kDa. In some embodiments, the first filter comprises a first cross-flow filter. In some embodiments, the second filter comprises a second cross-flow filter. In some embodiments, the method further comprises filtering a permeate of the first filter with the second filter. In some embodiments, the method further comprises collecting a retentate of the second filter. In some embodiments, the retentate of the second filter comprises the A2M enriched retentate. In some embodiments, the method further comprises storing the A2M enriched retentate in a second filter retentate reservoir in fluid connection with the second filter. In some embodiments, the method further comprises storing a retentate of the first filter in a reservoir in fluid connection with the first filter. In some embodiments, the two or more filters are fluidly connected in series between an inlet and an outlet of the flow filtration module. In some embodiments, the fluid sample passes through the two or more filters to produce the A2M enriched retentate. In some embodiments, the two or more filters comprise a first and a second filter, wherein the second filter is downstream of the first filter. In some embodiments, the first and the second of the two or more filters comprise a first and a second cross flow filter. In some embodiments, a retentate of the second filter comprises the A2M enriched retentate. In some embodiments, a retentate of the first filter comprises cells and particles from the fluid sample comprising a diameter of at least about 0.1 µm, 0.2 µm, 0.6 µm, or 1 µm. In some embodiments, in a retentate of the second filter the concentration of proteins with a molecular weight of at least about 10, 50, 100, 200, 300, 400, or 500 kDa is at least about 1.1 times their concentration in the biological sample. In some embodiments, a permeate from the second filter has a concentration of proteins having a molecular weight less than about 10, 50, 100, 200, 300, 400, or 500 kDa of more than about 99%, 95%, 90%, 80%, 60%, 30%, or 10% of the concentration of those proteins in the s biological ample. In some embodiments, a first permeate from the first filter flows through the second filter. In some embodiments, the flow filtration module further comprises a first and a second permeate collection reservoir. In some embodiments, the first permeate collection reservoir stores a permeate from the first filter and a retentate of the second filter. In some embodiments, the second permeate collection reservoir stores a permeate from the second filter. In some embodiments, the A2M enriched retentate remains in the first permeate collection reservoir. In some embodiments, the flow filtration module comprises and inlet and an outlet, and wherein the one or more filters are fluidly connected in series between the inlet and the outlet. In some embodiments, the flow filtration module comprises and inlet and an outlet, and wherein the two or more filters are fluidly connected in series between the inlet and the outlet. In some embodiments, the flowing comprises pumping with a pump, wherein the pump is fluidly connected to the flow filtration module upstream of the inlet or downstream of the outlet. In some embodiments, the pumping comprises manually actuating the pump. In some embodiments, the biological sample comprises plasma. In some embodiments, the method further comprises removing red blood cells from the biological sample. In some embodiments, the method further comprises removing white blood cells from the biological sample. In some embodiments, the method further comprises removing platelets from the biological sample. In some embodiments, the red blood cells, white blood cells, platelets, or any combination thereof, are removed by flowing or passing the sample through the filters. In some embodiments, the method further comprises adding one or more blood derived components to the biological sample or the A2M enriched retentate. In some embodiments, the one or more blood derived components comprise platelets. In some embodiments, a filter of the one or more filters is a hollow fiber tangential flow filter. In some embodiments, a filter of the two or more filters is a hollow fiber tangential flow filter. In some embodiments, a filter of the one or more filters comprises a charge, immobilized molecules, or a combination thereof, thereby enhancing the selectivity of the filter. In some embodiments, a filter of the two or more filters comprises a charge, immobilized molecules, or a combination thereof, thereby enhancing the selectivity of the filter. In some embodiments, the immobilized molecules comprise antibodies, proteins, receptors, ligands, carbohydrates, nucleotides, RNA, DNA, or any combination thereof. In some embodiments, enhancing the selectivity comprises enhancing the ability to retain A2M, enhancing the ability to not retain molecules that are not A2M, or a combination thereof. In some embodiments, the flowing comprises applying tangential force filtration, one or more centrifugation steps, gravitational forces, mechanical forces, or any combination thereof. In some embodiments, the mechanical force comprises a pump, centrifugal force, or gas pressure, or any combination thereof. In some embodiments, the method further comprises adding one or more non-blood derived components, one or more blood derived components, or a combination thereof, to the biological sample or the A2M enriched retentate. In some embodiments, the one or more additional non-blood derived components comprises an anti-coagulant, preservative, excipient, diluent, or other additive. In some embodiments, the anti-coagulant comprises EDTA, tri-sodium citrate, water for injection (WFI), saline, or ACD-A. In some embodiments, the diluent is a WFI solution or a saline solution. In some embodiments, the one or more additional blood derived components comprise platelets. In some embodiments, the biological sample is a mammalian sample. In some embodiments, the biological sample is a human sample. In some embodiments, the biological sample is collected with the aid of an additional absorbent, adsorbent, or capillary materials or devices selected from the group of needle-syringe combo, sponges, wicks, pledgets, sutures, hydrophilic catheters, hydrophobic catheters, hollow-lumen catheters, or any combination thereof. In some embodiments, the A2M enriched retentate is obtained in less than about 15 minutes, 30 minutes, 45 minutes, 1 hour, or 3 hours. In some embodiments, the concentration of A2M in the A2M enriched retentate is at least 1.1, 1.2, 1.3, 1.4, 1.5, 2, 3, 4, 5, 10, or 20 times higher than the concentration of A2M in the sample. In some embodiments, the concentration in the A2M enriched retentate of proteins having a molecular weight less than about 10, 50, 100, 200, 300, 400, or 500 kDa is less than 90%, 80%, 60%, 30%, or 10% of the concentration of those proteins in the sample. In some embodiments, the flow filtration module is a dead end and/or tangential flow filtration module.

In one aspect, provided herein is a system for manual flow of a biological sample comprising: a first retentate chamber comprising a flow path comprising a first end with a first inlet and second end with a second inlet; a first permeate chamber comprising a first outlet and optionally a second outlet; a first semi-permeable membrane oriented between the first retentate chamber and the first permeate chamber having an average pore size of at least about 10, 50, 100, 200, 300, 400, or 500 kDa that permits liquid flow from the first retentate chamber to the first permeate chamber; and a first injector comprising a manual actuator in fluid connection with the first end, and a second injector comprising a manual actuator in fluid connection with the second end.

In some embodiments, the system further comprises a second retentate chamber comprising a flow path comprising a third end with a third inlet and fourth end with a fourth inlet; a second permeate chamber comprising a second outlet, wherein the second outlet is optionally in fluid connection with the first retentate chamber; a second semi-permeable membrane oriented between the second retentate chamber and the second permeate chamber having an average pore size of at least about 0.1 µm, 0.2 µm, 0.6 µm, or 1 µm that permits liquid flow from the second retentate chamber to the second permeate chamber; and a third injector comprising a manual actuator in fluid connection with the third end, and a fourth injector comprising a manual actuator in fluid connection with the fourth end.

In some embodiments, the first injector is connected to the first inlet via an adapter. In some embodiments, the system further comprises a first vessel connected to the first inlet via the adapter. In some embodiments, the first vessel comprises sterile air. In some embodiments, the first vessel comprises a syringe. In some embodiments, the first vessel is disposed below the first membrane. In some embodiments, the first vessel is disposed above the first membrane. In some embodiments, the first vessel is oriented perpendicular to a surface of the first membrane. In some embodiments, the second injector is connected to the second inlet via an adapter. In some embodiments, the first outlet is connected to a first vessel. In some embodiments, the first vessel comprises a syringe. In some embodiments, the first vessel comprises a permeate of the biological sample. In some embodiments, the adapter is a valve. In some embodiments, the valve is a stopcock. In some embodiments, the first inlet, second inlet, third inlet, fourth inlet, first outlet, second outlet, or any combination thereof, comprises an adapter. In some embodiments, the adapter is a Luer-lock adapter, a Hose-Barb adapter, or a sanitary tri-clover adaptor. In some embodiments, the Luer-lock adapter is closed, capped, or sealed. In some embodiments, the first inlet, second inlet, third inlet, fourth inlet, first outlet, second outlet, or any combination thereof, is closed, capped, or sealed. In some embodiments, the third injector is connected to the third inlet via an adapter. In some embodiments, the system further comprises a second vessel connected to the third inlet via the adapter. In some embodiments, the second vessel comprises sterile air. In some embodiments, the second vessel comprises a syringe. In some embodiments, the second vessel is disposed below the second membrane. In some embodiments, the second vessel is disposed above the second membrane. In some embodiments, the second vessel is oriented perpendicular to a surface of the second membrane. In some embodiments, the fourth injector is connected to the fourth inlet via an adapter. In some embodiments, the second outlet is in fluid connection with the first retentate chamber. In some embodiments, the second outlet is in fluid communication with a second vessel. In some embodiments, the connection is via a second outlet flow path. In some embodiments, the second vessel comprises a container or bag. In some embodiments, the second vessel comprises a permeate of the biological sample. In some embodiments, the permeate of the biological sample does not comprise cells. In some embodiments, the adapter is a valve. In some embodiments, the valve is a stopcock. In some embodiments, the second outlet flow path is in fluid communication with the first retentate chamber via a connecting flow path. In some embodiments, the second outlet flow path is connected to the connecting flow path via a valve. In some embodiments, the valve allows fluid to flow from the second outlet flow path to the second vessel in a first orientation, and wherein the valve allows fluid to flow from the second vessel to the first retentate chamber in a second orientation. In some embodiments, the second outlet is in fluid connection with a collection vessel. In some embodiments, the collection vessel is adapted to fit the first or second inlet. In some embodiments, the collection vessel is adapted to fit an adapter connected to the first or second inlet. In some embodiments, the collection vessel is the first or second injector. In some embodiments, the system further comprises an A2M enriched retentate contained in the first injector or the second injector, the A2M enriched retentate comprising: A2M isolated from a biological sample from an animal, wherein the A2M is present at a concentration of at least 1.1 times higher than the concentration of A2M present in the biological sample from the animal; and plasma, bone marrow aspirate (BMA), or another body fluid from the biological sample. In some embodiments, the A2M enriched retentate comprises proteins with a molecular weight of at least about 10, 50, 100, 200, 300, 400, or 500 kDa present at a concentration of at least 1.1 times higher than found in the biological sample from the animal. In some embodiments, the A2M enriched retentate comprises a concentration of molecules with a molecular weight less than 10, 50, 100, 200, 300, 400, or 500 kDa is less than 90%, 70%, 50%, 30%, or 10% of the concentration of those proteins and/or fold concentration of A2M present in the biological sample from the animal. In some embodiments, the biological sample is a blood sample, BMA, or other body fluid. In some embodiments, the A2M enriched retentate is substantially free of cells and particles with a diameter of at least about 0.1 µm, 0.2 µm, 0.6 µm, or 1 µm, and comprises a reduced concentration of proteins and other molecules with a molecular weight of at least about 10, 50, 100, 200, 300, 400, or 500 kDa compared to the biological sample. In some embodiments, the A2M enriched retentate is for autologous delivery into or onto one or more wounds of the animal. In some embodiments, the A2M enriched retentate is an autologous composition. In some embodiments, the first inlet is disposed to introduce a biological sample into the first retentate chamber and parallel to the surface of the first membrane. In some embodiments, the second inlet is disposed to introduce a biological sample into the first retentate chamber and parallel to the surface of the first membrane. In some embodiments, the third and/or fourth inlet is disposed to introduce a biological sample into the second retentate chamber and parallel to the surface of the second membrane. In some embodiments, the system further comprises a means for providing the biological sample or permeate of the biological sample to the first or second inlet of the first retentate chamber, and a means for controlling a filtration rate of the biological sample through the first membrane and into the first permeate chamber. In some embodiments, the system further comprises a means for providing a the biological sample to the third or fourth inlet of the second retentate chamber, and a means for controlling a filtration rate of the biological sample through the second membrane and into the second permeate chamber. In some embodiments, the first retentate chamber is cylindrical, and wherein the first outlet is disposed perpendicular to a surface of the first and/or second membrane. In some embodiments, the second retentate chamber is cylindrical, and wherein the second outlet is disposed perpendicular to a surface of the second and/or first membrane. In some embodiments, the second retentate chamber is disposed above the first retentate chamber. In some embodiments, the second retentate chamber is parallel to the first retentate chamber. In some embodiments, the first inlet and/or the second inlet is disposed above the first membrane. In some embodiments, the third inlet and/or the fourth inlet is disposed above the second and/or first membrane. In some embodiments, the first inlet and/or the second inlet is oriented perpendicular to a surface of the first membrane. In some embodiments, the third inlet and/or the fourth inlet is oriented perpendicular to a surface of the second and/or first membrane. In some embodiments, the first inlet and/or the second inlet is oriented parallel to a surface of the first membrane. In some embodiments, the third inlet and/or the fourth inlet is oriented parallel to a surface of the second and/or first membrane. In some embodiments, the system is portable.

In one aspect, provided herein is a method for enrichment of A2M from a biological sample obtained from an animal comprising: flowing a biological sample into a system comprising: a first retentate chamber comprising a flow path comprising a first end with a first inlet and second end with a second inlet; a first permeate chamber comprising a first outlet; a first semi-permeable membrane oriented between the first retentate chamber and the first permeate chamber that permits liquid flow from the first retentate chamber to the first permeate chamber; and a first injector comprising a manual actuator in fluid connection with the first end, and a second injector comprising a manual actuator in fluid connection with the second end; through the first inlet, over the first membrane of the first retentate chamber, and through the second inlet, thereby separating the sample into a permeate and a retentate; and collecting the retentate in the first or second injector, wherein the retentate is enriched for A2M.

In some embodiments, the system of the method further comprises: a second retentate chamber comprising a flow path comprising a third end with a third inlet and fourth end with a fourth inlet; a second permeate chamber comprising a second outlet, wherein the second outlet is optionally in fluid connection with the first retentate chamber; a second semi-permeable membrane oriented between the second retentate chamber and the second permeate chamber that permits liquid flow from the second retentate chamber to the second permeate chamber; and a third injector comprising a manual actuator in fluid connection with the third end, and a fourth injector comprising a manual actuator in fluid connection with the fourth end; and wherein the method further comprises: flowing the sample through the third inlet, over the second membrane of the second retentate chamber, and through the fourth inlet, thereby retaining cells and other particles with an average diameter of at least about 0.1 µm, 0.2 µm, 0.6 µm, or 1 µm in the second retentate chamber; and flowing the permeate from the second membrane into the first retentate chamber.

In some embodiments, the concentration of A2M in the retentate is at least 1.1, 1.2, 1.3, 1.4, 1.5, 2, 3, 4, 5, 10, or 20 times higher than the concentration of A2M in the sample. In some embodiments, the retentate comprises a concentration of proteins with a molecular weight less than about 10, 50, 100, 300, or 500 kDa of less than 90%, 80%, 60%, 30%, or 10% the concentration of those proteins in the biological sample. In some embodiments, the flowing comprises flowing the permeate from the second membrane through a channel connecting the second outlet with the first retentate chamber. In some embodiments, the flowing comprises collecting the permeate from the second membrane in a collection vessel and flowing the collected permeate from the second membrane through the first or second inlet into the first retentate chamber. In some embodiments, the collection vessel is adapted to fit the first or second inlet. In some embodiments, the collection vessel is adapted to fit an adapter connected to the first or second inlet. In some embodiments, the collection vessel is the first or second injector. In some embodiments, the flowing comprises actuating the first injector. In some embodiments, the flowing further comprises actuating the second injector. In some embodiments, the first and second injectors are actuated on or more times. In some embodiments, the first and second injectors are actuated in sequence. In some embodiments, the biological sample comprises plasma. In some embodiments, red blood cells and white blood cells have been removed from the biological sample. In some embodiments, the biological sample or A2M enriched retentate further comprises one or more blood derived components. In some embodiments, the one or more blood derived components comprise platelets. In some embodiments, the second membrane is characterized by having a pore size of at least 0.1 µm, 0.2 µm, 0.6 µm, or 1 µm, or higher. In some embodiments, the first membrane comprises a hollow fiber tangential flow filter. In some embodiments, the first membrane has a molecular weight cut-off of at most 10, 50, 100, 200, 300, 400, or 500 kDa. In some embodiments, the first and/or second membranes comprise a charge, immobilized molecules, or a combination thereof, thereby enhancing the selectivity of the one or more filters. In some embodiments, the immobilized molecules comprise antibodies, proteins, receptors, ligands, carbohydrates, nucleotides, RNA, or DNA. In some embodiments, enhancing the selectivity of the one or more filters comprises enhancing the ability of the one or more filters to retain A2M, enhancing the ability of the one or more filters to not retain molecules that are not A2M, or a combination thereof. In some embodiments, the flowing comprises actuating on or more of the injectors, applying tangential force filtration, one or more centrifugation steps, gravitational forces, mechanical forces, or any combination thereof. In some embodiments, the mechanical force comprises a manual force, a pump, centrifugal force, gas pressure, or a combination thereof. In some embodiments, the method further comprises adding one or more non-blood derived components, one or more blood derived components, or a combination thereof, to the biological sample or A2M enriched retentate. In some embodiments, the one or more additional non-blood derived components comprises an anti-coagulant, preservative, excipient, diluent, or other additive. In some embodiments, the anti-coagulant comprises EDTA, tri-sodium citrate, water for injection (WFI), saline, or ACD-A. In some embodiments, the diluent is a WFI solution or a saline solution. In some embodiments, the one or more additional blood derived components comprise platelets. In some embodiments, the biological sample is from a human subject. In some embodiments, the human subject has a disease or condition treatable with the retentate. In some embodiments, the disease or condition is a wound. In some embodiments, the wound is a chronic wound. In some embodiments, the biological sample is collected with the aid of an additional absorbent, adsorbent, or capillary materials or systems selected from the group of needle-syringe combo, sponges, wicks, pledgets, sutures, hydrophilic catheters, hydrophobic catheters, hollow-lumen catheters, or any combination thereof. In some embodiments, the method further comprises centrifuging the sample to remove cells and particles.

In one aspect, provided herein is a method of manufacture of a medicament comprising bringing together an amount of a composition comprising A2M isolated from a biological sample from an animal, wherein the A2M is present at a concentration of at least 1.1 times higher than the concentration of A2M present in the biological sample from the animal, and plasma, BMA, or another body fluid from the biological sample; with a pharmaceutically acceptable carrier, wherein the medicament is effective to promote wound healing.

In one aspect, provided herein is an article of manufacture comprising package material containing a therapeutically effective amount of a composition comprising A2M isolated from a biological sample from an animal, wherein the A2M is present at a concentration of at least 1.1 times higher than the concentration of A2M present in the biological sample from the animal, and plasma, BMA, or another body fluid from the biological sample; together with instructions for use in the treatment of a wound in or on a subject.

In one aspect, provided herein is a method of manufacture of a medicament comprising bringing together an amount of a composition comprising a variant A2M polypeptide or portion thereof effective to promote wound healing and a pharmaceutically acceptable carrier.

In one aspect, provided herein is an article of manufacture comprising package material containing therapeutically effective amounts of a composition comprising a variant A2M polypeptide or portion thereof together with instructions for use in the treatment of a wound in or on a subject In one aspect, provided herein is a method of manufacture of a medicament comprising bringing together an amount a composition comprising an agent that inhibits one or more proteins or cells associated with formation of the FAC effective to promote wound healing and a pharmaceutically acceptable carrier.

In one aspect, provided herein is an article of manufacture comprising package material containing therapeutically effective amounts of a composition comprising an agent that inhibits one or more proteins or cells associated with formation of the FAC together with instructions for use in the treatment of a wound in or on a subject.

In some embodiments, the biological sample comprises a first biological sample from a first subject and a second biological sample from a second subject. In some embodiments, the first and second biological samples are blood samples or plasma samples. In some embodiments, the first and second biological samples do not substantially comprise blood cells. In some embodiments, the animal is a first animal and wherein the method further comprises combining the A2M enriched retentate with another A2M retentate obtained from another biological sample to form a pooled sample, wherein the another biological sample is from a second animal that is different from the first animal. In some embodiments, the biological samples are blood samples or plasma samples. In some embodiments, the A2M enriched retentates do not substantially comprise blood cells. In some embodiments, the method further comprises treating a subject in need thereof with the pooled sample. In some embodiments, the pooled sample is not immunogenic to the subject. In some embodiments, the fluid sample is a biological sample, wherein the biological sample comprises a first biological sample from a first subject and a second biological sample from a second subject. In some embodiments, the biological sample comprises a first biological sample from a first subject and a second biological sample from a second subject. In some embodiments, the first and second biological samples are blood samples or plasma samples. In some embodiments, the first and second biological samples do not substantially comprise blood cells. In some embodiments, the biological sample comprises a first biological sample from a first subject and a second biological sample from a second subject. In some embodiments, the first and second biological samples are blood samples or plasma samples. In some embodiments, the first and second biological samples do not substantially comprise blood cells. In some embodiments, the animal is a first animal and wherein the article further comprises an A2M enriched retentate obtained from another biological sample to form a pooled sample, wherein the another biological sample is from a second animal that is different from the first animal. In some embodiments, the biological samples are blood samples or plasma samples. In some embodiments, the article does not substantially comprise blood cells.

INCORPORATION BY REFERENCE

All publications, patents, and patent applications mentioned in this specification, including related International Application No. PCT/US2013/027159, are herein incorporated by reference to the same extent as if each individual publication, patent, or patent application was specifically and individually indicated to be incorporated by reference.

In the event of a conflict between a term herein and a term incorporated by reference, the term herein controls.

BRIEF DESCRIPTION OF THE DRAWINGS

The novel features are set forth with particularity in the appended claims. A better understanding of the features and advantages will be obtained by reference to the following detailed description that sets forth illustrative embodiments, in which the principles of devices, methods, and compositions are utilized, and the accompanying drawings of which:

FIGS. 9A-9G depict the flow of a sample through an exemplary system comprising two membranes.

FIG. 16A depicts a diagram of an exemplary APIC-HL system.

FIG. 16B depicts a diagram of an exemplary APIC-HH system.

FIGS. 36A and B depict graphs of collagenase activity in debridement tissues (A—140731DMB-DT; B—140731AW-DT) with and without A2M treatment. Serial dilutions of APIC-PRP were challenged to inhibit DT digestion of FITC-collagen. 1× means equal volumes of DT and APIC-PRP. A 1× concentration of APIC was able to inhibit 75% of the collagenases in the first 3 minutes of the digestion. Collagenase activity was reduced 10-fold when 3×APIC was added to wound fluid. No digestion of collagen was seen in APIC-only controls. Less protease activity in DT (compared to WF) was potently inhibited.

DETAILED DESCRIPTION OF THE DISCLOSURE

Figure 1:
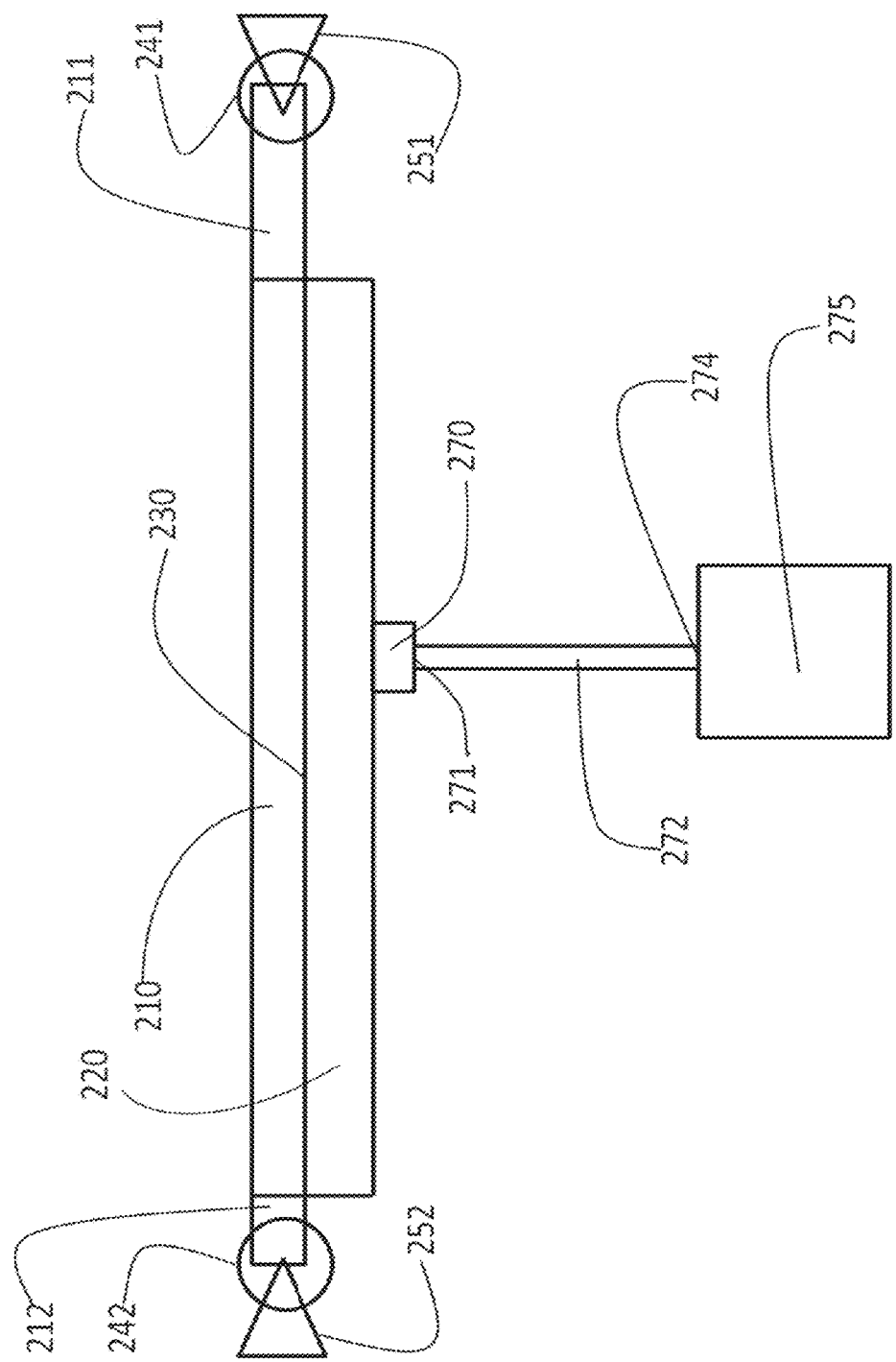
FIG. 1 depicts a schematic of an exemplary system. comprising one membrane
Figure 2:
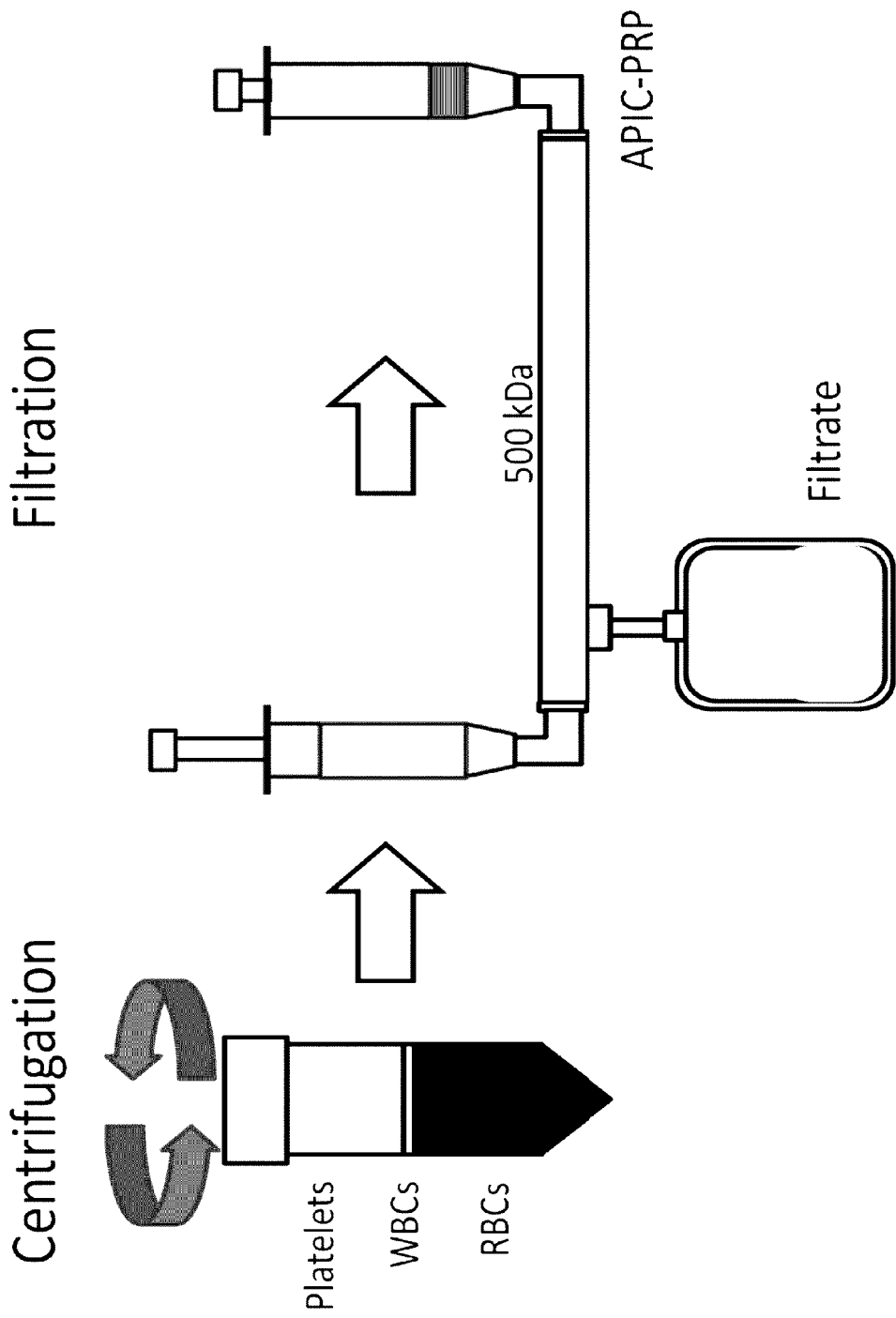
FIG. 2 depicts a schematic of an exemplary system comprising one membrane.
Figure 3:
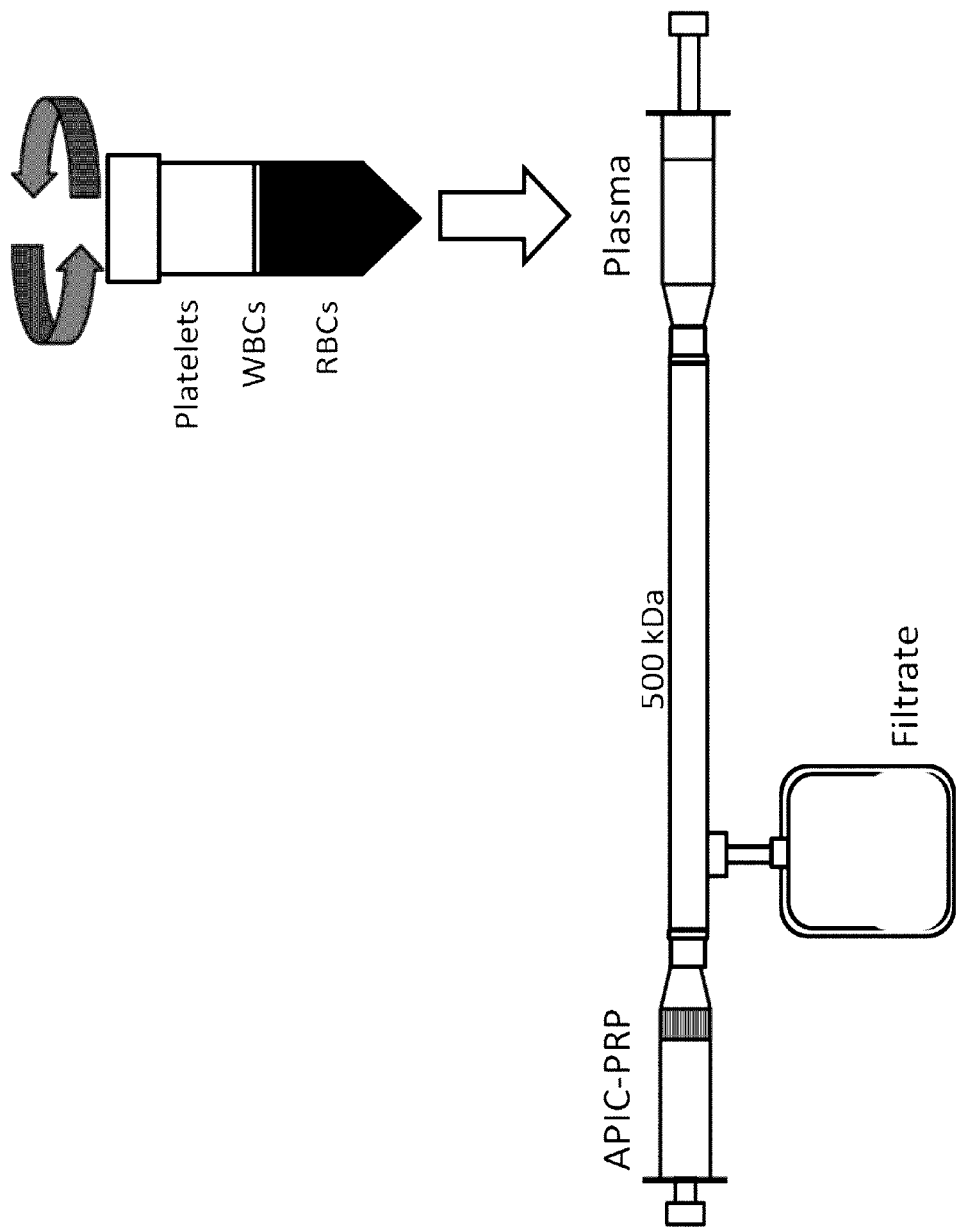
FIG. 3 depicts a schematic of an exemplary system comprising one membrane.

The details of one or more inventive embodiments are set forth in the accompanying drawings, the claims, and in the description herein. Other features, objects, and advantages of inventive embodiments disclosed and contemplated herein will be apparent from the description and drawings, and from the claims. As used herein, unless otherwise indicated, the article "a" means one or more unless explicitly otherwise provided for. As used herein, unless otherwise indicated, terms such as "contain," "containing," "include," "including," and the like mean "comprising." As used herein, unless otherwise indicated, the term "or" can be conjunctive or disjunctive. As used herein, unless otherwise indicated, any embodiment can be combined with any other embodiment. As used herein, unless otherwise indicated, some inventive embodiments herein contemplate numerical ranges. When ranges are present, the ranges include the range endpoints. Additionally, every sub-range and value within the range is present as if explicitly written out.

DEFINITIONS

The term "substantially non-immunogenic" or "substantially non-antigenic" means that the composition being administered to a subject does not elicit an immune response to the composition.

A "subject" refers to a donor, recipient or host of the composition of the present invention. In some embodiments, the donor and the recipient are the same. In some embodiments the subject is a human subject.

A "proteoglycan" refers to a special class of proteins that are heavily glycosylated. A proteoglycan is made up of a core protein with numerous covalently attached high sulphated glycosaminoglycan chain(s). Non-limiting example of extracellular matrix proteoglycans include aggrecan and certain collagens, such as collagen IX.

A "glycosaminoglycan" or "GAG" as used herein refers to a long unbranched polysaccharide molecules found on the cell surface or within the extracellular matrix. Non-limiting examples of glycosaminoglycan include heparin, chondroitin sulfate, dextran sulfate, dermatan sulfate, heparan sulfate, keratan sulfate, hyaluronic acid, hexuronyl hexosaminoglycan sulfate, and inositol hexasulfate.

The term "non-autologous" refers to tissue or cells which originate from a donor other than the recipient. Non-autologous can refer to, for example, allogeneic or xenogeneic. The term "autologous" as in an autologous composition, refers to a composition in which the donor and recipient is the same individual. Likewise, "allogeneic" refers to a donor and a recipient of the same species; "syngeneic" refers to a donor and recipient with identical genetic make-up (e.g., identical twins or autogenic) and "xenogeneic" refers to donor and recipient of different species.

The term "variant" (or "analog") refers to any molecule differing from the naturally occurring molecule.

The term "variant polynucleotide" (or "analog") refers to any polynucleotide differing from the naturally occurring polynucleotide. For example, "variant A2M polynucleotide" refers to any A2M polynucleotide differing from naturally occurring A2M polynucleotides. A variant A2M polynucleotide includes a polynucleotide sequence different from the wild-type A2M polynucleotide sequence (SEQ ID NO: 1). Variant polynucleotides can be characterized by nucleic acid insertions, deletions, and substitutions, created using, for example, recombinant DNA techniques. A variant A2M polynucleotide preferably includes a mutation, insertion, deletion, or a combination thereof, in the bait region of a wild-type A2M polynucleotide sequence. As used herein, when referring to polypeptides, the "bait region" includes the region of an A2M polynucleotide that encodes the region of the A2M polypeptide that binds to proteases, for example, regions that contain protease recognition sites. A variant A2M polynucleotide includes an "A2M acceptor sequence" (SEQ ID NO: 2) which includes a polynucleotide sequence of A2M with point mutations that can aid in creating variant A2M polynucleotides by recombinant DNA techniques, for example, by creating restriction enzyme cloning sites to aid in inserting various polynucleotide sequences encoding the variant bait regions. Bait regions include SEQ ID NOs: 5-66 and sequences substantially similar to SEQ ID NOs: 5-66.

The term "variant polypeptide" refers to any polypeptide differing from the naturally occurring polypeptide. For example, "variant A2M polypeptide" refers to any A2M polypeptide differing from naturally occurring A2M polypeptides. Variant polypeptides can be characterized by amino acid insertions, deletions, and substitutions, created using, for example, recombinant DNA techniques. A variant A2M polypeptide includes a polypeptide sequence different from the wild-type A2M polypeptide sequence. A variant A2M polypeptide preferably includes a mutation, insertion, deletion, or a combination thereof, in the bait region of a wild-type A2M protein. When referring to polypeptides, the "bait region" includes the region of an A2M polypeptide that binds to proteases, for example, a stretch of amino acids that contains one or more protease recognition sites. A variant A2M polypeptide includes a polypeptide (SEQ ID NO: 3) encoded by an A2M acceptor sequence (SEQ ID NO: 2). A "variant A2M polypeptide" can have at least one amino acid sequence alteration in the bait region as compared to the amino acid sequence of the corresponding wild-type polypeptide. An amino acid sequence alteration can be, for example, a substitution, a deletion, or an insertion of one or more amino acids. A variant A2M polypeptide can have any combination of amino acid substitutions, deletions or insertions.

Guidance in determining which amino acid residues may be replaced, added or deleted without abolishing activities of interest, may be found by comparing the sequence of the particular polypeptide with that of homologous peptides and minimizing the number of amino acid sequence changes made in regions of high homology (conserved regions) or by replacing amino acids with consensus sequence. Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as inhibition of proteases, ligand-binding affinities, interchain affinities, or degradation/turnover rate. Variant nucleotides can also be used to generate polypeptides that are better suited for expression, scale up and the like in the host cells chosen for expression. For example, cysteine residues can be deleted or substituted with another amino acid residue in order to eliminate disulfide bridges.

An amino acid "substitution" includes replacing one amino acid with another amino acid having similar structural and/or chemical properties, for example, conservative amino acid replacements. "Conservative" amino acid substitutions can be made on the basis of similarity in polarity, charge, solubility, hydrophobicity, hydrophilicity, the amphipathic nature of the residues involved, or a combination thereof. Nonpolar (hydrophobic) amino acids include alanine, leucine, isoleucine, valine, proline, phenylalanine, tryptophan, and methionine. Polar neutral amino acids include glycine, serine, threonine, cysteine, tyrosine, asparagine, and glutamine Positively charged (basic) amino acids include arginine, lysine, and histidine. Negatively charged (acidic) amino acids include aspartic acid and glutamic acid. "Insertions" or "deletions" are preferably in the range of about 1 to 50 amino acids, more preferably 1 to 30 amino acids. The variation allowed can be experimentally determined by inserting, deleting, or substituting amino acids in a polypeptide using recombinant DNA techniques and assaying the resulting recombinant variants for activity, for example, protease inhibition activity.

The terms "purified" or "substantially purified" as used herein denotes that the indicated nucleic acid or polypeptide is present in the substantial absence of other biological macromolecules, for example, polynucleotides, proteins, and the like. The polynucleotide or polypeptide can be purified such that it constitutes at least 95% by weight, for example, at least 99% by weight, of the indicated biological macromolecules present. Water, buffers, and other small molecules with a molecular weight of less than 1000 Daltons, can be present in any amount. The term "isolated" as used herein refers to a polynucleotide or polypeptide separated from at least one other component present with the polynucleotide or polypeptide in its natural source. In some embodiments, the polynucleotide or polypeptide can be found in the presence of only a solvent, buffer, ion, or other components normally present in a solution of the same. The terms "isolated" and "purified" do not encompass polynucleotides or polypeptides present in their natural source.

As used herein, "recombinant polypeptides" include polypeptides or proteins derived from recombinant expression systems, for example, microbial, insect, or mammalian expression systems. Polypeptides or proteins expressed in most bacterial cultures will be free of glycosylation modifications; polypeptides or proteins expressed in yeast can have a glycosylation pattern in general different from those expressed in mammalian cells.

The term "expression vector" refers to a plasmid or phage or virus or vector, for expressing a polypeptide from a DNA or RNA sequence. An expression vector can include a transcriptional unit comprising an assembly of a genetic element or elements having a regulatory role in gene expression, for example, promoters or enhancers, a structural or coding sequence which is transcribed into mRNA and translated into protein, and appropriate transcription initiation and termination sequences. Structural units intended for use in yeast or eukaryotic expression systems can include a leader sequence enabling extracellular secretion of translated protein by a host cell. Alternatively, where recombinant protein is expressed without a leader or transport sequence, it can include an amino terminal methionine residue. This residue may or may not be subsequently cleaved from the expressed recombinant protein to provide a final product.

The term "recombinant expression system" means host cells which have stably integrated a recombinant transcriptional unit into chromosomal DNA or carry the recombinant transcriptional unit extrachromosomally. Recombinant expression systems can be used to express heterologous polypeptides or proteins upon induction of the regulatory elements linked to the DNA segment or synthetic gene to be expressed. This term includes host cells which have stably integrated a recombinant genetic element or elements having a regulatory role in gene expression, for example, promoters or enhancers. Recombinant expression systems can be used to express polypeptides or proteins endogenous to the cell upon induction of the regulatory elements linked to the endogenous DNA segment or gene to be expressed. The cells can be prokaryotic or eukaryotic.

The term "secreted" includes a protein that is transported across or through a membrane, including transport as a result of signal sequences in its amino acid sequence when it is expressed in a suitable host cell. "Secreted" proteins include without limitation proteins secreted wholly, for example soluble proteins, or partially, for example receptors, from the cell in which they are expressed. "Secreted" proteins also include proteins transported across the membrane of the endoplasmic reticulum. "Secreted" proteins also include proteins containing non-typical signal sequences.

An expression vector may be designed to contain a "signal sequence" which will direct the polypeptide through the membrane of a cell. A signal sequence can be naturally present on the polypeptides described herein or provided from heterologous protein sources.

As used herein, "substantially equivalent" or "substantially similar" can refer both to nucleotide and amino acid sequences, for example a variant sequence, that varies from a reference sequence by one or more substitutions, deletions, or additions, the net effect of which does not result in an adverse functional dissimilarity between the reference and subject sequences. Typically, such a substantially equivalent sequence varies from one of those listed herein by no more than about 35%. For example, the number of individual residue substitutions, additions, and/or deletions in a substantially equivalent sequence, as compared to the corresponding reference sequence, divided by the total number of residues in the substantially equivalent sequence is about 0.35 or less. A substantially equivalent sequence includes sequences with 65% sequence identity to the reference sequence. A substantially equivalent sequence of the invention can vary from a reference sequence by no more than 30% (70% sequence identity), no more than 25% (75% sequence identity), no more than 20% (80% sequence identity), no more than 10% (90% sequence identity), or no more that 5% (95% sequence identity). Substantially equivalent amino acid sequences according to the invention preferably have at least 80% sequence identity with a reference amino acid sequence, at least 85% sequence identity, at least 90% sequence identity, at least 95% sequence identity, at least 98% sequence identity, or at least 99% sequence identity. Substantially equivalent polynucleotide sequences of the invention can have lower percent sequence identities, taking into account, for example, the redundancy or degeneracy of the genetic code. Preferably, the polynucleotide sequence has at least about 65%, at least about 75%, at least about 80%, at least 85%, at least 90%, at least 95%, at least 98%, or at least 99% sequence identity. Sequences having substantially equivalent biological activity and substantially equivalent expression characteristics are considered substantially equivalent. Identity between sequences can be determined by methods known in the art, such as by alignment of the sequences or varying hybridization conditions.

As used herein the term "effective amount" or "therapeutically effective amount" means a dosage sufficient to treat, inhibit, or alleviate chronic wounds such as pressure ulcers, venous ulcers, stasis ulcers, venous stasis ulcers, diabetic foot ulcers, arterial insufficiency ulcers or any combination thereof in a subject in need thereof.

By "degenerate variant" can be intended nucleotide fragments which differ from a nucleic acid fragment of the present invention (e.g., an ORF) by nucleotide sequence but, due to the degeneracy of the genetic code, encode an identical polypeptide sequence.

The terms polypeptide, peptide, and protein can be used interchangeably and can refer to a polymer of amino acid residues or a variant thereof. Amino acid polymers can have one or more amino acid residues and can be an artificial chemical mimetic of a corresponding naturally occurring amino acid, as well as to naturally occurring amino acid polymers, those containing modified residues, and non-naturally occurring amino acid polymers. A variant polypeptide can have at least one amino acid sequence alteration as compared to the amino acid sequence of the corresponding wild-type polypeptide. An amino acid sequence alteration can be, for example, a substitution, a deletion, or an insertion of one or more amino acids. A variant polypeptide can have any combination of amino acid substitutions, deletions or insertions. An amino acid sequence alteration can be formed by altering the nucleotide sequence from which it is derived, such as a mutation, for example, a frameshift mutation, nonsense mutation, missense mutation, neutral mutation, or silent mutation. For example, sequence differences, when compared to a wild-type nucleotide sequence, can include the insertion or deletion of a single nucleotide, or of more than one nucleotide, resulting in a frame shift; the change of at least one nucleotide, resulting in a change in the encoded amino acid; the change of at least one nucleotide, resulting in the generation of a premature stop codon; the deletion of several nucleotides, resulting in a deletion of one or more amino acids encoded by the nucleotides; the insertion of one or several nucleotides, such as by unequal recombination or gene conversion, resulting in an interruption of the coding sequence of a reading frame; duplication of all or a part of a sequence; transposition; or a rearrangement of a nucleotide sequence. Such sequence changes can alter the polypeptide encoded by the nucleic acid, for example, if the change in the nucleic acid sequence causes a frame shift, the frame shift can result in a change in the encoded amino acids, and/or can result in the generation of a premature stop codon, causing generation of a truncated polypeptide.

The term "fragment" can refer to any subset of the polypeptide that can be a shorter polypeptide of the full length protein. Fragments of A2M can include 20, 30, 40, 50 or more amino acids from A2M that can be detected with anti-A2M antibodies. Other fragments of A2M include various domains of A2M and combinations thereof.

"Platelet-rich plasma" ("PRP") can refer to blood plasma that has been enriched with platelets.

"Platelet-poor plasma" ("PPP") can refer to blood plasma that has been depleted of platelets.

Wounds and Wound Classification

Chronic wounds, slow healing wounds, and incomplete healing wounds often result in infection and can lead to amputation or death. It has been discovered that use of certain compounds, including those described or referenced herein, may block, inhibit, or alter cell communications, which may promote closure and healing in chronic, slow healing, and incomplete healing wounds.

By "wound" is meant an injury to any tissue, including, for example, acute, delayed, slow, or difficult to heal wounds, and chronic wounds. Examples of wounds may include both open and closed wounds. Wounds include, for example, burns, incisions, excisions, lacerations, abrasions, puncture or penetrating wounds, surgical wounds, contusions, hematomas, crushing injuries, and ulcers. Also included are wounds that do not heal at expected rates.

By a "slow healing wound" is meant an injury to any tissue that does not heal in an expected or typical time frame, including delayed, slow, or difficult to heal wounds (including delayed or incompletely healing wounds), and chronic wounds. Examples of wounds that do not heal at the expected rate include diabetic ulcers, diabetic foot ulcers, vasculitic ulcers, arterial ulcers, venous ulcers, venous stasis ulcers, pressure ulcers, decubitus ulcers, infectious ulcers, trauma-induced ulcers, burn ulcers, ulcerations associated with pyoderma gangrenosum, and mixed ulcers.

As described herein, a slow healing wound may include, for example, a wound that is characterized at least in part by one or more of 1) a prolonged inflammatory phase, 2) a slow forming extracellular matrix, and 3) a stalled or decreased rate of epithelialization.

In the art, the term "chronic wound" refers generally to a wound that has not healed within about three months, but can be wounds that have not healed within about one or two months. Chronic skin wounds include, for example, pressure ulcers, diabetic ulcers, venous ulcers, arterial ulcers, inflammatory ulcers, and mixed ulcers. The chronic wound may be an arterial ulcer that can include ulcerations resulting from complete or partial arterial blockage. The chronic wound may be a venous stasis ulcer, which can include ulcerations resulting from a malfunction of the venous valve and the associated vascular disease. The chronic wound may be a trauma-induced ulcer.

As used herein, chronic wound can also include, for example, a wound that is characterized at least in part by 1) a chronic self-perpetuating state of wound inflammation, 2) a deficient and defective wound extracellular matrix (ECM), 3) poorly responding (senescent) wound cells (e.g., fibroblasts), limited ECM production, and 4) failure of re-epithelialization due in part to lack of the necessary ECM orchestration and lack of scaffold for migration.

Chronic wounds can also be characterized, for example, by 1) prolonged inflammation and proteolytic activity, leading to ulcerative lesions, including, for example, diabetic, pressure (decubitus), venous, and arterial ulcers, 2) prolonged fibrosis in the wound leading to scarring, 3) progressive deposition of matrix in the affected area, 4) longer repair times, 5) less wound contraction, 6) slower re-epithelialization, and 7) increased thickness of granulation tissue.

Exemplary chronic wounds also include "pressure ulcers." Exemplary pressure ulcers may include all four stages of wound classifications based on AHCPR (Agency for Health Care Policy and Research, U.S. Department of Health and Human Services) guidelines, including for example, Stage 1. A Stage 1 pressure ulcer is an observable pressure related alteration of intact skin whose indicators as compared to the adjacent or opposite area on the body may include changes in one or more of the following: skin temperature (warmth or coolness), tissue consistency (firm or boggy feel), and/or sensation (pain, itching). The ulcer appears as a defined area of persistent redness in lightly pigmented skin, whereas in darker skin tones, the ulcer may appear with persistent red, blue, or purple hues. Stage 1 ulcerations may include non-blanchable erythema of intact skin and the heralding lesion of skin ulceration. In individuals with darker skin, discoloration of the skin, warmth, edema, induration, or hardness may also be indicators of stage 1 ulcerations. Stage 2 ulcerations may be characterized by partial thickness skin loss involving epidermis, dermis, or both. The ulcer is superficial and presents clinically as an abrasion, blister, or shallow crater. Stage 3 ulcerations may be characterized by full thickness skin loss involving damage to or necrosis of subcutaneous tissue that may extend down to, but not through, underlying fascia. The ulcer presents clinically as a deep crater with or without undermining of adjacent tissue. Stage 4 ulcerations may be characterized by full thickness skin loss with extensive destruction, tissue necrosis, or damage to muscle, bone, or supporting structures (e.g., tendon, joint capsule, etc.).

Exemplary chronic wounds also include "decubitus ulcers." Exemplary decubitus ulcer may arise as a result of prolonged and unrelieved pressure over a bony prominence that leads to ischemia. The wound tends to occur in patients who are unable to reposition themselves to off-load weight, such as paralyzed, unconscious, or severely debilitated persons. As defined by the U.S. Department of Health and Human Services, the major preventive measures include identification of high-risk patients; frequent assessment; and prophylactic measures such as scheduled repositioning, appropriate pressure-relief bedding, moisture barriers, and adequate nutritional status. Treatment options may include, for example, pressure relief, surgical and enzymatic debridement, moist wound care, and bacterial load control. Certain embodiments of the invention involve treating a chronic wound characterized by a decubitus ulcer or ulceration that results from prolonged, unrelieved pressure over a bony prominence that leads to ischemia.

Exemplary chronic wounds also include "arterial ulcers." Arterial ulcers include those characterized by complete or partial arterial blockage, which may lead to tissue necrosis and/or ulceration. Signs of arterial ulcer can include, for example, pulselessness of the extremity; painful ulceration; small, punctuate ulcers that are usually well circumscribed; cool or cold skin; delayed capillary return time (briefly push on the end of the toe and release, normal color should return to the toe in about 3 seconds or less); atrophic-appearing skin (for example, shiny, thin, dry); and loss of digital and pedal hair.

Exemplary chronic wounds also include "venous ulcers." Exemplary venous ulcers include the most common type of ulcer affecting the lower extremities and may be characterized by malfunction of the venous valve. The normal vein has valves that prevent the backflow of blood. When these valves become incompetent, the backflow of venous blood causes venous congestion. Hemoglobin from the red blood cells escapes and leaks into the extravascular space, causing the brownish discoloration commonly noted. It has been shown that the transcutaneous oxygen pressure of the skin surrounding a venous ulcer is decreased, indicating that there are forces obstructing the normal vascularity of the area. Lymphatic drainage and flow also plays a role in these ulcers. A venous ulcer can appear near the medial malleolus and usually occurs in combination with an edematous and indurated lower extremity; it may be shallow, not too painful, and may present with a weeping discharge from the affected site.

Exemplary chronic wounds also include "venous stasis ulcers." Exemplary venous stasis ulcers are characterized by chronic passive venous congestion of the lower extremities that results in local hypoxia. One possible mechanism of pathogenesis of these wounds includes the impediment of oxygen diffusion into the tissue across thick perivascular fibrin cuffs. Another mechanism is that macromolecules leaking into the perivascular tissue trap growth factors needed for the maintenance of skin integrity. Additionally, the flow of large white blood cells slows due to venous congestion, occluding capillaries, becoming activated, and damaging the vascular endothelium to predispose to ulcer formation.

Exemplary chronic wounds further include "diabetic foot ulcers." Diabetic patients with exemplary diabetic foot ulcer are prone to foot ulcerations due to both neurologic and vascular complications. Peripheral neuropathy can cause altered or complete loss of sensation in the foot and/or leg. Diabetic patients with advanced neuropathy lose all ability for sharp-dull discrimination. Any cuts or trauma to the foot may go completely unnoticed for days or weeks in a patient with neuropathy. A patient with advanced neuropathy can lose the ability to sense a sustained pressure insult and, as a result, tissue ischemia and necrosis may occur leading to, for example, plantar ulcerations. Additionally, microfractures in the bones of the foot, if unnoticed and untreated, may result in disfigurement, chronic swelling, and additional bony prominences. Microvascular disease is one of the significant complications for diabetics that may also lead to ulcerations.

Exemplary chronic wounds can include "traumatic ulcers." Formation of exemplary traumatic ulcers may occur as a result of traumatic injuries to the body. These injuries include, for example, compromises to the arterial, venous, or lymphatic systems; changes to the bony architecture of the skeleton; loss of tissue layers—epidermis, dermis, subcutaneous soft tissue, muscle or bone; damage to body parts or organs and loss of body parts or organs.

Exemplary chronic wounds can include "burn ulcers" including, for example, ulceration that occur as a result of a burn injury, including a first degree burn (i.e., superficial, reddened area of skin); a second degree burn (a blistered injury site which may heal spontaneously after the blister fluid has been removed); a third degree burn (burn through the entire skin and usually require surgical intervention for wound healing); scalding (may occur from scalding hot water, grease or radiator fluid); a thermal burn (may occur from flames, usually deep burns); a chemical burn (may come from acid and alkali, usually deep burns); an electrical burn (either low voltage around a house or high voltage at work); an explosion flash (usually superficial injuries); and contact burns (usually deep and may occur from muffler tail pipes, hot irons, and stoves).

Compositions for Autologous Treatment of Wounds

Provided herein are autologous compositions. The autologous compositions can be prepared from a biological sample from a subject and administered back to the same subject.

Also provided herein are therapeutic autologous compositions and methods for their preparation and use. Also provided herein are methods, systems, kits and compositions for the detection, diagnosis, and treatment of inflammation, ECM degradation, and chronic wounds such as pressure ulcers, venous ulcers, stasis ulcers, venous stasis ulcers, diabetic foot ulcers, arterial insufficiency ulcers or any combination thereof.

An autologous composition can comprise alpha-2-macroglobulin (A2M) and can be used to treat a subject with a condition. The A2M can be from a biological sample, such as from a human subject; or can be any fragment thereof. In preferred embodiments the autologous compositions of the present invention are substantially non-immunogenic, namely do not elicit an immune response.

An autologous composition can comprise an elevated concentration of A2M compared to the concentration of A2M found in a biological sample, such as the blood of normal subjects, or the blood from a subject in need of autologous treatment with the autologous composition. The concentration of A2M in an autologous composition can be at least about 1.1 times higher than the concentration of A2M found in a biological sample. For example, the concentration of A2M can be at least about 1.2, 1.3, 1.4, 1.5, 1.6, 1.7, 1.8, 1.9, 2, 2.1, 2.2, 2.3, 2.4, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of A2M found in a biological sample. For example, the concentration of A2M can be at least about 2 times higher than the concentration of A2M found in the biological sample.

In some embodiments, an autologous composition can further comprise a reduced concentration of components other than A2M compared to the normal concentration of the other components, such as the concentration in a sample from which the autologous compositions were prepared or an endogenous concentration of the other components in a biological sample. An autologous composition can comprise a reduced concentration of other components isolated from a biological sample compared to the normal concentration of the other components in the biological sample. The concentration of other components can be at least about 10% less than the concentration of the other components normally found in a biological sample. For example, the concentration of other components can be at least about 11%, 12%, 13%, 14%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% less than the concentration of the other components normally found in a biological sample. For example, the concentration of other components can be at least about 20% less than the concentration of the other components normally found in a biological sample. The concentration of other components can be at least about 0.1 times less than the concentration of the other components normally found in a biological sample. For example, the concentration of other components can be at least about 0.2, 0.3, 0.4, 0.5, 0.6, 0.7, 0.8, 0.9, 1, 2, 2, 3, 4, 5, 6, 7, 8, 9, 10, 15, 20, 25, 30, 35, 40, 45, 50, 55, 60, 65, 70, 75, 80, 85, 90, 95, 100, 150, 200, 300, 400, 500, 600, 700, 800, 900, or 1000 times less than the concentration of the other components normally found in a biological sample. For example, the concentration of other components can be at least about 2 times less than the concentration of the other components normally found in a biological sample.

In some embodiments, an autologous composition can comprise a reduced concentration of one or more proteins with a molecular weight lower than 50, 100, and/or 500 kDa. The concentration of one or more proteins with a molecular weight lower than 500 kDa can be at least about 1.1 times lower than the concentration of the one or more proteins with molecular weight lower than 50, 100, and/or 500 kDa found in a normal biological sample, such as blood from a subject. The concentration of one or more proteins with a molecular weight lower than 50, 100, and/or 500 kDa found in a normal biological sample can be the concentration of the endogenous level of the one or more proteins with a molecular weight lower than 50, 100, and/or 500 kDa in a biological sample, such as a normal or control biological sample. For example, the concentration of one or more proteins with molecular weight lower than 100 kDa can be at least about 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times lower than the concentration of the one or more proteins with molecular weight lower than 50, 100, and/or 500 kDa found in a normal biological sample or the endogenous concentration in a normal biological sample, or the blood from a subject in need of autologous treatment with the autologous composition. For example, the concentration of one or more proteins with molecular weight lower than 50, 100, and/or 500 kDa can be at least about 1.5 times lower than the concentration of the one or more proteins with molecular weight lower than 50, 100, and/or 500 kDa found in a normal biological sample or the endogenous concentration in a normal biological sample.

In some embodiments, an autologous composition can comprise an elevated concentration of one or more proteins with a molecular weight higher than 50, 100, and/or 500 kDa than normally found in a biological sample. The concentration of one or more proteins with a molecular weight higher than 50, 100, and/or 500 kDa can be at least about 1.1 times higher than the concentration of the one or more proteins with molecular weight higher than 50, 100, and/or 500 kDa found in a normal biological sample. The concentration of one or more proteins with a molecular weight higher than 50, 100, and/or 500 kDa found in a normal biological sample can be the concentration of the endogenous level of the one or more proteins with a molecular weight higher than 50, 100, and/or 500 kDa in the biological sample. For example, the concentration of one or more proteins with molecular weight higher than 50, 100, and/or 500 kDa can be at least about 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of the one or more proteins with molecular weight higher than 50, 100, and/or 500 kDa found in a normal biological sample or the endogenous concentration in a normal biological sample. For example, the concentration of one or more proteins with molecular weight higher than 50, 100, and/or 500 kDa can be at least about 1.5 times higher than the concentration of the one or more proteins with molecular weight higher than 50, 100, and/or 500 kDa found in a normal biological.

In some embodiments, proteins with a molecular weight from about 300-500 kDa, 100-500 kDa, and/or 50-500 kDa, such as fibronectin, fibrinogen, and fibrin monomers or polymers may be partially concentrated using the methods described herein. In some embodiments, an autologous composition can comprise an elevated concentration of one or more proteins with a molecular weight from about 300-500 kDa, 100-500 kDa, and/or 50-500 kDa. In some embodiments, the concentration of one or more proteins with a molecular weight higher than from about 300-500 kDa, 100-500 kDa, and/or 50-500 kDa can be at least about 1.1 times higher than the concentration of the one or more proteins with molecular weight from about 300-500 kDa, 100-500 kDa, and/or 50-500 kDa found in a normal biological sample, such as blood from a subject. The concentration of one or more proteins with a molecular weight from about 300-500 kDa, 100-500 kDa, and/or 50-500 kDa found in a normal biological sample can be the concentration of the endogenous level of the one or more proteins with a molecular weight from about 300-500 kDa, 100-500 kDa, and/or 50-500 kDa in a biological sample, such as a normal or control biological sample. For example, the concentration of one or more proteins with molecular weight from about 300-500 kDa, 100-500 kDa, and/or 50-500 kDa can be at least about 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of the one or more proteins with molecular weight from about 300-500 kDa, 100-500 kDa, and/or 50-500 kDa found in a normal biological sample or the endogenous concentration in a normal biological sample.

An autologous composition can comprise an elevated concentration of A2M compared to the concentration of A2M found in a biological sample and a reduced concentration of components other than A2M compared to the normal concentration of the other components found in a biological sample. The concentration of A2M in an autologous composition can be at least about 1.1 times higher than the concentration of A2M found in a biological sample and the concentration of other components other than A2M can be at least about 0.1 times less than the concentration of the other components normally found in a biological sample. For example, the concentration of A2M can be at least about 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of A2M found in a biological sample and the concentration of components other than A2M can be at least about 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 300, 400, 500, 600, 700, 800, 900, or 1000 times less than the concentration of the other components normally found in a biological sample. For example, the concentration of the concentration of A2M can be at least about 2 times higher than the concentration of A2M found in a biological sample and the concentration of components other than A2M can be at least about 2 times less than the concentration of the other components normally found in a biological sample. As another example, the concentration of A2M can be at least about 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of A2M found in a biological sample and the concentration of other components can be at least about 11%, 12%, 13%, 14%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% less than the concentration of the other components normally found in a biological sample. For example, the concentration of A2M can be at least about 2 times higher than the concentration of A2M found in a biological sample and the concentration of other components can be at least about 20% less than the concentration of the other components normally found in a biological sample.

In some embodiments, an autologous composition can comprise an elevated concentration of A2M compared to the concentration of A2M found in a biological sample and an elevated concentration of one or more proteins with molecular weight higher than 50, 100, and/or 500 kDa found in a biological sample. The concentration of A2M in an autologous composition can be at least about 1.1 times higher than the concentration of A2M found in a biological sample and the concentration of one or more proteins with molecular weight higher than 50, 100, and/or 500 kDa can be at least about 1.1 times higher than the concentration of the one or more proteins with molecular weight higher than 50, 100, and/or 500 kDa found in a biological sample. For example, the concentration of the concentration of A2M can be at least about 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of A2M found in a biological sample and the concentration of one or more proteins with molecular weight higher than 50, 100, and/or 500 kDa can be at least about 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of the one or more proteins with molecular weight higher than about 50, 100, and/or 500 kDa found in a biological sample. For example, the concentration of A2M can be at least about 2 times higher than the concentration of A2M found in a biological sample and the concentration of one or more proteins with molecular weight higher than 50, 100, and/or 500 kDa can be at least about 2 times higher than the concentration of the one or more proteins with molecular weight higher than about 100 kDa found in a biological sample.

The concentration of A2M and other proteins with a molecular weight higher than 50, 100, and/or 500 kDa can be present at a concentration of at least about 1.1 times higher than their concentration in a biological sample after retention by one or more filters using the methods or systems described herein. For example, the concentration of A2M and other proteins with a molecular weight higher than 50, 100, and/or 500 kDa can be present at a concentration of at least about 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than their concentration in a biological sample after retention by one or more filters using the methods or systems described herein. For example, the concentration of A2M and other proteins with a molecular weight higher than 50, 100, and/or 500 kDa can be present at a concentration of at least about 1.5 times higher than their concentration in a biological sample after retention by one or more filters using the methods or systems described herein.

The concentration of proteins with molecular weight less than about 50, 100, and/or 500 kDa can be less than about 10% of the concentrations of those proteins in a biological sample when retained by the one or more filters using the methods or systems described herein. For example, the concentration of proteins with molecular weight less than about 50, 100, and/or 500 kDa can be less than about 11%, 12%, 13%, 14%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% less than their concentration in a biological sample when retained by the one or more filters using the methods or systems described herein. For example, the concentration of proteins with molecular weight less than about 50, 100, and/or 500 kDa can be less than about 20% less than their concentration in a biological sample when retained by the one or more filters using the methods or systems described herein.

In some embodiments, the concentration of proteins with molecular weight less than about 50, 100, and/or 500 kDa can be less than about 10% of the concentrations of those proteins in a biological sample when retained by the one or more filters. For example, the concentration of proteins with molecular weight less than about 50, 100, and/or 500 kDa can be less than about 11%, 12%, 13%, 14%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% less than their concentration in a biological sample when retained by the one or more filters. For example, the concentration of proteins with molecular weight less than about 50, 100, and/or 500 kDa can be less than about 20% less than their concentration in a biological sample when retained by the one or more filters.

The concentration of A2M and other proteins with a molecular weight higher than 50, 100, and/or 500 kDa can be present at a concentration of at least about 1.1 times higher than their concentration in a biological sample after retention by one or more filters using the methods or systems described herein and the concentration of proteins with molecular weight less than about 50, 100, and/or 500 kDa can be less than about 10% of the concentrations of those proteins in a biological sample when retained by the one or more filters using the methods or systems described herein. For example, the concentration of A2M and other proteins with a molecular weight higher than 50, 100, and/or 500 kDa can be present at a concentration of at least about 1.2, 1.3, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than their concentration in a biological sample after retention by one or more filters using the methods or systems described herein, and the concentration of proteins with molecular weight less than about 50, 100, and/or 500 kDa can be less than about 11%, 12%, 13%, 14%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500%, 600%, 700%, 800%, 900%, or 1000% less than their concentration in a biological sample when retained by the one or more filters using the methods or systems described herein. For example, the concentration of A2M and other proteins with a molecular weight higher than 50, 100, and/or 500 kDa can be present at a concentration of at least about 1.5 times higher than their concentration in a biological sample after retention by one or more filters using the methods or systems described herein, and the concentration of proteins with molecular weight less than about 50, 100, and/or 500 kDa can be less than about 10% less than their concentration in a biological sample when retained by the one or more filters.

Proteins with a molecular weight higher than about 100 kDa can be, for example, proteins with a molecular weight at least about 110 kDa, 120 kDa, 130 kDa, 140 kDa, 150 kDa, 200 kDa, 250 kDa, 300 kDa, 350 kDa, 400 kDa, 450 kDa, 500 kDa, 550 kDa, 600 kDa, 650 kDa, 700 kDa, 750 kDa, 800 kDa, 850 kDa, 900 kDa, 950 kDa, 1000 kDa, 1050 kDa, 1100 kDa, 1150 kDa, 1200 kDa, 1250 kDa, 1300 kDa, 1350 kDa, 1400 kDa, 1450 kDa, 1500 kDa, 1550 kDa, 1600 kDa, 1650 kDa, 1700 kDa, 1750 kDa, 1800 kDa, 1850 kDa, 1900 kDa, 1950 kDa, 2000 kDa, or more.

Proteins with a molecular weight less than about 100 kDa can be, for example, proteins with a molecular weight of less than about 95 kDa, 90 kDa, 85 kDa, 80 kDa, 75 kDa, 70 kDa, 65 kDa, 60 kDa, 55 kDa, 50 kDa, 45 kDa, 40 kDa, 35 kDa, 30 kDa, 25 kDa, 20 kDa, 15 kDa, 10 kDa, 5 kDa, or less.

Proteins with a molecular weight higher than about 500 kDa can be, for example, proteins with a molecular weight higher than about 550 kDa, 600 kDa, 650 kDa, 700 kDa, 750 kDa, 800 kDa, 850 kDa, 900 kDa, 950 kDa, 1000 kDa, 1050 kDa, 1100 kDa, 1150 kDa, 1200 kDa, 1250 kDa, 1300 kDa, 1350 kDa, 1400 kDa, 1450 kDa, 1500 kDa, 1550 kDa, 1600 kDa, 1650 kDa, 1700 kDa, 1750 kDa, 1800 kDa, 1850 kDa, 1900 kDa, 1950 kDa, 2000 kDa, or higher. Proteins with a molecular weight less than about 500 kDa can be, for example, proteins with a molecular weight less than about 450 kDa, 400 kDa, 350 kDa, 300 kDa, 250 kDa, 200 kDa, 150 kDa, 100 kDa, 50 kDa, 45 kDa, 40 kDa, 35 kDa, 30 kDa, 25 kDa, 20 kDa, 15 kDa, 10 kDa, 5 kDa, or less.

Proteins with a molecular weight higher than 100 kDa can include, but are not limited to, immunoglobulin G, immunoglobulin M, fibronectin, fibrinogen and other proteins. Proteins with a molecular weight less than about 100 kDa can comprise cytokines, chemokines, proteases, pro-proteases, enzymes, pro-enzymes, immune-modulators and other proteins known in the art with a molecular weight of less than 100 kDa.

Proteins with a molecular weight higher than 500 kDa include, but are not limited to, IgM and Complement Component C4 binding proteins. Proteins with a molecular weight less than about 500 kDa can comprise cytokines, chemokines, proteases, pro-proteases, enzymes, pro-enzymes, immune-modulators and other proteins with a molecular weight of less than 500 kDa.

The concentration of A2M found in a biological sample, such as a blood sample from a normal subject, can be between about 0.1 mg/mL to about 6 mg/mL. For example, the concentration of A2M found in a blood sample from a normal subject or a normal biological sample can be between about 0.1 mg/mL to 5.5 mg/mL, 0.1 mg/mL to 5 mg/mL, 0.1 mg/mL to 4.5 mg/mL, 0.1 mg/mL to 4 mg/mL, 0.1 mg/mL to 3.5 mg/mL, 0.1 mg/mL to 3 mg/mL, 0.1 mg/mL to 2.5 mg/mL, 0.1 mg/mL to 2 mg/mL, 0.1 mg/mL to 1.5 mg/mL, 0.1 mg/mL to 1 mg/mL, 0.1 mg/mL to 0.75 mg/mL, 0.1 mg/mL to 0.5 mg/mL, 0.1 mg/mL to 0.25 mg/mL, 1 mg/mL to 6 mg/mL, 1 mg/mL to 5.5 mg/mL, 1 mg/mL to 5 mg/mL, 1 mg/mL to 4.5 mg/mL, 1 mg/mL to 4 mg/mL, 1 mg/mL to 3.5 mg/mL, 1 mg/mL to 3 mg/mL, 1 mg/mL to 2.5 mg/mL, 1 mg/mL to 2 mg/mL, 1 mg/mL to 1.5 mg/mL, 2 mg/mL to 6 mg/mL, 2 mg/mL to 5.5 mg/mL, 2 mg/mL to 5 mg/mL, 2 mg/mL to 4.5 mg/mL, 2 mg/mL to 4 mg/mL, 2 mg/mL to 3.5 mg/mL, 2 mg/mL to 3 mg/mL, 2 mg/mL to 2.5 mg/mL, 3 mg/mL to 6 mg/mL, 3 mg/mL to 5.5 mg/mL, 3 mg/mL to 5 mg/mL, 3 mg/mL to 4.5 mg/mL, 3 mg/mL to 4 mg/mL, 3 mg/mL to 3.5 mg/mL, 4 mg/mL to 6 mg/mL, 4 mg/mL to 5.5 mg/mL, 4 mg/mL to 5 mg/mL, 4 mg/mL to 4.5 mg/mL, 5 mg/mL to 6 mg/mL, or 5 mg/mL to 5.5 mg/mL.

In some embodiments, an autologous composition with an elevated concentration of A2M can be characterized by a reduction in the concentration of or a change in the ratios of cytokines, chemokines, other immunomodulatory mediators, for example, cytokines, chemokines, other immunomodulatory mediators with a molecular weight less than about 50, 100, and/or 500 kDa. In some embodiments, a retentate with an elevated concentration of A2M can be characterized by a reduction in the concentration of or a change in the ratios of cytokines, chemokines, other immunomodulatory mediators, for example, cytokines, chemokines, other immunomodulatory mediators with a molecular weight less than about 50, 100, and/or 500 kDa. Other immunomodulatory mediators can include peptides, proteins, DNA, RNA, carbohydrates, other small molecules, proteases, and other degradative proteins.

Cytokines, chemokines and other molecules in a composition with a reduction in concentration from a sample can be involved in inflammation. Cytokines can be small cell-signaling protein molecules that are secreted by one or more cells and are a category of signaling molecules that can be used in intercellular communication. Cytokines can be classified as proteins, peptides, or glycoproteins, chemokines, interleukins, tumor necrosis factors (TNFs), monocyte chemoattractant proteins (MCPs), IL-1-like cytokines, gamma chain cytokines, beta chain cytokines, IL-6-like cytokines, IL-10-like cytokines, interferons, tumor necrosis factors, TGF-beta, macrophage inflammatory proteins (MIPs), tumor growth factors (TGFs), and matrix metalloproteases (MMPs). For example, cytokines can be interleukins, such as IL-1-like, IL-1α (hematopoietin-1), IL-1β (catabolin), IL-1RA (IL-1 receptor antagonist), IL-18 (interferon-γ inducing factor), Common g chain (CD132), IL-2 (T cell growth factor), IL-4 (BSF-1), IL-7, IL-9 (T cell growth factor P40), IL-13 (P600), IL-15, Common b chain (CD131), IL-3 (multipotential CSF, MCGF), IL-5 (BCDF-1), GM-CSF (CSF-2), IL-6-like, IL-6 (IFN-β2, BSF-2), IL-11 (AGIF), G-CSF (CSF-3), IL-12 (NK cell stimulatory factor), LIF (leukemia inhibitory factor), OSM (oncostatin M), IL-10-like, IL-10 (CSIF), IL-20, IL-14 (HMW-BCGF), IL-16 (LCF), and IL-17 (CTLA-8); interferons, such as IFN-α, IFN-β, and IFN-γ, tumor necrosis factors (TNFs), such as CD154 (CD40L, TRAP), LT-β, TNF-α (cachectin), TNF-β (LT-α), 4-1BBL, APRIL (TALL-2), CD70 (CD27L), CD153 (CD30L), CD178 (FasL), GITRL, LIGHT, OX40L, TALL-1, TRAIL (Apo2L), TWEAK (Apo3L), and TRANCE (OPGL); tumor growth factors, such as TGF-β1, (TGF-β), TGF-β2, and TGF-β3; and hematopoietins, such as Epo (erythropoietin), Tpo (MGDF), Flt-3L, SCF (stem cell factor, c-kit ligand), M-CSF (CSF-1), and MSP (Macrophage stimulating factor). Other cytokines can include MST-1, CD40LG (TNFSF5), IFNA2, IL10, IL13, IL17C, IL1A, IL1B, IL1F10, IL36RN, IL36A, IL37, IL36B, IL36G, IL22, IL5, IL8, IL9, LTA, LTB, MIF, AIMP1, SPP1, and TNF. Exemplary, cytokine receptors can be IFNA2, IL10RA, IL10RB, IL13, IL13RA1, IL5RA, IL9, and IL9R.

Chemokines can be a family of small cytokines, or proteins secreted by cells. Some chemokines can be pro-inflammatory and can be induced during an immune response to recruit cells of an immune system to a site of infection, while others can be homeostatic and can be involved in controlling the migration of cells during normal processes of tissue maintenance or development. For example, chemokines can be XCL1 (lymphoactin a, SCM-1a, ATAC), XCL2 (lymphoactin b, SCM-1b, ATAC,) CCL1 (I-309), CCL2 (MCP-1, MCAF), CCL3 (MIP-1α, LD78α), CCL4 (MIP-1β, LAG-1, ACT-2), CCL5 (RANTES), CCL7 (MCP-3), CCL8 (MCP-2), CCL11 (eotaxin), CCL13 (MCP-4), CCL14 (HCC-1), CCL15 (HCC-2, Lkn-1, MIP-1d, MIP-5), CCL16 (HCC-4, LEC, LMC, LCC-1), CCL17 (TARC), CCL18 (DC-CK1, PARC, AMAC-a, MIP-4), CCL19 (MIP-3β, ELC, exodus-3), CCL20 (MIP-3α, LARC, exodus-1), CCL21 (6Ckine, SLC, exodus-2), CCL22 (MDC, STCP-1), CCL23 (MPIF-1, MIP-3, CKb-8), CCL24 (MPIF-2, eotaxin-2, CKb-6), CCL25 (TECK, MIP-4a), CCL26 (eotaxin-3), CCL27 (Eskine, CTACK, ILC), CXCL1 (GROa, MGSA-a), CXCL2 (GROb, MGSA-b, MIP-2a), CXCL3 (GROg, MGSA-g, MIP-2b), CXCL4 (PF4, oncostatin A), CXCL5 (ENA-78, CXCL6 (GCP-2), CXCL7 (NAP-2, PPBP), CXCL8 (IL-8, NAP-1, NAF, MDNCF), CXCL9 (Mig), CXCL10 (IP-10), CXCL11 (I-TAC), CXCL12 (SDF-1α/β), CXCL13 (BLC, BCA-1), CXCL14 (BRAK), CX3CL1 (fractaline). Chemokine receptors can be CCL13 (mcp-4), CCR1, CCR2, CCR3, CCR4, CCR5, CCR6, CCR7, CCR8, CCR9, CX3CR1, CXCR1, XCR1 (CCXCR1). Other proteins involved in inflammation can be ABCF1, BCL6, C3, C4A, CEBPB, CRP, CARD18, IL1R1, IL1RN, CXCR2, LTB4R, and TOLLIP.

Any of the autologous compositions described herein comprising A2M can further comprise one or more additional non-blood derived components. Non-blood derived components can be added before, during, or after isolation by any of the methods or using any of the systems described herein. A non-blood derived component can be obtained from non-blood tissues. A non-blood derived component can be an anti-coagulant. For example, a non-blood derived component or an anti-coagulant can be EDTA, tri-sodium citrate, water for injection (WFI), acid-citrate-dextrose (ACD), citrate-phosphate-dextrose (CPD), citrate-phosphate-double dextrose (CP2D), citrate-phosphate-dextrose-adenine (CPDA1), or saline.

Any of the autologous compositions described herein can comprise one or more additional blood products or blood-derived components. Blood products or blood-derived components can be added before, during, or after isolation by any of the methods described herein. Blood products or blood-derived components can be cells, peptides, proteins, DNA, RNA, carbohydrates, or other small molecules. For example, blood products or blood-derived components can be red blood cells, white blood cells, platelets, packed red blood cells, platelet-rich plasma, platelet concentrates, fresh plasma, fresh frozen plasma, frozen plasma, cryoprecipitate and cryosupernant.

In some embodiments, an autologous composition can contain PRP. PRP is an autologous blood product used by orthopedic healthcare providers due to the ability of platelet concentrates to release growth factors to a surgical site along with a bone graft. Platelets can be prepared by any means known in the art. The cellular components of PRP products generally include platelets with concentrations at least about 2 times the concentration of platelets in whole blood. For example, an autologous composition can contain platelets with a concentration of at least about 2, 3, 4, 5, 6, 7, 8, 9, 10, 11, 12, 13, 14, 15, 16, 17, 18, 19, 20, 25, 30, 40, or 50 times the concentration of platelets in whole blood. PRP products can also comprise variable concentrations of other growth factors released upon platelet degranulation, including, but not limited to, transforming growth factor-beta (TGF-β), insulin-like growth factor-1 (IGF-1), vascular endothelial growth factor (VEGF), EGF, fibroblast growth factor (FGF), and other factors. The growth factor content in various PRP products can vary between both patients and the method of preparation.

In some embodiments, an autologous composition can contain platelets. Typically, platelets can be prepared by separating platelets in blood from other blood components. In some embodiments, platelets can be obtained from any of the methods or systems described herein. In some embodiments, PRP can be separated or prepared from whole blood via centrifugation. Centrifugation can be used to separate plasma and platelets, which can be retained, from red and white blood cells, which can be discarded. In some embodiments, centrifugation parameters can be designed to achieve plasma containing approximately 70-100% of the platelets contained in the original blood sample, and to avoid the collection of leukocytes, such as less than 5%, for further processing. In some embodiments, concentrated platelets in blood plasma can be obtained by apheresis or pheresis (centrifugal separation during the donor process while other components are returned to the donor) or by selective removal from whole blood after gravity or centrifugal sedimentation of blood cells.

Though PRP preparations contain growth factors, other molecular mediators are also present, including cytokines, proteases and plasma proteins. Some of these mediators are potentially pro-inflammatory or catabolic, and are thought to be derived from leukocytes. Though all PRP preparations contain concentrated platelets, leukocytes and other blood derived cells may also be present and contribute to the molecular profile of the PRP products.

The compositions described herein can include one or more anti-oxidants or free radical scavengers to help minimize free radical damage and promote more rapid healing. When living tissue uses oxygen at the cellular level, unstable molecules termed free radicals are generated. Free radicals can include reactive oxygen species such as super-oxidants and hydrogen peroxide ($H2O2$) and reactive nitrogen species such as nitric oxide and peroxynitrites. Free radicals are unstable oxygen molecules that cause damage to cellular components such as DNA, proteins, or lipids and can induce cell death. The body naturally generates free radicals, which are generally neutralized in vivo by biochemical reactions. The concentration of free radicals is extremely high in a wound bed due to damage to the cells in wounded tissue. Immune cells migrating into the wound bed can induce inflammation and release more free radicals that do further damage to nearby cells. Inflammation can be directly proportional to the amount of scarring that can occur.

The anti-oxidants provided in the compositions described herein can include, but not limited to, vitamins such as vitamin C (ascorbic acid), vitamin E, vitamin A and other retinoids; and the carotenes such as 13-carotene.

In addition to its anti-oxidant functions, ascorbic acid can stimulate and organize the wound healing process due to its stimulatory effects on collagen production. Collagen can provide strength and structure to skin, cartilage and bone, and is the scaffold upon which the regenerated cellular and non-cellular elements of the wound can attach and grow. Ascorbic acid is known to have preservative properties, unless it is broken down such as occurs after exposure to sunlight or another source of ultraviolet (UV) light. Vitamin E is also known to break down upon exposure to sunlight or UV light. As such, coverings can be used to shield the components of the compositions from UV rays upon application.

The compositions described herein can also include one or more antiseptic, anti-infective, antibiotic, bacteriocidal, anti-fungal, anti-microbial agent or another agent that sanitizes the wound. Many wound sites are either already infected with bacteria or are susceptible to such infection. As such it is desirable that the composition be capable of either killing bacteria or preventing the mobility or the reproduction of bacteria already present in a wound. In an embodiment the antiseptic agent includes, but is not limited to, cetylpyridinium chloride (CPC) and other quaternary ammonium compounds or a combination thereof. In an embodiment, the composition includes an agent that is bacteriocidal to at least the *Pseudomonas* and Klebsella genera of bacteria. The agent can be effective against *E. coli*, species of *Streptococcus*, ShigeHa, *Salmonella* and most species of *Staphylococcus* including *S. aureus* and MRSA as well. The agent can include neosporin, vancomycin and gentamycin, and combinations thereof. The compositions described herein can include one or more plant components or plant extracts including, but not limited to, Aloe vera.

The compositions described herein can also include one or more growth factors, cytokines or chemokines. In an embodiment, the growth factors for use can include PDGF, platelet-derived angiogenesis factor (PDAF), VEGF, PDEGF, platelet factor 4 (PF-4), transforming growth factor 13 (TGF-13), acidic fibroblast growth factor (FGF-A), basic fibroblast growth factor (FGF-B), transforming growth factor a (TGF-A), insulin-like growth factors 1 and 2 (IGF-1 and IGF-2), p thromboglobulin-related proteins (f3 TG), thrombospondin (TSP), fibronectin, von Wallebrand factor (vWF), fibropeptide A, fibrinogen, albumin, plasminogen activator inhibitor 1 (PAI-1), osteonectin, regulated upon activation normal T cell expressed and presumably secreted (RANTES), gro-a, vitronectin, fibrin D-dimer, factor V, antithrombin ID, immunoglobulin-G (IgG), immunoglobulin-M (IgM), immunoglobulin-A (IgA), a2-macroglobulin, angiogenin, Fg-D, elastase, keratinocyte growth factor (KGF), EGF, FGF, tumor necrosis factor (TNF), FGF and interleukin-1 (IL-1), KGF-2 and combinations thereof. Each of these growth factors is known or believed to enhance cell or tissue growth. Moreover, said substances, or various combinations thereof, are known or believed to function together in an unexpected synergistic manner to promote wound healing. It should be appreciated that the growth factors can be derived from activated platelets, cultured cells, or from protein expression systems.

The compositions described herein can include concentrated platelets, or PRP as the growth factor source. The platelets can be separated from the red blood cells and white blood cells of whole blood, primarily through differential centrifugation, although any suitable method for separating platelets from whole blood may be employed. Incidental amounts of white blood cells can be present due to the fact that the platelets are rarely totally isolated from the other blood components. In an embodiment, the range of the mean platelet volume of the platelets being sequestered is in the range of about 6.6 to 8.4 femtoliters, with an average of about 7.7 femtoliters. In another embodiment, the range of the mean platelet volume of the platelets being sequestered is in the range of about $250 \times 10_{11}$ per cc blood or greater. In another embodiment, the range of the mean platelet volume of the platelets being sequestered is in the range of about $450 \times 10_{11}$ per cc blood. The concentrated platelets or PRP can be frozen or freeze-dried.

Some of the compositions described herein can include one or more biochemical platelet activators or agonists including, but not limited to, thrombin, including native thrombin, calcified thrombin, bovine thrombin (such as in Autologel), autologous thrombin, allogeneic thrombin, or recombinant human thrombin, tissue factor, von Willebrand factor, platelet factor 4, collagen, thromboxane A2, serotonin, adenosine diphosphate (ADP), acetylcholine (ACH), or combinations thereof to activate the platelets to release the contents of their stored granules into the plasma. Activators and agonists can be mixed with the plasma-containing compositions immediately prior to application to a patient.

In addition, the compositions described herein can include one or more activator co-factors including, but not limited to divalent cations such as calcium ions, sodium ions, calcium salts in order to implement the clotting cascade and activate platelets to release the alpha granules. Suitable calcium salts include, without limitation, $CaCO_3$, $CaSO_4$, $CaCl_2$, $CaCl_2$ which can be available as calcium chloride injection, USP 10% (American Regent Laboratories, Inc., Shirley, N.Y., USA).

Systems for Production of Autologous A2M Compositions

Provided herein are systems that can be used with the methods and can be used to produce any of the compositions. A system for enrichment of A2M from a sample is provided. A system can have one or more filters, a centrifuge, a pump, or a combination thereof. A system can have one or more waste, retentate, or filtrate (used synonymously with permeate) collection modules.

One aspect of the invention is directed at a system for concentrating A2M from a fluid sample, such as a biological sample. Typically, the fluid sample is blood derived from a subject, such as a patient with a chronic wound, and the system concentrates the A2M from the blood into a concentrated A2M blood serum or concentrated A2M blood plasma. The concentrated sample can then be administered back to the same subject to treat the chronic wound.

The systems described herein offer a number of advantages, including low cost and minimal parts. In some embodiments, the systems offer the advantage of not requiring the use of a pump, such as to flow blood through the system. In some embodiments, the systems provide control over the flow of fluids through the systems beyond that offered by the pump. There is also a need for faster processing times for preparations of therapeutic autologous blood compositions while maintaining sterility and/or minimizing foaming of the compositions so they are suitable for injection into a subject. Furthermore, there is a need for preparing effective therapeutic compositions for autologous treatment using smaller sample sizes to minimize the amount of blood drawn from a subject Importantly, there is also a need in the art for the minimization of platelet activation and/or degranulation during preparation of autologous therapeutic compositions, as platelet activation can lead to increased cytokine production and protease activation, which can lead to degradation of extracellular matrix proteins, a known cause of arthritis and other inflammatory diseases.

One advantage of the blood concentrating systems and methods described herein is that they do not require the use of a pump. Another advantage is that an operator can manually control the flow of fluids through the system through the use of injectors, such as syringes to move fluids through the system and through the one or more filters, such as Hollow Fiber Tangential Flow Filters (HFTFs) or polysulfone filters of the systems. Another advantage offered is that platelet activation and degranulation is minimized Because the biological samples concentrated are circulated through the filters employed a minimal number of times, or not at all, platelet activation and/or degranulation can be minimized Additionally, because a pump is not used in some embodiments, there is no crushing of tubing or chambers of the system by a pump head, which can further minimize platelet activation and/or degranulation. Syringes can be used to manually move a biological sample, such as plasma, back and forth through the one or more filters of the systems. Yet another advantage offered is that therapeutic autologous compositions suitable for injection into a subject can be generated in short amounts of time and from a minimal sample volume from a subject. The "dead space" of the systems is minimized by removing long tubing lines, bags, and the like. The systems are also amenable to using various volumes of biological samples because injectors with varying volumes can be readily used with the systems. Additionally, biological samples separated via centrifugation can be easily flowed into the systems, and processed. The systems utilize a minimal number of components, which minimizes cost as well. As the cost is minimized, the systems can also be made disposable. Additionally, recovery of desired material can be increased using a manual system. Table 1 depicts data of recovery of various components from samples from various subjects using a manual system.

Embodiments of the invention utilize minimal mechanization to concentrate and filter blood for autologous therapy. These less mechanized systems offer the advantage of easy handling, less dependency on mechanical and electrical components which may fail, and can be ultimately less expensive. One embodiment of the invention, for example, uses the force of gravity and/or pressure generated manually to accomplish concentration and filtration of a biological sample through a filter, such as a membrane, and to further process filtrate or drain waste filtrate. Gravity and manual manipulation of positive and negative pressure applied to the system can effectuates processing of the biological sample and washing fluid through the membrane for removing air and concentrating and filtering the biological sample.

By compartmentalization of the tangential flow filtration process, one can produce systems that may greatly improve processing of blood, convert the system into a disposable blood concentrator or be used for purification or isolation of certain components from biological fluids or other fluids. Other processes and uses are also possible as will become apparent.

One aspect of the invention is directed at a system for concentrating A2M from a fluid sample, such as a biological sample. Typically, the fluid sample is blood derived from a subject, such as a patient with pain, and the system concentrates the A2M from the blood into a concentrated A2M blood serum or concentrated A2M blood plasma. The concentrated sample can then be administered back into the same subject to treat the pain A system for purifying a blood component can comprise a filtration membrane. In some embodiments, the filtration membrane can be formed as a flat, elongated, sheet having a first surface and a second surface. The filtration membrane can have a preferred pore size to allow the selected blood components to traverse the membrane. The pore size of the filtration membrane can simultaneously prevent the passage of other blood components that exceed the size of the selected blood components.

TABLE 1

| Patient | Sample | % Conc Factor | Trypsin Inhib % of Plasma Avg | Trypsin Inhib % of Plasma SD | Trypsin Inhib % recovery Avg | Trypsin Inhib % recovery SD | A2M % of Plasma Avg | A2M % of Plasma SD | A2M % recovery Avg | A2M % recovery SD | Fibrinogen % Plasma | Fibrinogen % Rec | Total Protein % Plasma | Total Protein % Rec |
|---|---|---|---|---|---|---|---|---|---|---|---|---|---|---|
| 13-04-23 B D | APIC-PRP | 395 | 380 | 22.0 | 96.3 | 5.6 | 504 | 105 | 127.6 | 26.5 | 311 | 79 | 346 | 88 |
| 13-04-23 J R | APIC-PRP | 429 | 440 | 24.8 | 102.7 | 5.8 | 508 | 112 | 118.6 | 26.2 | 369 | 86 | 393 | 92 |
| 13-04-25 J H | APIC-PRP | 225 | 148 | 4.2 | 65.6 | 1.9 | 216 | 17 | 96.0 | 7.5 | 167 | 74 | 180 | 80 |
| 13-04-25 F S | APIC-PRP | 300 | 212 | 8.2 | 70.6 | 2.7 | 281 | 31 | 93.7 | 10.2 | 246 | 82 | 269 | 90 |
| 10-05-08 W F | APIC-PRP | 375 | 284 | 5.2 | 75.6 | 1.4 | 297 | 104 | 79.1 | 27.6 | | | 326 | 87 |
| AVERAGE | APIC-PRP | 345 | 293 | | 82 | | 361 | | 103 | | 273 | 80 | 303 | 87 |
| SD | APIC-PRP | 82 | 119 | | 16 | | 136 | | 20 | | 57 | 5 | 82 | 4 |
| 13-05-01 N Z | Manual APIC-PRP, 500 kDa | 400 | 265 | 5.8 | 66.4 | 1.5 | 296 | 25 | 73.9 | 6.3 | 237 | 59 | 289 | 72 |
| 13-05-03 P M | Manual APIC-PRP | 323 | 243 | 6.7 | 75.2 | 2.1 | 187 | 44 | 57.8 | 13.5 | 188 | 58 | 210 | 65 |
| 13-05-08 W F | Manual APIC-PRP, 500k U-shape | 375 | 305 | 5.2 | 81.3 | 1.6 | 272 | 43 | 72.4 | 11.5 | | | 302 | 80 |
| 13-05-08 W F | Manual APIC-PRP, 500k straight | 300 | 265 | 8.5 | 88.3 | 2.8 | 249 | 67 | 83.0 | 22.4 | | | 265 | 88 |
| AVERAGE | APIC-PRP | 349 | 270 | | 78 | | 251 | | 72 | | 213 | 59 | 266 | 76 |
| SD | APIC-PRP | 46 | 26 | | 9 | | 47 | | 10 | | 35 | 1 | 41 | 10 |
| 13-05-01 N Z | Manual APIC-PRP, HPH-Mini | 400 | 271 | 2.3 | 67.9 | 0.6 | 292 | 41 | 73.0 | 10.3 | 272 | 68 | 282 | 70 |
| 13-05-03 P M | Manual APIC-PRP, HPH-Mini | 265 | 261 | 9.5 | 98.6 | 3.6 | 259 | 30 | 97.9 | 11.3 | 209 | 79 | 230 | 87 |
| 13-05-08 W F | Manual APIC-PRP, HPH-Junior | 250 | 297 | 13.5 | 118.6 | 5.4 | 284 | 20 | 113.4 | 8.1 | | | 332 | 133 |
| AVERAGE | APIC-PRP | 305 | 276 | | 95 | | 278 | | 95 | | 240 | 73 | 281 | 97 |
| SD | APIC-PRP | 83 | 18 | | 26 | | 17 | | 20 | | 45 | 8 | 51 | 32 |

| Patient | Sample | Albumin % Plasma | Albumin % Rec | Globulin % Plasma | Globulin % Rec | Alk. Phos. % Plasma | Alk. Phos. % Rec | ALT % Plasma | ALT % Rec | AST % Plasma | AST % Rec |
|---|---|---|---|---|---|---|---|---|---|---|---|
| 13-04-23 B D | APIC-PRP | 329 | 83 | 368 | 93 | 71 | 18 | 514 | 130 | 373 | 95 |
| 13-04-23 J R | APIC-PRP | 380 | 89 | 421 | 98 | 88 | 21 | 471 | 110 | 486 | 113 |
| 13-04-25 J H | APIC-PRP | 162 | 72 | 209 | 93 | 29 | 13 | 200 | 89 | 320 | 142 |
| 13-04-25 F S | APIC-PRP | 274 | 91 | 262 | 87 | 70 | 23 | 338 | 113 | 400 | 133 |
| 10-05-08 W F | APIC-PRP | 312 | 83 | 350 | 93 | 106 | 28 | 500 | 133 | 1100 | 293 |
| AVERAGE | APIC-PRP | 291 | 84 | 322 | 93 | 73 | 21 | 405 | 115 | 536 | 155 |
| SD | APIC-PRP | 82 | 7 | 85 | 4 | 29 | 6 | 134 | 18 | 321 | 79 |
| 13-05-01 N Z | Manual APIC-PRP, 500 kDa | 295 | 74 | 278 | 70 | 123 | 31 | 267 | 67 | 267 | 67 |
| 13-05-03 P M | Manual APIC-PRP | 210 | 65 | 210 | 65 | 41 | 13 | 222 | 69 | 140 | 43 |
| 13-05-08 W F | Manual APIC-PRP, 500k U-shape | 302 | 81 | 300 | 80 | 118 | 31 | 500 | 133 | 700 | 187 |
| 13-05-08 W F | Manual APIC-PRP, 500k straight | 263 | 88 | 267 | 89 | 71 | 24 | 450 | 150 | 400 | 133 |
| AVERAGE | APIC-PRP | 268 | 77 | 264 | 76 | 88 | 25 | 360 | 105 | 377 | 108 |
| SD | APIC-PRP | 42 | 10 | 39 | 11 | 39 | 9 | 136 | 43 | 240 | 65 |
| 13-05-01 N Z | Manual APIC-PRP, HPH-Mini | 284 | 71 | 278 | 70 | 68 | 17 | 305 | 76 | 293 | 73 |
| 13-05-03 P M | Manual APIC-PRP, HPH-Mini | 130 | 87 | 229 | 86 | 51 | 19 | 222 | 84 | 200 | 76 |
| 13-05-08 W F | Manual APIC-PRP, HPH-Junior | 332 | 133 | 333 | 133 | 82 | 33 | 350 | 140 | 600 | 240 |
| AVERAGE | APIC-PRP | 282 | 97 | 280 | 96 | 67 | 23 | 292 | 100 | 364 | 130 |
| SD | APIC-PRP | 51 | 32 | 52 | 33 | 16 | 9 | 65 | 35 | 209 | 96 |

An exemplary embodiment of the systems comprises a filtration module comprising two or more inlets and one or more filters. A volume of a biological sample flows into the filtration module and through at least the inlet and one or more filters of the filtration module. The flow may also pass through another inlet of the module after passing through the first inlet and one or more filters. The one or more filters can be connected in series between the inlet and the outlet of the filter module. The inlets can have selectively closed valves to control flow of the fluid sample therein and the module may comprise multiple inlets or multiple outlets or any combination thereof. The filtration module may be a dead-end filtration module. Preferably, the filtration module may be a tangential flow filtration module.

In general, a biological sample, or separated components thereof, can be applied to the retentate side of a filter, or two or more filters in series. A pressure gradient can be applied across the filter wherein the pressure on the retentate side of the filter is greater than the pressure on the filtrate side of the filter. The difference in pressure can force certain blood components through the filter while other blood components, such as cells and high molecular weight molecules, which do not fit through the filter pores, can be retained. A pressure gradient can be provided by manually injecting fluid onto a retentate side of a filter. In one embodiment, a pressure gradient can be generated by applying a lower pressure or a vacuum, to a filtrate side of a filter. The filter of the invention can be a tangential flow filter, e.g., a hollow fiber filter. The filter of the invention can be a polysulfone filter. In some embodiments, the filter of the invention is not a polysulfone filter. The concentrator can have an ultrafiltration membrane with a molecular weight cut off of 50-500. 100-500, 50, 100, or 500 kDa. A pressure gradient across the membrane can be provided by a manual injector on the retentate side of the filter or from a manual injector on the filtrate side of the filter.

In one aspect, a system can comprise a first filtration module for removing a first blood component from a biological sample connected to a second filtration module for removing a second blood component and/or retaining a third blood component from the biological sample after processing through the first filtration module. The second filtration module can also be used to remove a third blood component from the biological sample. In some embodiments, a system can comprise a first filtration module comprising a first filter 30, a first channel 10 (first retentate chamber), and a second channel 20 (first filtrate chamber). The first channel 10 and the second channel 20 can be separated by a first filter 30, such as a membrane. The first channel 10 can comprise a first inlet end 11 and a second inlet end 12. The first channel 10 can have any suitable overall length. The first channel 10 can have a first suitable cross-sectional area measured at the first inlet end 11. The first channel 10 can have a second suitable cross-sectional area measured at the second inlet end 12. The first channel 10 can have a third suitable cross-sectional area measured between the first inlet end 11 and the second inlet end 12. The second channel 20 (first filtrate chamber) can receive blood components that flow within the first channel 10 (first retentate chamber) through the first filter 30. The first filter can have a preferred pore size chosen to allow the selected blood components, such as proteins, to traverse the membrane. The pore size of the first filter 30 can prevent the passage of other blood components, such as cells, that exceed the size of the selected blood components.

In some embodiments, a hollow fiber filter is used to separate the first channel 10 (first retentate chamber) and the second channel 20 (first filtrate chamber). In a preferred embodiment, the first filtrate chamber 20 can at least partially enclose the first retentate chamber 10. At least a portion of the first retentate chamber 10 wall can be the first membrane. The first filtrate chamber 20 can comprise an inner wall and an outer wall. At least a portion of the inner wall can be the first membrane portion 30 of the first retentate chamber 10 wall. The first filtrate chamber 20 outer wall can comprise an outer barrier impermeable to fluid. The first membrane portion 30 can comprise a hollow fiber filter, which can comprise multiple hollow fibers that run the length of the first channel 10 and/or second channel 20 in parallel. Hollow fibers can be embedded at each end of the channels. The hollow fiber's lumens can be retained open and can form a continuous passage through each of the lumens from one end of the channel to the other. The hollow fibers can be enclosed by the outer wall of the channels in the filtration modules. As a result, there can be a chamber bounded by the second channel 20 wall and the outer walls of the hollow fibers. That chamber can be used as the first filtrate chamber 20. The internal spaces of the hollow fibers can constitute part of the first retentate chamber 10 in the system described herein. The outer walls of the channels can have one or more ports from which the filtrate can be collected, flowed, and/or removed.

The first channel can be extended further than the internal spaces of the hollow fibers by a first adaptor 41 and/or a second adaptor 42 that fit to the first inlet 11 and second inlet 12, respectively, of the first channel 10. One or more adapters in conjunction with an inlet of the channel can be part of the retentate chamber. One or more adapters in conjunction with an inlet of the channel can be in fluid connection with the retentate chamber. Depending on the direction of fluid flow through the fibers, the retentate channel can collect fluid as it exits the hollow fibers Depending on the direction of fluid flow through the fibers, the retentate channel can allow fluid arriving through an inlet to interface with the hollow fiber's open ends and distribute through the fibers and flow towards the other end of the channel Each adapter can comprise a first and a second end. The first end can be fitted to the channel and the second end can comprise an opening connectable to an injector, vessel, or a pump. In one embodiment, the injector can be connected to the adapter via a line to allow for fluid flow. In one embodiment, the injector can be connected directly to the adapter. In some embodiments, the adapter may form part of the injector where part or the entire content of the injector may be contained within the adapter. The adapter can be connected directly to a manual injector but, if desired, a pump may be connected to the adaptor. When a connecting line is added to an adapter, the retentate chamber can include the space inside the connecting line. When a connecting line is connected at one end to an adapter and at its other end to a vessel, the interior of the vessel can be included as part of the first retentate chamber 10.

A first injector 51 can be connected to the first inlet end 11 of the first channel 10, optionally through an adaptor. A second injector 52 can be connected to the second inlet 12 of the first channel 10, optionally through an adaptor. The first injector 51 and/or the second injector 52 can hold, collect, or be used to inject fluid at various stages of the systems operation. The first injector 51 can comprise a biological sample, such as blood. Activation of the first injector 51 can cause the biological sample to flow through the first inlet 11, through the first channel 10 and over the first membrane 30. The injected biological sample can flow through the second inlet 12 into the second injector 52. Activation of the second injector 52 can cause the biological sample to flow back through the second inlet 12, through the first channel 10 and over the first membrane 30. The biological sample can flow back through the first inlet 11 and back into the first injector 51. This process can be repeated until a sufficient amount of the filtered blood sample has passed through the first filter 30 and into the second channel 20.

In some embodiments, the system comprises a first filtrate reservoir 75 connected to the first filtrate chamber 20. Fluid can flow between the first filtrate reservoir 75 and the first filtrate chamber 20. The reservoir can enclose the portion of the first filtrate chamber 20 that opens into the first filtrate reservoir 75 (e.g., a port). In some embodiments, the system comprises a second filtration module connected to the first filtrate reservoir 75. Flow of fluid from the first filtrate chamber 20 to the filtrate reservoir 75 and flow of fluid between the filtrate reservoir 75 and the second filtration module can be closed, open, or controlled through the use of a valve, such as a stop cock.

The second channel 20 can have any suitable overall length. The second channel 20 can have a cross-sectional area. The second channel 20 can have a port 70 connected thereto. The port 70 can be optionally fluidly connected to a third inlet 71 of a third channel 72. The third channel 72 can have any suitable overall length. The port 70 can be optionally fluidly connected to a collection vessel 300. The collection vessel 300 can be the third injector 53 or the fourth injector 54. The collection vessel 300 can be adapted to fit a first inlet end 11 and/or a second inlet end 12. The collection vessel 300 can be adapted to fit a first adaptor 41 and/or a second adaptor 42. The collection vessel 300 can be a syringe.

The third channel 72 can have a suitable cross-sectional area. In some embodiments, the third channel can be arranged substantially perpendicular to the first channel 10, second channel 20, or both. The third channel 72 can comprise a first outlet 74 connected to a vessel 75 (e.g., a filtrate reservoir). The third channel 72 can comprise a valve 76 situated between the first outlet 74 and third inlet 71 of the third channel. A fourth channel 80 can be connected to the valve 76 via a fourth inlet 81.

Blood components that flow from the first channel 10 through the first filter 30 into the second channel 20 and through the port 70 can flow through the third inlet of the third channel 71, the third channel 72, and the first outlet of the third channel 74 into the vessel 75 when the valve 76 is in a first open configuration. The fourth channel 80 can be in fluid connection with a third injector 53. In some embodiments, when the valve 76 is in the first open configuration, fluid is prevented from flowing into the fourth channel 80.

Blood components in the vessel 80 can flow through the third channel 72 and through the fourth channel 80 when the valve 76 is in a second open configuration. In some embodiments, this can be caused by activation of the third injector 53. The second open configuration can prevent flow of blood components from the vessel 75 through a portion of the third channel 72 upstream of the valve 76.

The system can have a fifth channel 90 (second retentate chamber) and a sixth channel 100 (second filtrate chamber). The fourth channel 80 can be connected to a fifth channel 90. The fifth channel can be connected to a third injector 53, such as through an adaptor 43. The fifth channel 90 and the sixth channel 100 can be separated by a second filter 110, such as a membrane. The fifth channel 90 can comprise a fifth inlet 13 and a sixth inlet 14.

A third injector 53 can be connected to the fifth inlet end 13, such as through an adaptor 43. A fourth injector 54 can be connected to the sixth inlet 14, such as through an adaptor 44. The third injector 53 and/or fourth injector 54 can hold, collect, or be used to inject fluid at various stages of the system's operation. The third injector 53 can comprise the filtered biological sample from the vessel 75. Activation of the third injector 53 can cause the filtered biological sample to flow through the fifth inlet 13, through the fifth channel 90 and over the second membrane 110. The injected biological sample can flow through the sixth inlet 14 into the fourth injector 54. Activation of the fourth injector 54 can cause the biological sample to flow back through the sixth inlet 14, through the fifth channel 90 and over the second membrane 110. The biological sample can flow back through the fifth inlet 13 and back into the third injector 53. This process can be repeated until a sufficient amount of the filtered blood sample has passed through the second filter 110 and into the sixth channel 100. This process can result in the formation of a concentrated biological sample in the fifth channel 90. The concentrated biological sample can be collected in the third injector 53 or the fourth injector 54.

The fifth channel 90 can have any suitable overall length. The fifth channel 90 can have a first cross-sectional area measured at the fifth inlet 13. The fifth channel 90 can have a second cross-sectional area measured at the sixth inlet 14. The fifth channel 90 can have a third cross-sectional area measured between the fifth inlet 13 and the sixth inlet 14. The sixth channel 100 can receive blood components that flow from the fifth channel 90 through the second filter 110.

The second filter 110 can have a preferred pore size chosen to prevent desired blood components, such as high molecular weight proteins, to traverse the membrane. The pore size of the second filter 110 can simultaneously allow the passage of other blood components, such as smaller molecular weight proteins that do not exceed the size of the desired blood components into the sixth channel 100.

The sixth channel 100 can have any suitable overall length. The sixth channel 100 can have a suitable cross-sectional area. The sixth channel 100 can have a port 120 connected thereto. The port 120 can be fluidly connected to a seventh inlet of a seventh channel 121. The seventh channel 122 can have any suitable overall length. The seventh channel 122 can have a suitable cross-sectional area. In some embodiments, the seventh channel can be arranged substantially perpendicular to the fifth channel 90, sixth channel 100, or both. The seventh channel 122 can comprise a second outlet 123 connected to a second vessel 124. Blood components that flow from the fifth channel 90 through the second filter 110 into the sixth channel 100 and through the second port 120 can flow through the seventh inlet of the seventh channel 121, the seventh channel 122, and the outlet of the seventh channel 123 into the vessel 124. In some embodiments, the seventh vessel 124 is a waste collection vessel.

In a preferred embodiment, a hollow fiber filter is used to separate the fifth channel 90 (second retentate chamber) and the sixth channel 100 (second filtrate chamber). In a preferred embodiment, the second filtrate chamber 100 can at least partially enclose the second retentate chamber 90. At least a portion of the second retentate chamber 90 wall can be the second membrane portion 110. The second filtrate chamber 100 can comprise an inner wall and an outer wall. At least a portion of the inner wall can be the second membrane portion 100 of the second filtrate chamber 90 wall. The second filtrate chamber 90 outer wall can comprise an outer barrier impermeable to fluid. The second membrane 110 portion can comprise a hollow fiber filter, which can comprise multiple hollow fibers that run the length of the fifth channel 90 and/or sixth channel 100 in parallel. Hollow fibers can be embedded at each end of the channels. The hollow fiber's lumens can be retained open and can form a continuous passage through each of the lumens from one end of the channel to the other. The hollow fibers can be enclosed by the outer wall of the channels in the filtration modules. As a result, there can be a chamber bounded by the sixth channel 100 wall and the outer walls of the hollow fibers. That chamber can be used as the second filtrate chamber 100. The internal spaces of the hollow fibers can constitute part of the second retentate chamber 90 in the system described herein. The outer walls of the channels can have one or more ports from which filtrate can be collected, flowed, and/or removed.

The fifth channel 90 can be extended further than the internal spaces of the hollow fibers by a third adapter 43 and/or fourth adapter 44 that fit to the third inlet 13 and/or fourth inlet 14 of the fifth channel 90, respectively. Each adapter in conjunction with an inlet of the channel can be part of the second retentate chamber 90. Depending on the direction of fluid flow through the fibers, the second retentate channel 90 can collect fluid as it exits the hollow fibers and/or allow fluid arriving through an inlet to interface with the hollow fiber's open ends and distribute itself among those hollow fibers for purposes of continuing its path towards the other end of the channel. Each adapter can comprise a first and a second end. The first end can be fitted to the channel 90 and the second end can comprise an opening connectable to an injector, vessel, or a pump. In one embodiment, the injector can be connected to the adapter via a line to allow for fluid flow but. In one embodiment, the injector can be connected directly to the adapter. In some embodiments, the adapter may form part of the injector where part or the entire content of the injector may be contained within the adapter. Normally the adapter is connected directly to a manual injector but, if desired, a pump mat be connected to the adaptor. When a connecting line is added to an adapter, the second retentate chamber 90 can include the space inside the connecting line. When a connecting line is connected at one end to an adapter and at its other end to a vessel, the interior of the vessel can be included as part of the second retentate chamber 90.

In some embodiments, a sample that flows through the first filter 30 can flow through port 70 and into a collection vessel 300. The collection vessel 300 can be the third injector 53 or the fourth injector 54. The collection vessel 300 can be adapted to fit a first inlet end 11 and/or a second inlet end 12. The collection vessel 300 can be adapted to fit a first adaptor 41 and/or a second adaptor 42. The collection vessel 300 can be a syringe. The collection vessel 300 can then be removed from the port, such as after collecting the first filtrate, and the collection vessel 300 can be connected to the first inlet end 11 or a second inlet end 12. The collected sample can then be flowed from the collection vessel 300 through the first inlet end 11 or a second inlet end 12 and into the first retentate chamber 10 and processed as described above. In such embodiments, there is no need for the second filtrate chamber 100 and first retentate chamber 10 to be in fluid connection.

In another aspect, a system can comprise a centrifuge and a device for removing a first blood component and/or retaining a second blood component from a portion of a biological sample after centrifugation. In some embodiments, a system can comprise a first filtration module for removing a first blood component from a portion of a centrifuged biological sample connected to a second filtration module for removing a second blood component and/or retaining a third blood component from a portion of a centrifuged biological sample after processing through the first filtration module. The second filtration module can also be used to remove a third blood component from a portion of a centrifuged biological sample. In some embodiments, a system can comprise a first filtration module comprising a first filter 230, a first channel 210 (first retentate chamber), and a second channel 220 (first filtrate chamber). The first channel 210 and the second channel 220 can be separated by a first filter 230, such as a membrane. The first channel 210 can comprise a first inlet end 211 and a second inlet end 212. The first channel 210 can have any suitable overall length. The first channel 210 can have a first suitable cross-sectional area measured at the first inlet end 211. The first channel 210 can have a second suitable cross-sectional area measured at the second inlet end 212. The first channel 210 can have a third suitable cross-sectional area measured between the first inlet end 211 and the second inlet end 212. The second channel 220 (first filtrate chamber) can receive blood components that flow within the first channel 210 (first retentate chamber) through the first filter 230. The first filter can have a preferred pore size chosen to allow the selected blood components, such as proteins, to traverse the membrane. The pore size of the first filter 230 can prevent the passage of other blood components, such as cells, that exceed the size of the selected blood components.

In a preferred embodiment, a hollow fiber filter is used to separate the first channel 210 (first retentate chamber) and the second channel 220 (first filtrate chamber). In a preferred embodiment, the first filtrate chamber 220 can at least partially enclose the first retentate chamber 210. At least a portion of the first retentate chamber 210 wall can be the first membrane portion 230. The first filtrate chamber 220 can comprise an inner wall and an outer wall. At least a portion of the inner wall can be the first membrane portion 230 of the first retentate chamber 210 wall. The first filtrate chamber 220 outer wall can comprise an outer barrier impermeable to fluid. The first membrane portion 230 can comprise a hollow fiber filter, which can comprise multiple hollow fibers that run the length of the first channel 210 and/or second channel 220 in parallel. Hollow fibers can be embedded at each end of the channels. The hollow fiber's lumens can be retained open and can form a continuous passage through each of the lumens from one end of the channel to the other. The hollow fibers can be enclosed by the outer wall of the channels in the filtration modules. As a result, there can be a chamber bounded by the second channel 220 wall and the outer walls of the hollow fibers. That chamber can be used as the first filtrate chamber 220. The internal spaces of the hollow fibers can constitute part of the first retentate chamber 210 in the system described herein. The outer walls of the channels can have one or more ports from which the filtrate can be collected, flowed, and/or removed.

The first channel can be extended further than the internal spaces of the hollow fibers by a first adaptor 241 and/or a second adaptor 242 that fit to the first inlet 211 and second inlet 212 respectively of the first channel 210. Each adapter in conjunction with an inlet of the channel can be part of the retentate chamber. Depending on the direction of fluid flow through the fibers, the retentate channel can collect fluid as it exits the hollow fibers and/or allow fluid arriving through an inlet to interface with the hollow fiber's open ends and distribute itself among those hollow fibers for purposes of continuing its path towards the other end of the channel Each adapter can comprise a first and a second end. The first end can be fitted to the channel and the second end can comprise an opening connectable to an injector, vessel, or a pump. In one embodiment, the injector can be connected to the adapter via a line to allow for fluid flow but. In one embodiment, the injector can be connected directly to the adapter. In some embodiments, the adapter may form part of the injector where part or the entire content of the injector may be contained within the adapter. Normally the adapter is connected directly to a manual injector but, if desired, a pump mat be connected to the adaptor. When a connecting line is added to an adapter, the retentate chamber can include the space inside the connecting line. When a connecting line is connected at one end to an adapter and at its other end to a vessel, the interior of the vessel can be included as part of the first retentate chamber 210.

A first injector 251 can be connected to the first inlet end 211 of the first channel 210, optionally through an adaptor. A second injector 252 can be connected to the second inlet 212 of the first channel 210, optionally through an adaptor. The first injector 251 and/or the second injector 252 can hold, collect, or be used to inject fluid at various stages of the systems operation. The first injector 251 can comprise a biological sample, such as blood. Activation of the first injector 251 can cause the biological sample to flow through the first inlet 211, through the first channel 210 and over the first membrane 230. The injected biological sample can flow through the second inlet 212 into the second injector 252. Activation of the second injector 252 can cause the biological sample to flow back through the second inlet 212, through the first channel 210 and over the first membrane 230. The biological sample can flow back through the first inlet 211 and back into the first injector 251. This process can be repeated until a sufficient amount of the filtered blood sample has passed through the first filter 230 and into the second channel 220.

In some embodiments, the system comprises a first filtrate reservoir 275 connected to the first filtrate chamber 220. Fluid can flow between the first filtrate reservoir 275 and the first filtrate chamber 220. The reservoir can enclose the portion of the first filtrate chamber 220 that opens into the first filtrate reservoir 275 (e.g., a port). In some embodiments, the system comprises a second filtration module connected to the first filtrate reservoir 275. Flow of fluid from the first filtrate chamber 220 to the filtrate reservoir 275 and flow of fluid between the filtrate reservoir 275 and the second filtration module can be closed, open, or controlled through the use of a valve, such as a stop cock.

The second channel 220 can have any suitable overall length. The second channel 220 can have a cross-sectional area. The second channel 220 can have a port 270 connected thereto. The port 270 can be fluidly connected to a third inlet 271 of a third channel 272. The third channel 272 can have any suitable overall length. The third channel 272 can have a suitable cross-sectional area. In some embodiments, the third channel can be arranged substantially perpendicular to the first channel 210, second channel 220, or both. The third channel 272 can comprise a first outlet 274 connected to a vessel 275 (e.g., a filtrate reservoir).

Blood components that flow from the first channel 210 through the first filter 230 into the second channel 220 and through the port 270 can flow through the third inlet of the third channel 271, the third channel 272, and the first outlet of the third channel 274 into the vessel 275 when the system is in use. In some embodiments, the vessel 275 is a waste collection vessel Any of the injectors described herein can be used for injecting a biological sample into the systems described herein. Any of the injectors described herein can be used to apply pressure to the systems described herein and to cause fluid to flow through the system. Any of the injectors described herein can be manually operated. Exemplary injectors include syringes. Any of the injectors described herein can also function as sample collection modules as the sample passes through various stages of the systems.

In some embodiments, a system can comprise one or more Luer-lock adapters. In some embodiments a Luer lock adapter can be capped or closed. In some embodiments, a system can comprise one or more dead-end filters. In some embodiments, one or more of the inlets can be closed or sealed.

In some embodiments, the sample can be processed through the system manually. For example, a sample can be processed through the system without the use of a pump. In some embodiments, the sample can be processed through the system by pushing or pulling the sample through the system using a pressure generating device, such as a syringe. Injectors can also be used as flow control devices to control the flow of the biological sample through one or more portions of the systems described herein. In some embodiments, other suitable flow control devices include actuators, clamps, ball valves, diaphragm valves, needle valves, and pumps. Flow control devices can be variable flow, i.e., capable of providing varying flow rates, and binary on/off that open to permit flow and close to block flow. Suitable pumps include, but are not limited to, vane pumps, tubing pumps, rotary pumps, and diaphragm pumps, and may be chosen based upon, for example, the desired flow rate.

In any of the systems described herein, a filtration membrane is positioned between, and separates, a retentate chamber and a filtrate chamber. Many configurations are possible for the retentate chamber and the filtrate chamber. For example the retentate chamber and the filtrate chamber can be configured in a side-by-side relationship. Alternatively, the retentate chamber and filtrate chamber can be configured to be coaxially disposed with either the retentate chamber or filtrate chamber positioned inside of the other. Any configuration of the retentate chamber and filtrate chamber that forces the biological sample to flow tangentially over opposite sides of a filtration membrane can be adapted for use in the present invention.

Changing pressure gradients and both axial flow and perpendicular flow to the membrane surface occur in the alternating tangential flow process. Upon activation of the injector on one side of the retentate chamber, the pressure in the injector is greater than the pressure in the retentate chamber. The retentate flows forward from the injector, i.e., through the retentate chamber and over the filter element. Also, some of the liquid is forced across the filter membrane into the filtrate chamber. When the filtrate chamber is enclosed, the entry of filtrate can pressurize the filtrate chamber. Conversely, upon activation of the injector on the opposite side of the retentate chamber, the pressure in the injector is greater than the pressure in the retentate chamber, so that sample flows in reverse, from the injector on one side of the retentate chamber to the injector on the other side of the retentate chamber. This reversal in flow maintains the membrane and inhibits clogging. This effect is further enhanced by another kind of transmembrane flow, one which forms when the resistance to axial flow inside the hollow fiber, or 1 μmen side, is greater than in the external, shell, side of the hollow fiber. Therefore, during the flow of the sample onto the filter, pressurized sample is forced into the hollow fibers and will take the path of least resistance and the sample will not only flow through the lumens, but also across the membrane, into the filtrate chamber. An axial pressure gradient forms on both sides of the filter causing fluid flow towards the exit end of the filter. As a result, the sample flow has the capacity to exchange fluids from the retentate chamber to the filtrate chamber. Such exchange can be highly beneficial for processing biological samples for generation of the composition described herein.

Another aspect of the invention reduces, eliminates, or substantially eliminates the introduction of air and/or generation of foam in the compositions produced using the methods or systems described herein.

Some of the key features of the system can utilize a fluid, such as sterile saline, to load the filter and purge air out of the systems and their various components before introduction and processing of the biological sample. This purging step can substantially eliminate introduction of air or bubbles (foaming) into the biological sample during the filtration and concentration process. Thus, the systems and methods are amenable to generate therapeutic compositions that can be readily administered into the blood stream of a subject.

In some embodiments, a pressure differential across a filter is not achieved by a vacuum applied to the system. In some embodiments, a system does not comprise a stopcock. In some embodiments, a system does not comprise an adaptor to an injector with a Luer lock fitting.

In some embodiments, the systems do not produce a composition comprising fibrinogen or concentrated fibrinogen. In some embodiments, a composition does not comprise fibrinogen or concentrated fibrinogen, such as at least about 1.1, 1.5, 2, 3, 4, 5, 10, or 20 fold concentrated fibrinogen. In some embodiments, a composition comprises concentrated fibrinogen at most about 1.1, 1.5, 2, 3, 4, 5, 10, or 20 fold concentrated fibrinogen. In some embodiments, the systems do not produce a composition comprising clotting factors or concentrated clotting factors such as Factor V and Factor X, and other undesired constituents, such as growth factors. In some embodiments, a composition does not comprise clotting factors or concentrated clotting factors such as Factor V and Factor X, and other undesired constituents, such as growth factors.

Injectors

Any of the injectors described herein can be used for injecting a biological sample into the systems described herein. Any of the injectors described herein can be used to apply pressure to the systems described herein and to cause fluid to flow through the system. Any of the injectors described herein can be manually operated. Exemplary injectors include syringes. Any of the injectors described herein can also function as sample collection modules as the sample passes through various stages of the systems.

According to one embodiment, the injector comprises a syringe. A typical syringe comprises a generally cylindrical barrel having opposed proximal and distal ends with at least one chamber formed between the ends for receiving a substance such as a biological sample. A plunger is typically sealably disposed within the barrel and movable with respect thereto, and sealing means may be sealably disposed approximate to the distal end of the barrel. A syringe can include an elongate barrel or cylinder having an open, proximal end and a distal end with at least one hollow chamber formed between the proximal and distal ends for receiving a biological sample. A plunger may be situated at the open, proximal end. A plunger can be moved by means of a plunger rod, which can be secured to the plunger, for example, by screwing or gluing. At the same end where the plunger is situated, the barrel may have a finger grip, which is secured to the barrel. A finger grip preferably consists of slightly resilient material, for example plastics. In another embodiment, the finger grip is a flange-like part of the barrel projecting radially outwards. Of course, other constructions known to those skilled in the art are possible. A stopper, which closes the barrel, may be situated in the end of the barrel remote from the plunger. The plunger and the stopper are preferably manufactured from an elastic material and, most preferably, from rubber of a pharmaceutical quality.

In preferred embodiments, an injection needle is not secured to the barrel. In further embodiments, the syringe is not stored with a needle in position, e.g., a needleless syringe. Although the syringe barrel can include a locking Luer-type collar, it is within the purview of the present invention to include syringe barrels without a collar, syringe barrels having an eccentrically positioned nozzle and various other nozzle-like structures. It is only required that there is an aperture on the distal end of the syringe barrel in fluid communication with the interior of the syringe barrel.

Vessels

Any of the reservoirs described herein can be any suitable vessel. Suitable vessels include any collection device including, but not limited to, tubes such as test tubes and centrifuge tubes; closed system blood collection devices, such as collection bags; syringes, catheters, such as central lines; microtiter and other multi-well plates; arrays; tubing; laboratory vessels such as flasks, spinner flasks, roller bottles, vials, microscope slides, microscope slide assemblies, coverslips, films and porous substrates and assemblies; pipettes and pipette tips, etc.; tissue and other biological sample collection containers; and any other container suitable for holding a biological sample, as well as containers and elements involved in transferring samples. In one aspect of the invention, a sample collection tube having a separating member (e.g., a mechanical separating element, a gel or a filter mechanism) for separating blood components is used. The vessel may also comprise a collection bag suitable for holding a biological sample such as, for example, a blood collecting bag, a blood plasma bag, a buffy coat bag, a platelet bag or the like.

Plastic or glass can be used to manufacture the reservoirs and vessels used in the present invention. Some preferred materials used to manufacture the vessels include polypropylene, polyethylene, polyethyleneterephthalate, polystyrene, polycarbonate and cellulosics. More expensive plastics such as polytetrafluoroethylene and other fluorinated polymers may also be used. In addition to the materials mentioned above, examples of other suitable materials for the vessels used in the present invention include polyolefins, polyamides, polyesters, silicones, polyurethanes, epoxies, acrylics, polyacrylates, polysulfones, polymethacrylates, PEEK, polyimide and fluoropolymers such as PTFE Teflon®, FEP Teflon®, Tefzel®, poly(vinylidene fluoride), PVDF and perfluoroalkoxy resins. Glass products including silica glass are also used to manufacture the vessels. One exemplary glass product is PYREX® (available from Coming Glass, Corning, N.Y.). Ceramic collection devices can be used according to embodiments of the invention. Cellulosic products such as paper and reinforced paper containers can also be used to form vessels according to the invention.

Filters/Membranes

TFF is a filtration process whereby the solution is constantly flowing over the membrane to prevent pores from becoming clogged by cells and proteins. As used in the systems and methods described herein, TFF can discourage unwanted particles, cells and/or other large proteins from blocking the membrane pores and allowing the flow of small molecules and proteins. The use of hollow fiber membranes can increase the surface area that is available for filtration. The 50, 100, or 500 kDa molecular weight cutoff of the membrane permits small molecules and proteins such as cytokines, chemokines, and proteases to pass through, eventually leading to waste, but retaining larger particles (>50, 100, or 500 kDa) such as platelets.

In some embodiments the one or more filters of the filtration module(s) comprise at least a first and a second filter. The first filter screens out cells, particles, and other molecules larger than 1 or 2 microns. The second filter screens out molecules having a weight less than about 50, 100, or 500 kDa. The second filter may also retain molecules having a weight of more than about 50, 100, or 500 kDa. In some embodiments the first and the second filters comprise cross-flow filters, such as hollow fiber filters.

Some embodiments of the invention further comprise a pump adapted to be fluidly coupled with the filtration module either upstream of the inlet of the filtration module or downstream of the outlet of the filtration module. The pump is further adapted to produce a flow of the fluid sample that passes through the one or more filters of the filter module. In some embodiments of the invention, the filter module further comprises at least one reservoir.

In an exemplary embodiment of the invention wherein the first filter comprises a cross-flow filter that screens out cells particles and other molecules lager than 1 or 2 microns. A retentate of this filter containing the cells, particles, and other molecules larger than 1 or 2 microns of the fluid sample is stored in a first retentate reservoir. Alternatively, the retentate of the first filter is discarded. A filtrate of the first filter is directed to a first filtrate reservoir, the first filtrate reservoir is then typically connected to the second filter. The filtrate of the first filter flows through the second filter. The second filter may typically be a cross flow filter adapted to retain molecules of weight more than about 50, 100, or 500 kDa. A retentate of the second filter comprises these molecules of weight more than about 50, 100, or 500 kDa may be retained in the first filtrate collection reservoir. The retentate of the second filter typically comprises the concentrated A2M of the fluid sample. A filtrate of the second filter can be directed to a separate second filter filtrate reservoir. Alternatively, the filtrate of the second reservoir may be redirected through the outlet of the filtration module and circulated back to the inlet of the filtration module such that the fluid sample is processed by the filtration module multiple times or continuously.

In some embodiments a system further comprises a centrifuge. A fluid sample can be centrifuged to produce a supernatant and a pellet, the supernatant containing small molecules and A2M but not large particles such as cells. The pellet contains the large particles such as cells present in the fluid sample. The supernatant can then be directed through a filtration module. The filtration module can comprise at least one filter adapted to retain molecules of weight more than about 50, 100, or 500 kDa. The at least one filter typically can comprise a 50, 100, or 500 kDa cross flow filter as describe above. The retentate of the 50, 100, or 500 kDa cross flow filter comprising the A2M of the supernatant can be retained in a retentate reservoir. The filtrate of the at least one filter can be directed to a waste reservoir or discarded. Alternatively, the filtrate of the at least one filter may be directed to the filter module outlet where can be redirected to the filter module inlet such that the supernatant of the fluid sample passes through the filter module on or more times.

A system can comprise a filtration module. The filtration module can comprise an inlet, an outlet and one or more filters fluidly connected in series between the inlet and the outlet. The filtration module can be enclosed in a housing, such as a column or jacket. A method employing a system can comprise removing cells from a sample. The method can further comprise manually pushing the fluid sample through the filtration module inlet and the one or more filters to produce a concentrated A2M serum or plasma. The fluid sample may also be manually pushed through the outlet. Pushing the fluid sample can be accomplished via use of an injector, such as a syringe, fluidly connected to the filtration module upstream of the inlet and/or downstream of the outlet. The one or more filters of the filtration module can comprise at least one 50, 100, or 500 kDa filter configured to retain molecules with a weight more than about 50, 100, or 500 kDa.

In some embodiments, removing cells from the fluid sample can comprise providing a centrifuge, centrifuging the fluid sample, and obtaining a resultant supernatant of the fluid sample. A resultant pellet of the fluid sample comprising cells and large molecules may be retained. The resultant supernatant of the fluid sample typically comprises A2M and small molecules but not cells and large molecules. The supernatant of the fluid sample can then be manually flowed through the filtration module to concentrate the A2M. The 50, 100, or 500 kDa filter of the filtration module can be a 50, 100, or 500 kDa cross-flow filter; a retentate of the 50, 100, or 500 kDa cross-flow filter can be retained and can comprise a concentrated A2M serum.

In some embodiments, removing cells from the fluid sample comprises filtering the fluid sample with a first filter of the filtration module adapted to screen out cells, particles, and molecules larger than at least about 1 or 2 microns, for example, at least about 3, 4, 5, 6, 7, 8, 9, or 10 microns. The first filter can be a cross-flow filter and a filtrate of the first filter can be directed to the at least one 50, 100, or 500 kDa filter of the filtration module. The filtrate of the first filter may be stored in a first filtrate reservoir. The 500 kDa filter of the filtration module can be a 50, 100, or 500 kDa cross-flow filter; a retentate of the 500 kDa cross-flow filter can be retained in the first filtrate reservoir and can comprise the concentrated A2M serum. A filtrate of the 50, 100, or 500 kDa cross flow filter may be stored, discarded, or directed to the inlet of the filtration module such that it can be further filtered.

A system can comprise one or more filters with a molecular weight cut-off of at most about 5 kDa, 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa, 80 kDa, 90 kDa, 100 kDa, 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 260 kDa, 270 kDa, 280 kDa, 290 kDa, 300 kDa, 310 kDa, 320 kDa, 330 kDa, 340 kDa, 350 kDa, 360 kDa, 370 kDa, 380 kDa, 390 kDa, 400 kDa, 410 kDa, 420 kDa, 430 kDa, 440 kDa, 450 kDa, 460 kDa, 470 kDa, 480 kDa, 490 kDa or lower to obtain one or more filtrates and retentates, such as an A2M enriched retentate or A2M concentrated retentate.

A system can comprise one or more filters with a pore size of at most about 0.6 µm, 0.7 µm, 0.8 µm, 0.9 µm, 1 µm, 2 µm, 3 µm, 4 µm, 5 µm, 6 µm, 7 µm, 8 µm, 9 µm, or 10 µm, for example, to remove or collect cells and/or particles.

It should be understood that features of the above described method and system embodiments may be combined and interchanged with one another.

Cells and particles with a size of 0.6 µm or more, and other molecules with a molecular weight of 50, 100, or 500 kDa or less can be removed from the sample by flowing or passing a sample through one or more filters contained within the system in sequence. Removed cells and particles can be disposed of or collected in a waste module. For example, cells and particles of 0.6 µm, 0.7 µm, 0.8 µm, 0.9 µm, 1 µm, 2 µm, or 3 µm or more, and other molecules with a molecular weight of 5 kDa, 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa, 80 kDa, 90 kDa, 100 kDa, 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 260 kDa, 270 kDa, 280 kDa, 290 kDa, 300 kDa, 310 kDa, 320 kDa, 330 kDa, 340 kDa, 350 kDa, 360 kDa, 370 kDa, 380 kDa, 390 kDa, 400 kDa, 410 kDa, 420 kDa, 430 kDa, 440 kDa, 450 kDa, 460 kDa, 470 kDa, 480 kDa, 490 kDa, or less can be removed by the one or more filters of the systems and can be further processed or deposited into one or more waste modules. A sample can be flowed through one or more filters by applying a pressure manually, such as by pushing and or pulling an injector of the system. In some embodiments, a sample can be flowed through one or more filters by applying centrifugal force using a centrifuge of the system, using a pump of the system, or a combination thereof. A system can further comprise a collection module or reservoir. A retentate or filtrate can be collected or isolated in the collection module, for example a retentate with an A2M enriched sample can be isolated in a collection module, after passing a sample through one or more filters. A system can further comprise a sample loading module. A sample loading module can be operable to introduce the sample into the system. A sample loading module can be directly or indirectly attached to the blood stream of a subject.

The first step in the system can be either a centrifugation step or filtration step. The collected blood can be centrifuged at a particular centrifugal force that allows the precipitation of the red blood cells and white blood cells and other particles and debris, allowing plasma proteins and platelets in the supernatant. This process can also be achieved by filtration using a hollow fiber membrane that will allow the plasma proteins and platelets to go through the membrane into the filtrate and prevent the red blood cells and white blood cells and other particles and debris to remain in the retentate. In some embodiments, the supernatant from the centrifugation step or the filtrate from the filtration step can be filtered on the second filter where proteins 50, 100, or 500 kDa or larger can be retained by the filter and smaller proteins than 50, 100, or 500 kDa and other molecules can pass through the membrane into the filtrate. The concentrated retentate can then be collected and injected into the patient.

In some embodiments, a collection receptacle with platelets and plasma can be connected to any of the systems described herein, such as with hematologic tubing, and manually passed through a filter, such as hollow fiber tangential flow filter (HFTFF), that uses a molecular weight cutoff membrane, such as a 50, 100, or 500 kDa molecular weight cutoff membrane, of modified polyethersulfone. In some embodiments, a pump, such as a peristaltic pump, can be used. In some embodiments, the flow-through port of the filter can be connected using hematologic tubing back to the collection bottle in a closed-loop. In some embodiments, the filtrate port of the filter can also be connected using tubing connected to waste. In some embodiments, no priming of the flow-circuit is necessary. In preferred embodiments, priming of the flow-circuit is accomplished by flowing a fluid through the system to remove air from the system. In some embodiments, priming of a system substantially prevents foaming of the compositions administered therapeutically, such as to a joint.

As a non-limiting example, a system, such as an APIC system (Autologous Platelet Integrated Concentrate system) can be run until the plasma reaches between 2-10 times the concentrations as found in whole blood. For example, a system can be run until the plasma reaches between 2-10, 1-9, 2-8, 2-7, 2-6, 2-5, 2-4, 2-3, 3-10, 1-9, 3-8, 3-7, 3-6, 3-5, 3-4, 4-10, 1-9, 4-8, 4-7, 4-6, 4-5, 5-10, 1-9, 5-8, 5-7, 5-6, 6-10, 1-9, 6-8, 6-7, 7-10, 7-9, 7-8, 8-10, 8-9, or 9-10 times the concentrations as found in whole blood. In some embodiments, the starting volume of the biological sample injected in to the systems described herein can be from about 10 mL to about 100 mL. For example, the starting volume of the biological sample injected in to the systems described herein can be from about 10-90 mL, 10-80 mL, 10-70 mL, 10-60 mL, 10-50 mL, 10-40 mL, 10-30 mL, 10-20 mL, 20-100 mL, 20-90 mL, 20-80 mL, 20-70 mL, 20-60 mL, 20-50 mL, 20-40 mL, 20-30 mL, 30-100 mL, 30-90 mL, 30-80 mL, 30-70 mL, 30-60 mL, 30-50 mL, 30-40 mL, 40-100 mL, 40-90 mL, 40-80 mL, 40-70 mL, 40-60 mL, 40-50 mL, 50-100 mL, 50-90 mL, 50-80 mL, 50-70 mL, 50-60 mL, 60-100 mL, 60-90 mL, 60-80 mL, 60-70 mL, 70-100 mL, 70-90 mL, 70-80 mL, 80-100 mL, 80-90 mL, or 90-100 mL. In some embodiments, this process or a similar process can be performed in approximately 1 to 5 minutes, 2 to 5 minutes, 3 to 6 minutes, 4 to 5 minutes, 5 to 10 minutes, 6 to 10 minutes, 7 to 10 minutes, 8 to 10 minutes, 9 to 10 minutes, 10 to 15 minutes, 15 to 20 minutes, 10 to 30 minutes, 15 to 35 minutes, 20 to 40 minutes, or 30 to 45 minutes. The waste volume, containing low molecular weight proteins, including potentially pro-inflammatory cytokines and proteases, can be discarded. The resulting autologous platelet concentrate can be drawn into a syringe and provided for mixing as needed for clinical administration, such as to a chronic wound.

Channels and Modules

The channels and modules and housings described herein can be made of any suitable material. Suitable materials include both liquid permeable and non-permeable materials, such as polyolefins, polyamides, polyesters, silicones, polyurethanes, epoxies, acrylics, polyacrylates, polysulfones, polymethacrylates, PEEK, polyimide and fluoropolymers such as PTFE Teflon®, FEP Teflon®, Tefzel®, poly(vinylidene fluoride), PVDF and perfluoroalkoxy resins. Glass products including silica glass can be used. Ceramic can be used according to embodiments of the invention. Cellulosic products such as paper and reinforced paper containers can also be used to form channels and modules according to the invention.

The size of the various modules and channels can be suitable for holding the volumes of samples described above. For example, the channels and modules can be from about 2-2000 cm, 2-1000 cm, 2-500 cm, 2-100 cm, 2-50 cm, 2-25 cm, 2-10 cm, 2-5 cm, 2-4 cm, 2-3 cm in length. For example, the channels and modules can be from about 0.1-200 cm, 0.1-100 cm, 0.1-50 cm, 0.1-10 cm, 0.1-5 cm, 0.1-2.5 cm, 0.1-1 cm, 0.1-0.5 cm, 0.1-0.4 cm, 0.1-0.3 cm, or 0.1-0.2 cm in width. For example, the channels and modules can have a diameter of from about 0.1-200 cm, 0.1-100 cm, 0.1-50 cm, 0.1-10 cm, 0.1-5 cm, 0.1-2.5 cm, 0.1-1 cm, 0.1-0.5 cm, 0.1-0.4 cm, 0.1-0.3 cm, or 0.1-0.2 cm.

Figure 34:
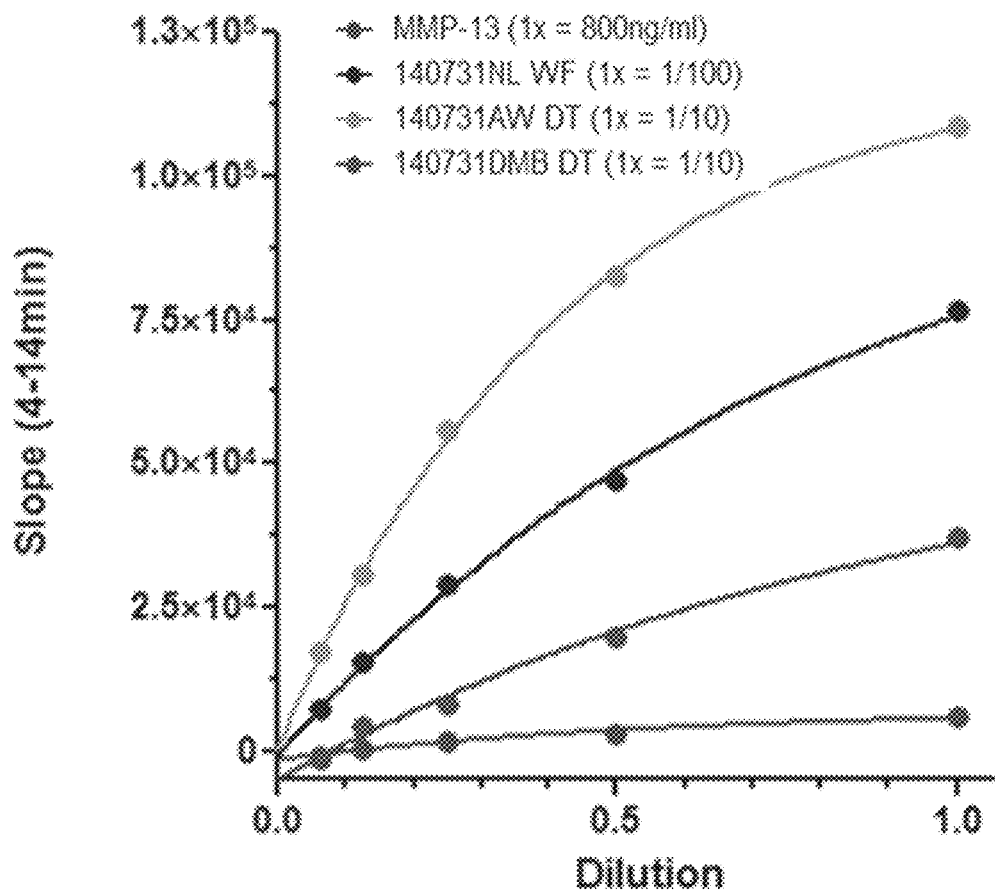
FIG. 34 depicts a graph of collagenase digestion of the indicated samples from a wound at the indicated serial dilutions. The samples depicted refer to the following: 140731NL—wound fluid (WF). 140731AW—debridement tissue (DT), 140731DMB-DT, and MMP-13—matrix metalloprotease-13. Chronic wound fluid had elevated protease activity (EPA). Debridement tissue contained relatively less collagenase activity.

Some embodiments of the invention further comprise a pump adapted to be fluidly coupled with the filtration module either upstream of the inlet of the filtration module or downstream of the outlet of the filtration module. The pump is further adapted to produce a flow of the fluid sample that passes through the one or more filters of the filter module. In some embodiments of the invention, the filter module further comprises at least one reservoir A particular embodiment of the filtration module is well suited to receive a supernatant 2409 of a fluid sample such as blood (not shown) that has been centrifuged (FIG. 34). The filter module 2401 has a first filter 2410 coupled to the filter module inlet 2402. The supernatant is 2409 received and pumped from a receiving reservoir 2405 into the first filter. The first filter 2410 is typically a cross-flow filter configured to retain molecules larger than about 500 kDa in a retentate reservoir 2406. The retentate reservoir 2406 may also be the same as the receiving reservoir 2405 for receiving the supernatant 2409 of the fluid sample. The permeate 2420 of the first filter 2410 containing molecules smaller than about 500 kDa is directed to a permeate reservoir 2430 which may be a waste bag 2431. A2M is concentrated in this retentate reservoir 2406. A filter module outlet 2450 maybe coupled to the retentate reservoir 2406 such that the concentrated A2M 2460 may be extracted from the retentate reservoir 2406 or pumped back through the first filter 2410.

Figure 35:
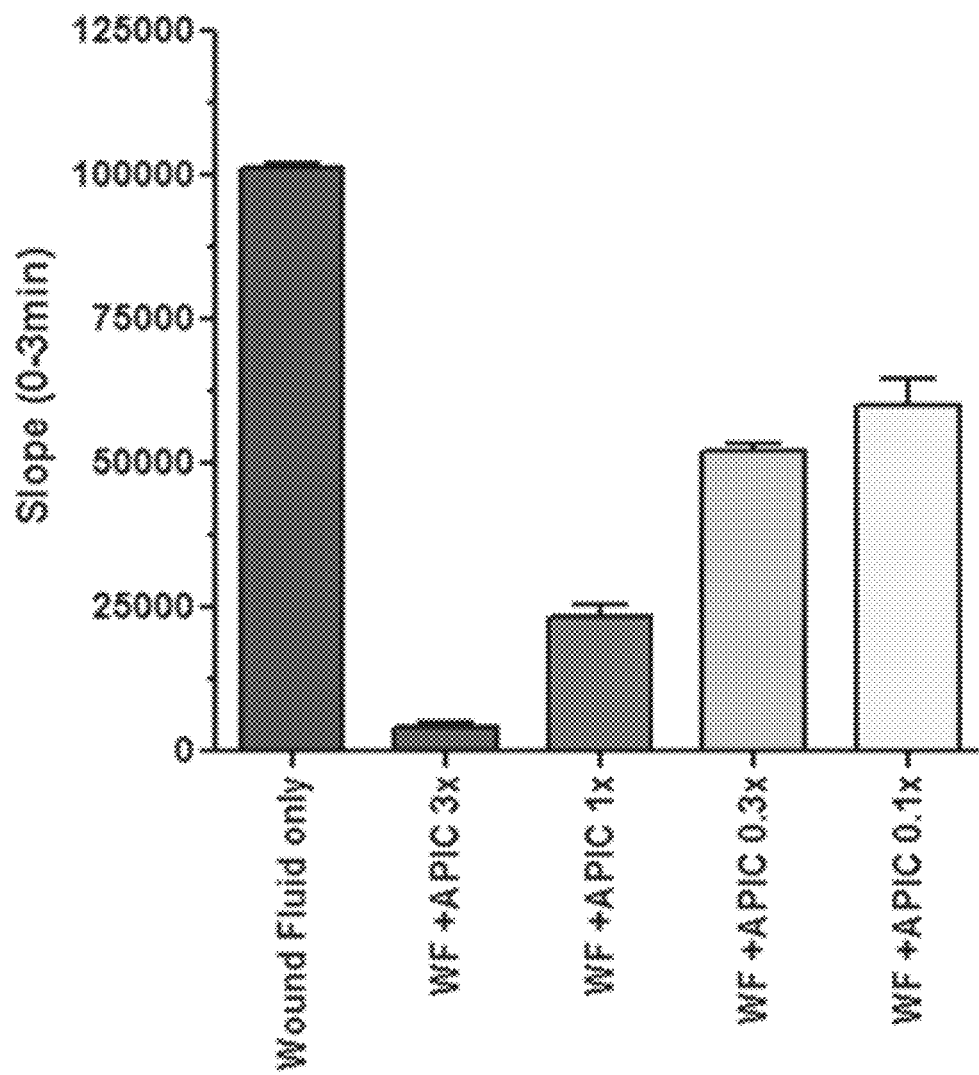
FIG. 35 depicts a graph of collagenase activity in the indicated samples with and without treatment of A2M at the indicated volumes (top) and corresponding table (bottom). Serial dilutions of Autologous Platelet Integrated Concentrate (APIC-PRP) (140224PD, 5.5 mg/ml of A2M) were challenged to inhibit WF digestion of FITC-collagen. 1× means equal volumes of WF and APIC-PRP. A 1× concentration of APIC was able to inhibit 75% of the collagenases in the first 3 minutes of the digestion. 3×APIC to wound fluid and collagenase activity was reduced 10-fold. No digestion of collagen was seen in APIC-only controls. A 1:1 mixture of APIC and EPA wound fluid is in the linear range of inhibition. An improperly made APIC, with less A2M concentration, may perform worse as an inhibitor.
Figures 37A, 37B:
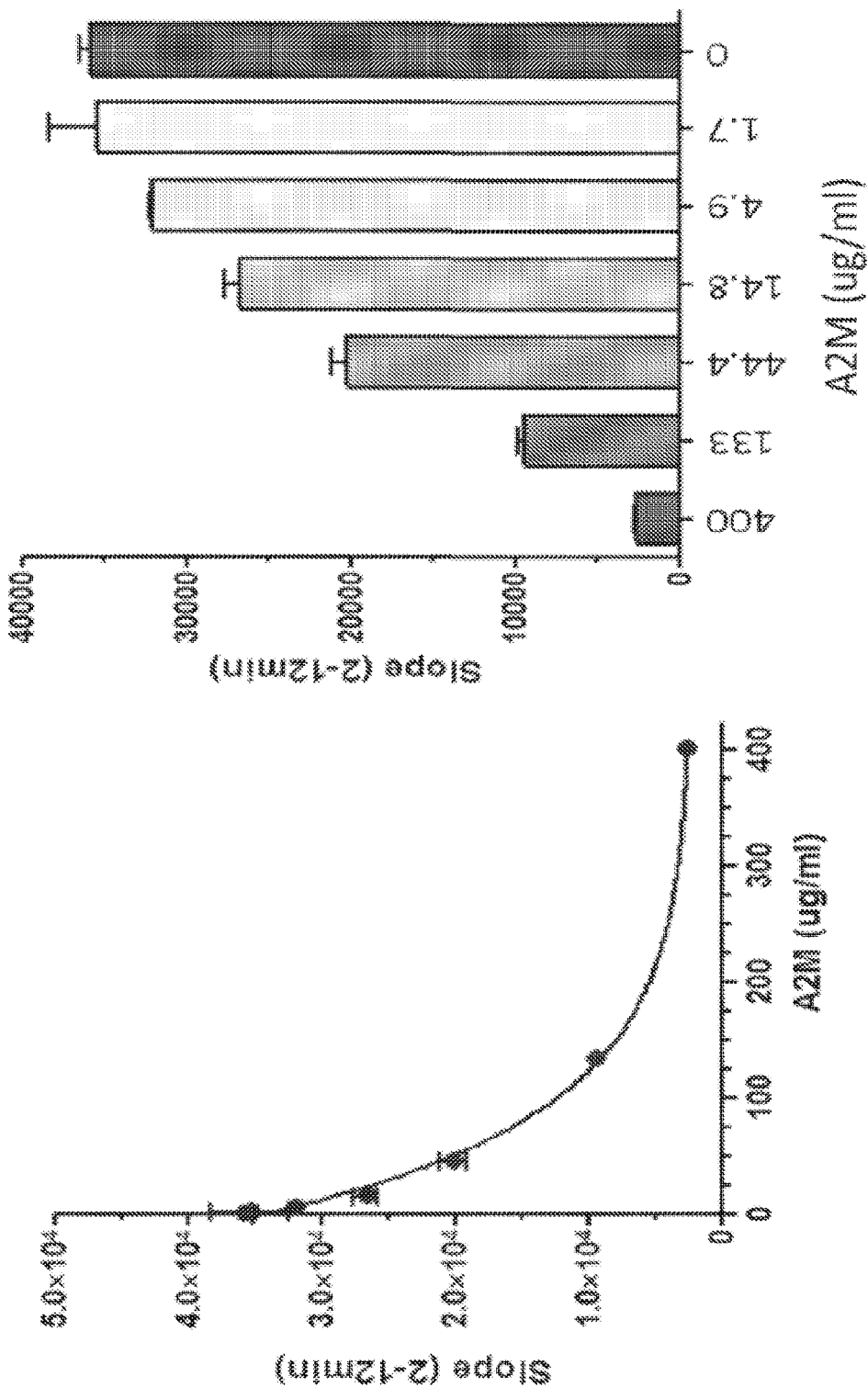
FIGS. 37A and B depict graphs (A—bar graph; B—line graph) of collagenase activity in the indicated samples with and without A2M treatment at the indicated amounts. 140731NL-WF (1/400) was used to digest FITC-collagen Type I in the presence or absence of a serial dilution of purified plasma A2M. Note that WF has numerous proteases that are inhibited by A2M, but only the collagenases would be visible in this experiment. Thus, A2M efficacy is under-represented.

An embodiment of the system for concentrating A2M is shown in FIGS. 35-37. A blood bag 2801 is shown containing the fluid sample 2802, which typically comprises blood. (FIG. 37). The fluid sample 2802 is extracted via syringe(s) 2803 and centrifuged with centrifuge 2804. The resultant supernatant 2805 containing A2M and other small molecules but not cells or large molecules is then directed to the filtration module 3209, where in the A2M is concentrated in to a serum 2810 or a plasma 2811 with at least one filter 2808 selected to retain molecules of larger in size than about 50, 100, and/or 500 kDa. The filtration module 3209 may be similar to the examples described herein.

An embodiment of the system for concentrating A2M is shown in (FIG. 39). A blood bag 3201 is shown containing the fluid sample 3202. The fluid sample 3202 is pumped via pump 3203 to the first filter 3210 of the filtration module 3204. The first filter 3210 shown here is a cross-flow filter configured to screen out cells, particles, and other molecules larger than 1 micron. The permeate 3212 of the first filter comprising components of the fluid sample smaller than 1 micron is directed to a first permeate reservoir 3215. The retentate 3216 of the first filter is directed to a first retentate reservoir 3216, in this particular embodiment the first retentate reservoir is also blood bag 3201. The permeate 3212 of the first filter is then directed via pump 3203 to the second filter 3220. The second filter is typically a cross-flow filter configured to retain molecules of weight more than about 500 kDa. Molecules of weight more than about 50, 100, and/or 500 kDa are retained as a second retentate 3223 in a second retentate reservoir 3225. The second retentate reservoir 3225 may be the same as the first permeate reservoir 3215. Permeate of the second filter 3224 is typically directed to a second permeate reservoir 3226 in some embodiments the second permeate reservoir 3226 is a waste bag 3230. The retentate of the second filter 3223 comprises the concentrated A2M. The pump 3203 may be fluidly connected to the filtration module up stream of the filtration module inlet 3206 or down-stream of the filtration module outlet 3207 or in-between inlet the filtration module 3206 and the filtration module outlet 3207 or any combination thereof. The second retentate reservoir 3225 has an access port 3229 for directing flow of the concentrated A2M (which is also the retentate of the second filter) back to the pump. Such port may be used to access the concentrated A2M, or the permeate of the first filter, or the retentate of the second filter for subsequent processing or harvesting of the concentrated A2M.

Methods of A2M Enrichment and Preparation of Autologous Compositions

Methods of enrichment of A2M from a subject are provided herein. The methods can be used to produce any of the autologous compositions. The systems can be used with any of the methods described herein.

A method for enrichment of A2M from a biological sample, such as a mammalian biological sample, can comprise flowing or passing a biological sample through one or more filters or membranes, such as one or more hollow fiber filters and/or membranes with a particular pore size. Flowing or passing a sample through one or more filters can comprise flowing the sample through 1, 2, 3, 4, 5, 6, 7, 8, 9, 10, or more filters. A sample can be separated into one or more filtrates and one or more retentates, for example a first filtrate and a first retentate. For example, a sample can be separated into 2, 3, 4, 5, 6, 7, 8, 9, 10, or more filtrates and 2, 3, 4, 5, 6, 7, 8, 9, 10, or more retentates upon flowing or passing the sample through one or more filters. For example, a sample can be separated into 2 or more filtrates and 2 or more retentates upon flowing or passing the sample through two or more filters. An A2M enriched sample can be a first, second, third, fourth, fifth, or more retentate upon flowing or passing a biological sample through one or more filters. One or more A2M enriched samples or retentates can be diluted, such as with a diluent. A diluent can be a liquid or a solution, such as a hypotonic, hypertonic, or isotonic solution. For example, a diluent can be a WFI solution or a saline solution.

A method for enrichment of A2M from a biological sample, such as a mammalian biological sample can comprise separating cells from a cellular biological sample, such as blood. In some embodiments, red blood cells can be separated from white blood cells and platelets by performing one or more centrifugation steps or by flowing a sample through a filter. White blood cells can be separated from platelets by performing one or more centrifugation steps. One or more centrifugation cycles can be used or applied to provide centrifugal force to flow or push a biological sample through one or more filters. Gravitational, centrifugal or mechanical force can also be used or applied to provide force to flow or push a biological by flowing a sample through one or more filters. Mechanical force can be a pump, centrifugal force, gas pressure, or any other force that is operable to provide enough force to flow a sample through one or more filters as described herein. A supernatant of a centrifuged or filtered blood sample can contain A2M. In some embodiments, the supernatant can contain A2M and platelets. In some embodiments, the supernatant can contain A2M and not contain platelets.

It is an object of the current invention to concentrate platelets and, in some embodiments, allow for the retention of platelet-released growth factors, while, in some embodiments, using a molecular weight cutoff of a filter and a tangential flow ultrafiltration (TFF) step to avoid the concentration of potentially proinflammatory cytokines and catabolic proteases. After obtaining PRP, tangential flow ultrafiltration (TFF) can be used to concentrate platelets to a desired concentration range using the methods described herein, resulting in an autologous platelet integrated concentrate in which low molecular weight proteins, such as cytokines and proteases, such as those less than about 50, 100, and/or 500 kDa in mass, have not been substantially concentrated. In some embodiments, filter parameters can be chosen to concentrate platelets and to avoid concentration of cytokines, proteases, and potentially undesirable plasma proteins.

In some embodiments, it is preferable to separate red blood cells and white blood cells from the biological sample and retain platelets within the biological sample prior to flowing the sample through one or more filters by performing one or more centrifugation steps. In some embodiments, it is preferable to separate red blood cells, white blood cells, and platelets from the biological sample prior to flowing or passing the sample through the one or more filter by performing one or more centrifugation steps.

In some embodiments, it is preferable to separate red blood cells and white blood cells from the biological sample and retain platelets within the biological sample by flowing or passing the biological sample through one or more filters or membranes. In some embodiments, it is preferable to separate red blood cells, white blood cells, and platelets from the biological sample by flowing or passing the biological sample through one or more filters. The one or more filters used to remove the cells and other large particles from the biological sample can have a pore size of at least about 0.1 μm. For example, the one or more filters used to remove the cells and other large particles from the biological sample can have a pore size of at least about 0.2 μm, 0.3 μm, 0.4 μm, 0.5 μm, 0.6 μm, 0.7 μm, 0.7 μm, 0.8 μm, 0.9 μm, 1 μm, 1.1 μm, 1.2 μm, 1.3 μm, 1.4 μm, 1.5 μm, 1.6 μm, 1.7 μm, 1.8 μm, 1.9 μm, 2 μm, 2.1 μm, 2.2 μm, 2.3 μm, 2.4 μm, 2.5 μm, 2.6 μm, 2.7 μm, 2.8 μm, 2.9 μm, or 3 μm, or higher. As a non-limiting example, a biological sample, such as blood, can be flowed through one or more filters with a pore size of at least about 0.2 μm wherein the red blood cells and white blood cells are retained by the filter and are in the retentate and non-cellular components and platelets are not retained by the filter and are in the filtrate. As another non-limiting example, a biological sample, such as blood, can be flowed through one or more filters with a pore size of at least about 0.2 µm wherein the red blood cells, white blood cells, and platelets are retained by the filter in the retentate and non-cellular components are not retained by the filter and are in the filtrate.

In some embodiments, one or more of the filters can have a charge, immobilized molecules, or a combination thereof and can thereby enhance the selectivity of the filters. Immobilized molecules can be antibodies, proteins, receptors, ligands, carbohydrates, nucleotides, RNA, DNA or any combination thereof. For example, enhancing the selectivity of filters can enhance the ability of a filter to retain A2M in the retentate upon flowing or passing a biological sample through the filter or, as another example, enhance the ability of a filter to not retain molecules that are not A2M upon flowing a biological sample through the filter.

Additionally, one or more filters with a molecular weight cut-off can be used and can allow a percentage of particles in the biological sample, such as cells and proteins, with a molecular weight higher than the molecular weight cut-off of the filter to be retained by the filter. The retained sample can be a retentate and the sample that flows through the filter can be a filtrate. A filter with a molecular weight cut-off can allow more than about 10%, 15%, 20%, 25%, 30%, 35%, 40%, 45%, 50%, 55%, 60%, 65%, 70%, 75%, 80%, 85%, 90%, 95%, or 100% of particles in a biological sample with a molecular weight higher than the molecular weight cut-off of the filter to be retained by the filter. For example, one or more filters can retain about 100% of cells, cellular debris, or a combination thereof, from a blood sample and can retain less than about 10%, 15%, 20%, 25%, 30%, 35%, 40%, 45%, 50%, 55%, 60%, 65%, 70%, 75%, 80%, 85%, 90%, 95%, or 100% of the proteins with a molecular weight less than about 50, 100, and/or 500 kDa from a biological sample containing A2M.

One or more filtrates can be passed through one or more other filters by applying a gravitational, centrifugal, or mechanical force to the one or more filtrates. A sample can be separated into one or more other filtrates and one or more other retentates, for example a second filtrate and a second retentate. For example, a sample can be separated into 2, 3, 4, 5, 6, 7, 8, 9, 10, or more other filtrates and 2, 3, 4, 5, 6, 7, 8, 9, 10, or more other retentates upon flowing the sample through 1, 2, 3, 4, 5, 6, 7, 8, 9, 10, or more other filters. For example, a sample can be separated into 2 other filtrates and 2 other retentates upon flowing or passing the sample through one or more other filters. An A2M enriched sample can be a first, second, third, fourth, fifth, or more other retentate upon flowing a biological sample through one or more other filters. One or more other retentates, filtrates, or A2M enriched samples can be diluted, such as with a diluent. For example, a diluent can be a liquid, such as a WFI solution or a saline solution.

In some embodiments, after separating the cells from a biological sample the resulting composition lacking red blood cells and white blood cells, and either lacking or containing a same, reduced or elevated platelet level, can be flowed or passed through one or more filters to obtain one or more filtrates and retentates, such as an A2M enriched retentate or A2M concentrated retentate. The resulting one or more filtrates can be flowed through one or more other filters with a molecular weight cut-off of at most about 50, 100, and/or 500 kDa to obtain one or more other filtrates and retentates, such as an A2M enriched or concentrated retentate. For example, a filtrate lacking red blood cells and white blood cells, and either lacking or containing a same, reduced or elevated platelet level, can be flowed through one or more filters with a molecular weight cut-off of at most about 50 kDa, 55 kDa, 60 kDa, 65 kDa, 70 kDa, 75 kDa, 80 kDa, 85 kDa, 90 kDa, 95 kDa, 100 kDa, 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 260 kDa, 270 kDa, 280 kDa, 290 kDa, 300 kDa, 310 kDa, 320 kDa, 330 kDa, 340 kDa, 350 kDa, 360 kDa, 370 kDa, 380 kDa, 390 kDa, 400 kDa, 410 kDa, 420 kDa, 430 kDa, 440 kDa, 450 kDa, 460 kDa, 470 kDa, 480 kDa, 490 kDa or lower to obtain one or more filtrates and retentates, such as an A2M enriched retentate or A2M concentrated retentate.

In some embodiments, a filtrate can comprise less than about 10%, 15%, 20%, 25%, 30%, 35%, 40%, 45%, 50%, 55%, 60%, 65%, 70%, 75%, 80%, 85%, 90%, 95%, or 100% of the red blood cells in a biological sample. In some embodiments, a filtrate can comprise less than about 10%, 15%, 20%, 25%, 30%, 35%, 40%, 45%, 50%, 55%, 60%, 65%, 70%, 75%, 80%, 85%, 90%, 95%, or 100% of the white blood cells in a biological sample. In some embodiments, a filtrate can comprise less than about 10%, 15%, 20%, 25%, 30%, 35%, 40%, 45%, 50%, 55%, 60%, 65%, 70%, 75%, 80%, 85%, 90%, 95%, or 100% of the red and white blood cells in a biological sample. In some embodiments, a filtrate can comprise less than about 10%, 15%, 20%, 25%, 30%, 35%, 40%, 45%, 50%, 55%, 60%, 65%, 70%, 75%, 80%, 85%, 90%, 95%, or 100% of the platelets in a biological sample. In some embodiments, a filtrate can comprise more than about or about 10%, 15%, 20%, 25%, 30%, 35%, 40%, 45%, 50%, 55%, 60%, 65%, 70%, 75%, 80%, 85%, 90%, 95%, or 100% of the platelets in a biological sample.

In some embodiments, a retentate can comprise more than about or about 10%, 15%, 20%, 25%, 30%, 35%, 40%, 45%, 50%, 55%, 60%, 65%, 70%, 75%, 80%, 85%, 90%, 95%, or 100% of the red blood cells in a biological sample. In some embodiments, a retentate can comprise more than about or about 10%, 15%, 20%, 25%, 30%, 35%, 40%, 45%, 50%, 55%, 60%, 65%, 70%, 75%, 80%, 85%, 90%, 95%, or 100% of the white blood cells in a biological sample. In some embodiments, a retentate can comprise more than about or about 10%, 15%, 20%, 25%, 30%, 35%, 40%, 45%, 50%, 55%, 60%, 65%, 70%, 75%, 80%, 85%, 90%, 95%, or 100% of the red and white blood cells in a biological sample. In some embodiments, a retentate can comprise less than about 10%, 15%, 20%, 25%, 30%, 35%, 40%, 45%, 50%, 55%, 60%, 65%, 70%, 75%, 80%, 85%, 90%, 95%, or 100% of the platelets in a biological sample. In some embodiments, a retentate can comprise more than about or about 10%, 15%, 20%, 25%, 30%, 35%, 40%, 45%, 50%, 55%, 60%, 65%, 70%, 75%, 80%, 85%, 90%, 95%, or 100% of the platelets in a biological sample.

A retentate can be or comprise any of the compositions described, such as an autologous A2M composition. For example, a retentate can comprise an elevated concentration of A2M compared to the concentration of A2M found in a biological sample. For example, a retentate can comprise an elevated concentration of A2M compared to the concentration of A2M found in a biological sample and an elevated concentration of one or more proteins with molecular weight higher than 50, 100, and/or 500 kDa found in a biological sample. For example, a retentate can comprise a reduced concentration of a protein with a molecular weight greater than about 50, 100, and/or 500 kDa compared to the concentration of the protein found in a biological sample and an elevated concentration of one or more proteins with molecular weight higher than 50, 100, and/or 500 kDa found in a biological sample. For example, a retentate can comprise an elevated concentration of A2M compared to the concentration of A2M found in a biological sample and a reduced concentration of a protein with a molecular weight greater than about 50, 100, and/or 500 kDa compared to the concentration of the protein found in a biological sample.

In some embodiments, a retentate can comprise less than about 10%, 15%, 20%, 25%, 30%, 35%, 40%, 45%, 50%, 55%, 60%, 65%, 70%, 75%, 80%, 85%, 90%, 95%, or 100% of the red blood cells in a biological sample. In some embodiments, a retentate can comprise less than about 10%, 15%, 20%, 25%, 30%, 35%, 40%, 45%, 50%, 55%, 60%, 65%, 70%, 75%, 80%, 85%, 90%, 95%, or 100% of the white blood cells in a biological sample. In some embodiments, a retentate can comprise less than about 10%, 15%, 20%, 25%, 30%, 35%, 40%, 45%, 50%, 55%, 60%, 65%, 70%, 75%, 80%, 85%, 90%, 95%, or 100% of the red and white blood cells in a biological sample. In some embodiments, a retentate can comprise less than about 10%, 15%, 20%, 25%, 30%, 35%, 40%, 45%, 50%, 55%, 60%, 65%, 70%, 75%, 80%, 85%, 90%, 95%, or 100% of the platelets in a biological sample. In some embodiments, a retentate can comprise more than about or about 10%, 15%, 20%, 25%, 30%, 35%, 40%, 45%, 50%, 55%, 60%, 65%, 70%, 75%, 80%, 85%, 90%, 95%, or 100% of the platelets in a biological sample.

For example, a concentration of A2M in a retentate obtained by flowing a biological sample lacking red blood cells, white blood cells and platelets through one or more filters with a molecular weight cut-off of at most about 50, 100, and/or 500 kDa can be at least about 1.1 times higher than the concentration of A2M found in a biological sample and the concentration of one or more proteins with molecular weight higher than 50, 100, and/or 500 kDa can be at least about 1.1 times higher than the concentration of the one or more proteins with molecular weight higher than 50, 100, and/or 500 kDa found in a biological sample. For example, the concentration of A2M in a retentate obtained by flowing a biological sample lacking red blood cells, white blood cells and platelets through one or more filters with a molecular weight cut-off of at most about 50 kDa, 55 kDa, 60 kDa, 65 kDa, 70 kDa, 75 kDa, 80 kDa, 85 kDa, 90 kDa, 95 kDa, 100 kDa, 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 260 kDa, 270 kDa, 280 kDa, 290 kDa, 300 kDa, 310 kDa, 320 kDa, 330 kDa, 340 kDa, 350 kDa, 360 kDa, 370 kDa, 380 kDa, 390 kDa, 400 kDa, 410 kDa, 420 kDa, 430 kDa, 440 kDa, 450 kDa, 460 kDa, 470 kDa, 480 kDa, 490 kDa, 500 kDa, or lower, can be at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of A2M found in a biological sample and the concentration of one or more proteins with molecular weight higher than 50, 100, and/or 500 kDa can be at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of the one or more proteins with molecular weight higher than about 50, 100, and/or 500 kDa found in a biological sample. For example, the concentration of A2M in a retentate obtained by flowing a biological sample lacking red blood cells, white blood cells and platelets through one or more filters with a molecular weight cut-off of at most about 50, 100, and/or 500 kDa can be at least about 2 times higher than the concentration of A2M found in a biological sample and the concentration of one or more proteins with molecular weight higher than 50, 100, and/or 500 kDa can be at least about 2 times higher than the concentration of the one or more proteins with molecular weight higher than about 50, 100, and/or 500 kDa found in a biological sample.

As another example, a retentate, such as an A2M enriched or concentrated retentate obtained by flowing or passing a composition, such as a filtrate lacking red blood cells and white blood cells, but not lacking platelets, through one or more filters with a molecular weight cut-off of at most about 50, 100, and/or 500 kDa, can comprise an elevated concentration of A2M compared to the concentration of A2M found in a biological sample and an elevated concentration of one or more proteins with molecular weight higher than 50, 100, and/or 500 kDa found in a biological sample. The concentration of A2M in a retentate obtained by flowing a biological sample lacking red blood cells and white blood cells, but not lacking platelets, through one or more filters with a molecular weight cut-off of at most about 50, 100, and/or 500 kDa can be at least about 1.1 times higher than the concentration of A2M found in a biological sample and the concentration of one or more proteins with molecular weight higher than 50, 100, and/or 500 kDa can be at least about 1.1 times higher than the concentration of the one or more proteins with molecular weight higher than 50, 100, and/or 500 kDa found in a biological sample. For example, The concentration of A2M in a retentate obtained by flowing a biological sample lacking red blood cells and white blood cells, but not lacking platelets, through one or more filters with a molecular weight cut-off of at most about 50 kDa, 55 kDa, 60 kDa, 65 kDa, 70 kDa, 75 kDa, 80 kDa, 85 kDa, 90 kDa, 95 kDa, 100 kDa, 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 260 kDa, 270 kDa, 280 kDa, 290 kDa, 300 kDa, 310 kDa, 320 kDa, 330 kDa, 340 kDa, 350 kDa, 360 kDa, 370 kDa, 380 kDa, 390 kDa, 400 kDa, 410 kDa, 420 kDa, 430 kDa, 440 kDa, 450 kDa, 460 kDa, 470 kDa, 480 kDa, 490 kDa, 500 kDa, or lower, can be at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of A2M found in a biological sample and the concentration of one or more proteins with molecular weight higher than 500 kDa can be at least about 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times higher than the concentration of the one or more proteins with molecular weight higher than about 500 kDa found in a biological sample. For example, the concentration of A2M in a retentate obtained by flowing a biological sample lacking red blood cells, white blood cells, but not lacking platelets, through one or more filters with a molecular weight cut-off of at most about 500 kDa can be at least about 2 times higher than the concentration of A2M found in a biological sample and the concentration of one or more proteins with molecular weight higher than 500 kDa can be at least about 2 times higher than the concentration of the one or more proteins with molecular weight higher than about 500 kDa found in a biological sample.

In some embodiments, after passing a sample, such as a biological sample or one or more filtrates, through one or more filters, at least about 10% of particles, and proteins with a molecular weight less than about 50, 100, and/or 500 kDa can be removed from the sample. For example, at least about 11%, 12%, 13%, 14%, 15%, 20%, 25%, 30%, 35%, 40%, 45%, 50%, 55%, 60%, 65%, 70%, 75%, 80%, 85%, 90%, 95%, or 100% of cells, particles, and small proteins with a molecular weight less than about 50, 100, and/or 500 kDa can be removed from the sample. For example, at least about 20% of particles and proteins with a molecular weight less than about 50, 100, and/or 500 kDa can be removed from the sample. At least about 11%, 12%, 13%, 14%, 15%, 20%, 25%, 30%, 35%, 40%, 45%, 50%, 55%, 60%, 65%, 70%, 75%, 80%, 85%, 90%, 95%, or 100% of cells, particles, and proteins with a molecular weight less than about 50 kDa, 55 kDa, 60 kDa, 65 kDa, 70 kDa, 75 kDa, 80 kDa, 85 kDa, 90 kDa, 95 kDa, 100 kDa, 110 kDa, 120 kDa, 130 kDa, 140 kDa, 150 kDa, 160 kDa, 170 kDa, 180 kDa, 190 kDa, 200 kDa, 210 kDa, 220 kDa, 230 kDa, 240 kDa, 250 kDa, 260 kDa, 270 kDa, 280 kDa, 290 kDa, 300 kDa, 310 kDa, 320 kDa, 330 kDa, 340 kDa, 350 kDa, 360 kDa, 370 kDa, 380 kDa, 390 kDa, 400 kDa, 410 kDa, 420 kDa, 430 kDa, 440 kDa, 450 kDa, 460 kDa, 470 kDa, 480 kDa, 490 kDa, or less can be removed from the sample. For example, at least about 20% of particles and small proteins with a molecular weight less than 50, 100, and/or 500 kDa, can be removed from the sample. An autologous composition described herein can be isolated after passing a sample through one or more filters.

One or more additional non-blood derived components can be added to the one or more filtrates or retentates. Non-blood derived components can be added before, during, or after isolation. A non-blood derived component can be an anti-coagulant. For example, an anti-coagulant can be EDTA, tri-sodium citrate, water for injection (WFI), or saline.

One or more additional blood products or blood-derived components can be added to the one or more filtrates or retentates. Blood products or blood-derived components can be added before, during, or after isolation. Blood products or blood derived components can be cells, peptides, proteins, DNA, RNA, carbohydrates, or other small molecules. For example, blood products or blood-derived components can be red blood cells, white blood cells, or platelets.

Platelets can be isolated from a biological sample according to any method known in the art, such as by centrifugation of a blood sample. Red blood cells and white blood cells can be sedimented by centrifugation at relatively low centrifugal force, for example, less than 1000 g. Platelets can be isolated by centrifugation of the platelet containing plasma obtained from a first centrifugation. A platelet containing plasma can be centrifuged, for example, between about 3000 g to 5000 g, to sediment platelets. The above procedure can also be performed in one or more centrifugation steps.

In some embodiments, one or more other filtrates or retentates, for example a second filtrate or second retentate can be collected. One or more additional non-blood derived components can be added to the one or more other filtrates or other retentates. Non-blood derived components can be added before, during, or after isolation. A non-blood derived component can be an anti-coagulant. For example, an anti-coagulant can be EDTA, tri-sodium citrate, water for injection (WFI), or saline.

One or more additional blood products or blood-derived components can be added to the one or more other filtrates or other retentates. Blood products or blood-derived components can be added before, during, or after flowing or passing the biological sample through one or more filters. Blood products or blood-derived components can be cells, peptides, proteins, DNA, RNA, carbohydrates, or other small molecules. For example, blood products or blood-derived components can be red blood cells, white blood cells, or platelets.

In some embodiments, an autologous composition produced from use of a system as described herein can have minimal foaming, and thus be suitable for injection into a subject. In some embodiments, a composition can have substantially no foaming. In some embodiments, a composition can have a volume wherein less than 20%, 19%, 18%, 17%, 16%, 15%, 14%, 13%, 12%, 11%, 10%, 9%, 8%, 7%, 6%, 5%, 4%, 3%, 2%, 1%, 0.5%, 0.1%, 0.05%, 0.01%, 0.005%, 0.001%, 0.0005%, 0.0001%, 0.00005%, 0.00001%, or less of the total volume of the composition is foam. Methods of measuring the amount of foam are known in the art. Examples include measuring specific conductivity, volume changes after removing foam, foam volumes, rate of foam degeneration over time, viscosity, optical absorption, specific surface, and other measurements. For example, in some embodiments, determining the amount of foam in a composition can comprise measuring the viscosity of the composition. In some embodiments, foaming measurements can be compared to foaming measurements taken from a reference sample. The reference sample can comprise a known amount of foaming.

Variant A2M Polypeptides Compositions for Treatment of Chronic Wounds

A2M is a general inhibitor of metalloproteases and other proteases such as ADAMTS 4 and ADAMTS 5. These proteases and others produced as a result of a wound, such as a chronic wound can be responsible for slow healing of the wound or persistence of the wound. Any of the recombinant compositions described herein can be used for treatment of a subject with a condition, disease, or chronic wound according to any of the methods described herein.

A2M is able to inactivate an enormous variety of proteases (including serine-, cysteine-, and aspartic-metalloproteases). A2M can function as an inhibitor of fibrinolysis by inhibiting plasmin and kallikrein. A2M can function as an inhibitor of coagulation by inhibiting thrombin. Human A2M has in its structure a 38 amino acid "bait" region. The bait region varies widely in the amino acid number (27-52 amino acids) and sequence between animal species. Proteases binding and cleaving of the bait region can become bound to A2M. The protease-A2M complex can be recognized by macrophage receptors and cleared from the organism's system. A2M is able to inhibit all four classes of proteases by a unique 'trapping' mechanism. When a protease cleaves the bait region, a conformational change can be induced in the protein which can trap the protease. The entrapped enzyme can remain active against low molecular weight substrates (activity against high molecular weight substrates can be greatly reduced). Following cleavage in the bait region a thioester bond can be hydrolyzed and can mediate the covalent binding of the protein to the protease.

In one aspect, provided herein is a composition that can be a variant A2M polypeptide. A variant A2M polypeptide can be a recombinant protein, or fragments thereof, and can be produced in a host cell and purified for use in treatment of chronic wounds. A variant A2M composition can be more efficient in inhibiting proteases, have longer half-life, have a slower clearance factor, or any combination thereof compared to a wild-type A2M. A variant A2M can be a recombinant protein, or a fragment thereof, and can be produced in a host cell and purified. For example, a variant A2M recombinant protein can be produced in a host comprising bacteria, yeast, fungi, insect, or mammalian cells, or a cell free system.

Variant A2M polypeptides or fragments thereof, can also be variants or posttranslationally modified variants of A2M. A2M variant polypeptides can have an integer number of amino acid alterations such that their amino acid sequence shares at least about 60%, 70%, 80%, 85%, 90%, 95%, 97%, 98%, 99%, 99.5% or 100% identity with an amino acid sequence of a wild type A2M polypeptide. In some embodiments, A2M variant polypeptides can have an amino acid sequence sharing at least about 60%, 70%, 80%, 85%, 90%, 95%, 97%, 98%, 99%, 99.5% or 100% identity with the amino acid sequence of a wild type A2M polypeptide.

Percent sequence identity can be calculated using computer programs or direct sequence comparison. Preferred computer program methods to determine identity between two sequences include, but are not limited to, the GCG program package, FASTA, BLASTP, and TBLASTN (see, e.g., D. W. Mount, 2001, Bioinformatics: Sequence and Genome Analysis, Cold Spring Harbor Laboratory Press, Cold Spring Harbor, N.Y.). The BLASTP and TBLASTN programs are publicly available from NCBI and other sources. The Smith Waterman algorithm can also be used to determine percent identity. Exemplary parameters for amino acid sequence comparison include the following: 1) algorithm from Needleman and Wunsch (J. Mol. Biol., 48:443-453 (1970)); 2) BLOSSUM62 comparison matrix from Hentikoff and Hentikoff (Proc. Nat. Acad. Sci. USA., 89:10915-10919 (1992)) 3) gap penalty=12; and 4) gap length penalty=4. A program useful with these parameters can be publicly available as the "gap" program (Genetics Computer Group, Madison, Wis.). The aforementioned parameters are the default parameters for polypeptide comparisons (with no penalty for end gaps). Alternatively, polypeptide sequence identity can be calculated using the following equation: % identity=(the number of identical residues)/(alignment length in amino acid residues)*100. For this calculation, alignment length includes internal gaps but does not include terminal gaps Variant A2M polypeptides, or fragments thereof, include but are not limited to, those containing as a primary amino acid sequence all or part of the amino acid sequence encoded by SEQ ID NOs: 5-66, and fragments of these proteins, including altered sequences in which functionally equivalent amino acid residues are substituted for residues within the sequence resulting in a silent change. The variant A2M polypeptides can include all or part of the amino acid sequence encoded by SEQ ID NO: 3. The variant A2M polypeptides can be, for example, any number of between 4-20, 20-50, 50-100, 100-300, 300-600, 600-1000, 1000-1450 consecutive amino acids containing the amino acids sequences of SEQ. ID NOs. 5-66. The variant A2M polypeptide can be less than or equal to 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 250, 300, 350, 400, 500, 600, 700, 800, 900, 1000, and 1450 amino acids in length and contain, as part of the sequence: SEQ ID NOs: 5-66. Variant A2M polypeptides includes polypeptide sequences having at least 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, or 60% sequence identity or similarity to any variant A2M polypeptide containing one of SEQ ID NOs: 5-66.

The variant A2M polypeptides provided herein also include proteins characterized by amino acid sequences similar to those of purified proteins but into which modification are naturally provided or deliberately engineered. For example, modifications, in the variant A2M peptide or variant A2M DNA sequence, can be made by those skilled in the art using known techniques. Modifications of interest in the protein sequences can include the alteration, substitution, replacement, insertion or deletion of a selected amino acid residue in the coding sequence. For example, one or more of the cysteine residues can be deleted or replaced with another amino acid to alter the conformation of the molecule. Techniques for such alteration, substitution, replacement, insertion or deletion are well known to those skilled in the art (see, e.g., U.S. Pat. No. 4,518,584). Preferably, such alteration, substitution, replacement, insertion or deletion retains the desired activity of the protein. Regions of the protein that are important for the protein function can be determined by various methods known in the art including the alanine-scanning method which involves systematic substitution of single or multiple amino acids with alanine, followed by testing the resulting alanine-containing variant for biological activity. This type of analysis can be used to determine the importance of the substituted amino acid(s) in biological activity.

The bait region of A2M is a segment that is susceptible to proteolytic cleavage, and which, upon cleavage, initiates a conformational change in the A2M molecule resulting in the collapse of the structure around the protease. For the exemplary A2M sequences set forth in SEQ ID NO: 3, the bait region corresponds to amino acids 690-728. For the exemplary A2M sequences set forth in SEQ ID NO: 1 and 2, the bait region corresponds to the nucleotides encoding amino acids 690-728.

A variant A2M polypeptide can comprise a bait region of a variant A2M polypeptide. For example, a bait region of a variant A2M polypeptide can be a mutant bait region, fragment of a bait region, a bait region from another species, an isoform of a bait region, or a bait region containing multiple copies of one or more bait regions described herein, or any combination thereof. A bait region of a variant A2M polypeptide can include a plurality of protease recognition sites arranged in series and can be arranged in any order.

A bait region of a variant A2M polypeptide can have one or more protease recognition sites. For example, a bait region of a variant A2M polypeptide can have 2 or more, or 3, 4, 5, 6, 7, 8, 9, or 10 or more protease recognition sites. Protease recognition sites or substrate bait regions can be consensus sequences for serine proteases, threonine proteases, cysteine proteases, aspartate proteases, metalloproteases, glutamic acid proteases, or any combination thereof compared to a wild type A2M protein. A variant A2M polypeptide can be characterized by an enhanced specific inhibition of serine proteases, threonine proteases, cysteine proteases, aspartate proteases, metalloproteases, glutamic acid proteases, or any combination thereof. A variant A2M polypeptide can be characterized by an enhanced nonspecific inhibition of serine proteases, threonine proteases, cysteine proteases, aspartate proteases, metalloproteases, glutamic acid proteases, or any combination thereof compared to a wild type A2M protein.

A bait region of a variant A2M polypeptide can have one or more mutant base regions. For example, a bait region of a variant A2M polypeptide can have 2 or more, or 3, 4, 5, 6, 7, 8, 9, or 10 or more mutant base regions. A bait region of a variant A2M polypeptide can have one or more bait region fragments. For example, a bait region of a variant A2M polypeptide can have 2 or more, or 3, 4, 5, 6, 7, 8, 9, or 10 or more bait region fragments. A fragment of a bait region of a variant A2M polypeptide can be a fragment of any of SEQ ID NOs: 5-66.

A bait region of a variant A2M polypeptide can have one or more mutant amino acids that are different than those amino acids in a wild-type A2M polypeptide. For example, a bait region of a variant A2M polypeptide can have 2 or more, or 3, 4, 5, 6, 7, 8, 9, or 10 or more mutant amino acids that are different than those amino acids in a wild-type A2M polypeptide. A bait region of a variant A2M polypeptide can have one or more mutant amino acid regions that are different than those regions in a wild-type A2M polypeptide. For example, a bait region of a variant A2M polypeptide can have 2 or more, or 3, 4, 5, 6, 7, 8, 9, or 10 or more mutant amino acid regions that are different than those regions in a wild-type A2M polypeptide. A mutant bait region of a variant A2M polypeptide can replace or substitute a bait region in a wild-type A2M polypeptide. A mutant bait region of a variant A2M polypeptide can be any of SEQ ID NOs: 5-66.

The A2M variant polypeptides provided herein also include A2M variant proteins characterized by amino acid sequences similar to those of purified A2M variant. Isolated or purified variant A2M polypeptides can have one or more amino acid residues within the polypeptide that are substituted by another amino acid of a similar polarity that acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic amino acids include phenylalanine, tryptophan, and tyrosine.

A bait region of a variant A2M polypeptide can have one or more bait region isoforms. For example, a bait region of a variant A2M polypeptide can have 2 or more, or 3, 4, 5, 6, 7, 8, 9, or 10 or more bait region isoforms. A bait region of a variant A2M polypeptide can have one or more mutant or engineered bait regions. For example, a bait region of a variant A2M polypeptide can have 2 or more, or 3, 4, 5, 6, 7, 8, 9, or 10 or more mutant or engineered bait regions.

A bait region of a variant A2M polypeptide can have one or more copies of one or more bait regions. The one or more bait regions can be the same bait regions (repeats), different bait regions, or any combination thereof. For example, a bait region of a variant A2M polypeptide can have 2 or more, or 3, 4, 5, 6, 7, 8, 9, or 10 or more copies of one or more bait regions, wherein the one or more bait regions can be the same bait regions (repeats), different bait regions, or any combination thereof.

A variant A2M polypeptide can comprise one or more bait regions derived from different organisms, different species of an organism, or a combination thereof. For example, a variant A2M polypeptide can have 2 or more, or 3, 4, 5, 6, 7, 8, 9, or 10 or more bait regions derived from different organisms, different species of an organism, or a combination thereof. One or more bait regions derived from different organisms can be derived from one or more different organisms and not from different species of an organism. For example, one or more modified bait regions can be derived from 2 or more, or 3, 4, 5, 6, 7, 8, 9, or 10 or more different organisms and not contain 2 or more bait regions derived from different species of an organism. One or more bait regions derived from different species of an organism can be derived from one or more different species of an organism and not from different organisms. For example, one or more modified bait regions can be derived from 2 or more, or 3, 4, 5, 6, 7, 8, 9, or 10 or more different species of an organism and not contain 2 or more bait regions derived from different organism. The modified bait regions can be derived from any animal, insect, plant, bacteria, viral, yeast, fish, reptile, amphibian, or fungi. The modified bait regions can be derived from any animal with A2M or homologous protein, such as pig, mouse, rat, rabbit, cat, dog, frog, monkey, horse or goat.

A variant A2M polypeptide can comprise one or more bait regions of variant A2M polypeptides. For example, a variant A2M polypeptide can have 2 or more, or 3, 4, 5, 6, 7, 8, 9, or 10 or more bait region of variant A2M polypeptides. One or more bait region of a variant A2M polypeptides can be derived from one or more different species. For example, one or more bait regions of variant A2M polypeptides can be derived from 2 or more, or 3, 4, 5, 6, 7, 8, 9, or 10 or more different species. The bait region of variant A2M polypeptides can be derived from any animal, insect, plant, bacteria, viral, yeast, fish, reptile, amphibian, or fungi species.

A variant A2M polypeptide can have a plurality of protease recognition sites that can be one or more protease substrate bait regions from one or more proteins other than A2M.

A variant A2M polypeptide can have a plurality of protease recognition sites that can be one or more protease substrate bait regions from A2M. A variant A2M polypeptide can have a plurality of protease recognition sites that can be one or more protease substrate bait regions from one or more non-natural protein sequences. The non-natural protein sequences can comprise one or more protease recognition sites in series and can function as bait for proteases. A variant A2M polypeptide can have a plurality of protease recognition sites that can be one or more protease substrate bait regions from or any of the combination of bait regions described herein. A variant A2M polypeptide can have any number of protease bait regions arranged in series. A variant A2M polypeptide can have any number of protease bait regions from any species and can be arranged in series. One or more protease substrate bait regions from one or more proteins other than A2M or from the one or more non-natural protein sequences can be a suicide inhibitor. For example, a variant A2M polypeptide can have 2, 3, 4, 5, 6, 7, 8, 9, 10, 11, 12, 13, 14, 15, or more suicide inhibitor bait regions. A suicide inhibitor can be operable to covalently attach a protease to A2M.

A variant A2M polypeptide can be characterized by at least about a 10% increase in protease inhibitory effectiveness compared to the protease inhibitory effectiveness of a wild type A2M protein. For example, a variant A2M polypeptide can be characterized by at least about a 20, 25%, 30%, 35%, 40%, 45%, 50%, 55%, 60%, 65%, 70%, 75%, 80%, 85%, 90%, 95%, or 100% increase in protease inhibitory effectiveness when compared to the protease inhibitory effectiveness of a wild type A2M protein. A variant A2M polypeptide can be characterized by an increase in protease inhibitory effectiveness compared to the protease inhibitory effectiveness of a wild type A2M protein. For example, a variant A2M polypeptide can be characterized by an 1.2, 1.2, 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times increase in protease inhibitory effectiveness compared to the protease inhibitory effectiveness of a wild type A2M protein.

A variant A2M polypeptide can be characterized as having an increased ability to inhibit one or more proteases compared to a wild-type A2M polypeptide. A variant A2M polypeptide can have an ability to inhibit one or more proteases that is at least 1.5 times higher than the ability of a wild-type A2M polypeptide to inhibit the one or more proteases. For example, a variant A2M polypeptide can have an ability to inhibit one or more proteases that is at least 1.5, 1.6, 1.7, 1.8, 1.9, 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 60, 70, 80, 90, or 100 times higher than the ability of a wild-type A2M polypeptide to inhibit the one or more proteases. A variant A2M polypeptide can have an ability to inhibit one or more proteases that is from 1.5-100 times higher than the ability of a wild-type A2M polypeptide to inhibit the one or more proteases. For example, a variant A2M polypeptide can have an ability to inhibit one or more proteases that is from 1.6-100, 1.7-100, 1.8-100, 1.9-100, 2-100, 2.1-100, 2.2-100, 2.3-100, 2.4-100, 2.5-100, 2.6-100, 2.7-100, 2.8-100, 2.9-100, 3.0-100, 3.1-100, 3.2-100, 3.3-100, 3.4-100, 3.5-100, 3.6-100, 3.7-100, 3.8-100, 3.9-100, 4-100, 5-100, 6-100, 7-100, 8-100, 9-100, 10-100, 11-100, 12-100, 13-100, 14-100, 15-100, 16-100, 17-100, 18-100, 19-100, 20-100, 25-100, 30-100, 35-100, 40-100, 45-100, 50-100, 60-100, 70-100, 80-100, 90-100, 1.5-90, 1.6-90, 1.7-90, 1.8-90, 1.9-90, 2-90, 2.1-90, 2.2-90, 2.3-90, 2.4-90, 2.5-90, 2.6-90, 2.7-90, 2.8-90, 2.9-90, 3.0-90, 3.1-90, 3.2-90, 3.3-90, 3.4-90, 3.5-90, 3.6-90, 3.7-90, 3.8-90, 3.9-90, 4-90, 5-90, 6-90, 7-90, 8-90, 9-90, 10-90, 11-90, 12-90, 13-90, 14-90, 15-90, 16-90, 17-90, 18-90, 19-90, 20-90, 25-90, 30-90, 35-90, 40-90, 45-90, 50-90, 60-90, 70-90, 80-90, 1.5-80, 1.6-80, 1.7-80, 1.8-80, 1.9-80, 2-80, 2.1-80, 2.2-80, 2.3-80, 2.4-80, 2.5-80, 2.6-80, 2.7-80, 2.8-80, 2.9-80, 3.0-80, 3.1-80, 3.2-80, 3.3-80, 3.4-80, 3.5-80, 3.6-80, 3.7-80, 3.8-80, 3.9-80, 4-80, 5-80, 6-80, 7-80, 8-80, 9-80, 10-80, 11-80, 12-80, 13-80, 14-80, 15-80, 16-80, 17-80, 18-80, 19-80, 20-80, 25-80, 30-80, 35-80, 40-80, 45-80, 50-80, 60-80, 70-80, 1.5-70, 1.6-70, 1.7-70, 1.8-70, 1.9-70, 2-70, 2.1-70, 2.2-70, 2.3-70, 2.4-70, 2.5-70, 2.6-70, 2.7-70, 2.8-70, 2.9-70, 3.0-70, 3.1-70, 3.2-70, 3.3-70, 3.4-70, 3.5-70, 3.6-70, 3.7-70, 3.8-70, 3.9-70, 4-70, 5-70, 6-70, 7-70, 8-70, 9-70, 10-70, 11-70, 12-70, 13-70, 14-70, 15-70, 16-70, 17-70, 18-70, 19-70, 20-70, 25-70, 30-70, 35-70, 40-70, 45-70, 50-70, 60-70, 1.5-60, 1.6-60, 1.7-60, 1.8-60, 1.9-60, 2-60, 2.1-60, 2.2-60, 2.3-60, 2.4-60, 2.5-60, 2.6-60, 2.7-60, 2.8-60, 2.9-60, 3.0-60, 3.1-60, 3.2-60, 3.3-60, 3.4-60, 3.5-60, 3.6-60, 3.7-60, 3.8-60, 3.9-60, 4-60, 5-60, 6-60, 7-60, 8-60, 9-60, 10-60, 11-60, 12-60, 13-60, 14-60, 15-60, 16-60, 17-60, 18-60, 19-60, 20-60, 25-60, 30-60, 35-60, 40-60, 45-60, 50-60, 1.5-50, 1.6-50, 1.7-50, 1.8-50, 1.9-50, 2-50, 2.1-50, 2.2-50, 2.3-50, 2.4-50, 2.5-50, 2.6-50, 2.7-50, 2.8-50, 2.9-50, 3.0-50, 3.1-50, 3.2-50, 3.3-50, 3.4-50, 3.5-50, 3.6-50, 3.7-50, 3.8-50, 3.9-50, 4-50, 5-50, 6-50, 7-50, 8-50, 9-50, 10-50, 11-50, 12-50, 13-50, 14-50, 15-50, 16-50, 17-50, 18-50, 19-50, 20-50, 25-50, 30-50, 35-50, 40-50, 1.5-40, 1.6-40, 1.7-40, 1.8-40, 1.9-40, 2-40, 2.1-40, 2.2-40, 2.3-40, 2.4-40, 2.5-40, 2.6-40, 2.7-40, 2.8-40, 2.9-40, 3.0-40, 3.1-40, 3.2-40, 3.3-40, 3.4-40, 3.5-40, 3.6-40, 3.7-40, 3.8-40, 3.9-40, 4-40, 5-40, 6-40, 7-40, 8-40, 9-40, 10-40, 11-40, 12-40, 13-40, 14-40, 15-40, 16-40, 17-40, 18-40, 19-40, 20-40, 25-40, 30-40, 1.5-30, 1.6-30, 1.7-30, 1.8-30, 1.9-30, 2-30, 2.1-30, 2.2-30, 2.3-30, 2.4-30, 2.5-30, 2.6-30, 2.7-30, 2.8-30, 2.9-30, 3.0-30, 3.1-30, 3.2-30, 3.3-30, 3.4-30, 3.5-30, 3.6-30, 3.7-30, 3.8-30, 3.9-30, 4-30, 5-30, 6-30, 7-30, 8-30, 9-30, 10-30, 11-30, 12-30, 13-30, 14-30, 15-30, 16-30, 17-30, 18-30, 19-30, 20-30, 1.5-20, 1.6-20, 1.7-20, 1.8-20, 1.9-20, 2-20, 2.1-20, 2.2-20, 2.3-20, 2.4-20, 2.5-20, 2.6-20, 2.7-20, 2.8-20, 2.9-20, 3.0-20, 3.1-20, 3.2-20, 3.3-20, 3.4-20, 3.5-20, 3.6-20, 3.7-20, 3.8-20, 3.9-20, 4-20, 5-20, 6-20, 7-20, 8-20, 9-20, 10-20, 11-20, 12-20, 13-20, 14-20, 15-20, 1.5-15, 1.6-15, 1.7-15, 1.8-15, 1.9-15, 2-15, 2.1-15, 2.2-15, 2.3-15, 2.4-15, 2.5-15, 2.6-15, 2.7-15, 2.8-15, 2.9-15, 3.0-15, 3.1-15, 3.2-15, 3.3-15, 3.4-15, 3.5-15, 3.6-15, 3.7-15, 3.8-15, 3.9-15, 4-15, 5-15, 6-15, 7-15, 8-15, 9-15, 10-15, 11-15, 12-15, 13-15, 14-15, 1.5-10, 1.6-10, 1.7-10, 1.8-10, 1.9-10, 2-10, 2.1-10, 2.2-10, 2.3-10, 2.4-10, 2.5-10, 2.6-10, 2.7-10, 2.8-10, 2.9-10, 3.0-10, 3.1-10, 3.2-10, 3.3-10, 3.4-10, 3.5-10, 3.6-10, 3.7-10, 3.8-10, 3.9-10, 4-10, 5-10, 6-10, 7-10, 8-10, 9-10, 1.5-9, 1.6-9, 1.7-9, 1.8-9, 1.9-9, 2-9, 2.1-9, 2.2-9, 2.3-9, 2.4-9, 2.5-9, 2.6-9, 2.7-9, 2.8-9, 2.9-9, 3.0-9, 3.1-9, 3.2-9, 3.3-9, 3.4-9, 3.5-9, 3.6-9, 3.7-9, 3.8-9, 3.9-9, 4-9, 5-9, 6-9, 7-9, 8-9, 1.5-8, 1.6-8, 1.7-8, 1.8-8, 1.9-8, 2-8, 2.1-8, 2.2-8, 2.3-8, 2.4-8, 2.5-8, 2.6-8, 2.7-8, 2.8-8, 2.9-8, 3.0-8, 3.1-8, 3.2-8, 3.3-8, 3.4-8, 3.5-8, 3.6-8, 3.7-8, 3.8-8, 3.9-8, 4-8, 5-8, 6-8, 7-8, 1.5-7, 1.6-7, 1.7-7, 1.8-7, 1.9-7, 2-7, 2.1-7, 2.2-7, 2.3-7, 2.4-7, 2.5-7, 2.6-7, 2.7-7, 2.8-7, 2.9-7, 3.0-7, 3.1-7, 3.2-7, 3.3-7, 3.4-7, 3.5-7, 3.6-7, 3.7-7, 3.8-7, 3.9-7, 4-7, 5-7, 6-7, 1.5-6, 1.6-6, 1.7-6, 1.8-6, 1.9-6, 2-6, 2.1-6, 2.2-6, 2.3-6, 2.4-6, 2.5-6, 2.6-6, 2.7-6, 2.8-6, 2.9-6, 3.0-6, 3.1-6, 3.2-6, 3.3-6, 3.4-6, 3.5-6, 3.6-6, 3.7-6, 3.8-6, 3.9-6, 4-6, 5-6, 1.5-5, 1.6-5, 1.7-5, 1.8-5, 1.9-5, 2-5, 2.1-5, 2.2-5, 2.3-5, 2.4-5, 2.5-5, 2.6-5, 2.7-5, 2.8-5, 2.9-5, 3.0-5, 3.1-5, 3.2-5, 3.3-5, 3.4-5, 3.5-5, 3.6-5, 3.7-5, 3.8-5, 3.9-5, 4-5, 1.5-4, 1.6-4, 1.7-4, 1.8-4, 1.9-4, 2-4, 2.1-4, 2.2-4, 2.3-4, 2.4-4, 2.5-4, 2.6-4, 2.7-4, 2.8-4, 2.9-4, 3.0-4, 3.1-4, 3.2-4, 3.3-4, 3.4-4, 3.5-4, 3.6-4, 3.7-4, 3.8-4, 3.9-4, 1.5-3, 1.6-3, 1.7-3, 1.8-3, 1.9-3, 2-3, 2.1-3, 2.2-3, 2.3-3, 2.4-3, 2.5-3, 2.6-3, 2.7-3, 2.8-3, 2.9-3, 1.5-2, 1.6-2, 1.7-2, 1.8-2, or 1.9-2 times higher than the ability of a wild-type A2M polypeptide to inhibit the one or more proteases.

The one or more proteases can include a matrix metalloprotease, such as MMP1 (Interstitial collagenase), MMP2 (Gelatinase-A), MMP3 (Stromelysin 1), MMP7 (Matrilysin, PUMP 1), MMP8 (Neutrophil collagenase), MMP9 (Gelatinase-B), MMP10 (Stromelysin 2), MMP11), Stromelysin 3), MMP12 (Macrophage metalloelastase), MMP13 (Collagenase 3), MMP14 (MT1-MMP), MMP15 (MT2-MMP), MMP16 (MT3-MMP), MMP17 (MT4-MMP), MMP18 (Collagenase 4, xcol4, xenopus collagenase), MMP19 (RASI-1, stromelysin-4), MMP20 (Enamelysin), MMP21 (X-MMP), MMP23A (CA-MMP), MMP23B MMP24 (MT5-MMP), MMP25 (MT6-MMP), MMP26 (Matrilysin-2, endometase), MMP27 (MMP-22, C-MMP), MMP28 (Epilysin); A Disintegrin and Metalloproteinase with Thrombospondin Motifs protease, such as ADAMTS1, ADAMTS2, ADAMTS3, ADAMTS4, ADAMTS5 (ADAMTS11), ADAMTS6, ADAMTS7, ADAMTS8 (METH-2), ADAMTS9, ADAMTS10, ADAMTS12, ADAMTS13, ADAMTS14, ADAMTS15, ADAMTS16, ADAMTS17, ADAMTS18, ADAMTS19, ADAMTS20; chymotrypsin; trypsin; elastase; compliment factors; clotting factors; thrombin; plasmin; subtilisin; Neprilysin; Procollagen peptidase; Thermolysin; Pregnancy-associated plasma protein A; Bone morphogenetic protein 1; Lysostaphin; Insulin degrading enzyme; ZMPSTE2; and acetylcholinesterase.

A variant A2M polypeptide can be characterized as having an increased ability to prevent FAC formation compared to a wild-type A2M polypeptide. A variant A2M polypeptide can have an ability to prevent FAC formation that is at least 1.5 times higher than the ability of a wild-type A2M polypeptide to prevent FAC formation. For example, a variant A2M polypeptide can have an ability to prevent FAC formation that is at least 1.5, 1.6, 1.7, 1.8, 1.9, 2, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4, 5, 6, 7, 8, 9, 10, 11, 12, 13, 14, 15, 16, 17, 18, 19, 20, 25, 30, 35, 40, 45, 50, 60, 70, 80, 90, or 100 times higher than the ability of a wild-type A2M polypeptide to prevent FAC formation. A variant A2M polypeptide can have an ability to prevent FAC formation that is from 1.5-100 times higher than the ability of a wild-type A2M polypeptide to prevent FAC formation. For example, a variant A2M polypeptide can have an ability to prevent FAC formation that is from 1.6-100, 1.7-100, 1.8-100, 1.9-100, 2-100, 2.1-100, 2.2-100, 2.3-100, 2.4-100, 2.5-100, 2.6-100, 2.7-100, 2.8-100, 2.9-100, 3.0-100, 3.1-100, 3.2-100, 3.3-100, 3.4-100, 3.5-100, 3.6-100, 3.7-100, 3.8-100, 3.9-100, 4-100, 5-100, 6-100, 7-100, 8-100, 9-100, 10-100, 11-100, 12-100, 13-100, 14-100, 15-100, 16-100, 17-100, 18-100, 19-100, 20-100, 25-100, 30-100, 35-100, 40-100, 45-100, 50-100, 60-100, 70-100, 80-100, 90-100, 1.5-90, 1.6-90, 1.7-90, 1.8-90, 1.9-90, 2-90, 2.1-90, 2.2-90, 2.3-90, 2.4-90, 2.5-90, 2.6-90, 2.7-90, 2.8-90, 2.9-90, 3.0-90, 3.1-90, 3.2-90, 3.3-90, 3.4-90, 3.5-90, 3.6-90, 3.7-90, 3.8-90, 3.9-90, 4-90, 5-90, 6-90, 7-90, 8-90, 9-90, 10-90, 11-90, 12-90, 13-90, 14-90, 15-90, 16-90, 17-90, 18-90, 19-90, 20-90, 25-90, 30-90, 35-90, 40-90, 45-90, 50-90, 60-90, 70-90, 80-90, 1.5-80, 1.6-80, 1.7-80, 1.8-80, 1.9-80, 2-80, 2.1-80, 2.2-80, 2.3-80, 2.4-80, 2.5-80, 2.6-80, 2.7-80, 2.8-80, 2.9-80, 3.0-80, 3.1-80, 3.2-80, 3.3-80, 3.4-80, 3.5-80, 3.6-80, 3.7-80, 3.8-80, 3.9-80, 4-80, 5-80, 6-80, 7-80, 8-80, 9-80, 10-80, 11-80, 12-80, 13-80, 14-80, 15-80, 16-80, 17-80, 18-80, 19-80, 20-80, 25-80, 30-80, 35-80, 40-80, 45-80, 50-80, 60-80, 70-80, 1.5-70, 1.6-70, 1.7-70, 1.8-70, 1.9-70, 2-70, 2.1-70, 2.2-70, 2.3-70, 2.4-70, 2.5-70, 2.6-70, 2.7-70, 2.8-70, 2.9-70, 3.0-70, 3.1-70, 3.2-70, 3.3-70, 3.4-70, 3.5-70, 3.6-70, 3.7-70, 3.8-70, 3.9-70, 4-70, 5-70, 6-70, 7-70, 8-70, 9-70, 10-70, 11-70, 12-70, 13-70, 14-70, 15-70, 16-70, 17-70, 18-70, 19-70, 20-70, 25-70, 30-70, 35-70, 40-70, 45-70, 50-70, 60-70, 1.5-60, 1.6-60, 1.7-60, 1.8-60, 1.9-60, 2-60, 2.1-60, 2.2-60, 2.3-60, 2.4-60, 2.5-60, 2.6-60, 2.7-60, 2.8-60, 2.9-60, 3.0-60, 3.1-60, 3.2-60, 3.3-60, 3.4-60, 3.5-60, 3.6-60, 3.7-60, 3.8-60, 3.9-60, 4-60, 5-60, 6-60, 7-60, 8-60, 9-60, 10-60, 11-60, 12-60, 13-60, 14-60, 15-60, 16-60, 17-60, 18-60, 19-60, 20-60, 25-60, 30-60, 35-60, 40-60, 45-60, 50-60, 1.5-50, 1.6-50, 1.7-50, 1.8-50, 1.9-50, 2-50, 2.1-50, 2.2-50, 2.3-50, 2.4-50, 2.5-50, 2.6-50, 2.7-50, 2.8-50, 2.9-50, 3.0-50, 3.1-50, 3.2-50, 3.3-50, 3.4-50, 3.5-50, 3.6-50, 3.7-50, 3.8-50, 3.9-50, 4-50, 5-50, 6-50, 7-50, 8-50, 9-50, 10-50, 11-50, 12-50, 13-50, 14-50, 15-50, 16-50, 17-50, 18-50, 19-50, 20-50, 25-50, 30-50, 35-50, 40-50, 1.5-40, 1.6-40, 1.7-40, 1.8-40, 1.9-40, 2-40, 2.1-40, 2.2-40, 2.3-40, 2.4-40, 2.5-40, 2.6-40, 2.7-40, 2.8-40, 2.9-40, 3.0-40, 3.1-40, 3.2-40, 3.3-40, 3.4-40, 3.5-40, 3.6-40, 3.7-40, 3.8-40, 3.9-40, 4-40, 5-40, 6-40, 7-40, 8-40, 9-40, 10-40, 11-40, 12-40, 13-40, 14-40, 15-40, 16-40, 17-40, 18-40, 19-40, 20-40, 25-40, 30-40, 1.5-30, 1.6-30, 1.7-30, 1.8-30, 1.9-30, 2-30, 2.1-30, 2.2-30, 2.3-30, 2.4-30, 2.5-30, 2.6-30, 2.7-30, 2.8-30, 2.9-30, 3.0-30, 3.1-30, 3.2-30, 3.3-30, 3.4-30, 3.5-30, 3.6-30, 3.7-30, 3.8-30, 3.9-30, 4-30, 5-30, 6-30, 7-30, 8-30, 9-30, 10-30, 11-30, 12-30, 13-30, 14-30, 15-30, 16-30, 17-30, 18-30, 19-30, 20-30, 1.5-20, 1.6-20, 1.7-20, 1.8-20, 1.9-20, 2-20, 2.1-20, 2.2-20, 2.3-20, 2.4-20, 2.5-20, 2.6-20, 2.7-20, 2.8-20, 2.9-20, 3.0-20, 3.1-20, 3.2-20, 3.3-20, 3.4-20, 3.5-20, 3.6-20, 3.7-20, 3.8-20, 3.9-20, 4-20, 5-20, 6-20, 7-20, 8-20, 9-20, 10-20, 11-20, 12-20, 13-20, 14-20, 15-20, 1.5-15, 1.6-15, 1.7-15, 1.8-15, 1.9-15, 2-15, 2.1-15, 2.2-15, 2.3-15, 2.4-15, 2.5-15, 2.6-15, 2.7-15, 2.8-15, 2.9-15, 3.0-15, 3.1-15, 3.2-15, 3.3-15, 3.4-15, 3.5-15, 3.6-15, 3.7-15, 3.8-15, 3.9-15, 4-15, 5-15, 6-15, 7-15, 8-15, 9-15, 10-15, 11-15, 12-15, 13-15, 14-15, 1.5-10, 1.6-10, 1.7-10, 1.8-10, 1.9-10, 2-10, 2.1-10, 2.2-10, 2.3-10, 2.4-10, 2.5-10, 2.6-10, 2.7-10, 2.8-10, 2.9-10, 3.0-10, 3.1-10, 3.2-10, 3.3-10, 3.4-10, 3.5-10, 3.6-10, 3.7-10, 3.8-10, 3.9-10, 4-10, 5-10, 6-10, 7-10, 8-10, 9-10, 1.5-9, 1.6-9, 1.7-9, 1.8-9, 1.9-9, 2-9, 2.1-9, 2.2-9, 2.3-9, 2.4-9, 2.5-9, 2.6-9, 2.7-9, 2.8-9, 2.9-9, 3.0-9, 3.1-9, 3.2-9, 3.3-9, 3.4-9, 3.5-9, 3.6-9, 3.7-9, 3.8-9, 3.9-9, 4-9, 5-9, 6-9, 7-9, 8-9, 1.5-8, 1.6-8, 1.7-8, 1.8-8, 1.9-8, 2-8, 2.1-8, 2.2-8, 2.3-8, 2.4-8, 2.5-8, 2.6-8, 2.7-8, 2.8-8, 2.9-8, 3.0-8, 3.1-8, 3.2-8, 3.3-8, 3.4-8, 3.5-8, 3.6-8, 3.7-8, 3.8-8, 3.9-8, 4-8, 5-8, 6-8, 7-8, 1.5-7, 1.6-7, 1.7-7, 1.8-7, 1.9-7, 2-7, 2.1-7, 2.2-7, 2.3-7, 2.4-7, 2.5-7, 2.6-7, 2.7-7, 2.8-7, 2.9-7, 3.0-7, 3.1-7, 3.2-7, 3.3-7, 3.4-7, 3.5-7, 3.6-7, 3.7-7, 3.8-7, 3.9-7, 4-7, 5-7, 6-7, 1.5-6, 1.6-6, 1.7-6, 1.8-6, 1.9-6, 2-6, 2.1-6, 2.2-6, 2.3-6, 2.4-6, 2.5-6, 2.6-6, 2.7-6, 2.8-6, 2.9-6, 3.0-6, 3.1-6, 3.2-6, 3.3-6, 3.4-6, 3.5-6, 3.6-6, 3.7-6, 3.8-6, 3.9-6, 4-6, 5-6, 1.5-5, 1.6-5, 1.7-5, 1.8-5, 1.9-5, 2-5, 2.1-5, 2.2-5, 2.3-5, 2.4-5, 2.5-5, 2.6-5, 2.7-5, 2.8-5, 2.9-5, 3.0-5, 3.1-5, 3.2-5, 3.3-5, 3.4-5, 3.5-5, 3.6-5, 3.7-5, 3.8-5, 3.9-5, 4-5, 1.5-4, 1.6-4, 1.7-4, 1.8-4, 1.9-4, 2-4, 2.1-4, 2.2-4, 2.3-4, 2.4-4, 2.5-4, 2.6-4, 2.7-4, 2.8-4, 2.9-4, 3.0-4, 3.1-4, 3.2-4, 3.3-4, 3.4-4, 3.5-4, 3.6-4, 3.7-4, 3.8-4, 3.9-4, 1.5-3, 1.6-3, 1.7-3, 1.8-3, 1.9-3, 2-3, 2.1-3, 2.2-3, 2.3-3, 2.4-3, 2.5-3, 2.6-3, 2.7-3, 2.8-3, 2.9-3, 1.5-2, 1.6-2, 1.7-2, 1.8-2, or 1.9-2 times higher than the ability of a wild-type A2M polypeptide to prevent FAC formation.

One aspect of the invention is a method for determining the enhanced inhibition of a protease by a variant A2M polypeptide comprising: a) providing a variant A2M polypeptide comprising a sequence of one or more of SEQ ID NOs 5-66; b) contacting the variant A2M polypeptide with the protease and a substrate cleaved by the protease; c) contacting a wild-type A2M polypeptide with the protease and the substrate cleaved by the protease; and d) comparing the amount of cleavage of the substrate from step b) to the amount of cleavage of the substrate from step c), thereby determining the enhanced inhibition of the protease by the variant A2M polypeptide.

Enzymatic glycoconjugation reactions can be targeted to glycosylation sites and to residues that are attached to glycosylation sites. The targeted glycosylation sites can be sites native to a wild-type A2M protein, native to a variant A2M polypeptide or, alternatively, they can be introduced into a wild-type A2M or variant A2M polypeptide by mutation. Thus, a method for increasing the in vivo half-life of a variant A2M polypeptide is provided by the methods of the invention.

A variant A2M polypeptide can include an amino acid sequence that mutated to insert, remove or relocate one or more glycosylation site in the protein. When a site is added or relocated, it is not present or not present in a selected location in the wild-type A2M peptide. The mutant glycosylation site can be a point of attachment for a modified glycosyl residue that can be enzymatically conjugated to the glycosylation site. Using the methods of the invention, the glycosylation site can be shifted to any efficacious position on the peptide. For example, if the native glycosylation site is sufficiently proximate or within the bait region of variant A2M polypeptide peptide that conjugation interferes with the ability to bind a protease, inhibit a protease, or a combination thereof, it is within the scope of the invention to engineer a variant A2M polypeptide that includes a glycosylation site as modified or removed from the bait as necessary to provide a biologically active variant A2M polypeptide.

Any glycosyltransferase or method of their use known in the art can be used for in vitro enzymatic synthesis of variant A2M polypeptides with custom designed glycosylation patterns, various glycosyl structures, or a combination thereof possible. See, for example, U.S. Pat. Nos. 5,876,980; 6,030,815; 5,728,554; 5,922,577; and WO/9831826; US2003180835; and WO 03/031464.

The present invention provides methods of improving or lengthening the in vivo half-lives of variant A2M polypeptides by conjugating a water-soluble polymer to the variant A2M polypeptides through an intact glycosyl linking group. In an exemplary embodiment, covalent attachment of polymers, such as polyethylene glycol (PEG), to such variant A2M polypeptides affords variant A2M polypeptides having in vivo residence times, and pharmacokinetic and pharmacodynamic properties, enhanced relative to the unconjugated variant A2M polypeptide.

The polymer backbone of the water-soluble polymer can be poly(ethylene glycol) (PEG). However, it should be understood that other related polymers are also suitable for use in the practice of this invention and that the use of the term PEG or poly(ethylene glycol) is intended to be inclusive and not exclusive in this respect. The term PEG includes poly(ethylene glycol) in any of its forms, including alkoxy PEG, difunctional PEG, multiarmed PEG, forked PEG, branched PEG, pendent PEG (i.e. PEG or related polymers having one or more functional groups pendent to the polymer backbone), or PEG with degradable linkages therein. The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, pentaerythritol and sorbitol. The central branch moiety can also be derived from several amino acids, such as lysine. The branched poly(ethylene glycol) can be represented in general form as R(-PEG-OH)$_n$ in which R represents the core moiety, such as glycerol or pentaerythritol, and n represents the number of arms. Many other polymers are also suitable for the invention. Examples of suitable polymers include, but are not limited to, other poly(alkylene glycols), such as poly(propylene glycol) ("PPG"), copolymers of ethylene glycol and propylene glycol and the like, poly(oxyethylated polyol), poly(olefinic alcohol), polyvinylpyrrolidone), poly(hydroxypropylmethacrylamide), poly(α-hydroxy acid), poly(vinyl alcohol), polyphosphazene, polyoxazoline, poly(N-acryloylmorpholine) and copolymers, terpolymers, and mixtures thereof. Although the molecular weight of each chain of the polymer backbone can vary, it is typically in the range of from about 100 Da to about 100,000 Da often from about 6,000 Da to about 80,000 Da.

A variant A2M polypeptide can further comprise PEG. A variant A2M polypeptide can have one or more mutant or modified glycosylation sites. The modified glycosylation sites can comprise PEG. For example, a variant A2M polypeptide can have 2, 3, 4, 5, 6, 7, 8, 9, 10, 11, 12, 13, 14, 15, or more mutant or modified glycosylation sites. The conjugation or addition of PEG to a variant A2M polypeptide with one or more modified or abnormal glycosylation sites can result in a variant A2M polypeptide with a longer half-life than the half-life of a wild-type A2M protein without PEG when disposed within or on a wound of a subject, such as a chronic wound of a subject. The conjugation or addition of PEG to a variant A2M polypeptide with one or more modified or abnormal glycosylation sites can result in a variant A2M polypeptide with a longer half-life than the half-life of a variant A2M polypeptide without one or more modified glycosylation sites without PEG when disposed w within or on a wound of a subject, such as a chronic wound of a subject. The conjugation or addition of PEG to a variant A2M polypeptide with one or more modified or abnormal glycosylation sites can result in a variant A2M polypeptide with a longer half-life than the half-life of a variant A2M polypeptide with one or more modified glycosylation sites without PEG when within or on a wound of a subject, such as a chronic wound of a subject. For example, a variant A2M polypeptide with one or more modified or abnormal glycosylation sites with PEG can have half-life that is 1.4, 1.5, 1.6, 1.7, 1.8, 1.9, 2, 2.5, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20, 25, 30, 35, 40, 45, 50, 55, 60, 65, 70, 75, 80, 85, 90, 95, 100, 200, 300, 400, 500, 600, 700, 800, 900, or 1000 times the half-life of a wild type A2M protein without PEG, a variant A2M polypeptide with one or more modified glycosylation sites without PEG, or a variant A2M polypeptide without one or more modified glycosylation sites without PEG. For example, a variant A2M polypeptide with one or more modified or abnormal glycosylation sites with PEG can have half-life that is 2 times the half-life of a wild type A2M protein composition with one or more modified or abnormal glycosylation sites without PEG when disposed within or on a wound of a subject, such as a chronic wound of a subject.

The present invention further provides isolated polypeptides encoded by the nucleic acid fragments of the present invention or by degenerate variants of the nucleic acid fragments of the present invention. By "degenerate variant" can be intended nucleotide fragments which differ from a nucleic acid fragment of the present invention (e.g., an ORF) by nucleotide sequence but, due to the degeneracy of the genetic code, encode an identical polypeptide sequence. Preferred nucleic acid fragments of the present invention are the ORFs that encode proteins.

Fragments of the A2M variants of the present invention which are capable of exhibiting biological activity are also encompassed by the present invention. Fragments of the A2M variants can be in linear form or they can be cyclized using known methods, for example, as described in H. U. Saragovi, et al., Bio/Technology 10, 773-778 (1992) and in R. S. McDowell, et al., J. Amer. Chem. Soc. 114, 9245-9253 (1992), both of which are incorporated herein by reference. Such fragments can be fused to carrier molecules such as immunoglobulins for many purposes, including increasing the valency of protein binding sites. The present invention also provides both full-length and mature forms (for example, without a signal sequence or precursor sequence) of the disclosed A2M variants. The protein coding sequence can be identified in the sequence listing by translation of the disclosed nucleotide sequences. The mature form of such A2M variants can be obtained by expression of a full-length polynucleotide in a suitable mammalian cell or other host cell. The sequence of the mature form of the A2M variants can be also determinable from the amino acid sequence of the full-length form. Where A2M variants of the present invention are membrane bound, soluble forms of the A2M variants are also provided. In such forms, part or all of the regions causing the A2M variants to be membrane bound are deleted so that the A2M variants are fully secreted from the cell in which it can be expressed. A2M variant compositions of the present invention can further comprise an acceptable carrier, such as a hydrophilic, e.g., pharmaceutically acceptable, carrier.

Variant A2M Polynucleotide Compositions

As used herein, "A2M polynucleotide," when used with reference to SEQ ID NOs: 1 or 2, means the polynucleotide sequence of SEQ ID NO: 1 or 2, or fragments thereof, as well as any nucleic acid variants which include one or more insertions, deletions, mutations, or a combination thereof. The insertions, deletions, and mutations are preferably within the polynucleotide sequence encoding the bait region of the A2M protein. Similarly, "A2M cDNA", "A2M coding sequence" or "A2M coding nucleic acid", when used with reference to SEQ ID NOs: 1 or 2, means the nucleic acid sequences of SEQ ID NOs: 1 or 2, or fragments thereof, as well as nucleic acid variants which include one or more mutations, insertions, deletions, or a combination thereof. The A2M polynucleotides, or fragments thereof, can be manipulated using conventional techniques in molecular biology so as to create variant A2M recombinant polynucleotide constructs, encoding the variant A2M polypeptides that express variant A2M polypeptides. Variant A2M polynucleotides include nucleotide sequences having at least 99%, 98%, 97%, 96%, 95%, 94%, 93%, 92%, 91%, 90%, 89%, 88%, 87%, 86%, or 85% sequence identity to SEQ ID NOs: 1 and 2. A2M coding sequences includes nucleotide sequences having at least 99%, 98%, 97%, 96%, 95%, 94%, 93%, 92%, 91%, 90%, 89%, 88%, 87%, 86%, or 85% sequence identity to any one of SEQ ID NOs: 1 and 2.

In one aspect, provided herein is a variant A2M polynucleotide nucleotide composition. Numerous polynucleotide sequences encoding wild-type A2M proteins from various organisms have been determined Any A2M DNA sequence identified can be subsequently obtained by chemical synthesis and/or a polymerase chain reaction (PCR) technique such as overlap extension method. For a short sequence, completely de novo synthesis may be sufficient; whereas further isolation of full length coding sequence from a human cDNA or genomic library using a synthetic probe may be necessary to obtain a larger gene. Alternatively, a nucleic acid sequence encoding an A2M polypeptide can be isolated from a human cDNA or genomic DNA library using standard cloning techniques such as polymerase chain reaction (PCR), where homology-based primers can often be derived from a known nucleic acid sequence encoding an A2M polypeptide.

cDNA libraries suitable for obtaining a coding sequence for a wild-type A2M polypeptide can be obtained commercially or can be constructed. The general methods of isolating mRNA, making cDNA by reverse transcription, ligating cDNA into a recombinant vector, transfecting into a recombinant host for propagation, screening, and cloning are well known. Upon obtaining an amplified segment of nucleotide sequence by PCR, the segment can be further used as a probe to isolate the full-length polynucleotide sequence encoding the wild-type A2M protein from the cDNA library. A similar procedure can be followed to obtain a full length sequence encoding a wild-type A2M protein from a human genomic library. Human genomic libraries are commercially available or can be constructed according to various art-recognized methods. In general, to construct a genomic library, the DNA is first extracted from a tissue where a peptide is likely found. The DNA is then either mechanically sheared or enzymatically digested to yield fragments of about 12-20 kb in length. The fragments are subsequently separated by gradient centrifugation from polynucleotide fragments of undesired sizes and are inserted in bacteriophage λ vectors. These vectors and phages are packaged in vitro. Recombinant phages are analyzed by plaque hybridization.

Based on sequence homology, degenerate oligonucleotides can be designed as primer sets and PCR can be performed under suitable conditions to amplify a segment of nucleotide sequence from a cDNA or genomic library. Using the amplified segment as a probe, the full-length nucleic acid encoding a wild-type A2M protein can be obtained Upon acquiring a nucleic acid sequence encoding a wild-type A2M protein, the coding sequence can be subcloned into a vector, for instance, an expression vector, so that a recombinant wild-type A2M protein can be expressed mutated into a variant A2M polypeptide of the invention produced from the resulting construct. Further modifications to the wild-type A2M protein coding sequence, for example, nucleotide substitutions, may be subsequently made to alter the bait region of the A2M protein.

The present invention further provides isolated polypeptides encoded by the polynucleotides, or fragments thereof, of the present invention or by degenerate variants of the polynucleotides, or fragments thereof, of the present invention. Preferred polynucleotides, or fragments thereof, of the present invention are the ORFs that encode A2M variants.

A variant A2M polynucleotide can be made by mutating the polynucleotide sequence encoding a wild-type A2M protein. This can be achieved by using any known mutagenesis methods. Exemplary modifications to a wild-type A2M polynucleotide for accepting variant bait regions described herein include those in SEQ ID NO 2. Exemplary modifications to an A2M nucleotide include inserting or substituting a nucleotide sequence encoding a variant bait region of SEQ ID NO 5-66 into the wild-type A2M polynucleotide sequence of SEQ ID NO: 1 and the variant A2M acceptor polynucleotide sequence of SEQ ID NO 2. Mutagenesis procedures can be used separately or in combination to produce variants of a set of nucleic acids, and hence variants of encoded polypeptides. Kits for mutagenesis are commercially available.

In one aspect, provided herein are methods of making any of the variant A2M polynucleotides. A method of making a variant A2M polynucleotide can comprise inserting or substituting a variant bait region into a wild-type A2M polynucleotide sequence or substantially similar sequence. The substantially similar sequence can be SEQ ID NO 2. One aspect of the invention is a method for making a variant A2M polynucleotide comprising: a) providing a vector containing a variant A2M polynucleotide comprising a sequence of SEQ ID NO 2; b) digesting the vector containing a variant A2M polynucleotide with restriction endonucleases to form a linear vector; c) ligating one end of the one or more polynucleotides encoding one or more of the non-natural bait regions of SEQ ID NOs 5-66 to one end of the linear vector; and d) ligating the other end of the one or more polynucleotides encoding one or more of the non-natural bait regions of SEQ ID NOs 5-66 to the other end of the linear vector, thereby forming a vector containing a variant A2M polynucleotide comprising the non-natural bait regions of SEQ ID NOs 5-66.

Protein Production

A variety of methodologies known in the art can be utilized to obtain any one of the isolated A2M variant proteins of the present invention. At the simplest level, the amino acid sequence can be synthesized using commercially available peptide synthesizers. Such polypeptides can be synthesized with or without a methionine on the amino terminus Chemically synthesized polypeptides can be oxidized using methods set forth in these references to form disulfide bridges. The synthetically constructed A2M variant sequences, by virtue of sharing primary, secondary or tertiary structural and/or conformational characteristics with A2M variants can possess biological properties in common therewith, including protease inhibitory activity. This technique can be particularly useful in producing small peptides and fragments of larger polypeptides. Fragments are useful, for example, in generating antibodies against the A2M variants. Thus, they can be employed as biologically active or immunological substitutes for natural, purified A2M variants in screening of therapeutic compounds and in immunological processes for the development of antibodies.

The A2M variant polypeptides of the present invention can alternatively be purified from cells which have been altered to express the desired A2M variant. As used herein, a cell can be said to be altered to express a desired A2M variant polypeptide or protein when the cell, through genetic manipulation, can be made to produce a A2M variant polypeptide which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the A2M variant polypeptides of the present invention.

A variant A2M polypeptide can be a recombinant protein, or fragments thereof, and can be produced in a host cell or in vitro system. Recombinant polypeptides and protein promoters can be inserted in such a manner that it can be operatively produced in a host cell, for example, a bacterial culture or lower eukaryotes such as yeast or insects or in prokaryotes or any host know in the art. A variant A2M recombinant protein can be produced in a bacterium, yeast, fungi, insect, or mammalian host cell, or a cell free system. For example, a variant A2M polypeptide can be produced in *Escherichia coli, Bacillus subtilis, Salmonella typhimurium, Corynebacterium, Saccharomyces cerevisiae, Schizosaccharomyces pombe Kluyveromyces* strains, *Candida, Pichia pastoris*, baculovirus-infected insect cells, or mammalian cells such as COS cells, BHK cells, 293 cells, 3T3 cells, NS0 hybridoma cells, baby hamster kidney (BHK) cells, PER.C6™ human cells, HEK293 cells or *Cricetulus griseus* (CHO) cells. A variant A2M polypeptide can be produced by transient expression, stable cell lines, BacMam-mediated transient transduction, or cell-free protein production.

The variant A2M polypeptides can also be produced by operably linking the isolated variant A2M polynucleotides to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBat™ kit), and such methods are well known in the art, as described in Summers and Smith, Texas Agricultural Experiment Station Bulletin No. 1555 (1987), incorporated herein by reference.

In mammalian host cells, a number of viral-based expression systems can be utilized. In cases where an adenovirus is used as an expression vector, the variant A2M nucleotide sequence of interest can be ligated to an adenovirus transcription/translation control complex, for example, the late promoter and tripartite leader sequence. This chimeric gene can then be inserted in the adenovirus genome by in vitro or in vivo recombination. Insertion in a non-essential region of the viral genome can result in a recombinant virus that is viable and capable of expressing the variant A2M gene product in infected hosts. Specific initiation signals can also be required for efficient translation of inserted nucleotide sequences. These signals include the ATG initiation codon and adjacent sequences. In cases where an entire variant A2M gene or cDNA, including its own initiation codon and adjacent sequences, is inserted into the appropriate expression vector, for example, a pJ608 mammalian expression vector no additional translational control signals are needed. Exogenous translational control signals, such as the ATG initiation codon, can be provided.

Host cells can be genetically engineered to contain the variant A2M polynucleotides of the invention. For example, such host cells can contain variant A2M polynucleotides introduced into the host cell using known transformation, transfection or infection methods. As used herein, a cell capable of expressing a variant A2M polynucleotide can be "transformed." The variant A2M polypeptides of the invention can be prepared by culturing transformed host cells under culture conditions suitable to express the recombinant protein. Any procedure for introducing foreign nucleotide sequences into host cells may be used. Non-limiting examples include the use of calcium phosphate transfection, transfection, DEAE, dextran-mediated transfection, microinjection, lipofection, polybrene, protoplast fusion, electroporation (Davis, L. et al., *Basic Methods in Molecular Biology* (1986)), liposomes, microinjection, plasma vectors, viral vectors, and any other well-known methods for introducing cloned genomic DNA, cDNA, synthetic DNA, or other foreign genetic material into a host cell. A genetic engineering procedure capable of successfully introducing at least one gene into the host cell capable of expressing the variant A2M polynucleotide can be used.

The present invention still further provides host cells engineered to express the variant A2M polynucleotides of the invention, wherein the variant A2M polynucleotides are operative with a regulatory sequence heterologous to the host cell which drives expression of the variant A2M polynucleotides in the cell. Knowledge of A2M-like DNA allows for modification of cells to permit, or increase, expression of A2M-like polypeptide. Cells can be modified, for example, by homologous recombination, to provide increased variant A2M polypeptide expression by replacing, in whole or in part, the naturally occurring A2M derived from the SV40 viral genome, for example, SV40 macroglobulin-like promoter with all or part of a heterologous promoter so that the cells' variant A2M sites can be used to provide the required non-transcribed polypeptide and can be expressed at higher levels.

For long-term, high-yield production of recombinant variant A2M polypeptides, stable expression is preferred. For example, cell lines that stably express the variant A2M sequences described herein can be engineered. Rather than using expression vectors that contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells are allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn are cloned and expanded into cell lines. This method is advantageously used to engineer cell lines which express the variant A2M gene product. Such engineered cell lines are particularly useful in screening and evaluation of compounds that affect the endogenous activity of the variant A2M gene product. A number of selection systems can be used, including but not limited to the herpes simplex virus thymidine kinase, hypoxanthine-guanine phosphoribosyltransferase, and adenine phosphoribosyltransferase genes can be employed in tk⁻, hgprt⁻ or aprt⁻ cells, respectively. Also, antimetabolite resistance can be used as the basis of selection for the following genes: dhfr, which confers resistance to methotrexate; gpt, which confers resistance to mycophenolic acid; neo, which confers resistance to the aminoglycoside G-418; and hygro, which confers resistance to hygromycin.

Variant A2M polynucleotide sequences can be engineered so as to modify processing or expression of the protein. For example, and not by way of limitation, the variant A2M polynucleotides can be combined with a promoter sequence and/or ribosome binding site, or a signal sequence can be inserted upstream of variant A2M polynucleotide sequences to permit secretion of the variant A2M polypeptide and thereby facilitate harvesting or bioavailability. Additionally, a variant A2M polynucleotide can be mutated in vitro or in vivo, to create and/or destroy translation, initiation, and/or termination sequences, or to create variations in coding regions and/or form new restriction sites or destroy preexisting ones, or to facilitate further in vitro modification. Any technique for mutagenesis known in the art can be used, including but not limited to, in vitro site-directed mutagenesis.

Further, nucleic acids encoding other proteins or domains of other proteins can be joined to nucleic acids encoding variant A2M polypeptides or fragments thereof so as to create a fusion protein. Nucleotides encoding fusion proteins can include, but are not limited to, a full length variant or wild-type A2M protein, a truncated variant or wild-type A2M protein or a peptide fragment of a variant or wild type A2M protein fused to an unrelated protein or peptide, such as for example, a transmembrane sequence, which anchors the A2M peptide fragment to the cell membrane; an Ig Fc domain which increases the stability and half-life of the resulting fusion protein; maltose binding protein (MBP), glutathione-S-transferase (GST) or thioredoxin (TRX), a His tag, an enzyme, fluorescent protein, luminescent protein which can be used as a marker, for example, an A2M-Green Fluorescent Protein fusion protein. The fusion proteins can be used for affinity purification.

The variant A2M nucleic acids and polypeptides can also be expressed in organisms so as to create a transgenic organism. Desirable transgenic plant systems having one or more of these sequences include Arabadopsis, Maize, and *Chlamydomonas*. Desirable insect systems having one or more of the variant A2M polynucleotides and/or polypeptides include, for example, *D. melanogaster* and *C. elegans* Animals of any species, including, but not limited to, amphibians, reptiles, birds, mice, rats, rabbits, guinea pigs, pigs, micro-pigs, goats, dogs, cats, and non-human primates, e.g., baboons, monkeys, and chimpanzees can be used to generate variant A2M containing transgenic animals. Transgenic organisms desirably exhibit germline transfer of variant A2M nucleic acids and polypeptides described herein.

A variety of methodologies known in the art can be utilized to obtain any one of the isolated polypeptides or proteins of the present invention. At the simplest level, the amino acid sequence can be synthesized using commercially available peptide synthesizers. The synthetically constructed protein sequences, by virtue of sharing primary, secondary or tertiary structural and/or conformational characteristics with proteins can possess biological properties in common therewith, including protein activity. This technique can be particularly useful in producing small peptides and fragments of larger polypeptides. Fragments are useful, for example, in generating antibodies against the native polypeptide. Thus, they can be employed as biologically active or immunological substitutes for natural, purified proteins in screening of therapeutic compounds and in immunological processes for the development of antibodies. The polypeptides and proteins of the present invention can alternatively be purified from cells which have been altered to express the desired polypeptide or protein. As used herein, a cell can be said to be altered to express a desired polypeptide or protein when the cell, through genetic manipulation, can be made to produce a polypeptide or protein which it normally does not produce or which the cell normally produces at a lower level. One skilled in the art can readily adapt procedures for introducing and expressing either recombinant or synthetic sequences into eukaryotic or prokaryotic cells in order to generate a cell which produces one of the polypeptides or proteins of the present invention.

The invention also relates to methods for producing a polypeptide comprising growing a culture of host cells in a suitable culture medium, and purifying the protein from the cells or the culture in which the cells are grown. For example, the methods can include a process for producing a polypeptide in which a host cell containing a suitable expression vector that includes a polynucleotide of the invention can be cultured under conditions that allow expression of the encoded polypeptide. The polypeptide can be recovered from the culture, conveniently from the culture medium, or from a lysate prepared from the host cells and further purified. Preferred embodiments include those in which the protein produced by such process can be a full length or mature form of the protein, such as A2M. In an alternative method, the polypeptide or protein can be purified from bacterial cells which naturally produce the polypeptide or protein. One skilled in the art can readily follow known methods for isolating polypeptides and proteins in order to obtain one of the isolated polypeptides or proteins of the present invention. These include, but are not limited to, immunochromatography, HPLC, size-exclusion chromatography, ion-exchange chromatography, and immuno-affinity chromatography. See, e.g., Scopes, *Protein Purification: Principles and Practice*, Springer-Verlag (1994); Sambrook, et al., in Molecular Cloning: A *Laboratory Manual*; Ausubel et al., *Current Protocols in Molecular Biology*. Polypeptide fragments that retain biological or immunological activity include fragments comprising greater than about 100 amino acids, or greater than about 200 amino acids, and fragments that encode specific protein domains. The purified polypeptides can be used in in vitro binding assays which are well known in the art to identify molecules which bind to the polypeptides. These molecules include but are not limited to, for example, small molecules, molecules from combinatorial libraries, antibodies or other proteins. The molecules identified in a binding assay can then be tested for antagonist or agonist activity in in vivo tissue culture or animal models that are well known in the art. In brief, the molecules can be titrated into a plurality of cell cultures or animals and then tested for either cell or animal death or prolonged survival of the animal or cells.

The resulting expressed variant A2M polypeptides can then be purified from a culture, for example, from culture medium or cell extracts, using known purification processes, such as affinity chromatography, gel filtration, and ion exchange chromatography. The purification of the variant A2M polypeptides can also include an affinity column containing agents which will bind to the protein; one or more column steps over such affinity resins as concanavalin A-agarose, heparin-Toyopearl™ or Cibacron blue 3GA Sepharose™; one or more steps involving hydrophobic interaction chromatography using such resins as phenyl ether, butyl ether, or propyl ether; or immunoaffinity chromatography. Alternatively, the protein of the invention can also be expressed in a form which will facilitate purification. For example, a protein can be expressed as a fusion protein, such as those of maltose binding protein (MBP), glutathione-S-transferase (GST) or thioredoxin (TRX), or as a His tag. Kits for expression and purification of such fusion proteins are commercially available from New England BioLab (Beverly, Mass.), Pharmacia (Piscataway, N.J.) and Invitrogen, respectively. The protein can also be tagged with an epitope and subsequently purified by using a specific antibody directed to such epitope. One such epitope ("FLAG®") is commercially available from Kodak (New Haven, Conn.). Finally, one or more reverse-phase high performance liquid chromatography (RP-HPLC) steps employing hydrophobic RP-HPLC media, for example, silica gel having pendant methyl or other aliphatic groups, can be employed to further purify the protein. Any combination of the foregoing purification procedures can also be employed to provide a substantially homogeneous isolated or purified recombinant variant A2M polypeptide. The variant A2M polypeptides purified can be substantially free of other mammalian proteins and can be defined in accordance with the present invention as an "isolated protein."

Agents for Inhibition of FAC Formation and Treatment of Chronic Wounds

Also provided herein are methods to inhibit the one or more steps of the fibronectin-aggrecan complex formation cycle (FACC) in a human with a condition or disease, such as a chronic wound. An agent can be administered to a subject with a condition or disease. An agent can be wild-type A2M protein or a composition described herein, such as a purified form of A2M, or an A2M enriched sample, or a variant A2M polypeptide as described herein. An agent can be an agent that is not a purified form of A2M concentrated from autologous blood. An agent can be an inhibitor or an antagonist. An inhibitor or antagonist can be a compound or composition that directly or indirectly, partially or totally blocks activity, decreases, prevents, delays activation, inactivates, desensitizes, or down regulates the activity or expression of a target biomarker. Antagonists can be, for example, polypeptides, such as antibodies, and soluble receptors, as well as nucleic acids such as siRNA or antisense RNA, as well as naturally occurring and synthetic biomarker antagonists, including small chemical molecules.

An agent can be compound that has a pharmacological activity. Agents can include compositions described herein or compounds that are known drugs, compounds for which pharmacological activity has been identified but that are undergoing further therapeutic evaluation, and compounds that are members of collections and libraries that are to be screened for a pharmacological activity. An agent can be organic or inorganic chemical such a peptide, protein, including antibodies, small molecules and natural products.

An agent can comprise an antibody. An antibody can be a polypeptide comprising a framework region from an immunoglobulin gene or fragments thereof that specifically binds and recognizes an antigen. The recognized immunoglobulin genes can include the kappa, lambda, alpha, gamma, delta, epsilon, and mu constant region genes, as well as the myriad immunoglobulin variable region genes. Light chains can be classified as either kappa or lambda. Heavy chains can be classified as gamma, mu, alpha, delta, or epsilon, which in turn define the immunoglobulin classes, IgG, IgM, IgA, IgD and IgE, respectively. An antibody can encompass plural referents unless the context clearly indicates otherwise. In some instances a plurality of the antibodies can belong to the same antibody species, e.g., in the case of monoclonal antibodies, while in some cases different antibodies species are encompassed the by phrase "an antibody", e.g., a polyclonal antibodies. An exemplary immunoglobulin (antibody) structural unit can comprise a tetramer. Each tetramer can be composed of two identical pairs of polypeptide chains, each pair having one "light" (about 25 kDa) and one "heavy" chain (about 50-70 kDa). The N-terminus of each chain can define a variable region of about 100 to 110 or more amino acids primarily responsible for antigen recognition. The terms variable light chain ($V_l$) and variable heavy chain (VH) can refer to these light and heavy chains respectively. Antibodies can exist, e.g., as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer can be a Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. An antibody can also be an antibody fragment either produced by the modification of whole antibodies, or those synthesized de novo using recombinant DNA methodologies (e.g., single chain Fv) or those identified using phage display libraries (see, e.g., McCafferty et al., Nature 348:552-554 (1990)). When referring to treatment methods, antibodies that are chimeric, human, humanized or otherwise specific to the species to be treated can be used.

An agent can be an antibody that binds to the FAC but not to the individual components of the complex separately. An agent can comprise an antibody that binds to aggrecan or any variation thereof, thereby inhibiting formation of the FAC complex. An agent can comprise an antibody, such as a monoclonal antibody, that binds to aggrecan G3 lectin domain. The antibody can bind to aggrecan G3 and prevent the formation of FAC and inflammation. An agent can comprise an antibody that binds to fibronectin or any variant thereof, thereby inhibiting formation of the FAC complex. An agent can comprise an antibody that binds to a PAMP receptor recognition domain of aggrecan, a DAMP receptor recognition domain of aggrecan, or both, thereby inhibiting activation of monocytes and other cells. Other cells can be macrophages, fibroblast, T-cells, B-cells, neutrophils, platelets, synoviocytes, chondrocytes and other cells involved in inflammation. An agent can comprise an antibody that binds to a PAMP receptor recognition domain of fibronectin, a DAMP receptor recognition domain of fibronectin, or both, thereby inhibiting activation of monocytes and other cells.

An agent that prevents or inhibits FAC formation can be a recombinant aggrecan G3 domain, wherein the domain contains the aggrecan G3 lectin domain and competitively binds to fibronectin; wherein the domain lacks the Pathogen Associated Molecular Patterns (PAMP) and the Damage Associated Molecular Patterns (DAMP) receptor recognition domains Recombinant aggrecan G3 lectin domain can competitively bind to fibronectin. A recombinant aggrecan G3 domain can lack the cell activation domain and can slow down, inhibit, or prevent FAC formation and inflammation.

An agent that prevents or inhibits FAC formation can be a wild-type A2M protein or a recombinant fibronectin fragment, wherein the fragment comprises a G3 binding domain and binds to aggrecan, wherein the G3 binding domain the PAMP, receptor recognition domain, the DAMP receptor recognition domain, or both. A recombinant fibronectin fragment can competitively bind to aggrecan.

An agent that prevents or inhibits FAC formation can be a soluble form of the PAMP receptor or DAMP receptor that binds to the PAMP domain of aggrecan G3, the DAMP domain of aggrecan G3, or both, thereby inhibiting activation of monocytes and other cells to produce proinflammatory cytokines, chemokines, proteases, or any combination thereof.

An agent that prevents or inhibits FAC formation can be a soluble form of the PAMP receptor or DAMP receptor that binds to the PAMP domain of fibronectin, the DAMP domain of fibronectin, or both, thereby inhibiting activation of monocytes and other cells to produce proinflammatory cytokines, chemokines, proteases, or any combination thereof. An agent can be an inhibitor of fibroblast cells and can inhibit production of increased levels fibronectin, recruitment of other fibroblast cells, or both.

An agent that prevents or inhibits FAC formation can be a small molecule. A small molecule can be identified using one or more high-throughput screening methods. A small molecule can inhibit FAC formation, inhibit activation of monocytes; inhibit increased production of fibronectin; inhibit recruitment of fibroblast cells; or bind to the DAMP domain of fibronectin, bind to the DAMP domain of aggrecan G3, bind to the PAMP domain of fibronectin, or bind to the PAMP domain of aggrecan G3, thereby inhibiting activation of cells to produce proinflammatory cytokines, chemokines, proteases, or any combination thereof. In A small molecule can inhibit FAC formation by competitively binding to fibronectin or aggrecan. In some embodiments, the small molecule binds to the FAC complex and resulting in dissociation or degradation of the FAC complex Inhibiting the formation of the fibronectin-aggrecan complex (FAC) can comprise inhibiting one or more steps in FAC formation or a step in the FAC formation cycle (FACC).

One or more steps in FAC formation or the FACC can comprise production of fibronectin in the ECM, production of proteases and metalloproteases, production of inflammatory cytokines and chemokines, degradation of aggrecan in cartilage, or increasing the aggrecan G3 domain fragment concentration.

In any of the methods herein, an agent can be a medicament used to treat chronic wounds such as pressure ulcers, venous ulcers, stasis ulcers, venous stasis ulcers, diabetic foot ulcers, arterial insufficiency ulcers or any combination thereof. Thus, one can administer to a subject, along with a composition comprising an elevated concentration of A2M, a variant A2M polypeptide, or a wild-type A2M protein, an effective amount of one or more other medicament (where a composition comprising an elevated concentration of A2M or variant A2M polynucleotide (e.g., compositions described herein) can be a first medicament). The one or more other medicaments can include, for example, an immunosuppressive agent, a cytokine antagonist such as a cytokine antibody, an integrin antagonist (e.g., antibody), a corticosteroid, or any combination thereof. The type of such second medicament can depend on various factors, including the type of chronic wound, extent of the wound, the severity of the wound, the condition and age of the subject, the type and dose of the first medicament employed, etc. Examples of such additional medicaments include an immunosuppressive agent (such as mitoxantrone (NOVANTRONE®), MTX, cyclophosphamide, chlorambucil, leflunomide, and azathioprine), intravenous immunoglobulin (gamma globulin), lymphocyte-depleting therapy (e.g., mitoxantrone, cyclophosphamide, CAMPATH™ antibodies, anti-CD4, cladribine, a polypeptide construct with at least two domains comprising a de-immunized, autoreactive antigen or its fragment that can be specifically recognized by the Ig receptors of autoreactive B-cells (WO 2003/68822), total body irradiation, and bone marrow transplantation), integrin antagonist or antibody (e.g., an LFA-1 antibody such as efalizumab/RAPTIVA® commercially available from Genentech, or an alpha 4 integrin antibody such as natalizumab/ANTEGREN® available from Biogen, or others as noted above), drugs that treat symptoms secondary or related to chronic wound healing such as those noted herein, steroids such as corticosteroid (e.g., prednisolone, methylprednisolone such as SOLU-MEDROL™ methylprednisolone sodium succinate for injection, prednisone such as low-dose prednisone, dexamethasone, or glucocorticoid, e.g., via injection, including systemic corticosteroid therapy), nonlymphocyte-depleting immunosuppressive therapy (e.g., MMF or cyclosporine), a TNF-$\alpha$ inhibitor such as an antibody to TNF-$\alpha$ or its receptor or TNFR-Ig (e.g., etanercept), DMARD, NSAID, plasmapheresis or plasma exchange, trimethoprim-sulfamethoxazole (BACTRIM™, SEPTRA™), MMF, H2-blockers or proton-pump inhibitors (during the use of potentially ulcerogenic immunosuppressive therapy), levothyroxine, cyclosporin A (e.g., SANDIMMUNE®), somatostatin analogue, a DMARD or NSAID, cytokine 25 antagonist such as antibody, anti-metabolite, immunosuppressive agent, rehabilitative surgery, radioiodine, thyroidectomy, anti-IL-6 receptor antagonist/antibody (e.g., ACTEMRA™ (tocilizumab)), or another B-cell antagonist such as BR3-Fc, TACI-Ig, anti-BR3 antibody, anti-CD40 receptor or anti-CD40 ligand (CD154), agent blocking CD4O-CD40 ligand, epratuzumab (anti-CD22 antibody), lumiliximab (anti-CD23 30 antibody), or anti-CD20 antibody such as rituximab or 2H7 antibody. Known inhibitors such as chelators of known aggrecanases or MMP's can be administered to a subject in need thereof in amount effective to inhibit or slow down the release of aggrecan fragments which in effect will reduce or eliminate the formation of the fibronectin aggrecan complexes thereby giving relief to the subject from the chronic wound.

Diagnostic Methods

Methods for detecting biomarkers, such as a wild-type A2M protein, to identify sites in the subject that are a source of chronic wounds can be used to diagnose, or assist in the diagnosis be of, subjects with chronic wounds related to the anatomic structure and physiologic function of the wound. For example, the identification of fibronectin-aggrecan complexes in a biological sample, such as a biological sample from the wound can be used to diagnose, or assist in the diagnosis of a chronic wound.

The amount of a biomarker, such as A2M, that can indicate a specific location in the subject as a source of a chronic wound for a particular subject can depend on numerous factors, including, but not limited to, the age, sex, medical history, etc., of the patient, the site that the biological sample was extracted from, and the assay format used to detect the biomarker. In some embodiments, the level and/or concentration of A2M in a biological sample may be quantified or directly compared with a control sample. In some embodiments, the level and/or concentration of A2M in a biological sample may not be quantified or directly compared with a control sample, but can rather be detected relative to a "diagnostic absence" or "diagnostic presence" of A2M.

A "diagnostic absence" can refer to an amount and/or concentration of A2M in a biological that indicates the absence or likelihood of the absence of a chronic wound or inflammation causing pathology or injury at the location from which the sample was taken. A diagnostic absence can be detectable in a simple assay giving a positive or negative result. A positive or negative result can be determined based on the amount and/or concentration of A2M in the biological sample. Detection of a level and/or concentration of A2M corresponding to a diagnostic absence of A2M indicates the absence of a chronic wound-causing pathology or injury at the location from which the sample was taken. In some embodiments, a diagnostic absence of A2M can be a concentration of A2M in a biological sample from about 0-30 µg/ml. For example, a diagnostic absence of A2M can be a concentration of A2M in a biological sample from about 0-30 µg/ml, 0-25 µg/ml, 0-20 µg/ml, 0-15 µg/ml, 0-10 µg/ml, 0-5 µg/ml, 5-30 µg/ml, 5-25 µg/ml, 5-20 µg/ml, 5-15 µg/ml, 5-10 µg/ml, 10-30 µg/ml, 10-25 µg/ml, 10-20 µg/ml, 10-15 µg/ml, 15-30 µg/ml, 15-25 µg/ml, 15-20 µg/ml, 20-30 µg/ml, or 20-25 µg/ml. In some embodiments, a diagnostic absence of A2M can be a concentration of A2M in a biological sample from about 0-40 µg/ml. For example, a diagnostic absence of A2M can be a concentration of A2M in a biological sample from about 0-40 µg/ml, 5-40 µg/ml, 10-40 µg/ml, 15-40 µg/ml, 20-40 µg/ml, 25-40 µg/ml, 30-40 µg/ml, or 35-40 µg/ml.

In some embodiments, a diagnostic absence of A2M in a biological sample can be at least about 1.5, 2, 3, 4, 5, 6, 7, 8, 9, 10, 20, 30, 40, 50, 60, 70, 80, 90, 100, 200, 500, 1000 or more fold lower than a control sample.

A "diagnostic presence" can refer to an amount and/or concentration of A2M in a biological that indicates the presence or likelihood of the presence of a chronic wound or inflammation causing pathology or injury at the location from which the sample was taken. A diagnostic presence can be detectable in a simple assay giving a positive or negative result. A positive or negative result can be determined based on the amount and/or concentration of A2M in the biological sample. Detection of a level and/or concentration of A2M corresponding to a diagnostic presence of A2M indicates the presence of a chronic wound-causing pathology or injury at the location from which the sample was taken. In some embodiments, a diagnostic presence of A2M can be a concentration of A2M in a biological sample of at least about 31 µg/ml, 32 µg/ml, 33 µg/ml, 34 µg/ml, 35 µg/ml, 36 µg/ml, 37 µg/ml, 38 µg/ml, or 39 µg/ml. In some embodiments, a diagnostic presence of A2M can be a concentration of A2M in a biological sample of at least about 40 µg/ml. For example, a diagnostic presence of A2M can be a concentration of A2M in a biological sample of at least about 45 µg/ml, 50 µg/ml, 55 µg/ml, 60 µg/ml, 65 µg/ml, 70 µg/ml, 75 µg/ml, 80 µg/ml, 85 µg/ml, 90 µg/ml, 95 µg/ml, 100 µg/ml, 110 µg/ml, 120 µg/ml, 130 µg/ml, 140 µg/ml, 145 µg/ml, 150 µg/ml, 160 µg/ml, 170 µg/ml, 180 µg/ml, 190 µg/ml, 200 µg/ml, 220 µg/ml, 240 µg/ml, 250 µg/ml, 260 µg/ml, 280 µg/ml, 300 µg/ml, 320 µg/ml, 340 µg/ml, 360 µg/ml, 380 µg/ml, 400 µg/ml, 420 µg/ml, 440 µg/ml, 460 µg/ml, 480 µg/ml, 500 µg/ml, or more.

In some embodiments, a diagnostic presence of A2M can be a concentration of A2M in a biological sample from about 40-500 µg/ml. For example, a diagnostic presence of A2M can be a concentration of A2M in a biological sample from about 50-500 µg/ml, 60-500 µg/ml, 70-500 µg/ml, 80-500 µg/ml, 90-500 µg/ml, 100-500 µg/ml, 125-500 µg/ml, 150-500 µg/ml, 175-500, 200-500 µg/ml, 250-500 µg/ml, 300-500 µg/ml, 400-500 µg/ml, 50-60 µg/ml, 50-70 µg/ml, 50-80 µg/ml, 50-90 µg/ml, 50-100 µg/ml, 50-125 µg/ml, 50-150 µg/ml, 50-175 µg/ml, 50-200 µg/ml, 50-250 µg/ml, 50-300 µg/ml, 50-400 µg/ml, 60-70 µg/ml, 60-80 µg/ml, 60-90 µg/ml, 60-100 µg/ml, 60-125 µg/ml, 60-150 µg/ml, 60-175 µg/ml, 60-200 µg/ml, 60-250 µg/ml, 60-300 µg/ml, 60-400 µg/ml, 70-80 µg/ml, 70-90 µg/ml, 70-100 µg/ml, 70-125 µg/ml, 70-150 µg/ml, 70-175 µg/ml, 70-200 µg/ml, 70-250 µg/ml, 70-300 µg/ml, 70-400 µg/ml, 80-90 µg/ml, 80-100 µg/ml, 80-125 µg/ml, 80-150 µg/ml, 80-175 µg/ml, 80-200 µg/ml, 80-250 µg/ml, 80-300 µg/ml, 80-400 µg/ml, 90-100 µg/ml, 90-125 µg/ml, 90-150 µg/ml, 90-175 µg/ml, 90-200 µg/ml, 90-250 µg/ml, 90-300 µg/ml, 90-400 µg/ml, 100-125 µg/ml, 100-150 µg/ml, 100-175 µg/ml, 100-200 µg/ml, 100-250 µg/ml, 100-300 µg/ml, 100-400 µg/ml, 125-150 µg/ml, 125-175 µg/ml, 125-200 µg/ml, 125-250 µg/ml, 125-300 µg/ml, 125-400 µg/ml, 150-175 µg/ml, 150-200 µg/ml, 150-250 µg/ml, 150-300 µg/ml, 150-400 µg/ml, 175-200 µg/ml, 175-250 µg/ml, 175-300 µg/ml, 175-400 µg/ml, 200-250 µg/ml, 200-300 µg/ml, 200-400 µg/ml, 250-300 µg/ml, 250-400 µg/ml, or 300-400 µg/ml.

In some embodiments, a diagnostic presence of A2M in a biological sample can be at least about 1.5, 2, 3, 4, 5, 6, 7, 8, 9, 10, 20, 30, 40, 50, 60, 70, 80, 90, 100, 200, 500, 1000 or more fold higher than a control sample.

The disclosed methods can be used regardless of whether A2M is normally present, or expected to be present, in a particular control sample. For example, A2M may not be detectable in certain normal wound samples using a particular assay, resulting in a complete absence of A2M complexes in a control biological sample. For example, A2M cannot be detectable in certain normal wound samples (such as, for example, in a synovial fluid sample) using a particular assay, resulting in a complete absence of A2M in a control biological sample. For such biological samples, a diagnostic presence can refer to any detectable amount of A2M using that same assay. In other instances, however, there can be a detectable level of A2M present in normal or control samples and a diagnostic absence represents a level that can be lower than the normal level, preferably representing a statistically significant decrease over the normal level.

Control samples can be samples that are taken from an individual or a group of individuals not experiencing inflammation or a chronic wound, such as pressure ulcers, venous ulcers, stasis ulcers, venous stasis ulcers, diabetic foot ulcers, arterial insufficiency ulcers or any combination thereof. Alternatively, control samples can be obtained from a source not suspected to be a source of a chronic wound or inflammation, such as a level of the wound not suspected to be a source of chronic wound. For example, in a subject experiencing a wound, the control sample can be obtained from an unaffected or asymptomatic region of the same patient. Control samples can be samples that are taken from an individual or a group of individuals not experiencing a chronic wound. Alternatively, control samples can be obtained from unaffected or asymptomatic wounds from the subject being tested.

The level of a biomarker, such as A2M, need not be quantified for a diagnostic absence or presence to be detected. Rather, any method of determining whether A2M is present at levels lower or higher than in a normal or control can be used. In addition, a diagnostic absence or presence does not refer to any absolute quantity of A2M, but rather to an amount that, depending on the biological sample, assay conditions, medical condition of the patient, etc., can be sufficient to distinguish the level in an affected patient from a normal or control patient.

The presence, absence or level of A2M present at a particular level within the wound can be used to diagnose, or assist in the diagnosis be of, a particular type of chronic wounds such as pressure ulcers, venous ulcers, stasis ulcers, venous stasis ulcers, diabetic foot ulcers, arterial insufficiency ulcers or any combination thereof. Additionally, or alternatively, the presence, absence, or level of A2M in a wound sample can be used to distinguish wounds that results from wound pathology or injury originating from another source, such as non-chronic-wound.

The presence, absence, or change over time in the level of A2M in a biological sample can be used to designate a patient as candidate for a particular treatment. A sample obtained from the patient can be analyzed for the presence or absence of A2M. The patient can be selected for treatment if A2M is not detected in the sample. The type of treatment can be then tailored to the severity of the condition as determined by the presence, absence, or level of A2M.

The level A2M present at a specific site can also be useful to determine a prognosis for the subject being tested. For example, the level of A2M present in a sample can indicate the extent of an acute injury to the subject and can assist a practitioner in determining to what extent successful repair or healing of the injury or pathology can be achieved.

Methods for Detecting A2M to Identify Wounds as Sites for Treating Chronic Wounds can be Used to Diagnose, or Assist in the Diagnosis of, Subjects Detection of A2M can be used alone, or in combination with other diagnostic approaches to diagnose chronic wounds. Exemplary diagnostic approaches include, but are not limited to, medical history and physical examination, x-ray radiography, MRI and intra-articular injection. The presence of A2M can however be used to diagnose injury and administer treatment at a particular location irrespective of whether injury was detectable by other methods, e.g., an MRI. The patient will typically be treated by administration of a therapeutic agent to the site of injury or pathology, i.e., the site of presence of A2M.

The diagnostic methods of the present invention can include determination of the expression levels of a set of nucleic acid molecules comprising polynucleotide sequences coding for a protein marker. The diagnostic methods of the present invention can include the determination of expression levels of a plurality (i.e., one or more, e.g., at least 2, at least 3, at least 4, at least 5, at least 6, at least 7, at least 8, at least 9, at least 10 or more) of polypeptides in a biological sample obtained from a subject. Determination of protein expression levels in the practice of the inventive methods can be performed by any suitable method (see, for example, E. Harlow and A. Lane, "Antibodies: A Laboratories Manual", 1988, Cold Spring Harbor Laboratory: Cold Spring Harbor, N.Y.).

The disclosed methods can also be used to assess the efficacy of a treatment or a course of treatment. For example, in a patient with wound testing positive for a diagnostic positive of A2M, such as wild-type A2M protein, indicative of a chronic wound, the efficacy of a chronic wound treatment can be assessed by monitoring, over time, the levels of A2M. A decrease in the levels of A2M in a biological sample taken from a patient following a treatment, compared to a level in a sample taken from the same patient before, or earlier in, the treatment, can indicate efficacious treatment. An increase or lack of change in the levels of A2M in a biological sample taken from a patient following a treatment, compared to a level in a sample taken from the same patient before, or earlier in, the treatment, can indicate a non-efficacious treatment.

Inflammation biomarkers for diagnostic methods can be A2M, chemokines, cytokines, fibronectin, or aggrecan polypeptides in any ratio, in addition to other inflammatory mediators, extracellular matrix molecules or their breakdown products, signal transduction mediators, proteases and their inhibitors, and neurotransmitter receptors including, but not limited to IL-6, Prostaglandin E2, NO, IFN gamma, 5HT, RANTES, MIP-1a, MCP-1, IL-1ra, TNF-$\alpha$, Procollagens, CTX II, ARGS, aggrecan fragments, fibronectin fragments, FAC, COMP, CS 846, chondroitin fragments, sRAGE, MMP-3, MMP-13 and other MMPs, ADAMTS-4, aggrecanases, NF-kappa-B, p38 MAP kinase, DR5/DcR2. The biomarkers can include full length polypeptides or can include fragments of polypeptides.

Any known method for detecting the presence of polypeptides in a biological sample can be used to qualitatively or quantitatively detect the presence of A2M in biological samples, such as chronic wound samples. Suitable methods include, but are not limited to, chromatographic methods, selective binding assays, mass spectrometry, spectrophotometry, or combinations thereof.

Exemplary binding assays include immunoassays, such as enzyme-linked immunosorbent assays Immunoassays can be used to qualitatively or quantitatively analyze a sample for the presence of A2M. A general overview of the applicable technology can be found in a number of readily available manuals, e.g., Harlow & Lane, Cold Spring Harbor Laboratory Press, Using Antibodies: A Laboratory Manual (1999).

The disclosed methods and kits can utilize selective binding partners of inflammation biomarkers to identify their presence or determine their levels in samples from the wound. The selective binding partners can be antibodies, or other biomolecules that specifically bind to A2M, or fragments or complexes thereof.

Monoclonal or polyclonal antibodies can be used. The antibodies can be any known in the art, including commercially available antibodies. It is well known to those of skill in the art that the type, source and other aspects of an antibody to be used can be a consideration to be made in light of the assay in which the antibody can be used. In some instances, antibodies that will recognize its antigen target (for instance, an epitope or multiple epitopes from A2M) on a Western blot might not be applicable to all ELISA or ELISpot assay and vice versa.

Antibodies, antibody fragments, or single chain antibodies to be used can be produced using techniques for producing monoclonal or polyclonal antibodies that are well known in the art (see, e.g., Coligan, Current Protocols in Immunology (1991); Harlow & Lane, supra; Goding, Monoclonal Antibodies: Principles and Practice (2d ed. 1986); and Kohler & Milstein, Nature 256: 495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., Science 246:1275-1281 (1989); Ward et al., Nature 341:544-546 (1989)).

A number of immunogens from A2M can be used to produce antibodies specifically reactive with A2M and fragments thereof. For example, a recombinant A2M or an antigenic fragment thereof, can be isolated using methods well known to those of skill in the art. Recombinant protein can be expressed in eukaryotic or prokaryotic cells. Recombinant protein can be the typically used immunogen for the production of monoclonal or polyclonal antibodies. Alternatively, synthetic peptides derived from the known sequences A2M and conjugated to a carrier protein can be used as an immunogen. Naturally-occurring protein can also be used either in pure or impure form. The product can be then injected into an animal capable of producing antibodies. Either monoclonal or polyclonal antibodies can be generated, for subsequent use in immunoassays to measure the protein.

Antibodies that specifically bind to complexes containing A2M can be used as specific binding partners.

Non-antibody polypeptides can be used as specific binding agents for the detection of A2M, or fragments or complexes thereof. A large number of proteins that specifically bind to A2M are known in the art. Exemplary proteins that can be used as selective binding partners of A2M include, but are not limited to soluble receptors, cytokines and growth factors that are known to bind A2M, modified proteases that can bind to A2M and not trigger the conformation change.

Once selective binding partners are available, each specific biomarker can be detected by a variety of selective binding assays, including immunoassay methods. For a review of immunological and immunoassay procedures, see Basic and Clinical Immunology (Stites & Terr eds., 7th ed. 1991). Moreover, the disclosed selective binding assays can be performed in any of several configurations. Several immunoassay configurations are reviewed extensively in Enzyme Immunoassay (Maggio, ed., 1980).

Methods for detecting the presence and/or measuring a level of A2M in a sample, can use specific binding partners A2M, or fragments or complexes thereof. The methods generally include contacting the sample with specific binding partner for A2M, or fragments or complexes thereof, purifying a desired fraction from the sample, and detecting binding between the specific binding partner and molecules of the sample.

Detection of specific binding of the specific binding partners with molecules of the sample, when compared to a suitable control, can be an indication that biomarkers are present in the sample. A variety of methods to detect specific protein interactions are known in the art and can be used in the method. Methods include competitive assays and non-competitive assays.

Suitable methods include, but are not limited to, Western blot, immunoprecipitation, ELISA and radio-immunoassays. Methods for performing these and other suitable assays are known in the art. In general, the specific binding partner used to detect the biomarker will be delectably labeled, either directly or indirectly. The chronic wound sample can be brought into contact with and immobilized on a solid support or carrier, such as a membrane (i.e. nitrocellulose) or polystyrene or magnetic beads that can be capable of immobilizing cells, cell particles, or soluble proteins. The support can then be washed with suitable buffers, followed by contacting with a detectably-labeled selective binding partner.

In specific binding assays, it can be desirable to minimize the amount of non-specific binding that occurs, particularly when the specific binding partner can be attached to a substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used. In addition to, or in place of proteinaceous material, various detergents and/or salt can be incorporated into the immunoassay to minimize non-specific interactions. Throughout the assays, incubation and/or washing steps can be required after each combination of reagents. Incubation and washing times will depend upon several factors, including the assay format, the affinity of the specific binding partner for the biomarker, the volume of solution, concentrations.

A positive control for an inflammation biomarker can be used in the detection assays, for example to calibrate the detection assay. A2M can be from different sources, for example from different species. A2M can be recombinant, natural or a combination thereof.

In general, protein expression levels can be determined by contacting a biological sample isolated from a subject with binding agents for one or more of the protein markers; detecting, in the sample, the levels of polypeptides that bind to the binding agents; and comparing the levels of polypeptides in the sample with the levels of polypeptides in a control sample. A binding agent can be an entity or composition such as a polypeptide or antibody that specifically binds to a protein marker. A binding agent can specifically bind to a polypeptide if it reacts and/or interacts at a detectable level with the polypeptide, but does not react and/or interact detectably with peptides containing unrelated sequences or sequences of different polypeptides.

The binding agent can be a ribosome, with or without a peptide component, an RNA molecule, or a polypeptide (e.g., a polypeptide that comprises a polypeptide sequence of a protein marker, a peptide variant thereof, or a non-peptide mimetic of such a sequence).

The binding agent can be an antibody specific for a protein marker of the invention. Suitable antibodies for use in the methods of the present invention include monoclonal and polyclonal antibodies, immunologically active fragments (e.g., Fab or (Fab)$_2$ fragments), antibody heavy chains, humanized antibodies, antibody light chains, and chimeric antibodies. Antibodies, including monoclonal and polyclonal antibodies, fragments and chimeras, can be prepared using methods known in the art (see, for example, R. G. Mage and E. Lamoyi, in "Monoclonal Antibody Production Techniques and Applications", 1987, Marcel Dekker, Inc.: New York, pp. 79-97; G. Kohler and C. Milstein, Nature, 1975, 256: 495-497; D. Kozbor et al., J. Immunol. Methods, 1985, 81: 31-42; and R. J. Cote et al., Proc. Natl. Acad. Sci. 1983, 80: 2026-203; R. A. Lerner, Nature, 1982, 299: 593-596; A. C. Nairn et al., Nature, 1982, 299: 734-736; A. J. Czernik et al., Methods Enzymol. 1991, 201: 264-283; A. J. Czernik et al., Neuromethods: Regulatory Protein Modification: Techniques & Protocols, 1997, 30: 219-250; A. J. Czernik et al., Neuroprotocols, 1995, 6: 56-61; H. Zhang et al., J. Biol. Chem. 2002, 277: 39379-39387; S. L. Morrison et al., Proc. Natl. Acad. Sci., 1984, 81: 6851-6855; M. S. Neuberger et al., Nature, 1984, 312: 604-608; S. Takeda et al., Nature, 1985, 314: 452-454). Antibodies to be used in the methods of the invention can be purified by methods well known in the art (see, for example, S. A. Minden, "Monoclonal Antibody Purification", 1996, IBC Biomedical Library Series: Southbridge, Mass.). For example, antibodies can be affinity purified by passage over a column to which a protein marker or fragment thereof can be bound. The bound antibodies can then be eluted from the column using a buffer with a high salt concentration.

Instead of being prepared, antibodies to be used in the methods of the present invention can be obtained from scientific or commercial sources.

The binding agent can be directly or indirectly labeled with a detectable moiety. The role of a detectable agent can be to facilitate the detection step of the diagnostic method by allowing visualization of the complex formed by binding of the binding agent to the protein marker (or analog or fragment thereof). The detectable agent can be selected such that it generates a signal which can be measured and whose intensity can be related or proportional to the amount of protein marker present in the sample being analyzed. Methods for labeling biological molecules such as polypeptides and antibodies are well-known in the art (see, for example, "Affinity Techniques. Enzyme Purification B", Methods in Enzymol., 1974, Vol. 34, W. B. Jakoby and M. Wilneck (Eds.), Academic Press: New York, N.Y.; and M. Wilchek and E. A. Bayer, Anal. Biochem., 1988, 171: 1-32).

Specific binding to an antibody, for example, when referring to a protein or peptide, can be a binding reaction that can be determinative of the presence of the protein in a heterogeneous population of proteins and other biologics. Thus, under designated immunoassay conditions, the specified antibodies can bind to a particular protein or protein complex at least two times the background and do not substantially bind in a significant amount to other proteins present in the sample. Specific binding between a binding agent, e.g., an antibody and a protein, for instance, a biomarker, can be the ability of a capture- or detection-agent to preferentially bind to a particular antigen that can be present in a mixture; e.g., a biological sample. In some embodiments, specific binding can refer to a dissociation constant ($K_D$) that can be less than about $10^{-6}$ M; preferably, less than about $10^{-s}$ M; and, most preferably, less than about $10^{-9}$ M.

Specific binding assays, including immunoassays, can use a labeling agent to specifically bind to and allow for the detection of the complex formed by the specific binding partner and the detected analyte. A label or detectable moiety can be a composition detectable by spectroscopic, photochemical, biochemical, radiographic, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins or other entities which can be made detectable, e.g., by incorporating a radiolabel into the peptide or used to detect antibodies specifically reactive with the peptide. The labels can be incorporated into nucleic acids, proteins and antibodies at any position. Any method known in the art for conjugating the antibody to the label can be employed, e.g., using methods described in Hermanson, Bioconjugate Techniques 1996, Academic Press, Inc., San Diego.

The labeling agent can be a part of the specific binding partner used to detect the analyte. Alternatively, the labeling agent can be a third moiety, such a secondary antibody, which specifically binds to the complex formed by the specific binding partner and the detected analyte. Other proteins capable of specifically binding immunoglobulin constant regions, such as protein A or protein G, can also be used as the label agent. These proteins exhibit a strong affinity for immunoglobulin constant regions from a variety of species (see, e.g., Kronval et al., J. Immunol. 111: 1401-1406 (1973); Akerstrom et al., J. Immunol. 135:2589-2542 (1985)). The labeling agent can be modified with a detectable moiety, such as biotin, to which another molecule can specifically bind, such as streptavidin. A variety of detectable moieties are well-known to those skilled in the art.

The detectable label can be any material having a detectable physical or chemical property. Many useful detectable labels are known in the art and include any label that can be detectable by spectroscopic, photochemical, biochemical, immunochemical, radiographic, electrical, optical or chemical means. The choice of label can depend on the sensitivity required, the ease of conjugation with the compound, stability requirements, available instrumentation, and disposal provisions. Useful labels include magnetic beads (e.g., DYNABEADS®), fluorescent dyes (e.g., fluorescein isothiocyanate, Texas red, rhodamine, and the like), radiolabels (e.g., 3H, 125I, 35S, 14C, or 32P), enzymes (e.g., horseradish peroxidase, alkaline phosphatase and others commonly used in an ELISA), and calorimetric labels such as colloidal gold or colored glass or plastic beads (e.g., polystyrene, polypropylene, latex, etc.).

Non-radioactive labels are often attached by indirect means. Generally, a ligand molecule (e.g., biotin) can be covalently bound to the molecule. The ligand then binds to another molecules (e.g., streptavidin) molecule, which can be either inherently detectable or covalently bound to a signal system, such as a detectable enzyme, a fluorescent compound, or a chemiluminescent compound. The ligands and their targets can be used in any suitable combination with antibodies that recognize the biomarkers, or secondary antibodies that recognize the antibodies to the biomarkers.

The molecules can also be conjugated directly to signal generating compounds, for example, by conjugation with an enzyme or fluorophore. Enzymes that can be used as labels will primarily be hydrolases, particularly phosphatases, esterases and glycosidases, or oxidotases, particularly peroxidases. Exemplary fluorescent compounds include, but are not limited to, fluorescein and its derivatives, rhodamine and its derivatives, dansyl and µM belliferone. Exemplary chemiluminescent compounds include, but are not limited to, luciferin and 2,3-dihydrophthalazinediones. Means of detecting labels are well known to those of skill in the art.

Any of a wide variety of detectable agents can be used in the practice of the present invention. Suitable detectable agents include, but are not limited to: various ligands, radionuclides, fluorescent dyes, chemiluminescent agents, microparticles (such as, for example, quantum dots, nanocrystals, phosphors and the like), enzymes (such as, for example, those used in an ELISA, i.e., horseradish peroxidase, beta-galactosidase, luciferase, alkaline phosphatase), colorimetric labels, magnetic labels, and biotin, dioxigenin or other haptens and proteins for which antisera or monoclonal antibodies are available.

In certain embodiments, the binding agents (e.g., antibodies) can be immobilized on a carrier or support (e.g., a bead, a magnetic particle, a latex particle, a microtiter plate well, a cuvette, or other reaction vessel). Examples of suitable carrier or support materials include agarose, cellulose, nitrocellulose, dextran, Sephadex, Sepharose, liposomes, carboxymethyl cellulose, polyacrylamides, polystyrene, gabbros, filter paper, magnetite, ion-exchange resin, plastic film, plastic tube, glass, polyamine-methyl vinylether-maleic acid copolymer, amino acid copolymer, ethylene-maleic acid copolymer, nylon, silk, and the like. Binding agents can be indirectly immobilized using second binding agents specific for the first binding agents (e.g., mouse antibodies specific for the protein markers can be immobilized using sheep anti-mouse IgG Fc fragment specific antibody coated on the carrier or support).

Protein expression levels in the diagnostic methods of the present invention can be determined using immunoassays. Examples of such assays are radioimmunoassays, enzyme immunoassays (e.g., ELISA), immunofluorescence immunoprecipitation, latex agglutination, hemagglutination, and histochemical tests, which are conventional methods well-known in the art. As will be appreciated by one skilled in the art, the immunoassay can be competitive or noncompetitive. Methods of detection and quantification of the signal generated by the complex formed by binding of the binding agent with the protein marker will depend on the nature of the assay and of the detectable moiety (e.g., fluorescent moiety). Alternatively, the protein expression levels can be determined using mass spectrometry based methods or image (including use of labeled ligand) based methods known in the art for the detection of proteins. Other suitable methods include proteomics-based methods.

Determination of expression levels of nucleic acid molecules in the practice of the inventive methods can be performed by any suitable method, including, but not limited to, Southern analysis, Northern analysis, polymerase chain reaction (PCR) (see, for example, U.S. Pat. Nos. 4,683,195; 4,683,202, and 6,040,166; "PCR Protocols: A Guide to Methods and Applications", Innis et al. (Eds.), 1990, Academic Press: New York), reverse transcriptase PCR(RT-PCT), anchored PCR, competitive PCR (see, for example, U.S. Pat. No. 5,747,251), rapid amplification of cDNA ends (RACE) (see, for example, "Gene Cloning and Analysis: Current Innovations, 1997, pp. 99-115); ligase chain reaction (LCR) (see, for example, EP 01 320308), one-sided PCR (Ohara et al., Proc. Natl. Acad. Sci., 1989, 86: 5673-5677), in situ hybridization, Taqman based assays (Holland et al., Proc. Natl. Acad. Sci., 1991, 88:7276-7280), differential display (see, for example, Liang et al., Nucl. Acid. Res., 1993, 21: 3269-3275) and other RNA fingerprinting techniques, nucleic acid sequence based amplification (NASBA) and other transcription based amplification systems (see, for example, U.S. Pat. Nos. 5,409,818 and 5,554,527), Qbeta Replicase, Strand Displacement Amplification (SDA), Repair Chain Reaction (RCR), nuclease protection assays, subtraction-based methods, Rapid-Scan™, and the like.

Nucleic acid probes for use in the detection of polynucleotide sequences in biological samples can be constructed using conventional methods known in the art. Suitable probes can be based on nucleic acid sequences encoding at least about 5 sequential amino acids from regions of nucleic acids encoding a protein marker, and preferably comprise about 15 to about 50 nucleotides. A nucleic acid probe can be labeled with a detectable moiety, as mentioned above in the case of binding agents. The association between the nucleic acid probe and detectable moiety can be covalent or non-covalent. Detectable moieties can be attached directly to nucleic acid probes or indirectly through a linker (E. S. Mansfield et al., Mol. Cell. Probes, 1995, 9: 145-156). Methods for labeling nucleic acid molecules are well known in the art (for a review of labeling protocols, label detection techniques and recent developments in the field, see, for example, L. J. Kricka, Ann Clin. Biochem. 2002, 39: 114-129; R. P. van Gijlswijk et al., Expert Rev. Mol. Diagn. 2001, 1: 81-91; and S. Joos et al., J. Biotechnol. 1994, 35:135-153).

Nucleic acid probes can be used in hybridization techniques to detect polynucleotides encoding the protein markers. The technique can generally involve contacting an incubating nucleic acid molecules in a biological sample obtained from a subject with the nucleic acid probes under conditions such that specific hybridization takes place between the nucleic acid probes and the complementary sequences in the nucleic acid molecules. After incubation, the non-hybridized nucleic acids are removed, and the presence and amount of nucleic acids that have hybridized to the probes are detected and quantified.

Detection of nucleic acid molecules comprising polynucleotide sequences coding for a protein marker can involve amplification of specific polynucleotide sequences using an amplification method such as PCR, followed by analysis of the amplified molecules using techniques known in the art. Suitable primers can be routinely designed by one skilled in the art. In order to maximize hybridization under assay conditions, primers and probes employed in the methods of the invention generally have at least about 60%, preferably at least about 75% and more preferably at least about 90% identity to a portion of nucleic acids encoding a protein marker.

Hybridization and amplification techniques described herein can be used to assay qualitative and quantitative aspects of expression of nucleic acid molecules comprising polynucleotide sequences coding for the inventive protein markers.

Alternatively, oligonucleotides or longer fragments derived from nucleic acids encoding each protein marker can be used as targets in a microarray. A number of different array configurations and methods of their production are known to those skilled in the art (see, for example, U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637). Microarray technology allows for the measurement of the steady-state level of large numbers of polynucleotide sequences simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; 1. 1. Chen et al., Genomics, 1998, 51: 313324; U.S. Pat. Nos. 5,143,854; 5,445,934; 5,807,522; 5,837, 832; 6,040,138; 6,045,996; 6,284,460; and 6,607,885).

Any biomarker binding agent, such as an antibody, can be labeled with a radiolabel or a fluorescent label. A labeled biomarker binding agent can be administered into a subject, by any suitable method, such as by injection. In some embodiments, a labeled biomarker binding agent can be administered locally, such as to a chronic wounds such as pressure ulcers, venous ulcers, stasis ulcers, venous stasis ulcers, diabetic foot ulcers, arterial insufficiency ulcers or any combination thereof. The labeled biomarker binding agent can be detected by any suitable means known in the art. Exemplary instruments that can be used to detect radiolabeled agents or fluorescent agents after administration to a subject include, but are not limited to, instruments for IVIS Imaging™ (Calipur), bioluminescence imaging (BLI), fluorescence-lifetime imaging (FLI) microscopy, X-ray radiography, ultrasound imaging, computed tomography (CT) imaging, single-photon emission computed tomography (SPECT), positron emission tomography (PET), magnetic resonance imaging (MRI), or any combination thereof. A labeled biomarker agent can bind to its respective biomarker upon administration of the agent into a subject. In some embodiments, the intensity of the signal from the label and the region in a subject's body where the label accumulates can indicate a chronic wound such as pressure ulcers, venous ulcers, stasis ulcers, venous stasis ulcers, diabetic foot ulcers, arterial insufficiency ulcers or any combination thereof, where treatment is needed.

Therapeutic Methods

Any method known in the art can be used to treat the chronic wound, or to treat the pathology that can be causing the chronic wound. A method can comprise treatment of a chronic wound in a mammal, such as a neuropathic ulcer decubitus ulcer, a venous ulcer or a diabetic ulcer or an infected wound. The method can comprise applying an A2M composition to the wound. A2M compositions and formulations can be used for inhibiting proteases. A2M compositions can be used to prevent, slow, or alter FAC formation. A variant A2M can be more efficient than a wild-type A2M polypeptide in inhibiting proteases, have a longer half-life, have a slower clearance factor, or any combination thereof.

In some embodiments, the wound is a decubital ulcer, a pressure ulcer, a lower extremity ulcer, a deep sternal wound, a post-operative wound, a refractory post-operative wound of the trunk area, a wound to the great saphenous vein following harvesting of the great saphenous vein, a venous ulcer, or an anal fissure. In those embodiments involving a lower extremity ulcer, the ulcer may be in a diabetic patient. In other embodiments, the wound is a venous ulcer, pressure ulcer, or post-operative ulcer.

The A2M composition can be comprised on a wound dressing. Dry and hydrated, i.e. wet wound dressings and delivery systems can be used and can also be suitable for active ingredients, their use for the treatment of wounds and skin diseases, preferably chronic wounds. A wound dressing can be applied to the chronic wound for a period of at least 1 hour, at least 24 hours, at least 48 hours, or at least 72 hours. The treatment may be extended for several days, weeks or months, with dressing changes as appropriate, if necessary for chronic wounds.

Another aspect of the invention relates to articles of manufacture comprising a composition of the invention and a dressing. In some embodiments, the dressing is a dry dressing, moisture-keeping barrier dressing, or bioactive dressing. In those embodiments involving a dry dressing, the dressing may be a gauze, a bandage, a non-adhesive mesh, a membrane, foils, foam, or a tissue adhesive. In those embodiments involving a moisture-keeping barrier dressing, the dressing may be a paste, a cream, an ointment, a nonpermeable or semi-permeable membrane or foil, a hydrocolloid, a hydrogel, or combinations thereof. In those embodiments involving a bioactive dressing, the dressing may be an antimicrobial dressing. For example, the wound dressing may be a woven, nonwoven or knitted fabric having the A2M composition coated thereon, or it may be a bioresorbable polymer film or sponge having the A2M composition dispersed therein for sustained release at the ulcer site.

Dressings and Matrices

In one aspect, one or more active agents are provided in the form of a dressing or matrix. In certain embodiments, the one or more agents of the invention are provided in the form of a liquid, semi-solid or solid composition for application directly, or the composition is applied to the surface of, or incorporated into, a solid contacting layer such as a dressing gauze or matrix. The dressing composition may be provided for example, in the form of a fluid or a gel. One or more active agents may be provided in combination with conventional pharmaceutical excipients for topical application. Suitable carriers include: Pluronic gels, Poloxamer gels, Hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (Carbopols). Suitable carriers also include creams/ointments used for topical pharmaceutical preparations, e.g., creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilizers such as EDTA.

Suitable dressings or matrices may include, for example, the following with A2M compositions or formulations:

Suitable absorptives may include, for example, absorptive dressings, which can provide, for example, a semi-adherent quality or a non-adherent layer, combined with highly absorptive layers of fibers, such as for example, cellulose, cotton or rayon. Alternatively, absorptives may be used as a primary or secondary dressing.

Suitable alginates include, for example, dressings that are non-woven, non-adhesive pads and ribbons composed of natural polysaccharide fibers or xerogel derived from seaweed. Suitable alginates dressings may, for example, form a moist gel through a process of ion exchange upon contact with exudate. In certain embodiments, alginate dressings are designed to be soft and conformable, easy to pack, tuck or apply over irregular-shaped areas. In certain embodiments, alginate dressings may be used with a second dressing.

Suitable antimicrobial dressings may include, for example, dressings that can facilitate delivery of bioactive agents, such as, for example, silver and polyhexamethylene biguanide (PHMB), to maintain efficacy against infection, where this is needed or desirable. In certain embodiments, suitable antimicrobial dressings may be available as for example, as sponges, impregnated woven gauzes, film dressings, absorptive products, island dressings, nylon fabric, non-adherent barriers, or a combination of materials.

Suitable biological dressings or biosynthetic dressings may include, for example, gels, solutions or semi-permeable sheets derived from a natural source, e.g., pigs or cows. In certain embodiments, a gel or solution is applied to the treatment site and covered with a dressing for barrier protection. In another embodiment, a biological-based or biosynthetic-based sheet is placed in situ which may act as membrane, remaining in place after a single application, or the biological dressings or biosynthetic dressings may be prepared in advance to include the therapeutics agents.

Suitable collagen dressings may include, for example, gels, pads, particles, pastes, powders, sheets or solutions derived from for example, bovine, porcine or avian sources or other natural sources or donors. In certain embodiments, the collagen dressing may interact with treatment site exudate to form a gel. In certain embodiments, collagen dressing may be used in combination with a secondary dressing.

Suitable composite dressings may include, for example, dressings that combine physically distinct components into a single product to provide multiple functions, such as, for example, a bacterial barrier, absorption, and adhesion. In certain embodiments, the composite dressings are comprised of, for example, multiple layers and incorporate a semi- or non-adherent pad. In certain embodiments, the composite may also include for example, an adhesive border of non-woven fabric tape or transparent film. In certain other embodiments, the composite dressing may function as for example, either a primary or a secondary dressing and in yet another embodiment, the dressing may be used in combination with topical pharmaceutical composition.

Suitable contact layer dressings may include, for example, thin, non-adherent sheets placed on an area to protect tissue from for example, direct contact with other agents or dressings applied to the treatment site. In certain embodiments, contact layers may be deployed to conform to the shape of the area of the treatment site and are porous to allow exudate to pass through for absorption by an overlying, secondary dressing. In yet another embodiment, the contact layer dressing may be used in combination with topical pharmaceutical composition.

Suitable elastic bandages may include, for example, dressings that stretch and conform to the body contours. In certain embodiments, the fabric composition may include for example, cotton, polyester, rayon, or nylon. In certain other embodiments, the elastic bandage may for example, provide absorption as a second layer or dressing, to hold a cover in place, to apply pressure or to cushion a treatment site.

Suitable foam dressings may include, for example, sheets and other shapes of foamed polymer solutions (including polyurethane) with small, open cells capable of holding fluids. Exemplary foams may be for example, impregnated or layered in combination with other materials. In certain embodiments, the absorption capability may be adjusted based on the thickness and composition of the foam. In certain other embodiments, the area in contact with the treatment site may be non-adhesive for easy removal. In yet another embodiment, the foam may be used in combination with an adhesive border and/or a transparent film coating that can serve as an anti-infective barrier.

Suitable gauze dressings and woven dressings may include, for example, dry woven or non-woven sponges and wraps with varying degrees of absorbency. Exemplary fabric composition may include, for example, cotton, polyester, or rayon. In certain embodiments, gauzes and non-woven dressing may be available sterile or non-sterile in bulk and with or without an adhesive border. Exemplary gauze dressings and woven dressings may be used for cleansing, packing and covering a variety of treatment sites.

Suitable hydrocolloid dressings may include, for example, wafers, powders or pastes composed of gelatin, pectin, or carboxymethylcellulose. In certain embodiment, wafers are self-adhering and available with or without an adhesive border and in a wide variety of shapes and sizes. Exemplary hydrocolloids are useful on areas that require contouring. In certain embodiments, powders and pastes hydrocolloids may use used in combination with a secondary dressing.

Suitable amorphous hydrogel dressings may include, for example, formulations of water, polymers and other ingredients with no shape, designed to donate moisture and to maintain a moist healing environments and or to rehydrate the treatment site. In certain embodiments, hydrogels may be used in combination with a secondary dressing cover.

Suitable impregnated hydrogel dressings may include, for example, gauzes and non-woven sponges, ropes and strips saturated with an amorphous hydrogel. Amorphous hydrogels may include for example, formulations of water, polymers and other ingredients with no shape, designed to donate moisture to a dry treatment site and to maintain a moist healing environment.

Suitable hydrogel sheets may include for example, three-dimensional networks of cross-linked hydrophilic polymers that are insoluble in water and interact with aqueous solutions by swelling. Exemplary hydrogels are highly conformable and permeable and can absorb varying amounts of drainage, depending on their composition. In some embodiments, the hydrogel is non-adhesive against the treatment site or treated for easy removal.

Suitable impregnated dressings may include, for example, gauzes and non-woven sponges, ropes and strips saturated with a solution, an emulsion, oil, gel or some other pharmaceutically active compound or carrier agent, including for example, saline, oil, zinc salts, petrolatum, xeroform, and scarlet red as well as the compounds described herein. Silicone Gel Sheets: suitable silicone gel sheet dressings may include, for example, soft covers composed of cross-linked polymers reinforced with or bonded to mesh or fabric.

Suitable liquid dressings may include, for example, mixtures of multiprotein material and other elements found in the extracellular matrix. In certain embodiments, exemplary solutions may be applied to the treatment site after debridement and cleansing and then covered with an absorbent dressing or a nonadherent pad. Transparent Films: suitable transparent film dressings may include polymer membranes of varying thickness coated on one side with an adhesive. In certain embodiments, transparent films are impermeable to liquid, water and bacteria but permeable to moisture vapor and atmospheric gases. In certain embodiments, the transparency allows visualization of the treatment site.

Suitable filler dressings may include, for example, beads, creams, foams, gels, ointments, pads, pastes, pillows, powders, strands, or other formulations. In certain embodiments, fillers are non-adherent and may include a time-released antimicrobial. Exemplary fillers may be useful to maintain a moist environment, manage exudate, and for treatment of for example, partial- and full-thickness wounds, infected wounds, draining wounds, and deep wounds that require packing. Where the A2M composition is used for prophylaxis of chronic wounds, conventional transdermal pharmaceutical forms may be appropriate, such as slow-release skin patches to prevent or minimize ulcer formation or breakout. More conventional systemic administration, such as oral or parenteral administration, may be preferable.

In still another aspect, a composition of the invention may further comprise as a matrix or scaffold a material suitable for implantation in a person. In some embodiments, the material is a solid before implantation. In some embodiments, the material is a gel that solidifies following implantation.

The A2M compositions may be suitable for local or systemic, oral or parenteral administration. However, preferably, the composition is in the form of an ointment for topical administration to a chronic wound or ulcer. The ointment can comprise an A2M composition in a pharmaceutically acceptable carrier. Suitable carriers include: Hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (Carbopols). Suitable carriers also including creams/ointments used for topical pharmaceutical preparations, e.g., creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, and stabilizers such as EDTA.

Wound dressing compositions can be located on an inert support, such as an adhesive strip, adhesive wrap, bandage, gauze bandage or compress system. Wound dressing compositions, systems and packages can be used for the treatment of wounds, especially badly healing wounds like chronic wounds, in particular for the treatment of diabetic, venous, decubitus or neuropathic ulcers or infected wounds. For example, A2M compositions or formulation can be directly smeared 1 to 3 mm thick or thinner than 2 mm thick on the wound surface. The wound surface can be covered and/or bound, such as with cotton gauze or a ventilative material. The dressing can be removed one or more times during a time period. For example, the dressing can be removed 1, 2, 3, 4, 5, 6, 7, 8, 9, 10 or more times over a 12-96 hours. The dressing change can remove metabolites in wound surfaces. The wound can then be covered with an A2M composition and bound with gauze dressing. Necrotic musculotendinous tissue can be removed. In some embodiments, disinfectants are not applied to the surface of the wound.

Any number of methods known in the art for treating chronic wounds can be applied to treat the patient. Suitable methods include surgical and non-surgical methods including, but not limited to, arthroscopic debridement or administration of steroidal or non-steroidal anti-inflammatory agents. Suitable methods include but are not limited to, laminotomy, laminectomy, discectomy, microdiscectomy, percutaneous discectomy, endoscopic discectomy, laser discectomy, foramenotomy, fusion, prolotherapy, other surgical decompressions, decompression with fusion with or without instrumentation.

Chronic wounds can also be treated by standard non-surgical methods, including administration of steroidal or non-steroidal anti-inflammatory agents. Non-steroidal anti-inflammatory (NSAID) agents are well known in the art. Non-steroidal agents, including NSAIDs such as ibuprofen, aspirin or paracetamol can be used. Steroids, such as glucocorticoids, which reduce inflammation by binding to cortisol receptors, can also be used for treatment.

Other wound healing therapeutic substances can be used, such as non-steroidal anti-inflammatory drugs, e.g., acetaminophen, steroids, like hydrocortisone or betamethosone, local anesthetics, antimicrobial agents, growth factors (e.g., fibroblast growth factors or platelet derived growth factor), or protease inhibitors. The antimicrobial agent may, for example, comprise an antiseptic, an antibiotic, or mixtures thereof. Preferred antibiotics include cephalosporins (cephalexin, cefoxytin, and others), penicillins (amoxycillin, ampicillin, phenoxymethylpenicillin, and others), tetracyclines (minocycline, doxycycline, and others), aminoglycosides (gentamicin, neomycin, and others), antifungals (isoconazole, clotrimazole, amphotericin, and others), sulphadiazine, chloramphenicol, erythromycin, vancomycin, trimethoprim, and others. Preferred antiseptics include silver, including colloidal silver, silver salts including one or more silver salts of one or more of the anionic polymers making up the material, silver sulfadiazine, chlorhexidine, povidone iodine, triclosan, sucralfate, quarternary ammonium salts and mixtures thereof.

A2M compositions and formulations can be used for enhancing the nonspecific inhibition of one or more proteases in a human or non-human animal experiencing or susceptible to one or more conditions selected from the group of chronic wounds such as pressure ulcers, venous ulcers, stasis ulcers, venous stasis ulcers, diabetic foot ulcers, arterial insufficiency ulcers or any combination thereof. For example, A2M compositions can be administered to an animal to reduce one or more protease activities in an animal.

Any of the compositions or formulations can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual), oral, intra-articular or inhalation routes of administration. A2M compositions and formulations can also be administered using bioerodible inserts, bare-metal stents (BMS), or drug-eluting stents (DES or coated stents, or medicated stents), and can be delivered directly to chronic wounds such as pressure ulcers, venous ulcers, stasis ulcers, venous stasis ulcers, diabetic foot ulcers, arterial insufficiency ulcers or any combination thereof. A2M compositions and formulations can be formulated in dosage forms appropriate for each route of administration. An A2M containing an agent that is not peptides or polypeptides, can additionally be formulated for enteral administration.

In some embodiments, the A2M compositions can be delivered by injection (peripherally or directly to a site). In one aspect, the injection is made at or adjacent to a site or wound, e.g., 1-10 mm from the site or wound edge. In other embodiments, the injection is made about 1-8, 1-7, 1-6, 1-5, 1-4, 1-3 and 1-2 mm from the site or wound edge. In still other embodiments, the injection is made about 2-8, 2-7, 2-6, 2-5, 2-4 and 2-3 mm from the site or wound edge. In one embodiment, the injection is made 2-4 or 2-5 mm from the site or wound edge. In sites of administration, including wounds, which have length greater than about 1 cm, the injections can occur once every linear centimeter. In one embodiment, the injection is angled in toward a wound or other site of administration, or the injection is made into the dermis of a wound, or by intradermal, intra-tissue or intra-organ injection.

The A2M compositions and formulations can be administered to a subject in a therapeutically effective amount. The precise dosage will vary according to a variety of factors such as subject dependent variables, such as age, the injury or pathology being treated, and the treatment being affected. The exact dosage can be chosen by the individual physician in view of the patient to be treated. Dosage and administration are adjusted to provide sufficient levels of the active moiety or to maintain the desired effect. Additional factors that can be taken into account include the severity of the disease, age of the organism, and weight or size of the organism; diet, time and frequency of administration, drug combination(s), reaction sensitivities, and tolerance/response to therapy. Short acting pharmaceutical compositions are administered daily whereas long acting pharmaceutical compositions are administered every 2, 3 to 4 days, every week, or once every two weeks. Depending on half-life and clearance rate of the particular formulation, the pharmaceutical compositions of the invention are administered once, twice, three, four, five, six, seven, eight, nine, ten or more times per day.

For some compositions, the selected dosage depends upon the route of administration, and on the duration of the treatment desired. Generally dosage levels can include 0.1 to 40 mg/kg of body weight daily. Generally, for local injection or infusion, dosages can be lower. Depending on the composition and site of administration, dosage levels can be between about 1 to 500,000 mg, in a volume between about 0.1 to 10 mL. For example, dosage levels can be between about 5 to 450 mg, 5 to 400 mg, 5 to 350 mg, 5 to 300 mg, 5 to 250 mg, 5 to 200 mg, 5 to 150 mg, 5 to 100 mg, 5 to 500 mg, 5 to 25 mg, 100 to 150 mg, 100 to 200 mg, 100 to 250 mg, 100 to 300 mg, 100 to 350 mg, 100 to 400 mg, 100 to 450 mg, or 100 to 500 mg in a volume between about 0.1 to 9 mL, 0.1 to 8 mL, 0.1 to 7 mL, 0.1 to 6 mL, 0.1 to 5 mL, 0.1 to 4 mL, 0.1 to 3 mL, 0.1 to 2 mL, 0.1 to 1 mL, 0.1 to 0.9 mL, 0.1 to 0.7 mL, 0.1 to 0.6 mL, 0.1 to 0.5 mL, 0.1 to 0.4 mL, 0.1 to 0.3 mL, 0.1 to 0.2 mL, 1 to 9 mL, 1 to 8 mL, 1 to 7 mL, 1 to 6 mL, 1 to 5 mL, 1 to 4 mL, 1 to 3 mL, or 1 to 2 mL. Normal dosage amounts of various variant A2M polypeptides or nucleic acids, or fragment thereof can vary from any number between approximately 1 to 500,000 micrograms, up to a total dose of about 50 grams, depending upon the route of administration. Desirable dosages include, for example, 250 µg, 500 µg, 1 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1.8 g, 1.9 g, 2 g, 3 g, 4 g, 5, 6 g, 7 g, 8 g, 9 g, 10 g, 20 g, 30 g, 40 g, and 50 g.

The dose of the composition can be administered to produce a tissue or blood concentration from approximately any number between 0.1 µM to 500 mM. Desirable doses produce a tissue or blood concentration of about any number from 1 to 800 µM. Preferable doses produce a tissue or blood concentration of greater than about any number from 10 µM to about 500 µM. For example, a dose can comprise the amount of active ingredient required to achieve a tissue or blood concentration of 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 110 µM, 120 µM, 130 µM, 140 µM, 145 µM, 150 µM, 160 µM, 170 µM, 180 µM, 190 µM, 200 µM, 220 µM, 240 µM, 250 µM, 260 µM, 280 µM, 300 µM, 320 µM, 340 µM, 360 µM, 380 µM, 400 µM, 420 µM, 440 µM, 460 µM, 480 µM, and 500 µM. Although doses that produce a tissue concentration of greater than 800 µM are not preferred, they can be used with some embodiments of the invention. A constant infusion can also be provided so as to maintain a stable concentration in the tissues as measured by blood levels.

Any of the A2M compositions or formulations can be administered in an aqueous solution by parenteral, intradiscal, intrafacet, intrathecal, epidural or topical application. Any composition described herein can be administered directly to the chronic wound. For example, when fibronectin-aggrecan complexes are detected in the wound, an A2M composition can be administered by direct injection into the wound. Alternatively, the compositions can be administered by direct application to the wound when FACs or protease activity or other suitable biomarkers are detected in these spaces. For example, aggrecan can include any naturally-occurring variants and splice variants of aggrecan, versican, brevican and neurocan, and any variants of aggrecan, versican, brevican and neurocan due to splicing by different cell types. Fibronectin can include any naturally occurring fibronectin variants including approximately 20 known splice variants associated with a disease or a disorder and fibronectin variants due to different splicing by different cell types.

A composition or formulation can also be in the form of a suspension or emulsion. In general, pharmaceutical compositions are provided including effective amounts of a peptide or polypeptide, and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80, Polysorbate 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations can be lyophilized and redissolved or resuspended immediately before use. The formulation can be sterilized by, for example, filtration through a bacteria retaining filter, by incorporating sterilizing agents into the compositions, by irradiating the compositions, or by heating the compositions. In some embodiments, linoleic acid can be used in the A2M compositions, for example, to treat a diabetic ulcer.

Any composition or formulation can also be administered in controlled release formulations. Controlled release polymeric devices can be made for long term release systemically following implantation of a polymeric device (rod, cylinder, film, or disc) or injection (microparticles). The matrix can be in the form of microparticles such as microspheres, where peptides are dispersed within a solid polymeric matrix or microcapsules, where the core can be of a different material than the polymeric shell, and the peptide can be dispersed or suspended in the core, which can be liquid or solid in nature. Unless specifically defined herein, microparticles, microspheres, and microcapsules are used interchangeably. Alternatively, the polymer can be cast as a thin slab or film, ranging from nanometers to four centimeters, a powder produced by grinding or other standard techniques, or even a gel such as a hydrogel.

Either non-biodegradable or biodegradable matrices can be used for delivery of any composition or formulation described herein, although biodegradable matrices are preferred. These can be natural or synthetic polymers, although synthetic polymers are preferred due to the better characterization of degradation and release profiles. The polymer can be selected based on the period over which release can be desired. In some cases linear release can be most useful, although in others a pulse release or "bulk release" can provide more effective results. The polymer can be in the form of a hydro gel (typically in absorbing up to about 90% by weight of water), and can optionally be crosslinked with multivalent ions or polymers. The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, *J. Controlled Release*, 5:13-22 (1987); Mathiowitz, et al., *Reactive Polymers*, 6:275-283 (1987); and Mathiowitz, et al., *J. Appl. Polymer Sci.*, 35:755-774 (1988).

Devices can be formulated for local release to treat the area of implantation or injection which will typically deliver a dosage that can be much less than the dosage for treatment of an entire body or systemic delivery. These can be implanted or injected subcutaneously, into the muscle, fat, or swallowed.

Any A2M composition or formulation can be used in the treatment of a condition or a disease. For example, a condition or disease can be chronic wounds such as pressure ulcers, venous ulcers, stasis ulcers, venous stasis ulcers, diabetic foot ulcers, arterial insufficiency ulcers or any combination thereof.

In some embodiments, agents that are not peptides or polypeptides, can be used in the treatment of a condition or a disease. For example, an agent, can be administered directly onto a chronic wound such as pressure ulcers, venous ulcers, stasis ulcers, venous stasis ulcers, diabetic foot ulcers, arterial insufficiency ulcers or any combination thereof.

Any of the compositions described herein can be isolated from a blood sample and can be suitable for administration to chronic wounds such as pressure ulcers, venous ulcers, stasis ulcers, venous stasis ulcers, diabetic foot ulcers, or arterial insufficiency ulcers.

In other aspects, the invention is directed to a method of inhibiting the onset of infection in a wound, comprising administering to the wound a composition of the invention. In one embodiment, the wound is caused by trauma. In another embodiment, the wound is caused by surgery.

In those aspects involving methods of treating a wound, the wound may also be treated by administering to the wound an article of manufacture comprising a composition of the invention.

For purposes of the present invention, wounds include tattoos. Accordingly, a further aspect of the present invention is directed to a method of tattoo removal, which includes administering or otherwise applying the A2M composition or an article of manufacture comprising the A2M composition, to a tattoo.

A wound dressing can be packaged in a microorganism-impermeable container. Such packages can represent single or multi-unit dosage forms of the present compositions. These packages can be used by the subject himself.

The A2M composition may be used in conjunction with any other conventional wound treatment, such as negative pressure, warming (therapeutic heat), electrical stimulation, magnetism, laser phototherapy, cycloidal vibration therapy and ultrasound. It also can be used with biological therapy such as larva therapy, skin substitutes, cultured keratinocytes (Epicel, Genzyme biosurgery), human dermal replacement (Dermagraft, Smith and Nephew Inc.), cadaver derived processed dermis (Alloderm, Life Cell Corporation), Bilayered Skin Equivalent (Apligraf, Organogenesis Inc.), TransCyte (Smith and Nephew Inc.), Growth Factors (PDGF is currently the only growth factor licensed for topical use), and fibrin sealant. In some embodiments, the A2M composition is used in conjunction with negative pressure wound therapy (NPWT) (one example being the V.A.C., which is a commercially available wound therapy manufactured by KCI). Negative pressure therapy promotes wound healing by applying negative pressure to a wound. In these embodiments, A2M composition can be applied to a wound prior to negative pressure therapy. In yet other embodiments, the A2M composition is used in conjunction with hyperbaric oxygen therapy (Thackham, 2008) or ozone therapy. For example, the A2M composition can be applied to a wound just prior to a patient receiving hyperbaric therapy. The A2M composition may also be used in conjunction with low-energy shock wave therapy (e.g., impulses of about 0.1 mJ/mm2; 5 Hz) per centimeter of wound length). See, e.g., Dumfarth, et al., Ann Thorac. Surg. 86:1909-13 (2008).

Subjects

Any subject in need of treatment for a condition or disease described herein, such as a subject with a chronic wound, can be treated with any composition or formulation described herein.

As used herein, a "condition" or "disease" is any disorder, disease, or condition that would benefit from an agent that initiates, accelerates, promotes or enhances wound healing (including acute wounds, dehiscent wounds, and slow-healing delayed-healing and chronic wounds), reduces inflammation, reduces or lessens scarring, improves scar quality, reduces fibrosis, and/or reduces adhesions. For example, diseases, disorders, and conditions include acute wounds. Diseases, disorders, and conditions also include dehiscent wounds, and slow-healing delayed-healing and chronic wounds. Also included are diseases, disorders, and conditions characterized by excess production of fibrous material, including excess production of fibrous material within the extracellular matrix. Also included are diseases, disorders and conditions characterized by replacement of normal tissue elements by abnormal, non-functional, and/or excessive accumulation of matrix-associated components. Also included are diseases, disorders and conditions characterized by adhesion formation. Also included is any disorder, disease, or condition that would benefit from an agent that promotes wound healing and/or reduces swelling, inflammation, and/or scar formation (including abnormal and excessive scarring, including keloid scars, hypertrophic scars, widespread (stretched) scars, and atrophic (depressed) scars). For example, included are wounds resulting from surgery or trauma, wounds that do not heal at expected rates (such as delayed-healing wounds, incompletely healing wounds, chronic wounds, and dehiscent wounds), and wounds associated abnormalities in connection with neuropathic, ischemic, microvascular pathology, pressure over bony area (tailbone (sacral), hip (trochanteric), buttocks (ischial), or heel of the foot), reperfusion injury, and valve reflux etiology and conditions. Also included are diseases, disorders and conditions that would benefit from enhanced cellular migration, lessened cellular adhesion, scarring and inflammation as described herein. In some embodiments, a subject can be diagnosed with a condition or disease before or after being diagnosed with a condition or disease, such as by the methods described in U.S. Pat. No. 7,709,215 and U.S. Publication No.: US 2010/0098684A1. In some embodiments, a subject can be diagnosed as needing treatment with any of the compositions or formulations described herein.

Subjects can include any subject that presents with a chronic wound such as pressure ulcers, venous ulcers, stasis ulcers, venous stasis ulcers, diabetic foot ulcers, arterial insufficiency ulcers or any combination thereof. In some embodiments, a subject can be selected for the detection of A2M. Subjects can have chronic wounds such as pressure ulcers, venous ulcers, stasis ulcers, venous stasis ulcers, diabetic foot ulcers, arterial insufficiency ulcers or any combination thereof.

At the time of treatment, a subject may have been experiencing chronic wounds for 30 or 25 weeks or less. For example, a subject may have been experiencing chronic wounds for 20, 15, 10, 8, or 6 weeks, or less.

Subjects can be of either sex and can be of any age.

A subject can be human or non-human animal. A subject can be a mammal, such as a mouse, rat, rabbit, cat, dog, monkey, horse or goat. Preferably the subject is human. A subject can be a non-human primate, rodent, caprine, bovine, ovine, equine, canine, feline, mouse, rat, rabbit, horse or goat.

Samples

Any of the autologous compositions described herein can be derived from a biological sample. Preferably, the autologous compositions described herein are isolated from a biological sample and suitable for delivery into or onto a chronic wound. Biological samples include blood, sections of tissues such as biopsy samples, frozen sections taken for histologic purposes, and lavage samples.

A biological sample can be a tissue sample or bodily fluid, such as a human bodily fluid. For example, the bodily fluid can be blood, sera, plasma, lavage, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, Cowper's fluid, pre-ejaculatory fluid, female ejaculate, sweat, tears, cyst fluid, pleural fluid, peritoneal fluid, pericardial fluid, lymph, chyme, chyle, bile, interstitial fluid, menses, pus, sebum, vaginal secretion, mucosal secretion, stool water, pancreatic juice, lavage fluid from sinus cavities, bronchopulmonary aspirate, blastocyl cavity fluid, fluid from a chronic wound or umbilical cord blood. One or more of the biological sample(s) can comprise a cell, such as a stem cell, undifferentiated cell, differentiated cell, or cell from a diseased subject or subject with a specific condition. A biological sample can be blood, a cell, a population of cells, a quantity of tissue, fluid, or a sample from a chronic wound. A biological sample can comprise cells from cartilaginous tissue or can be free of cells. A biological sample can be substantially depleted of a common serum protein, such as, but not limited to, albumin or IgG. Depletion can comprise filtration, fractionation, or affinity purification. A biological sample can be from animal, such as a mammal, for example, a human, non-human primate, rodent, caprine, bovine, ovine, equine, canine, feline, mouse, rat, rabbit, horse or goat Pooled Samples In some embodiments, pooled samples can be used to treat a disease or condition, such as a wound. In some embodiments, two or more samples can be obtained from two or more sources, such as two or more subjects, and pooled together before or after being processed into the A2M concentrated compositions described herein. However, such pooled samples should not be immunogenic to the subject being treated. For example, a first blood sample can be obtained from a first subject and a second blood sample can be obtained from a second subject. The blood samples can be processed using a system containing two or more filters as described herein. The processed samples can be substantially free of blood cells. These samples can be pooled together and can be used to treat the first subject, the second subject, or a third subject, as long as the pooled sample is not immunogenic to the subject being treated.

A sample for the preparation of an autologous composition can be from a single subject. For example, a blood sample taken from a single subject can be used to prepare an autologous sample described herein. A sample can also include multiple sample taken from the same individual. For example, two or more blood samples can be obtained from a subject, and each of the two or more samples taken from the subject can be used to prepare 2 or more autologous samples containing a concentrated amount of A2M. These samples can be pooled together and used to treat the subject from whom they were obtained.

Samples can also be obtained from two or more subjects, pooled together, and used to treat one of the subjects from which they were obtained. The samples can be pooled prior to or after being processed into a composition containing concentrated A2M, such as using a method or system described herein. For example, blood from two or more subjects can be pooled, or concentrated A2M samples obtained from two or more different people can be pooled. The pooled samples can then be used to treat one of the subjects from which they were obtained, so long as the pooled sample is not immunogenic to the subject being treated with the pooled samples.

Samples can also be obtained from two or more subjects, pooled together, and used to treat a different subject than the subjects from whom they were obtained. The samples can be pooled prior to or after being processed into a composition containing concentrated A2M, such as using a method or system described herein. For example, blood from two or more subjects can be pooled, or concentrated A2M samples obtained from two or more different people can be pooled. The pooled samples can then be used to treat a different subject than the subjects from which they were obtained, so long as the pooled sample is not immunogenic to the subject being treated with the pooled samples.

Biological samples can be collected by any non-invasive means, such as, for example, by drawing blood from a subject, or using fine needle aspiration, swabbing a wound, or taking a sample from a wound, or needle biopsy. Alternatively, biological samples can be collected by an invasive method, including, for example, surgical biopsy.

A biological sample can comprise disease or condition specific proteins. A biological sample can be from a subject with a disease or condition or from a subject without a disease or condition. In some embodiments, a biological sample can be from a subject diagnosed with a disease or condition or from a subject not diagnosed with or without a disease or condition. A diagnosis can be made by any of the methods described herein. A biological sample can be from a subject at one time point and another biological sample can be from a subject at a later or earlier time point, wherein the subject can be the same or a different subject. For example, the subject may have a disease or condition or have been diagnosed with a disease or condition, and samples can be taken as the disease or condition progresses. A biological sample can be from a subject pretreatment and another biological sample can be from a subject at post treatment, wherein the subject can be the same or different subject. A biological sample can be from a subject non-responsive to treatment and another biological sample can be from a subject responsive to a treatment. Biological samples can be from the same or different species. One or more biological samples can be from the same subject or from a different subject from which one or more other biological samples were obtained.

The methods of the invention can be applied to the study of any type of biological samples allowing one or more biomarkers to be assayed. A biological sample can be a fresh or frozen sample collected from a subject, or archival samples with known diagnosis, treatment and/or outcome history.

The inventive methods can be performed on the biological sample itself without or with limited processing of the sample. The inventive methods can be performed at the single cell level (e.g., isolation of cells from the biological sample). Multiple biological samples can be taken from the same tissue/body part in order to obtain a representative sampling of the tissue.

Any of the method described herein can be performed on a protein extract prepared from the biological sample. The methods can also be performed on extracts containing one or more of: membrane proteins, nuclear proteins, and cytosolic proteins. Methods of protein extraction are well known in the art (see, for example "Protein Methods", D. M. Bollag et al., 2nd Ed., 1996, Wiley-Liss; "Protein Purification Methods: A Practical Approach", E. L. Harris and S. Angal (Eds.), 1989; "Protein Purification Techniques: A Practical Approach", S. Roe, 2nd Ed., 2001, Oxford University Press; "Principles and Reactions o/Protein Extraction, Purification, and Characterization", H. Ahmed, 2005, CRC Press: Boca Raton, Fla.). Numerous different and versatile kits can be used to extract proteins from bodily fluids and tissues, and are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.). After the protein extract has been obtained, the protein concentration of the extract can be standardized to a value being the same as that of the control sample in order to allow signals of the protein markers to be quantitated. Such standardization can be made using photometric or spectrometric methods or gel electrophoresis.

Any of the method described herein can be performed on nucleic acid molecules extracted from the biological sample. For example, RNA can be extracted from the sample before analysis. Methods of RNA extraction are well known in the art (see, for example, J. Sambrook et al., "Molecular Cloning: A Laboratory Manual", 1989, 2nd Ed., Cold Spring Harbor Laboratory Press: Cold Spring Harbor, N.Y.). Most methods of RNA isolation from bodily fluids or tissues are based on the disruption of the tissue in the presence of protein denaturants to quickly and effectively inactivate RNAses. Isolated total RNA can then be further purified from the protein contaminants and concentrated by selective ethanol precipitations, phenol/chloroform extractions followed by isopropanol precipitation or cesium chloride, lithium chloride or cesium trifluoroacetate gradient centrifugations. Kits are also available to extract RNA (i.e., total RNA or mRNA) from bodily fluids or tissues and are commercially available from, for example, Ambion, Inc. (Austin, Tex.), Amersham Biosciences (Piscataway, N.J.), BD Biosciences Clontech (Palo Alto, Calif.), BioRad Laboratories (Hercules, Calif.), GIBCO BRL (Gaithersburg, Md.), and Qiagen, Inc. (Valencia, Calif.).

After extraction, mRNA can be amplified, and transcribed into cDNA, which can then serve as template for multiple rounds of transcription by the appropriate RNA polymerase. Amplification methods are well known in the art (see, for example, A. R. Kimmel and S. L. Berger, Methods Enzymol. 1987, 152: 307-316; J. Sambrook et al., "Molecular Cloning: A Laboratory Manual", 1989, 2nd Ed., Cold Spring Harbour Laboratory Press: New York; "Short Protocols in Molecular Biology", F. M. Ausubel (Ed.), 2002, 5th Ed., John Wiley & Sons; U.S. Pat. Nos. 4,683,195; 4,683,202 and 4,800,159). Reverse transcription reactions can be carried out using non-specific primers, such as an anchored oligo-dT primer, or random sequence primers, or using a target-specific primer complementary to the RNA for each probe being monitored, or using thermostable DNA polymerases (such as avian myeloblastosis virus reverse transcriptase or Moloney murine leukemia virus reverse transcriptase).

Other Embodiments

Disclosed herein are molecules, materials, compositions, and components that can be used for, can be used in conjunction with, can be used in preparation for, or are products of methods and compositions disclosed herein. It is understood that when combinations, subsets, interactions, groups, etc. of these materials are disclosed and while specific reference of each various individual and collective combinations and permutation of these molecules and compounds cannot be explicitly disclosed, each is specifically contemplated and described herein. For example, if a nucleotide or nucleic acid is disclosed and discussed and a number of modifications that can be made to a number of molecules including the nucleotide or nucleic acid are discussed, each and every combination and permutation of nucleotide or nucleic acid and the modifications that are possible are specifically contemplated unless specifically indicated to the contrary. This concept applies to all aspects of this application including, but not limited to, steps in methods of making and using the disclosed molecules and compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art can recognize, or be able to ascertain using no more than routine experimentation, many equivalents to the specific embodiments of the method and compositions described herein. Such equivalents are intended to be encompassed by the following claims.

It is understood that the disclosed methods and compositions are not limited to the particular methodology, protocols, and reagents described as these can vary. It is also to be understood that the terminology used herein is for the purpose of describing particular embodiments only, and is not intended to limit the scope of the present disclosure which can be limited only by the appended claims.

Various modifications and variations of the described method and system of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. Other embodiments are in the claims.

Unless otherwise explained, all technical and scientific terms used herein have the same meaning as commonly understood by one of ordinary skill in the art to which this disclosure belongs. The following references contain embodiments of the methods and compositions that can be used herein: The Merck Manual of Diagnosis and Therapy, 18th Edition, published by Merck Research Laboratories, 2006 (ISBN 0-911910-18-2); Benjamin Lewin, Genes IX, published by Jones & Bartlett Publishing, 2007 (ISBN-13: 9780763740634); Kendrew et al. (eds.), The Encyclopedia of Mol. Biology, published by Blackwell Science Ltd., 1994 (ISBN 0-632-02182-9); and Robert A. Meyers (ed.), Mol. Biology and Biotechnology: a Comprehensive Desk Reference, published by VCH Publishers, Inc., 1995 (ISBN 1-56081-569-8).

Standard procedures of the present disclosure are described, e.g., in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol. 152, S. L. Berger and A. R. Kimmerl (eds.), Academic Press Inc., San Diego, USA (1987)). Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), and Animal Cell Culture Methods (Methods in Cell Biology, Vol. 57, Jennie P. Mather and David Barnes editors, Academic Press, 1st edition, 1998), which are all incorporated by reference herein in their entireties.

It should be understood that the following examples should not be construed as being limiting to the particular methodology, protocols, and compositions, etc., described herein and, as such, can vary. The following terms used herein are for the purpose of describing particular embodiments only, and are not intended to limit the scope of the embodiments disclosed herein.

EXAMPLES

Example 1

A study was conducted to define the cell composition and Alpha-2-Macroglobulin (A2M) concentrations of concentrated plasma products using different methods of production. Concentrated products were produced by
1. pre-mixing RBC-reduced (RBC-R) PRP and PPP before filter concentration,
2. post-mixing RBC-reduced PRP with filter concentrated PPP, or
3. adapting a centrifuge for an Autologous Platelet Integrated Concentrate (APIC) 50 ml conical and filter-concentrating the PRP obtained.

Concentration was performed with each method using a Hemacor Polysulphone Hemaconcentrator Junior (APIC-HL HPH-Jr) or APIC-HH filter. The platelet, red blood cell, and white blood cells were counted in each product and their intermediates. A2M concentration was obtained by Enzyme-Linked Immunosorbent Assay (ELISA) for each product as well.

From the study, it was concluded that:
1. Concentrated products made with the APIC-HH filter had higher concentrations of platelets and A2M than in the HPH-Jr in each method.
2. The highest A2M concentration achieved was by pre-mixing RBC-R and PPP then concentrating on the APIC-HH filter (~3.5×A2M over PPP, ~7×A2M over WB). The HPH-Jr filter had approximately a 2× drop in A2M concentration with the same protocol (~2.5×A2M over PPP, ~5×A2M over WB)
3. Post-mixing the RBC-R and concentrated PPP resulted in significantly reduced levels of platelet and A2M, (1-2.5× less than pre-mixing).
4. Centrifuging a 50 ml conical within the parameters of a centrifuge resulted in an ~18 min spin time as well as much increased WBC concentrations (1-1.5× of whole blood) compared to their RBCR counterparts.

Example 2

Protocol

Figure 4:
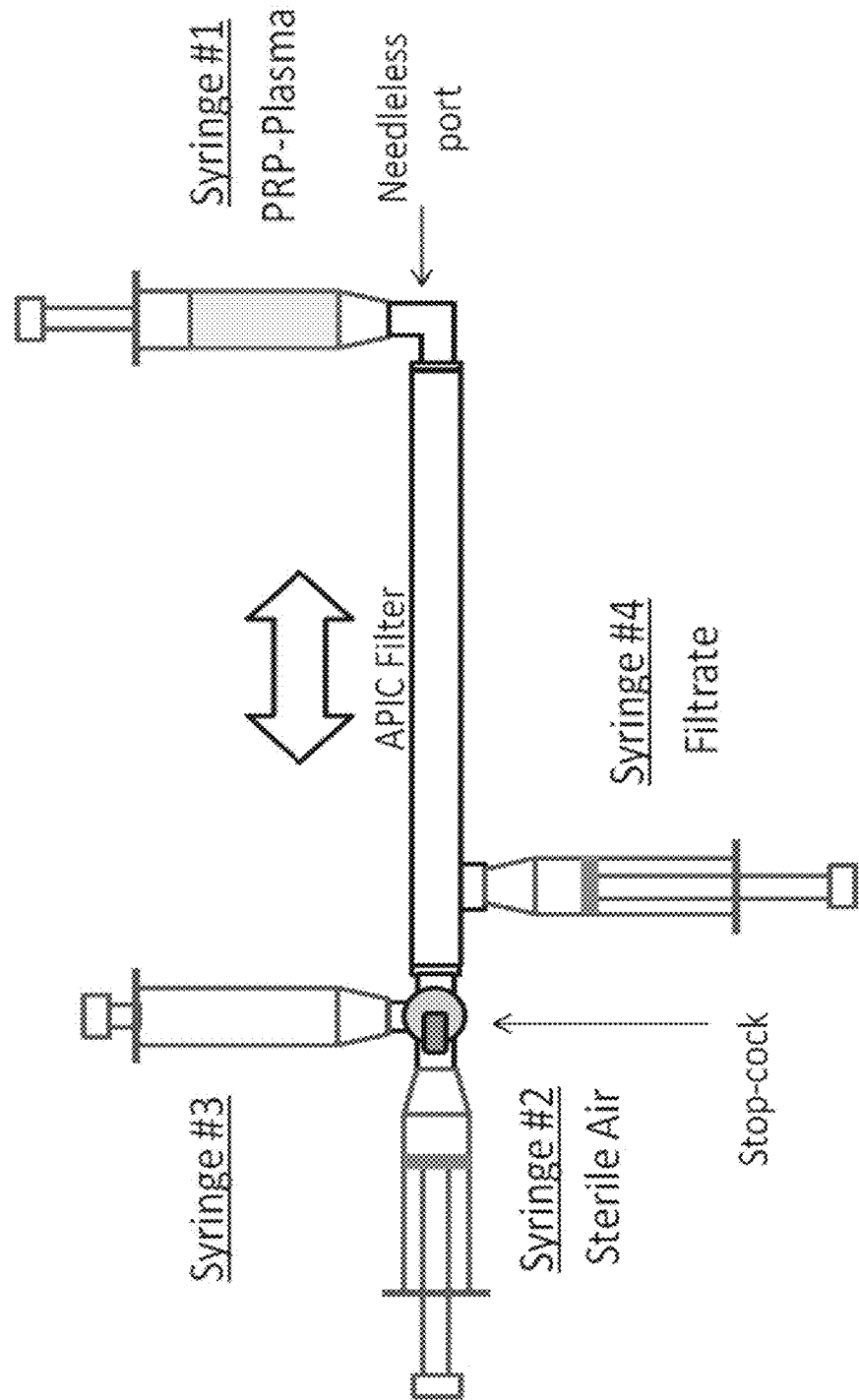
FIG. 4 depicts a schematic of an exemplary system comprising one membrane.
Figure 5:
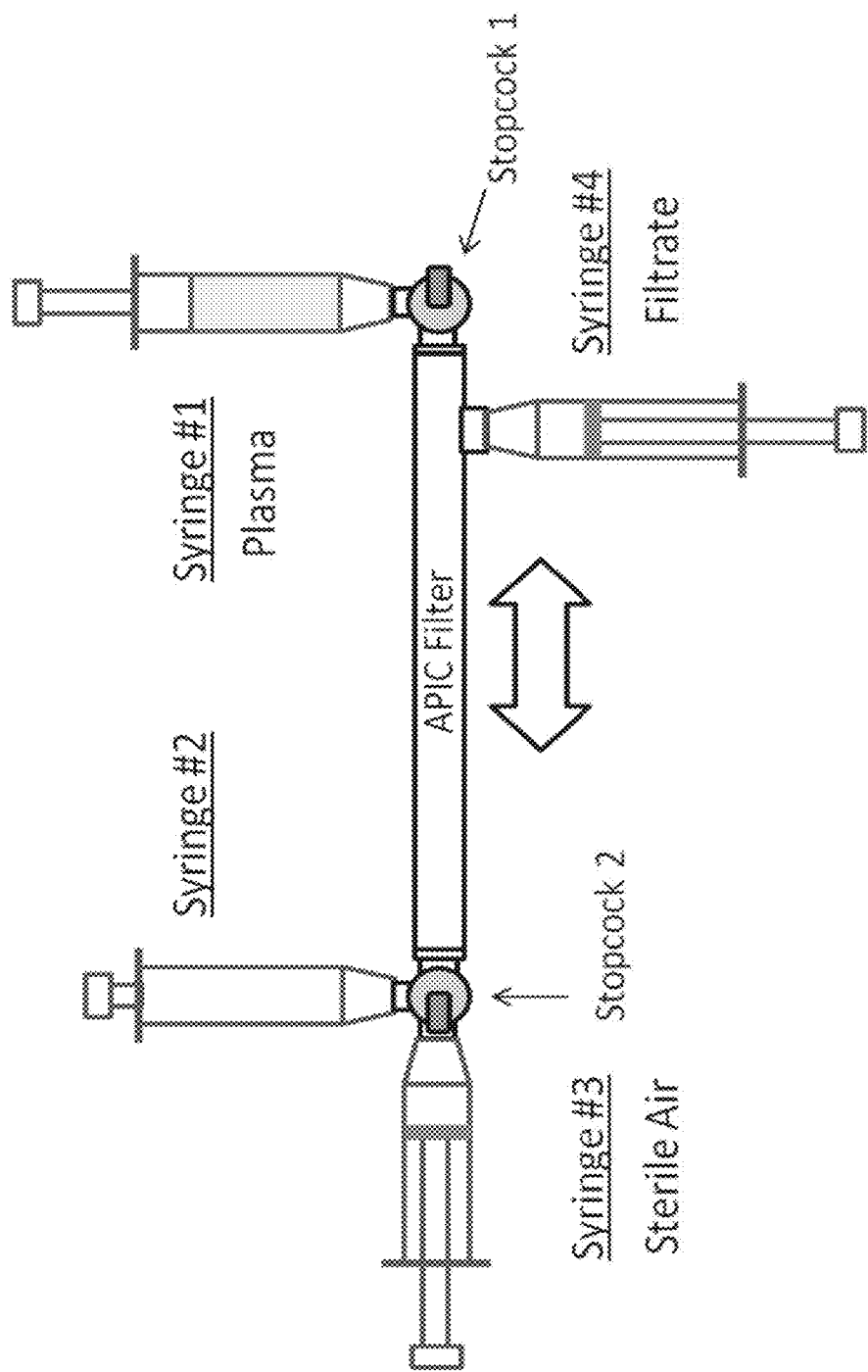
FIG. 5 depicts a schematic of an exemplary system comprising one membrane.
Figure 6:
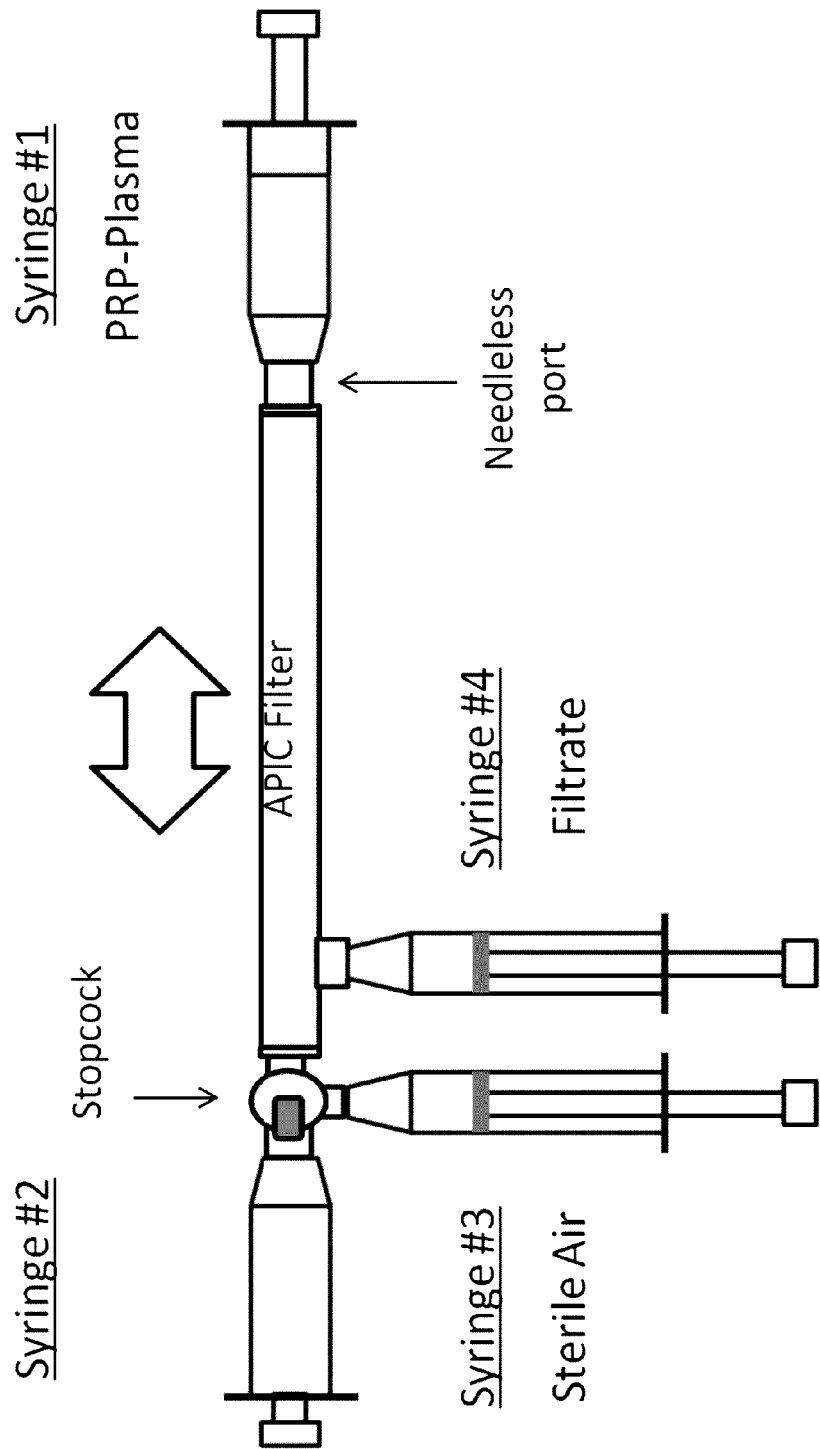
FIG. 6 depicts a schematic of an exemplary system comprising one membrane.
Figure 7:
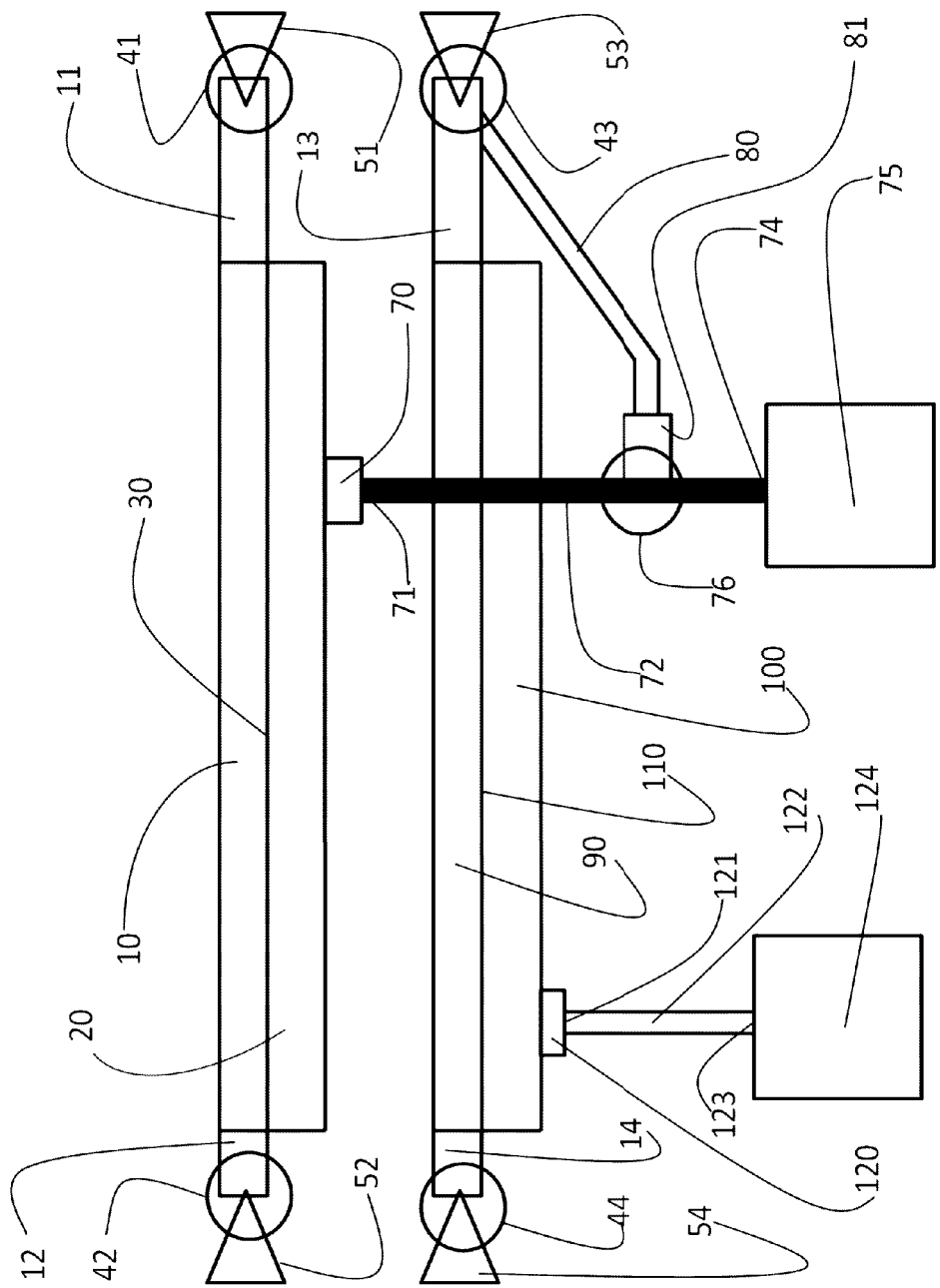
FIG. 7 depicts a schematic of an exemplary system comprising two membranes.
Figure 8:
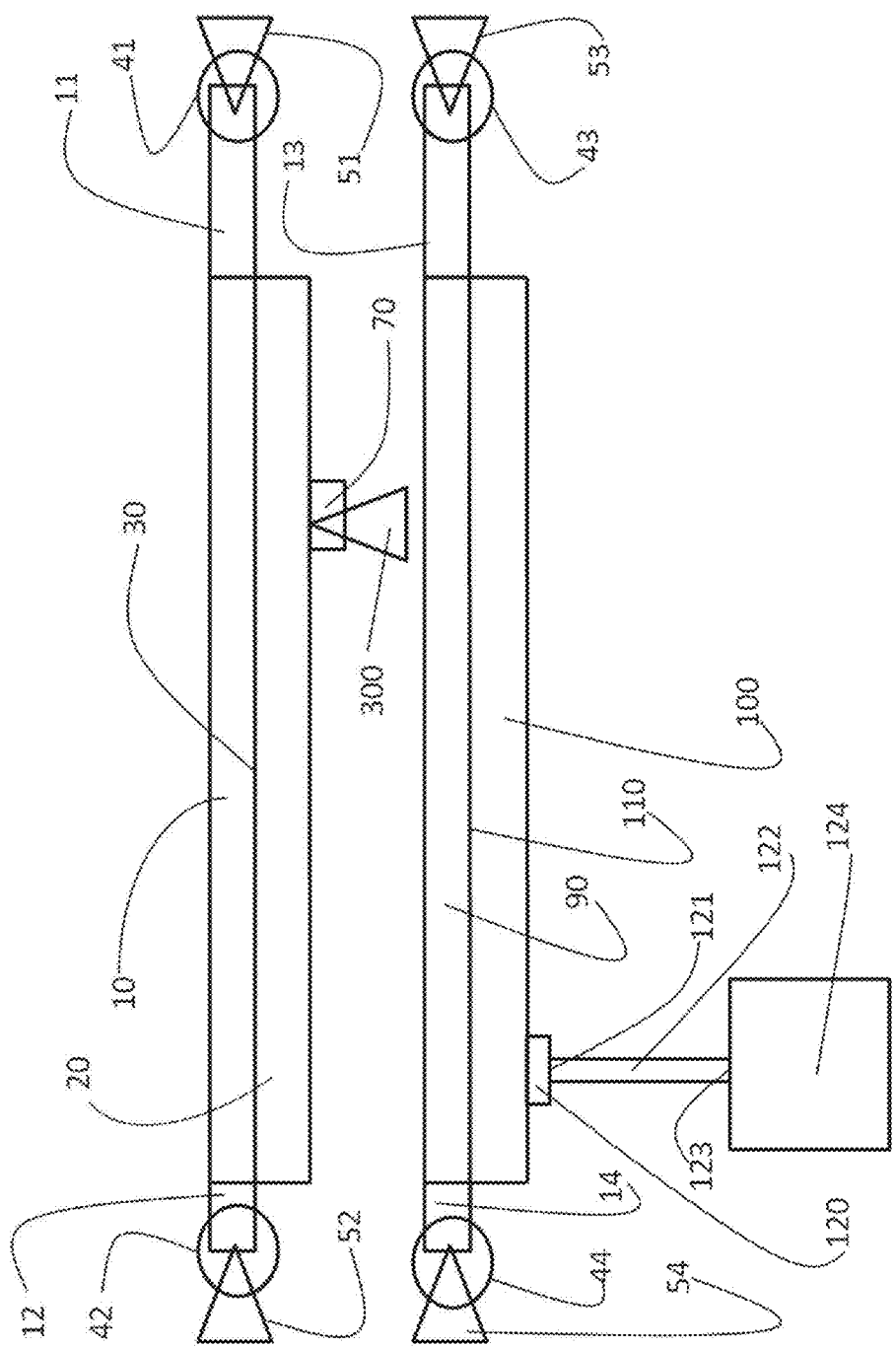
FIG. 8 depicts a schematic of an exemplary system comprising two membranes.
Figure 9A:
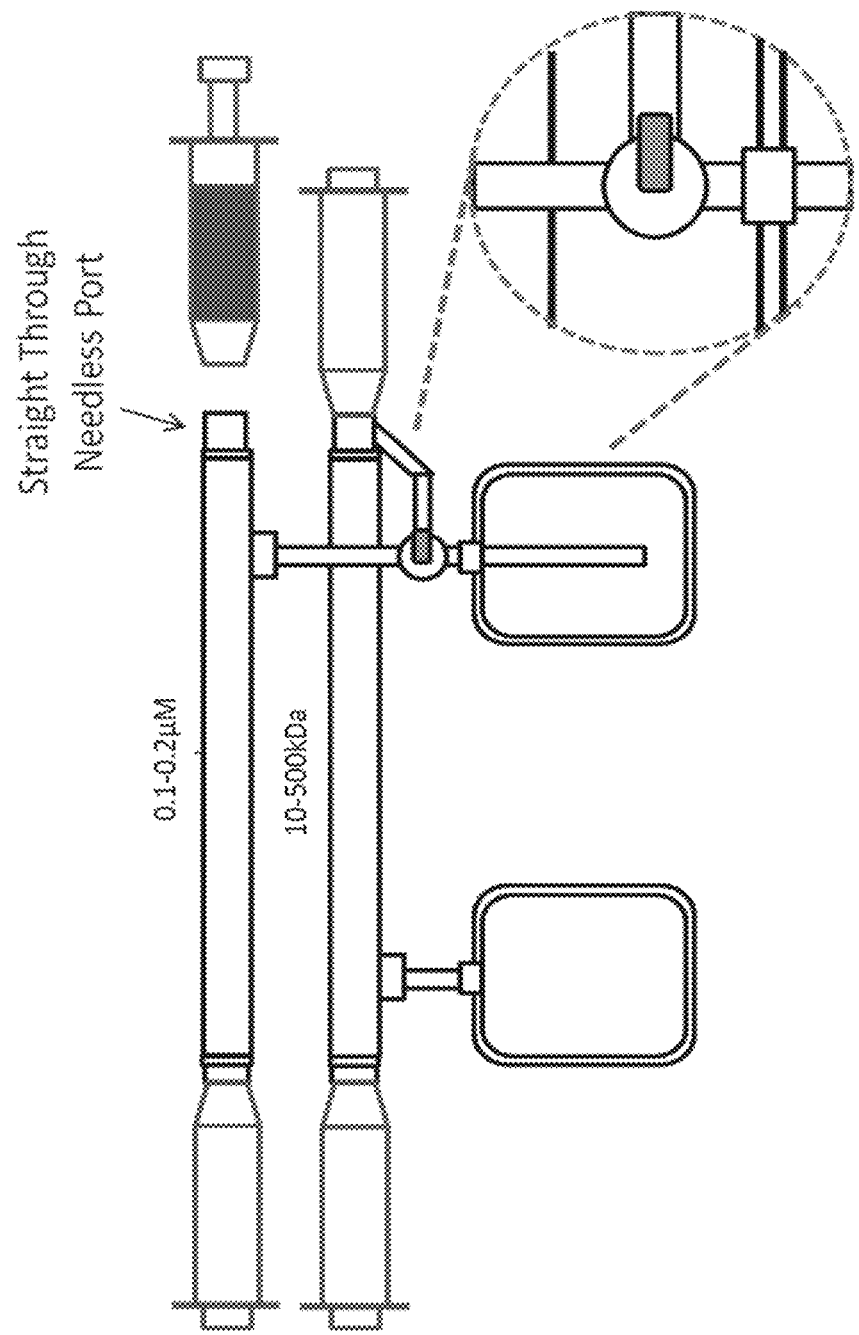
Figure 9C:
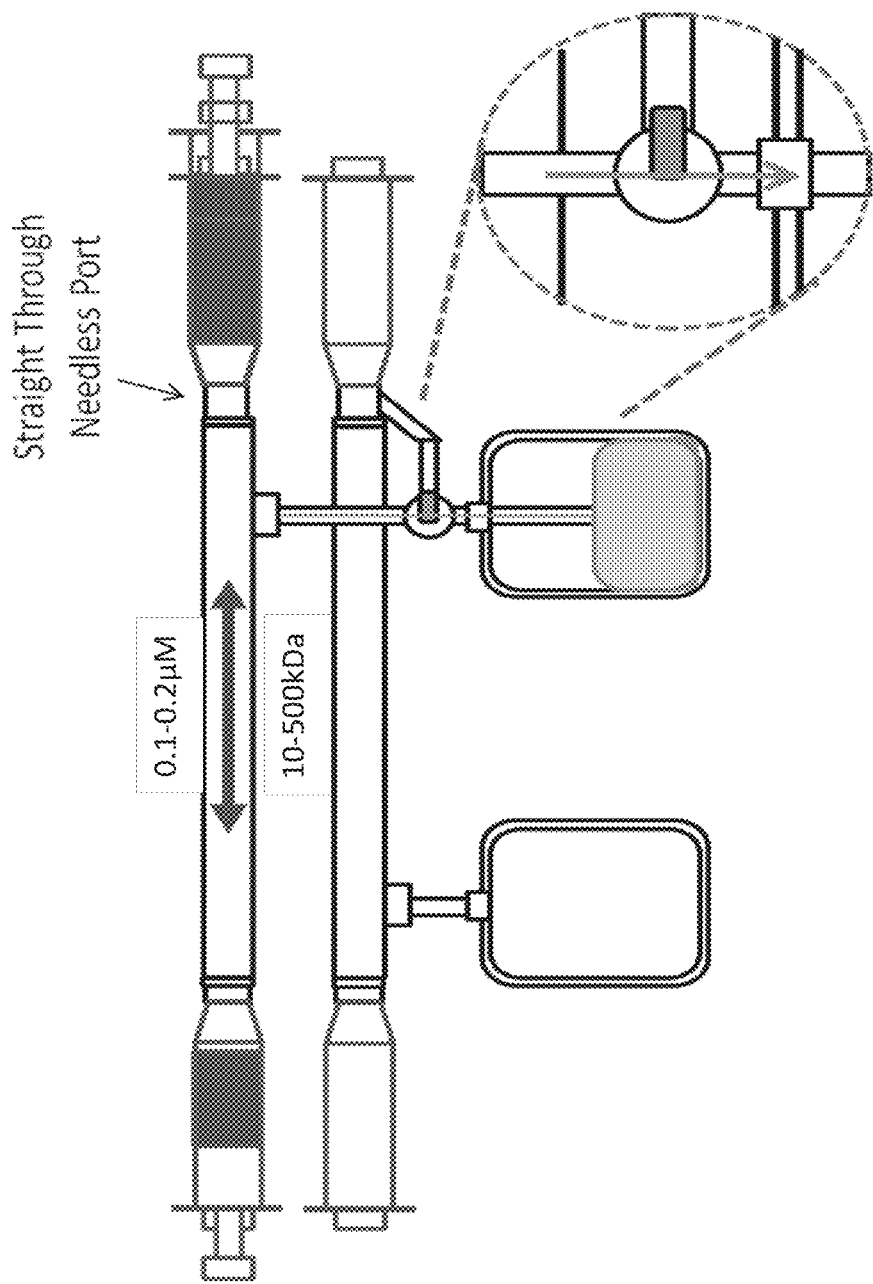
Figure 9D:
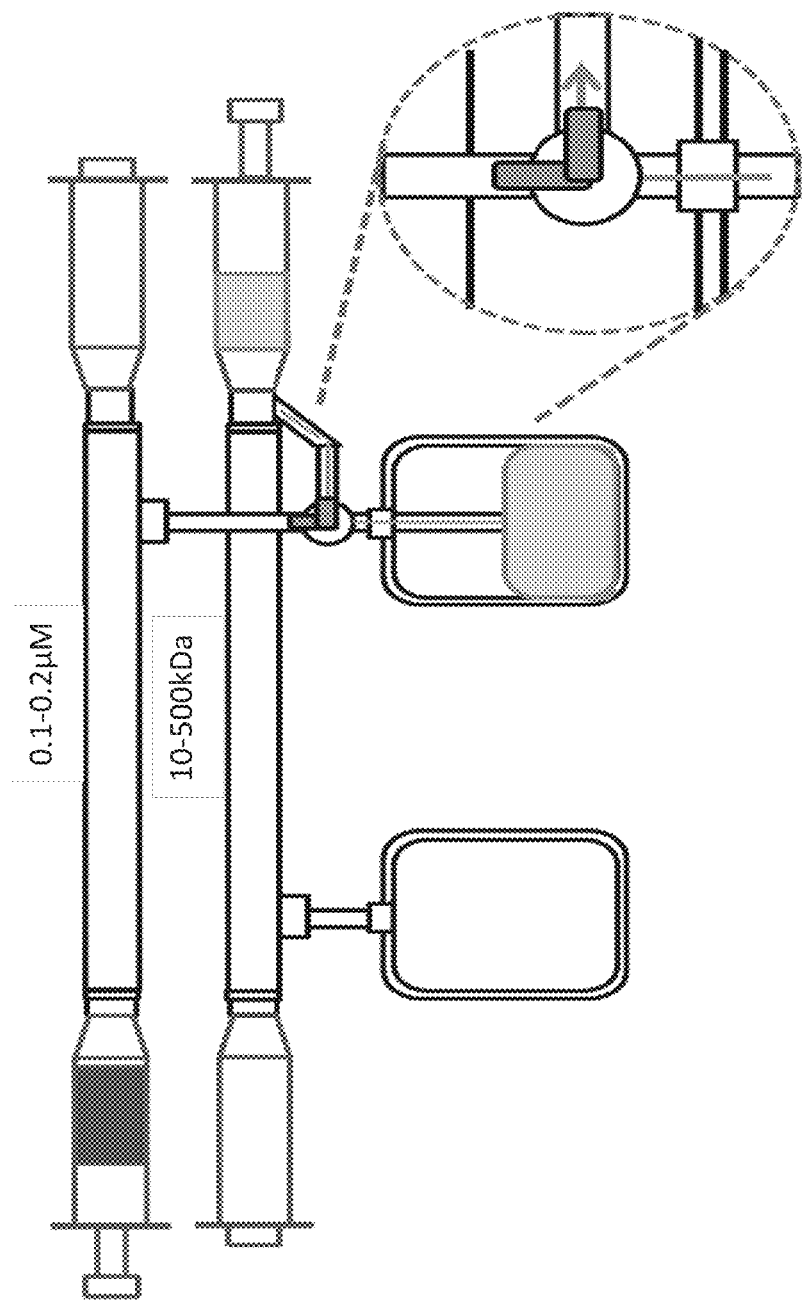
Figure 9F:
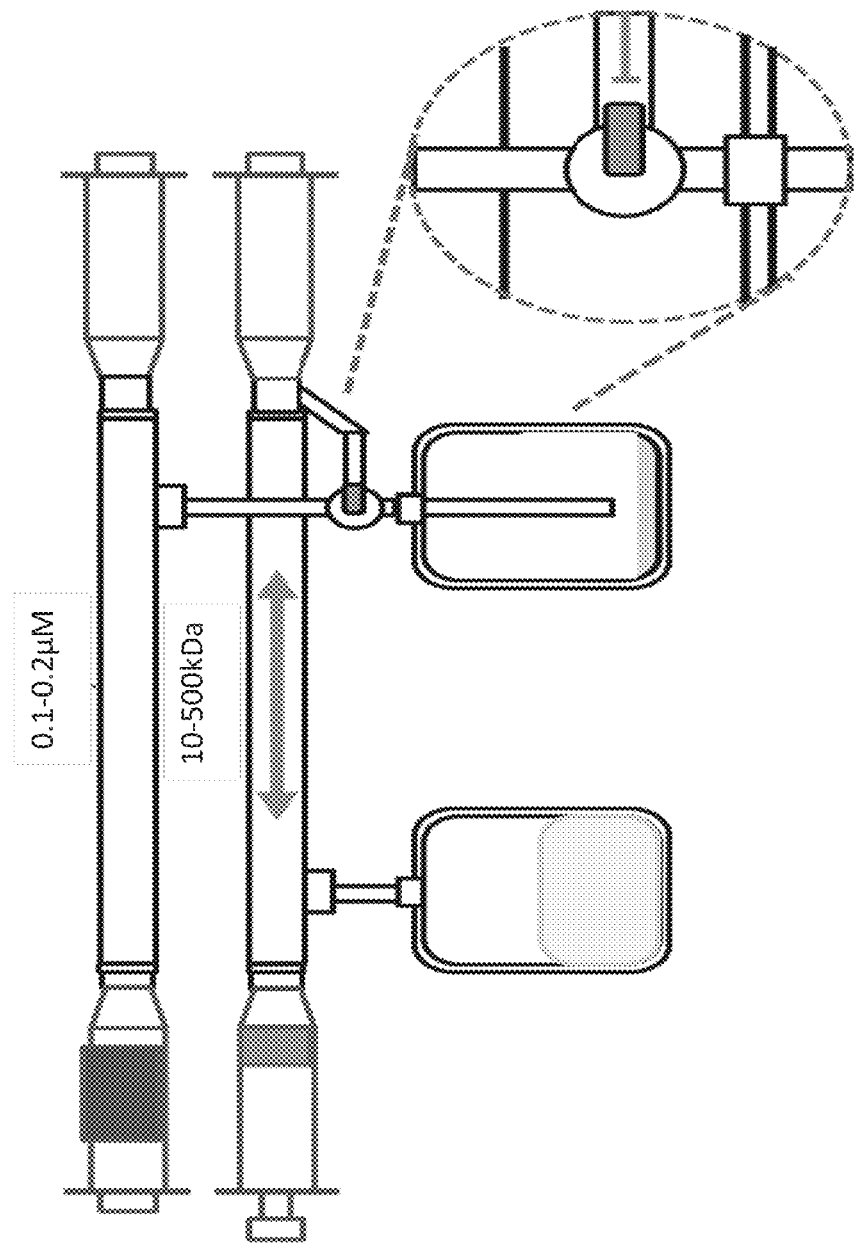
Figure 9G:
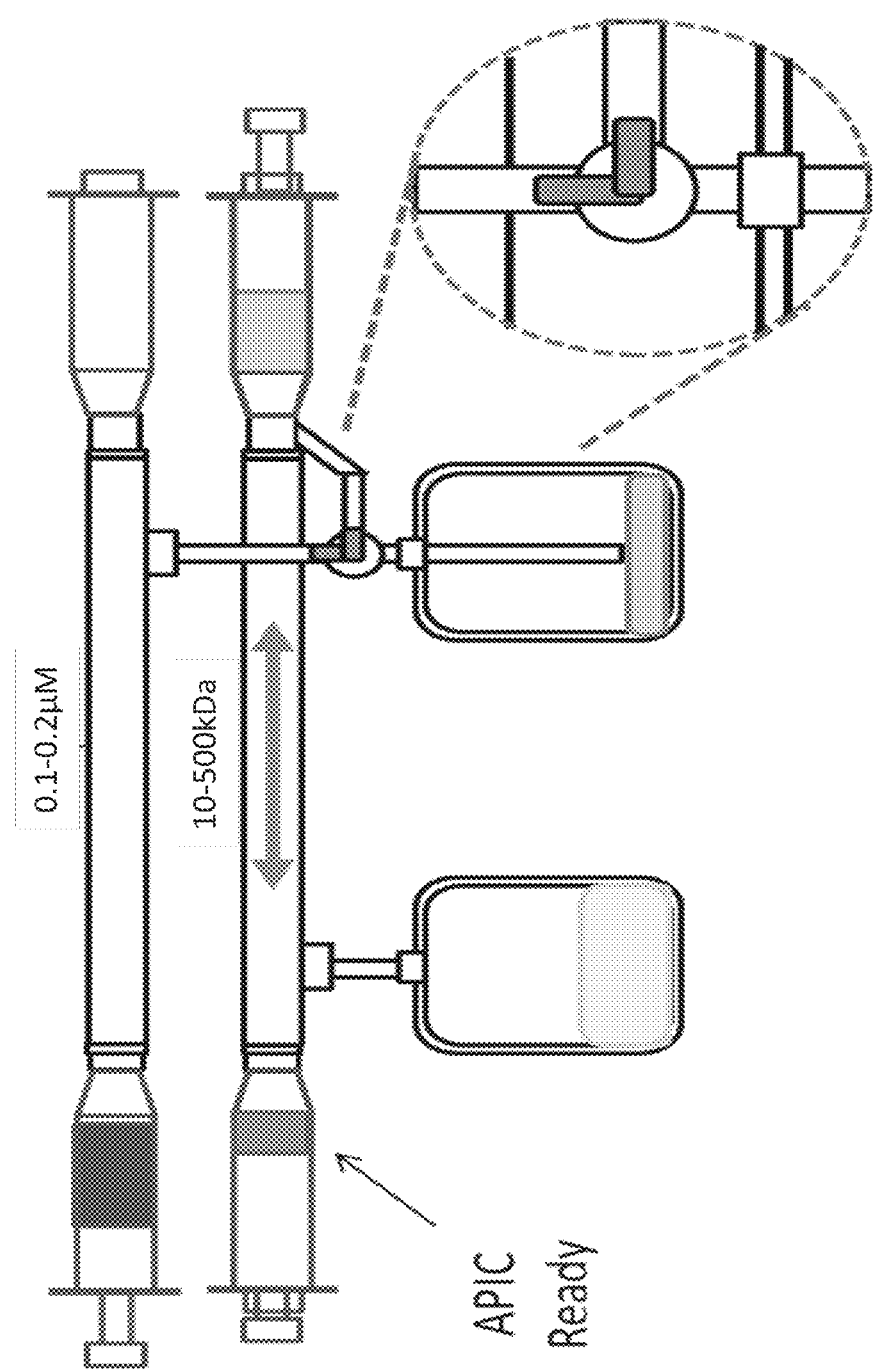
Figure 10:
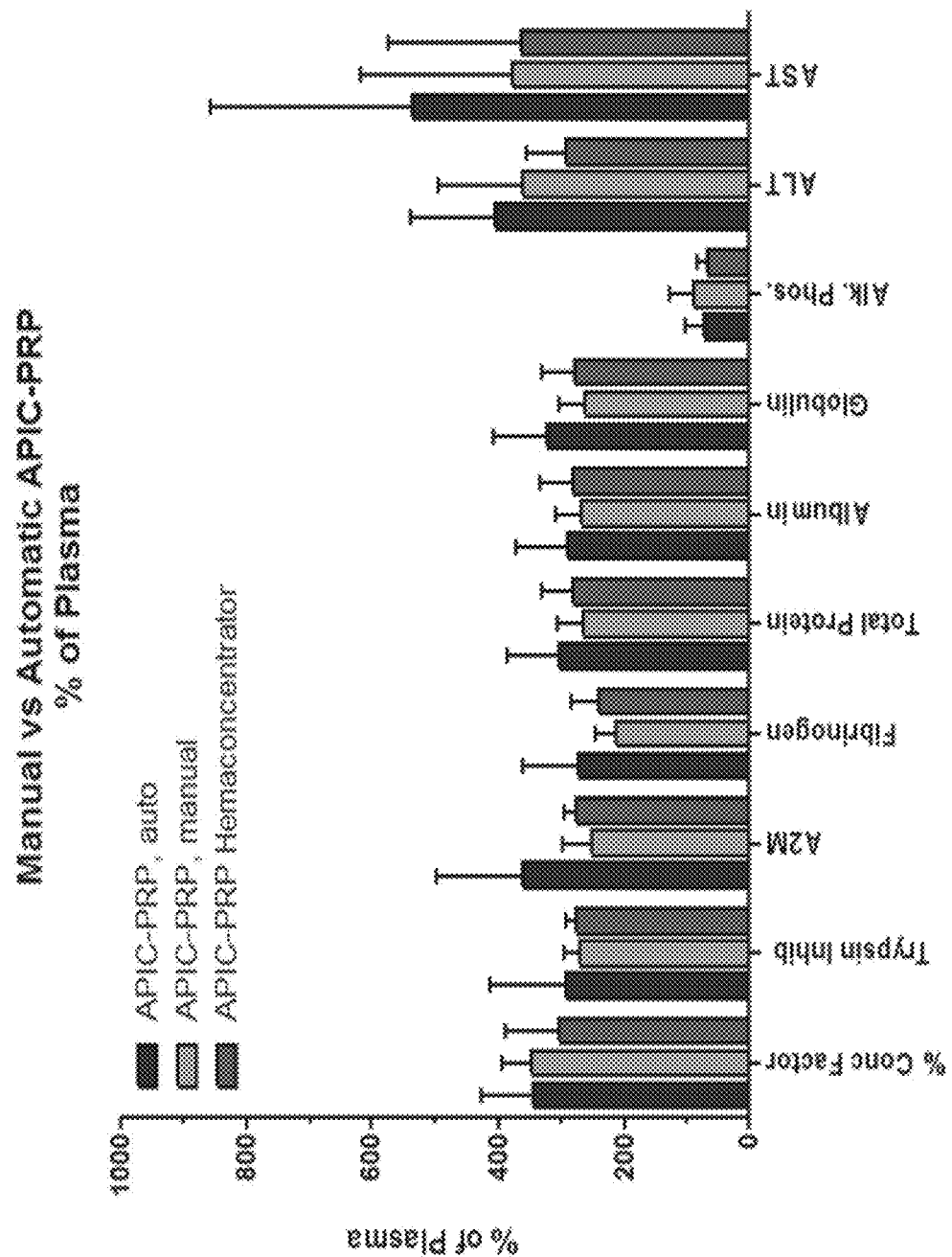
FIG. 10 depicts a graph comparing recovery of various components from a sample using an automatic system, a manual system, and a system comprising a hemaconcentrator.
Figure 11:
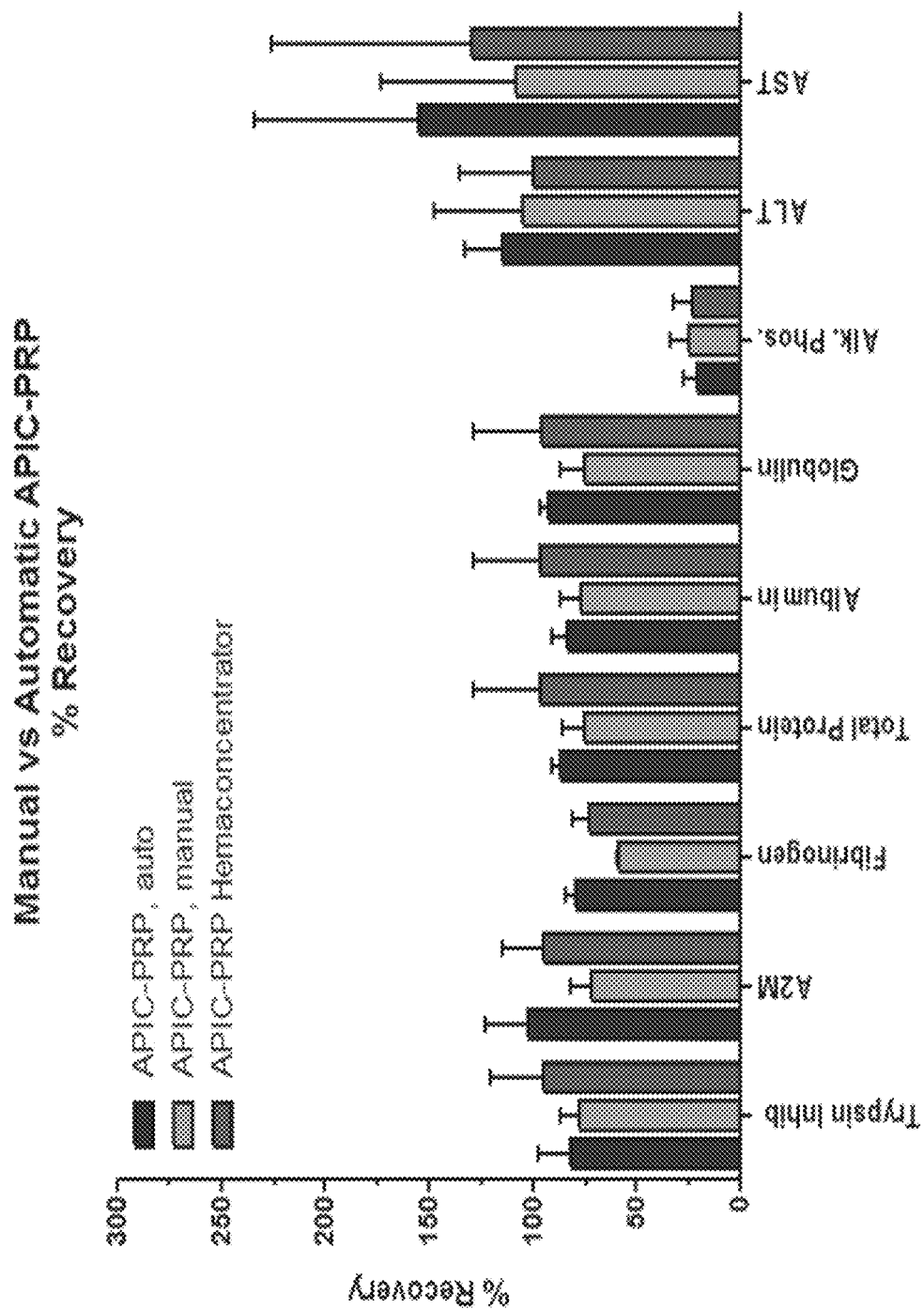
FIG. 11 depicts a graph comparing recovery of various components from a sample using an automatic system, a manual system, and a system comprising a hemaconcentrator.
Figure 12:
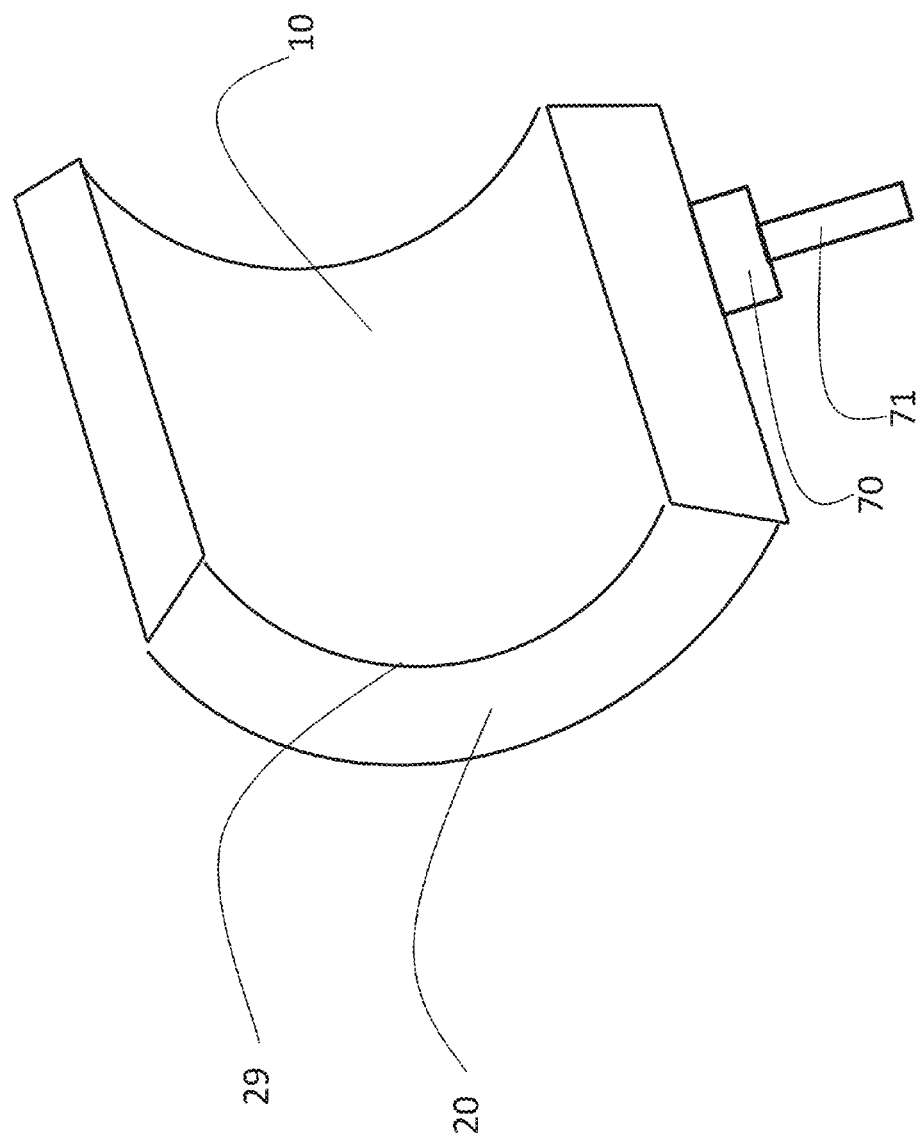
FIG. 12 depicts a schematic of view of a filtration module of a system.
Figure 13:
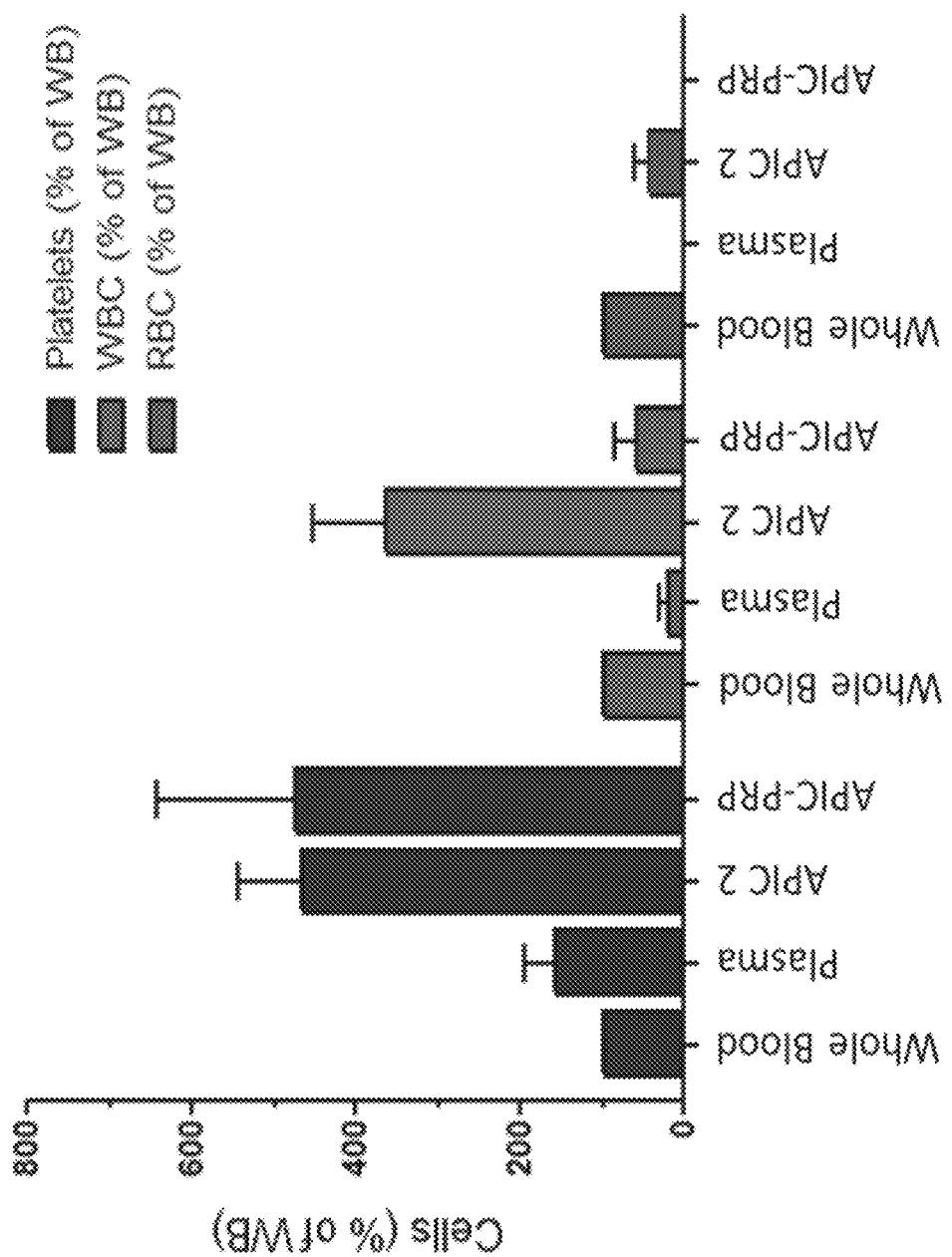
FIG. 13 depicts a bar graph of the % of the indicated cells compared to whole blood (WB)) using the indicated methods.
Figure 14:
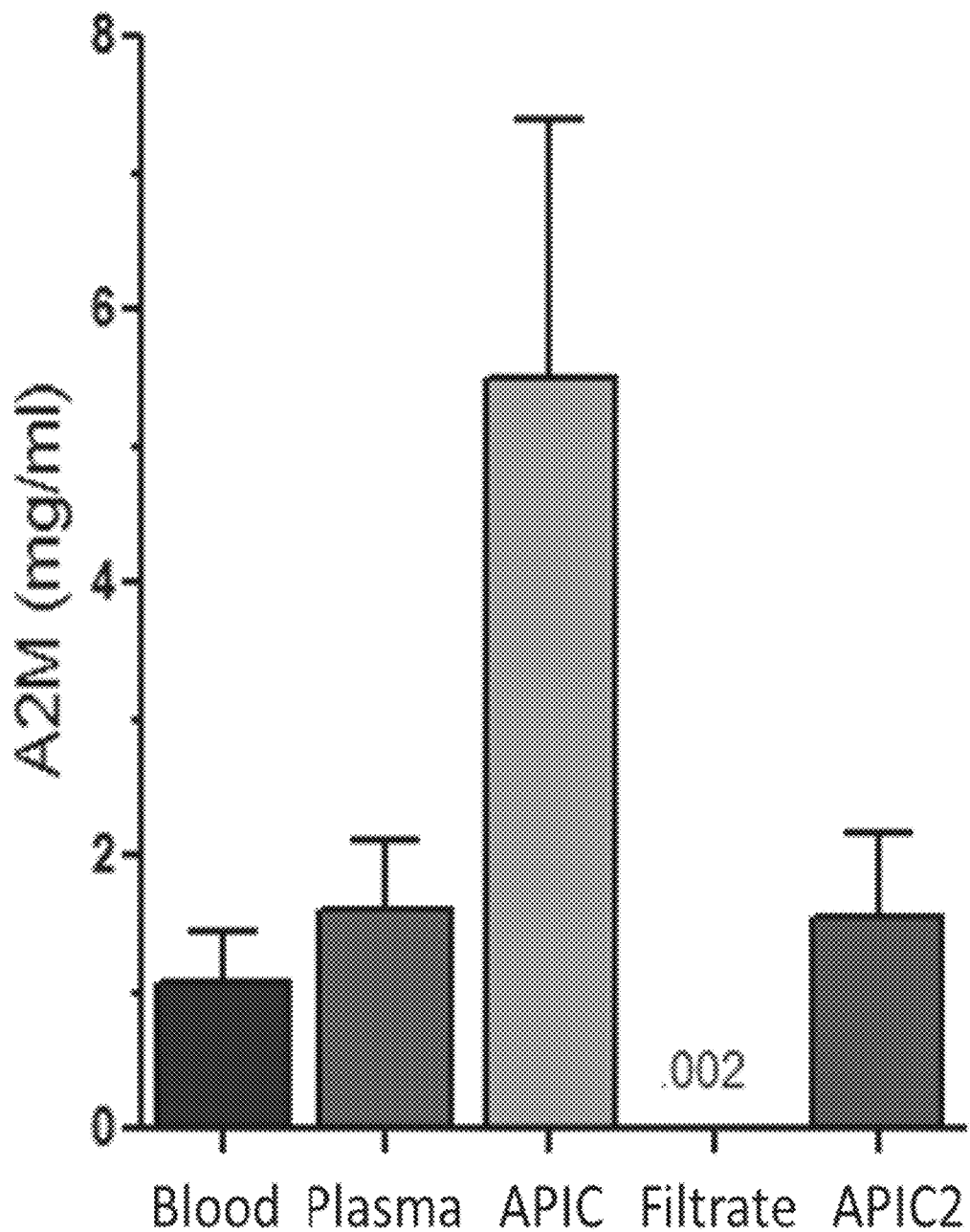
FIG. 14 depicts a bar graph of the concentration of A2M (mg/mL) in blood, plasma, and concentrated compositions produced using the indicated methods.
Figure 15A:
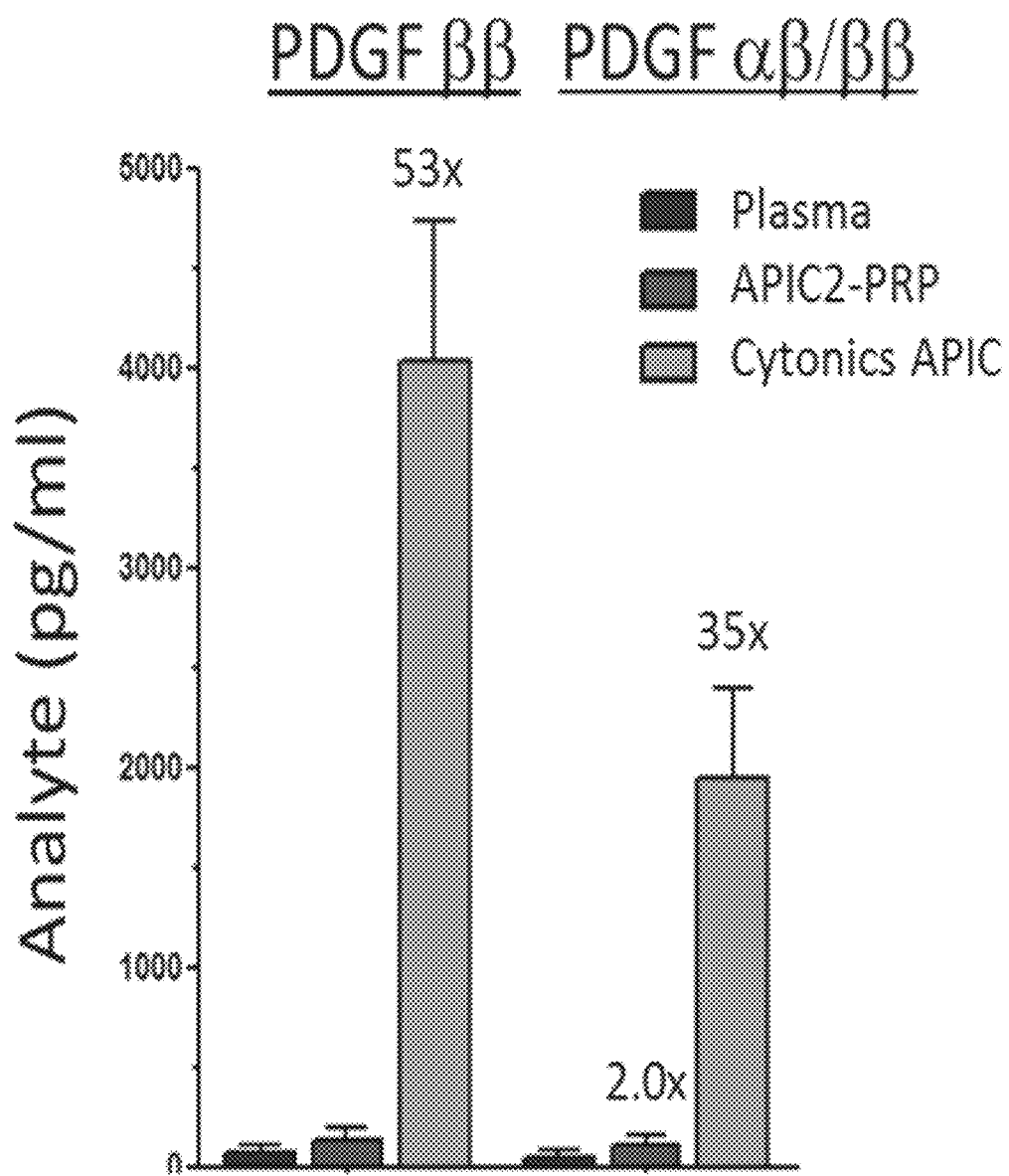
FIGS. 15A-C depict bar graphs of the concentration of the indicated analytes in plasma and concentrated compositions produced using the indicated methods.
Figure 15B:
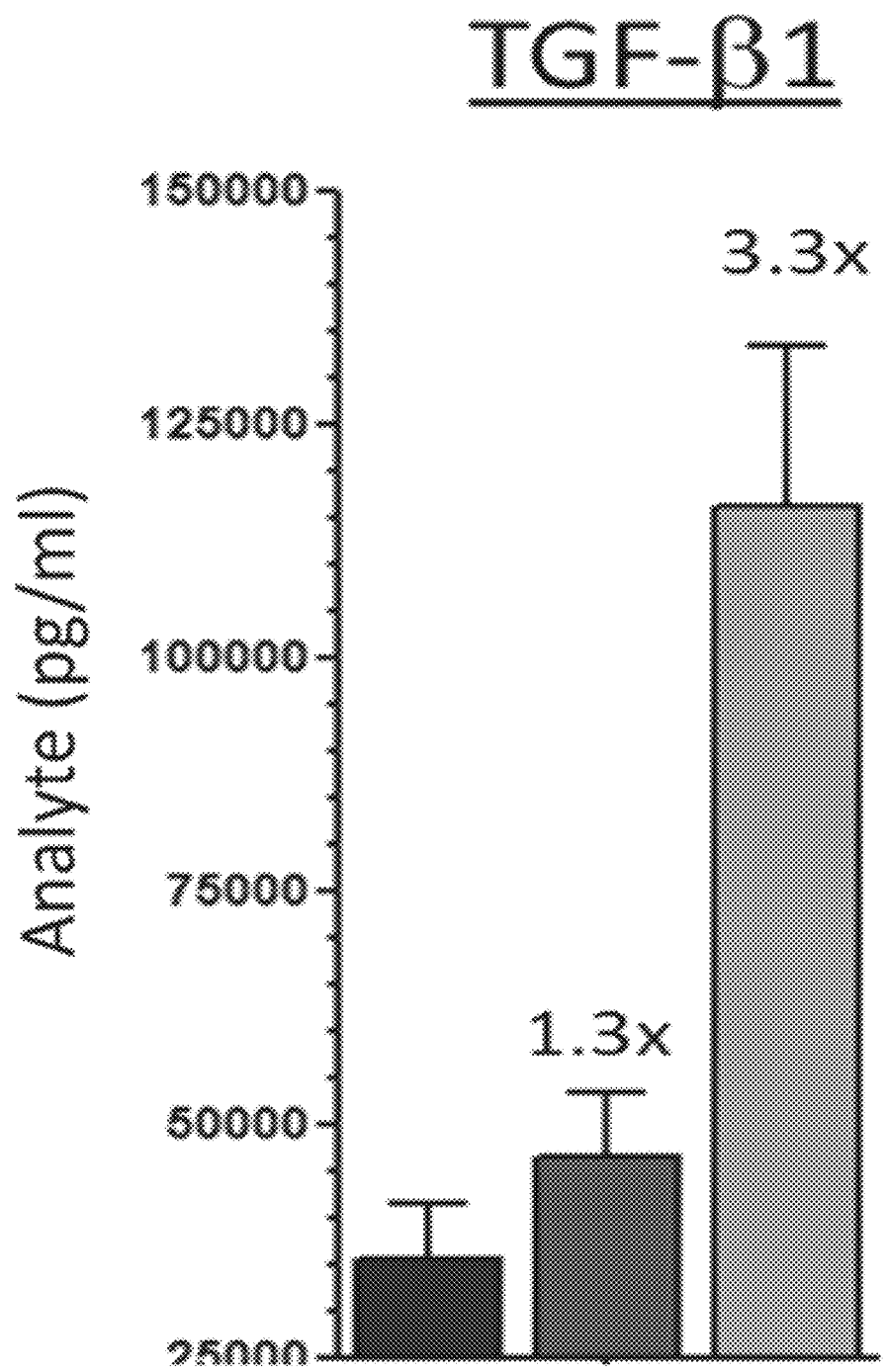
Figure 15C:
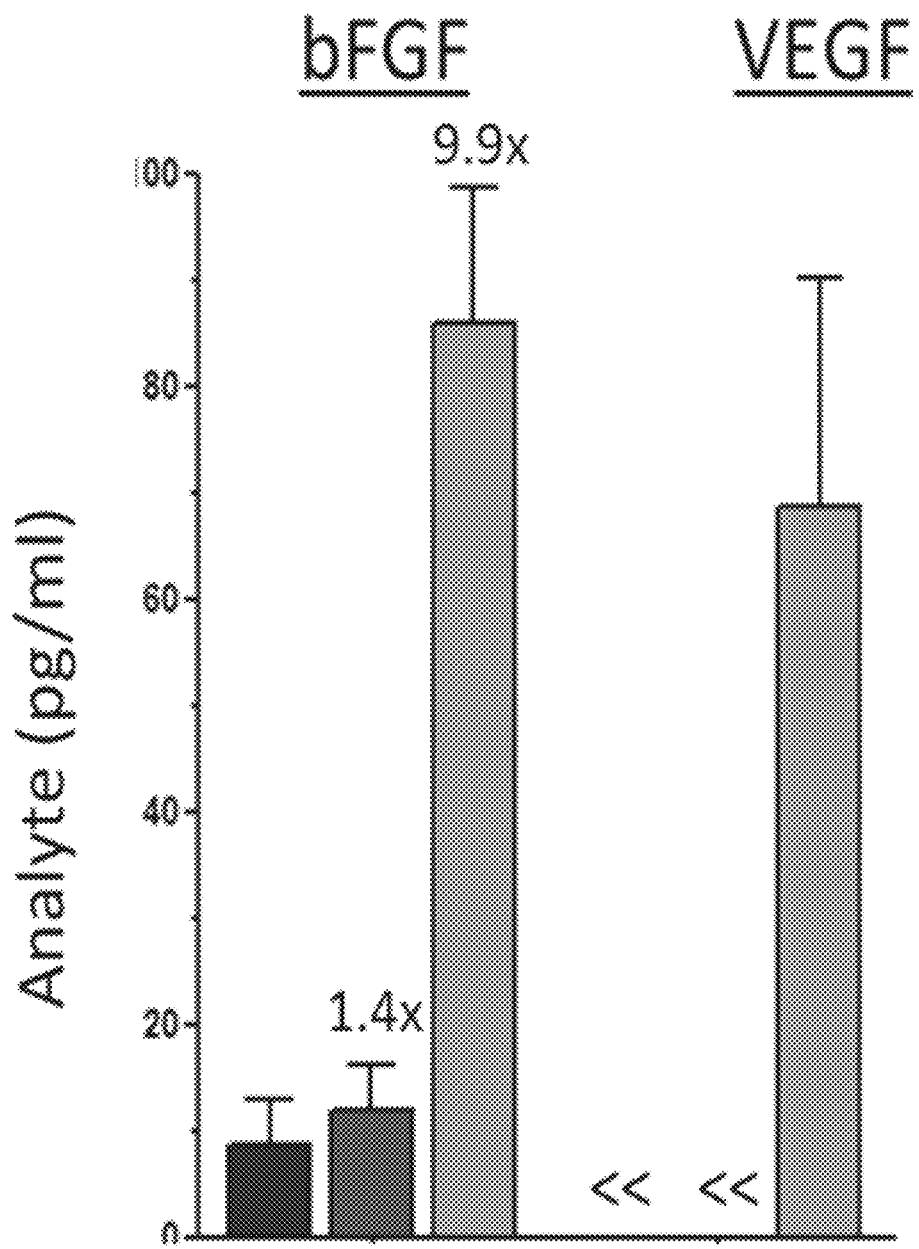
Figure 17:
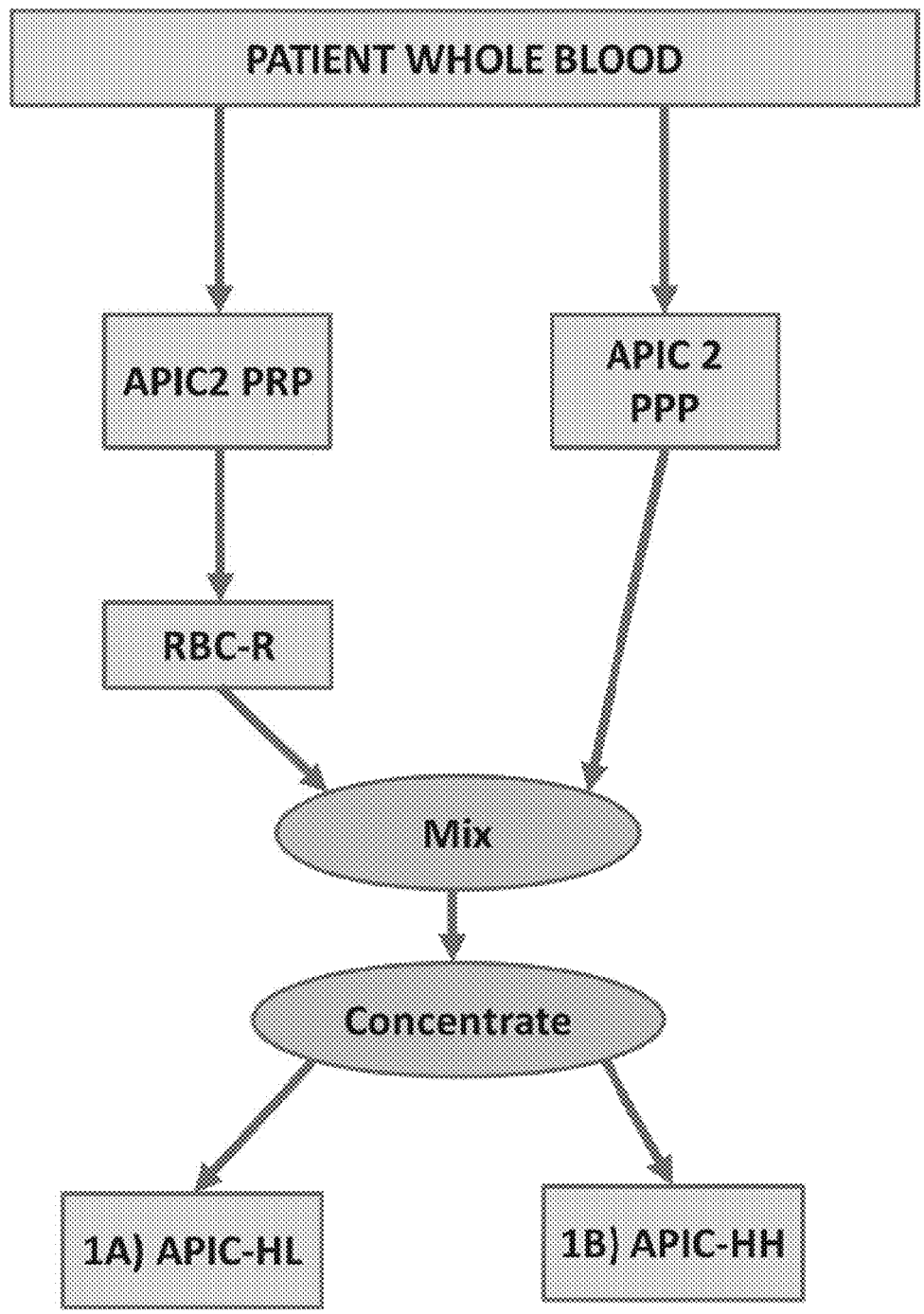
FIG. 17 depicts a flow chart of the steps for exemplary methods of preparing therapeutic compositions described herein.
Figure 18:
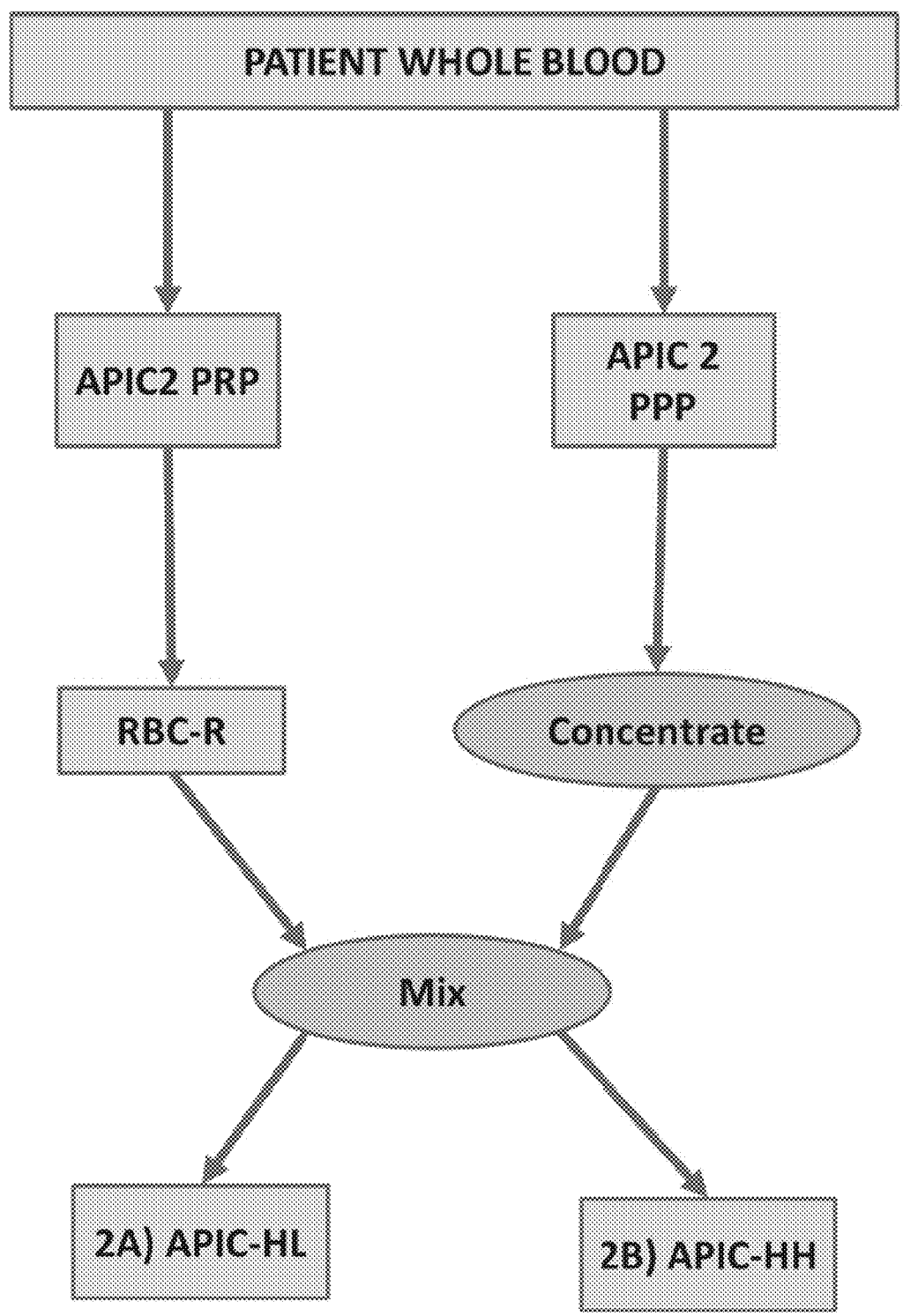
FIG. 18 depicts a flow chart of the steps for exemplary methods of preparing therapeutic compositions described herein.
Figure 19:
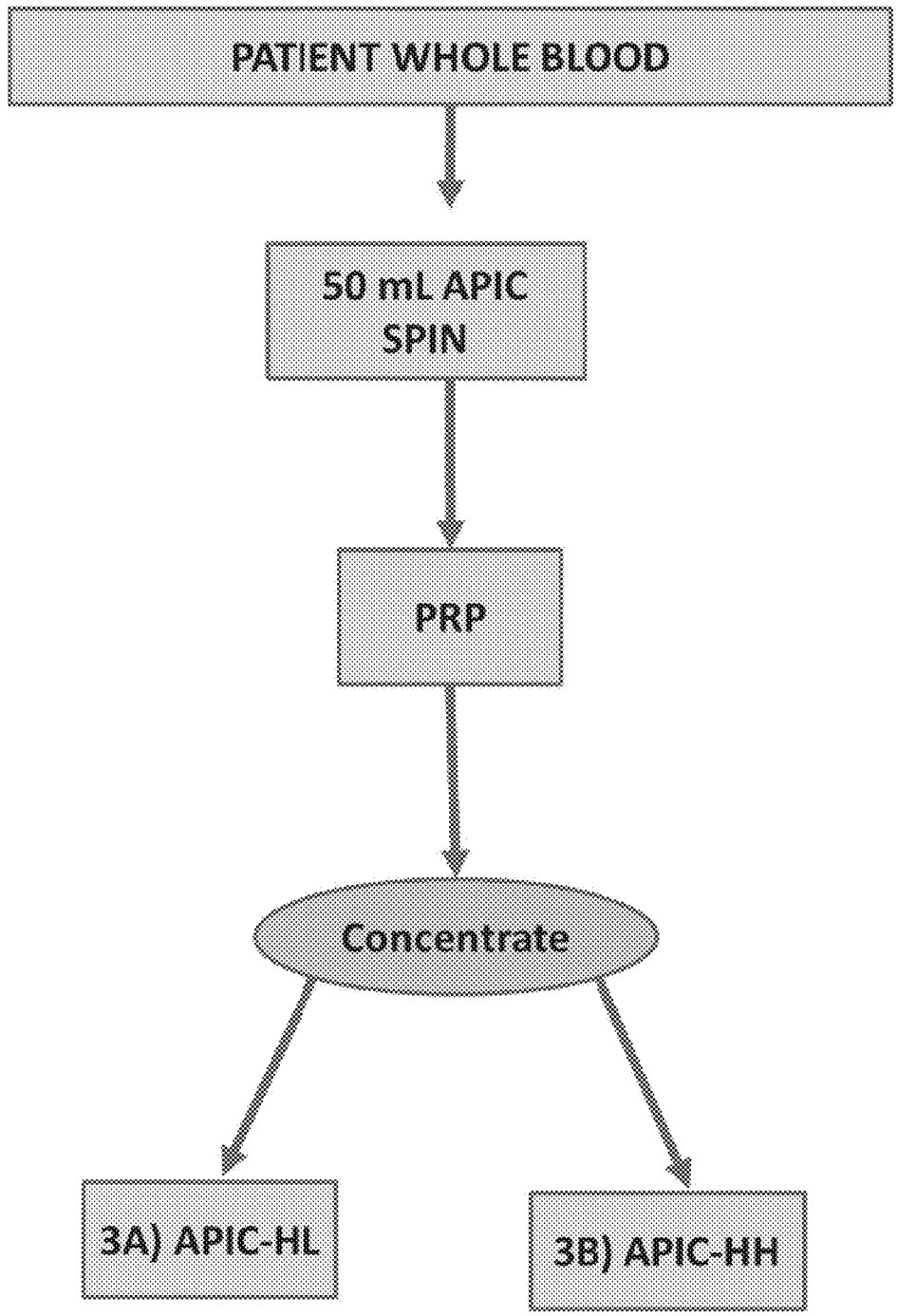
FIG. 19 depicts a flow chart of the steps for exemplary methods of preparing therapeutic compositions described herein.
Figure 20A:
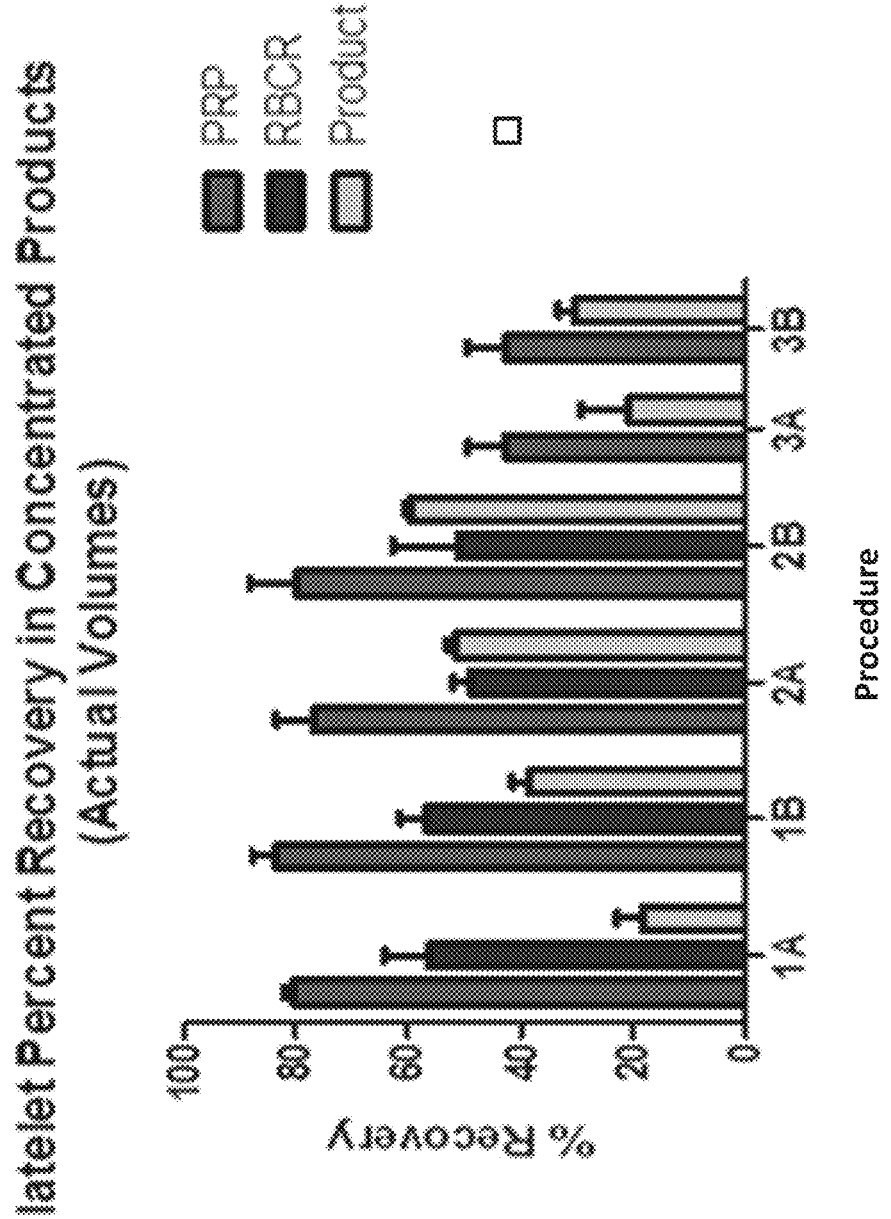
FIG. 20A depicts a bar graph of the percent recovery of platelets from whole blood in concentrated products produced using the indicated method.
Figure 20B:
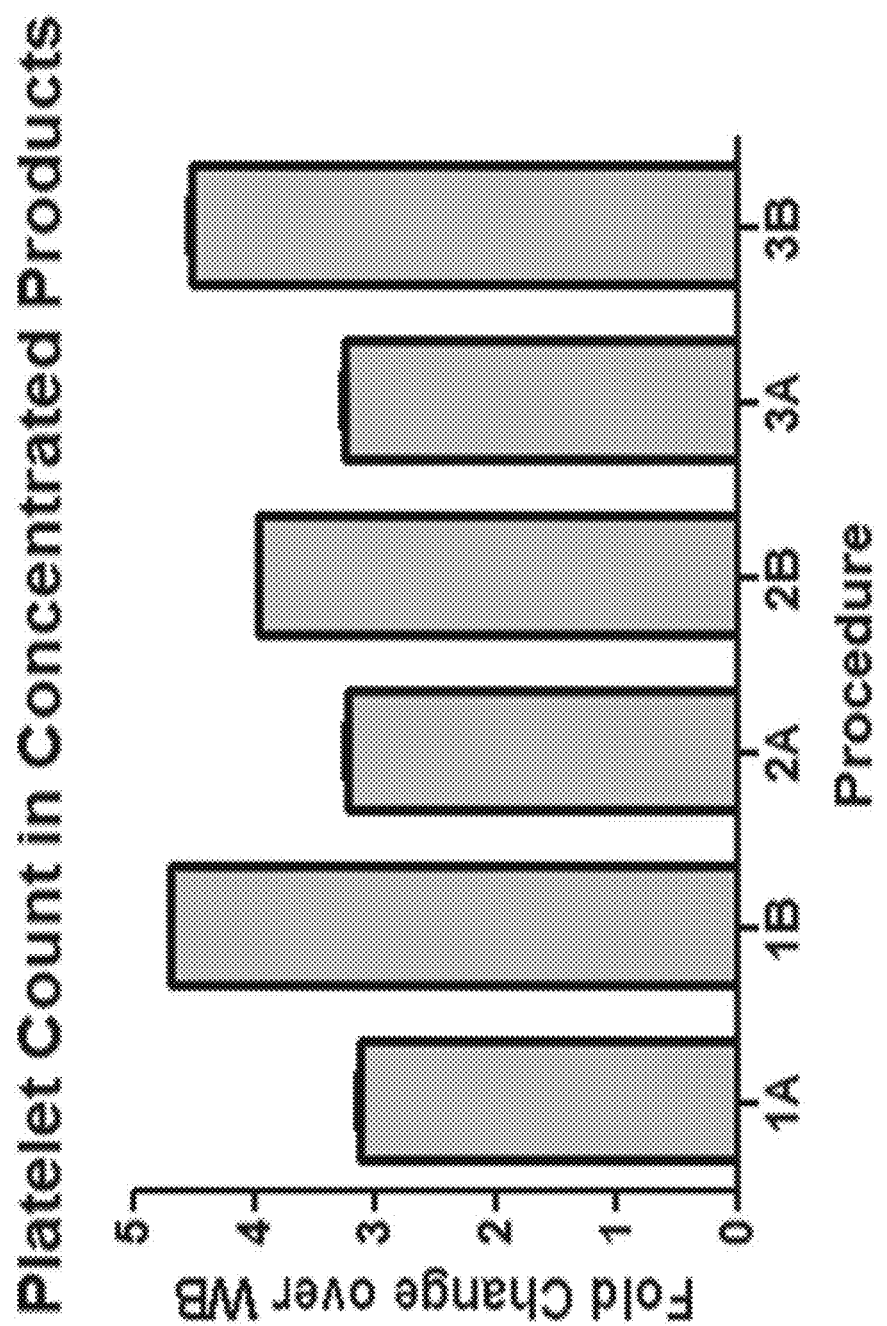
FIG. 20B depicts a bar graph of the fold change of platelets in concentrated products produced using the indicated method compared to whole blood.
Figure 21A:
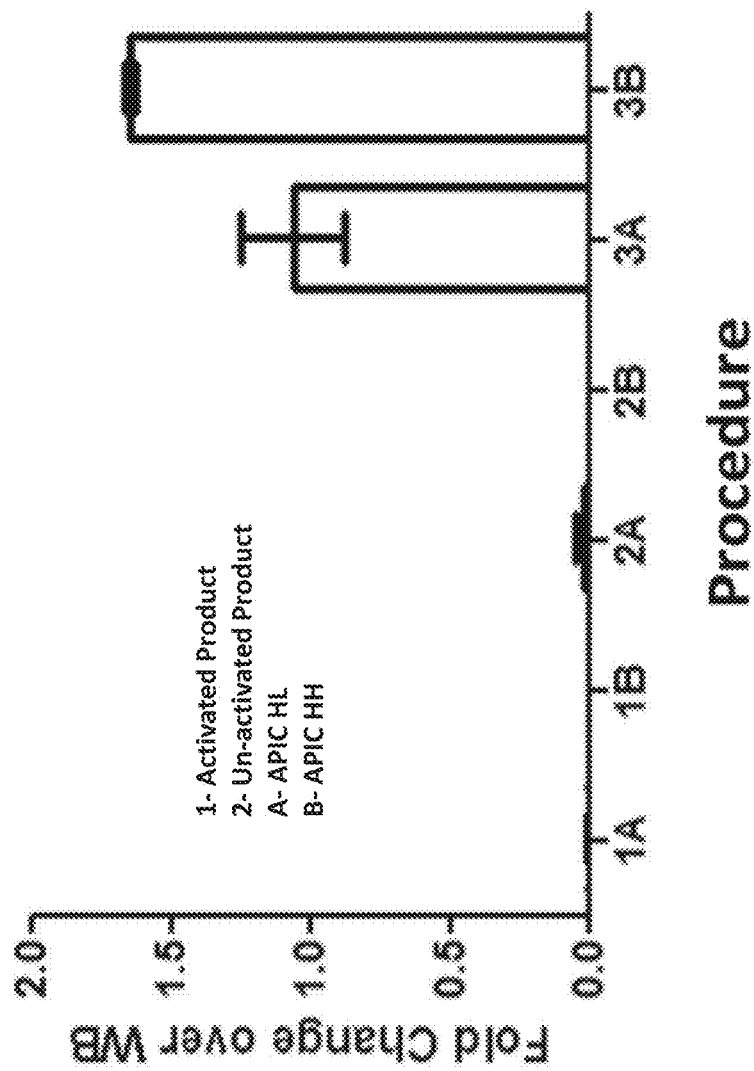
FIG. 21A depicts a bar graph of the fold change of white blood cells in concentrated products produced using the indicated method compared to whole.
Figure 21B:
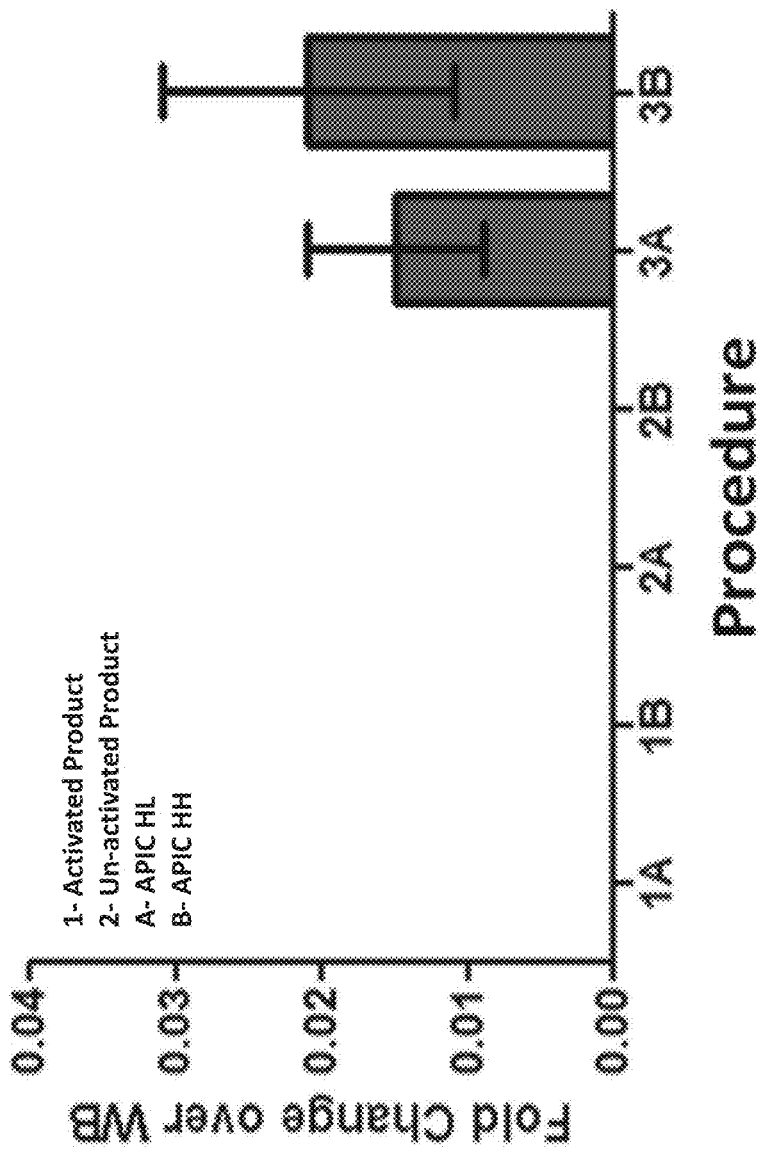
FIG. 21B depicts a bar graph of the fold change of red blood cells in concentrated products produced using the indicated method compared to whole blood.
Figure 22:
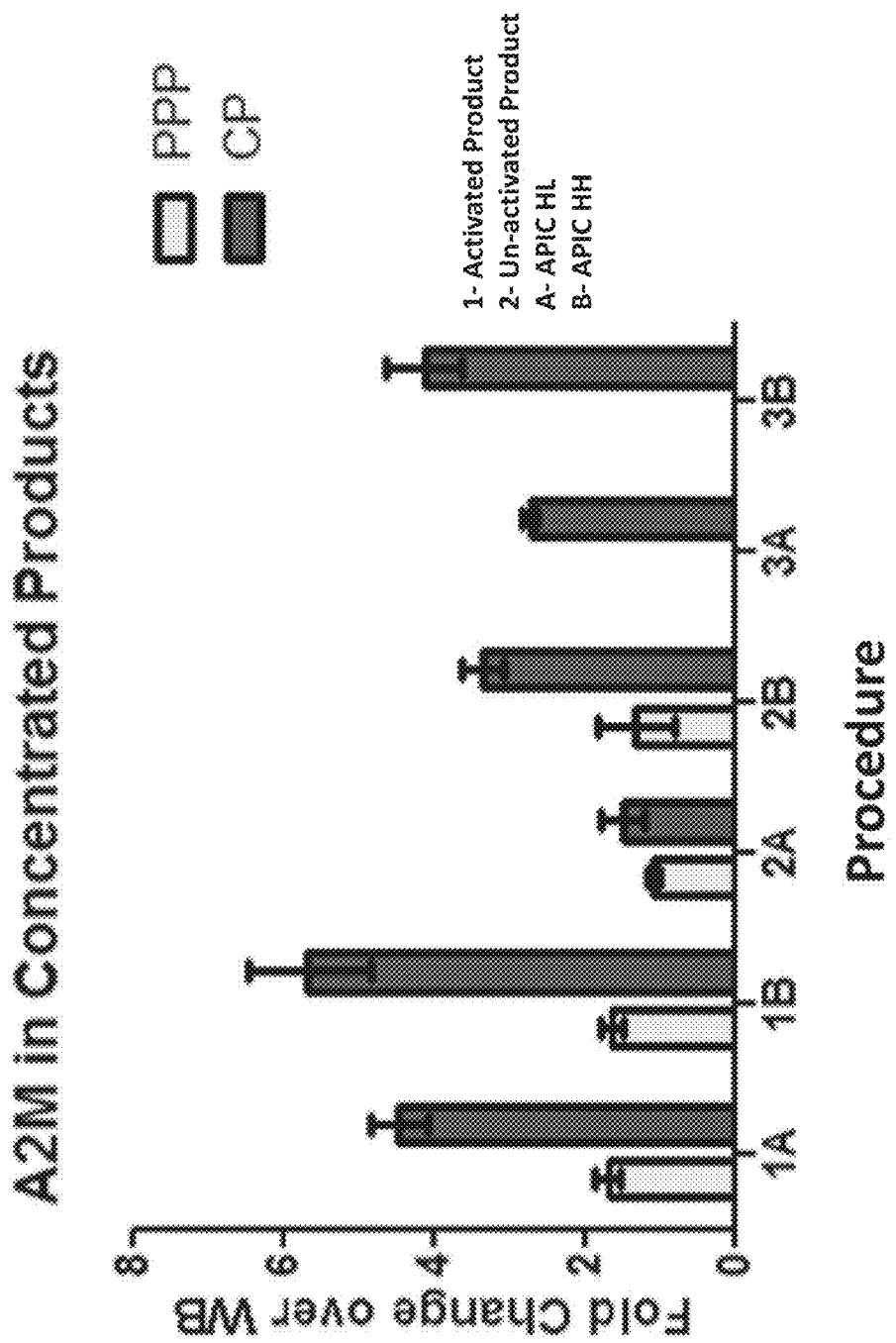
FIG. 22 depicts a bar graph of the fold change of A2M in concentrated products produced using the indicated method compared to whole blood.
Figure 23:
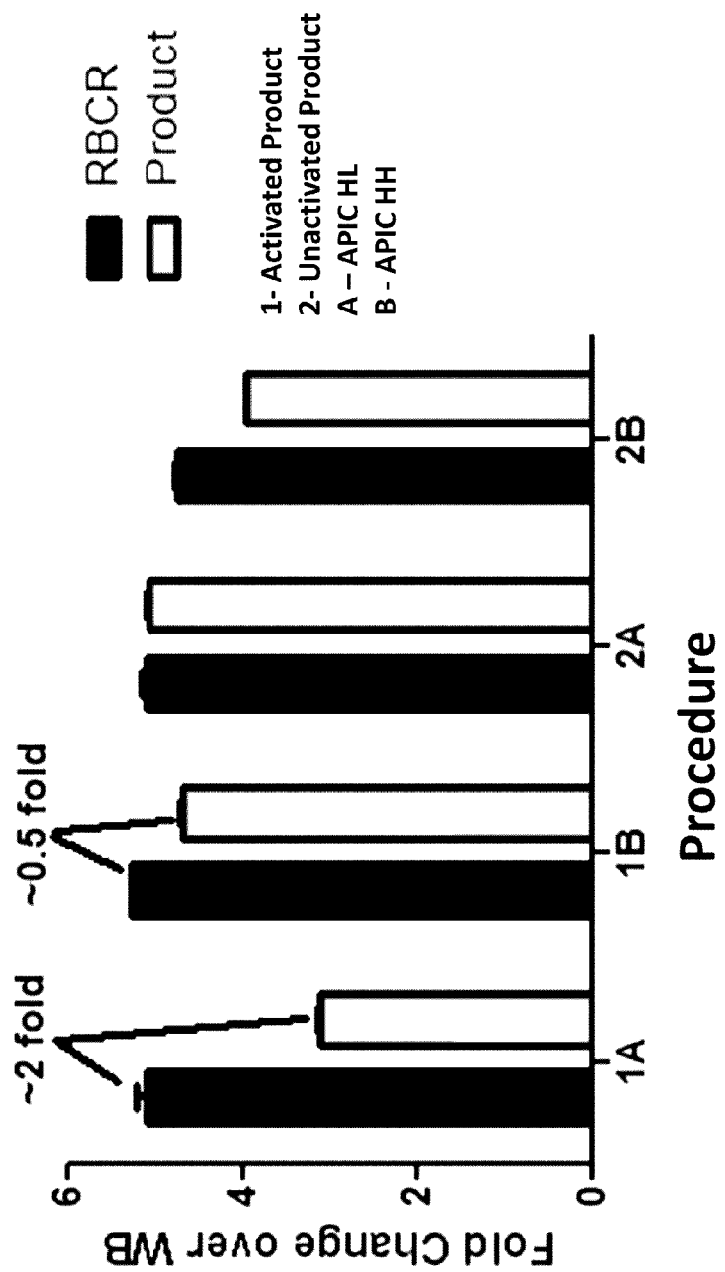
FIG. 23 depicts a bar graph of the fold change of platelets in concentrated products produced using the indicated method compared to whole blood
Figure 24:
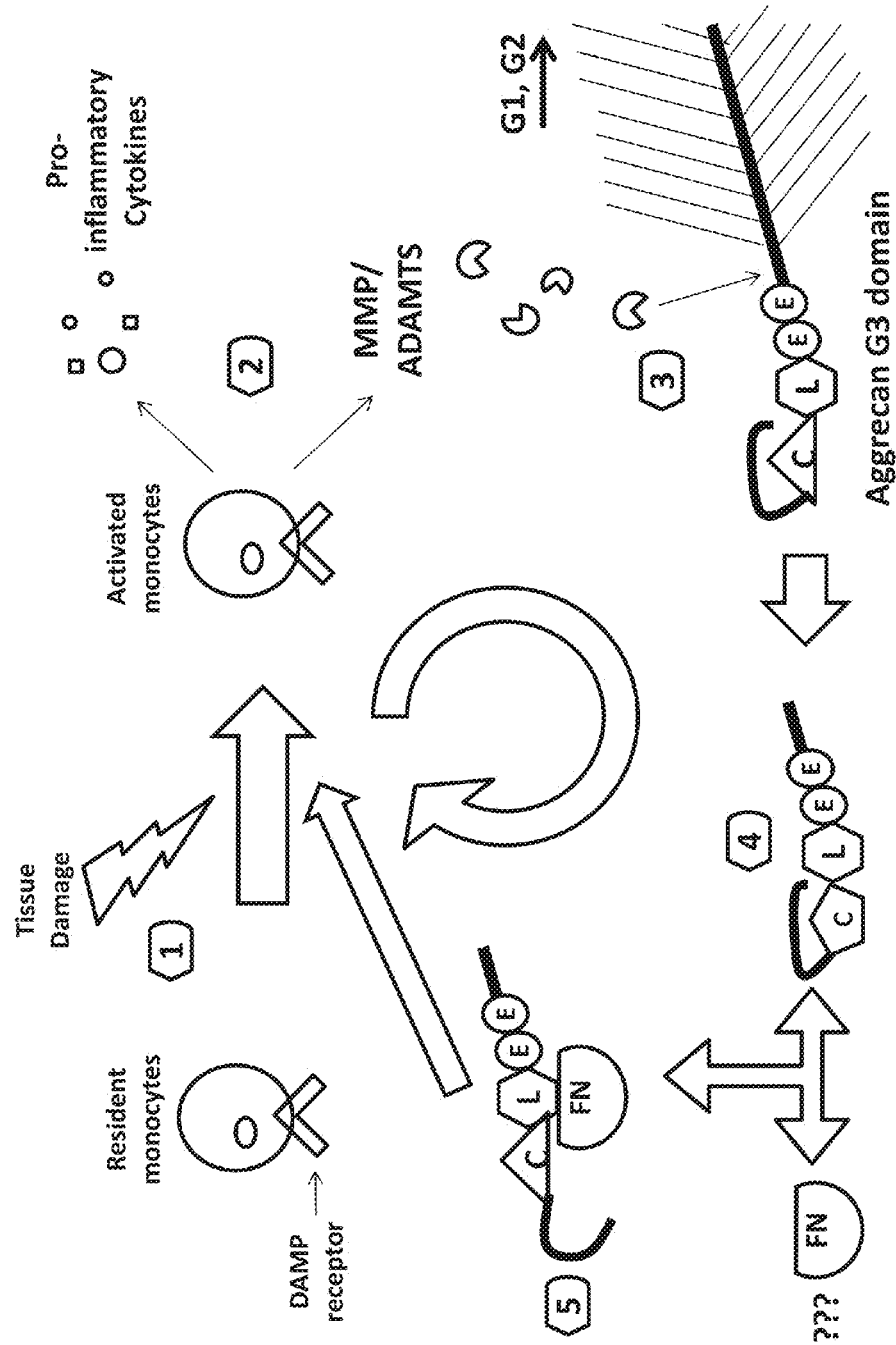
FIG. 24 depicts a schematic of the steps and signaling pathways associated with formation of a fibronectin-aggrecan complex (FAC) and the FAC-induced activation of Damage-Associated-Molecular Pattern (DAMP) receptor signaling in cells. The combination of the two processes creates a cyclic process that continually degrades cartilage.
Figure 25:
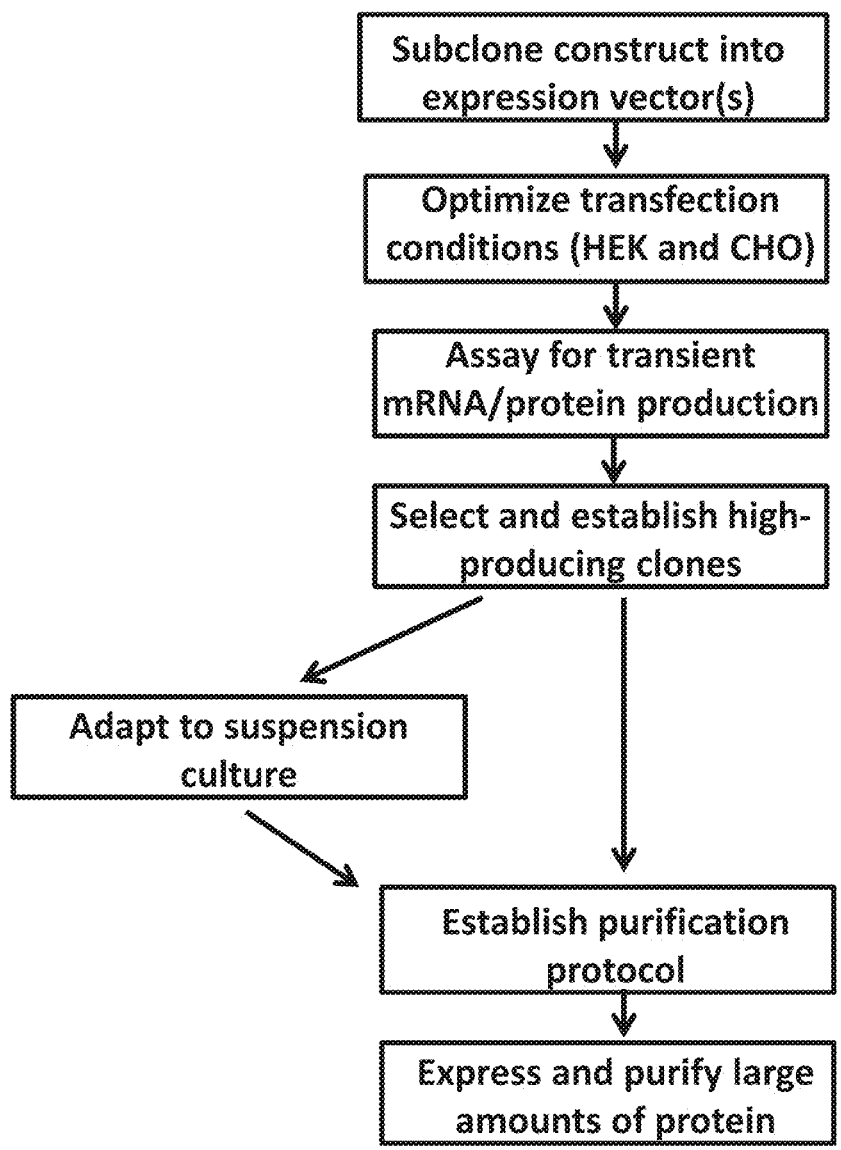
FIG. 25 depicts a flow chart of the steps for construct or protein expression.
Figure 26:
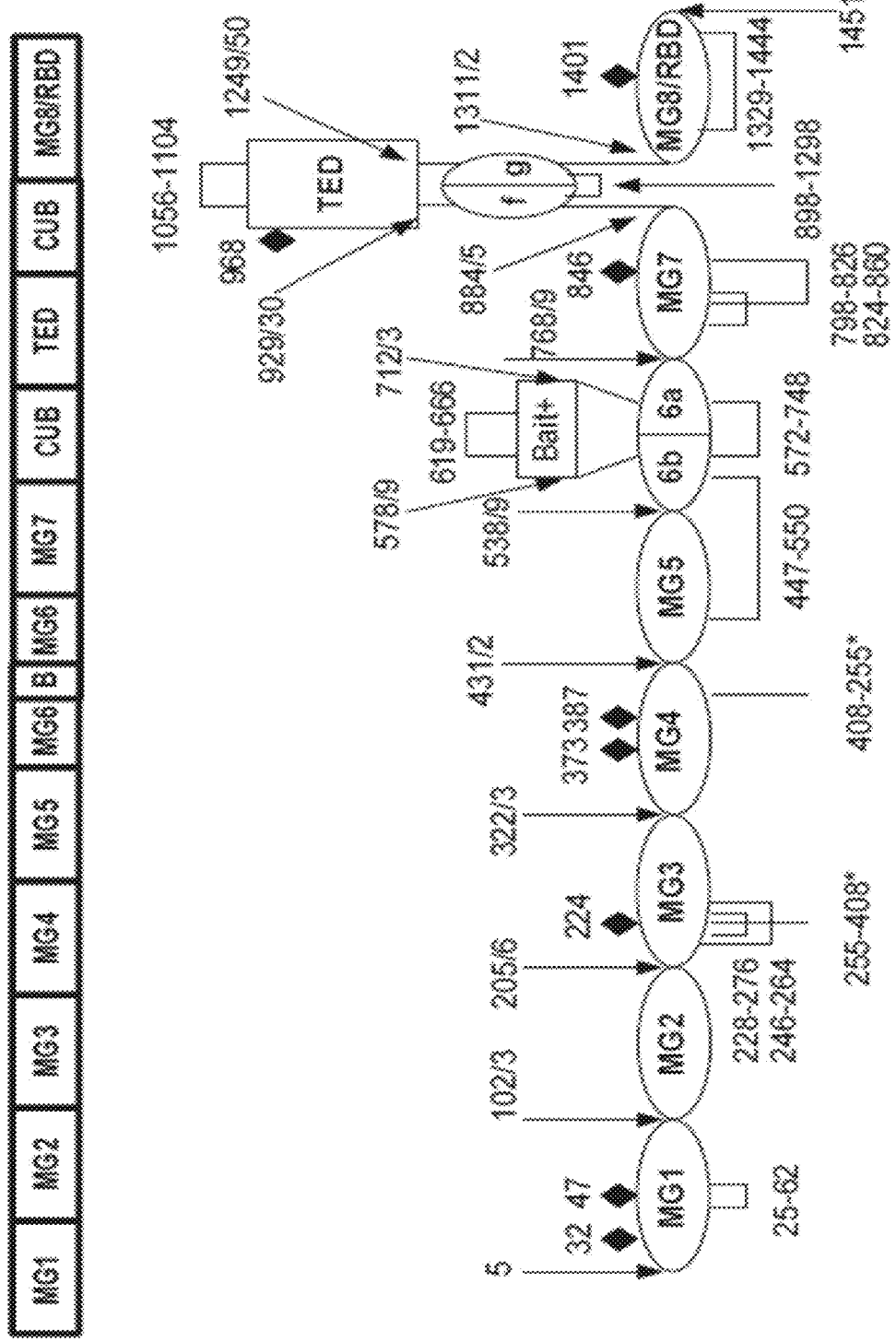
FIG. 26 depicts the A2M structure and various domains of A2M.
Figure 27:
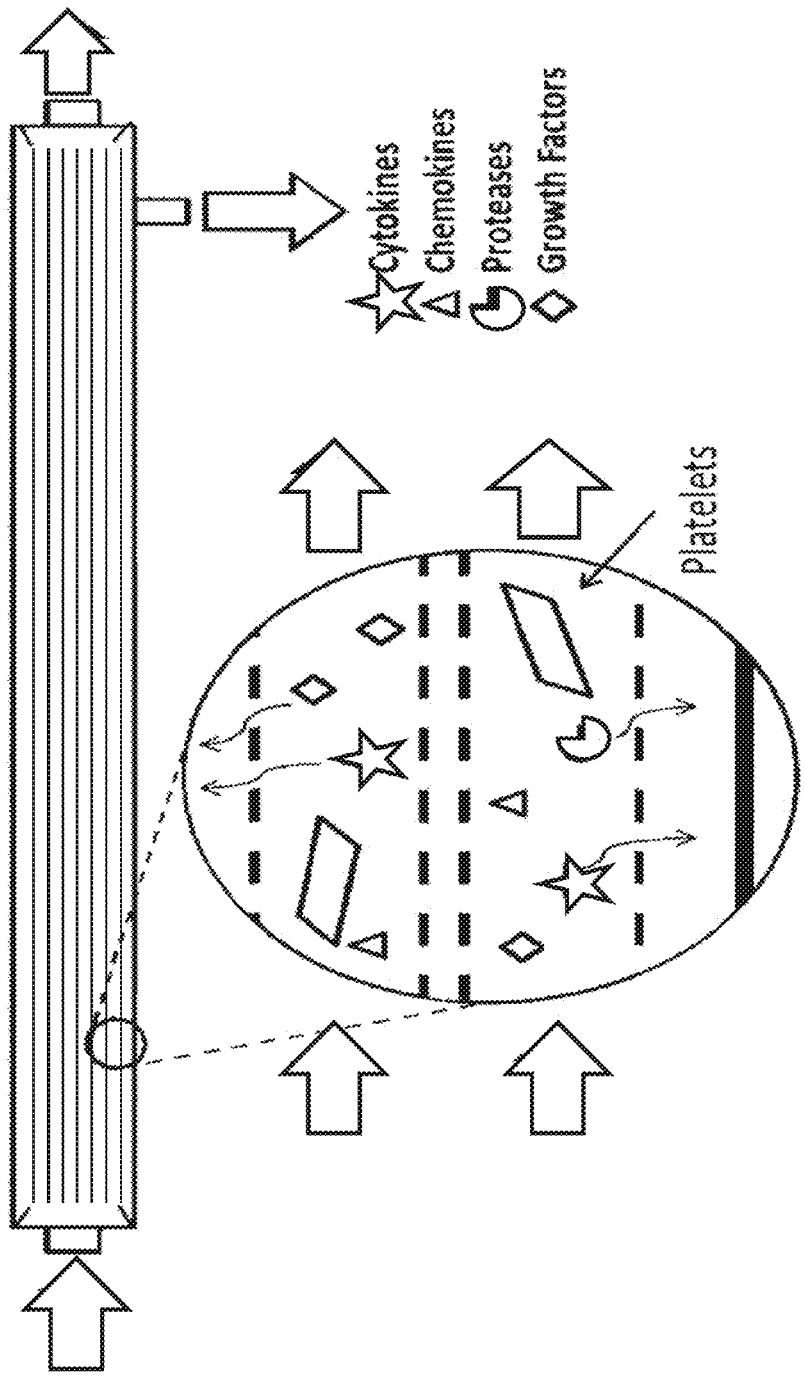
FIG. 27 depicts the process of tangential flow filtration using hollow fiber filters.
Figure 28:
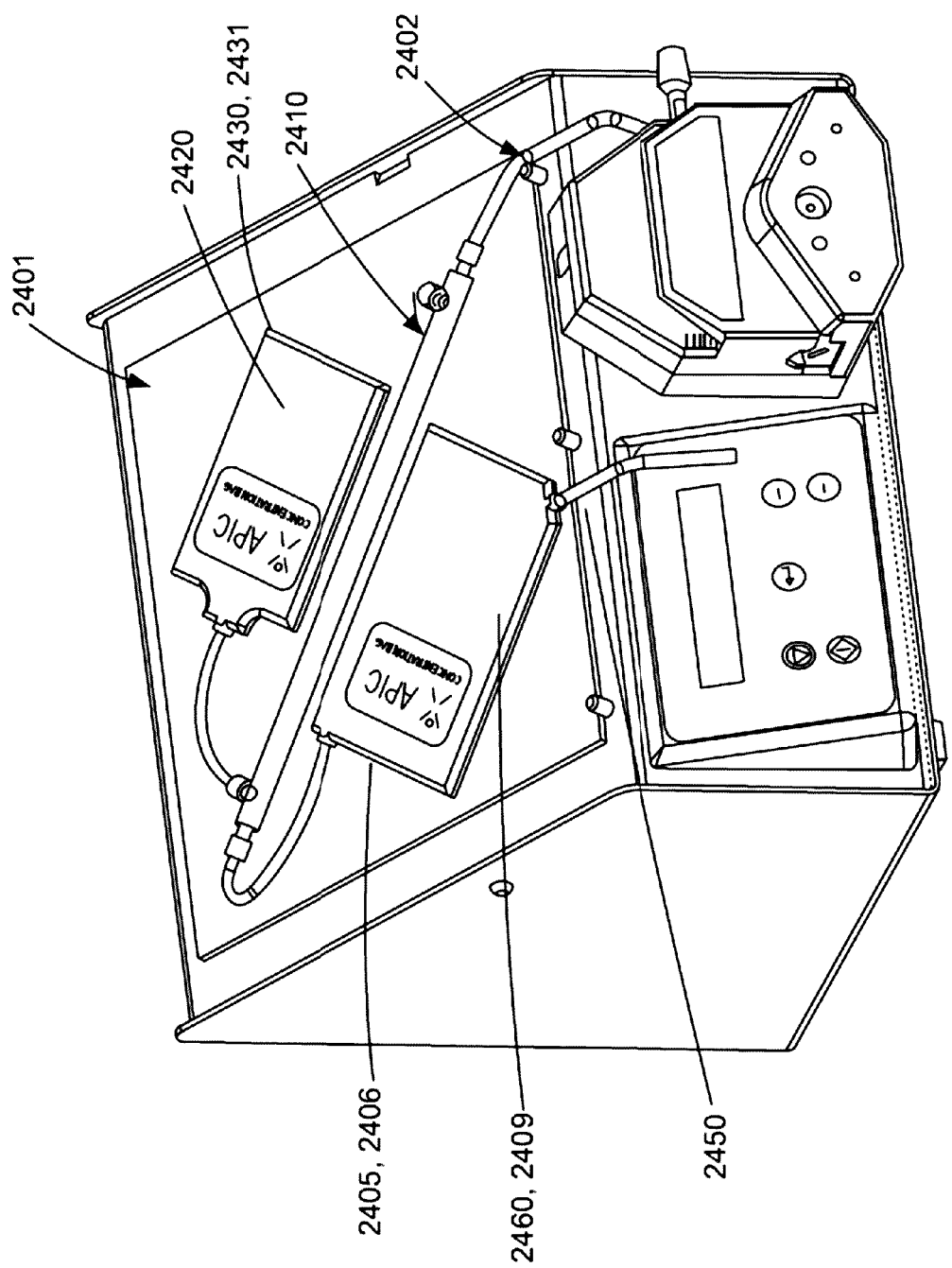
FIG. 28 depicts a schematic of a system as described herein.
Figure 29:
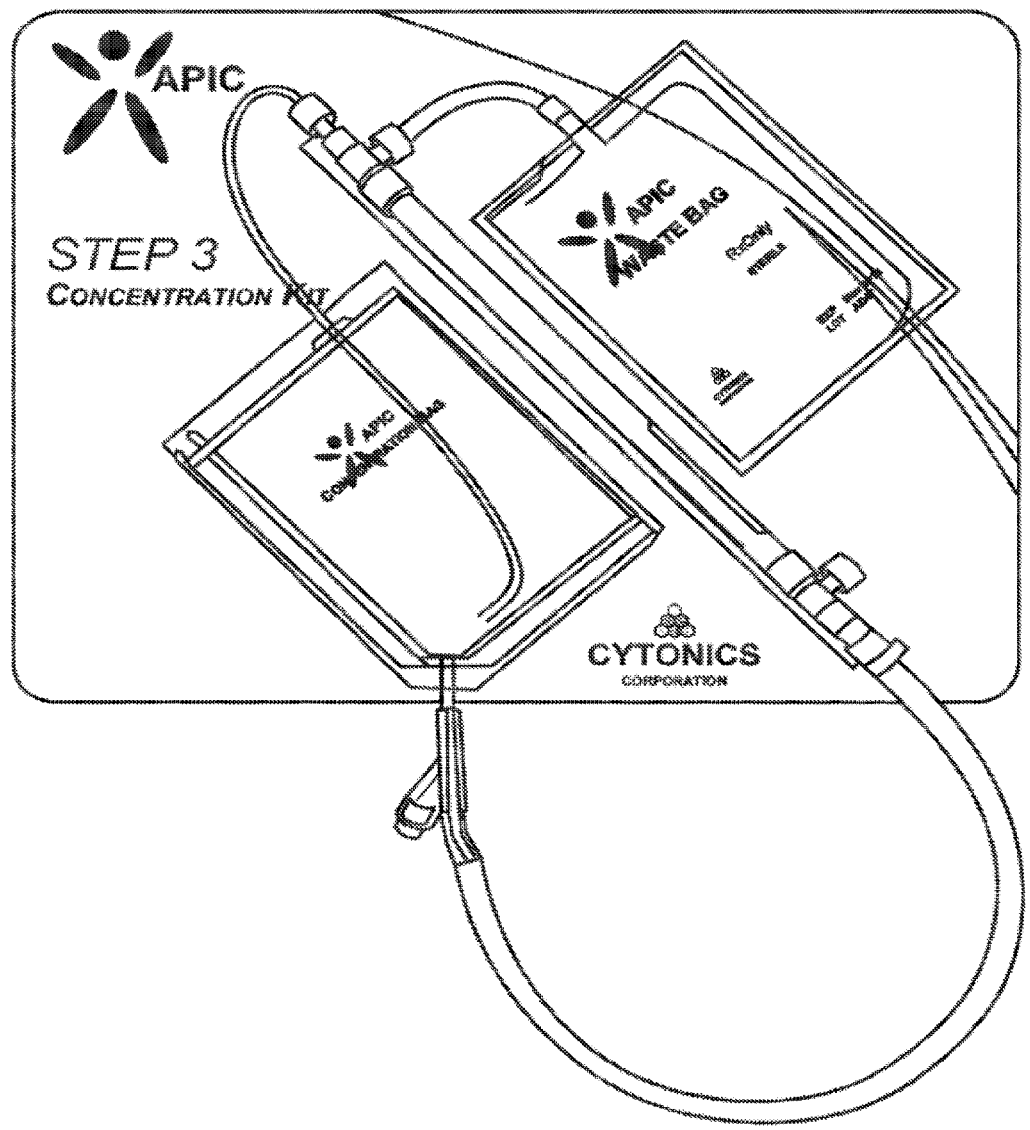
FIG. 29 a picture of the concentration kit/tray of a system described herein showing one filter, a concentration bag and the filtrate bag.
Figure 30:
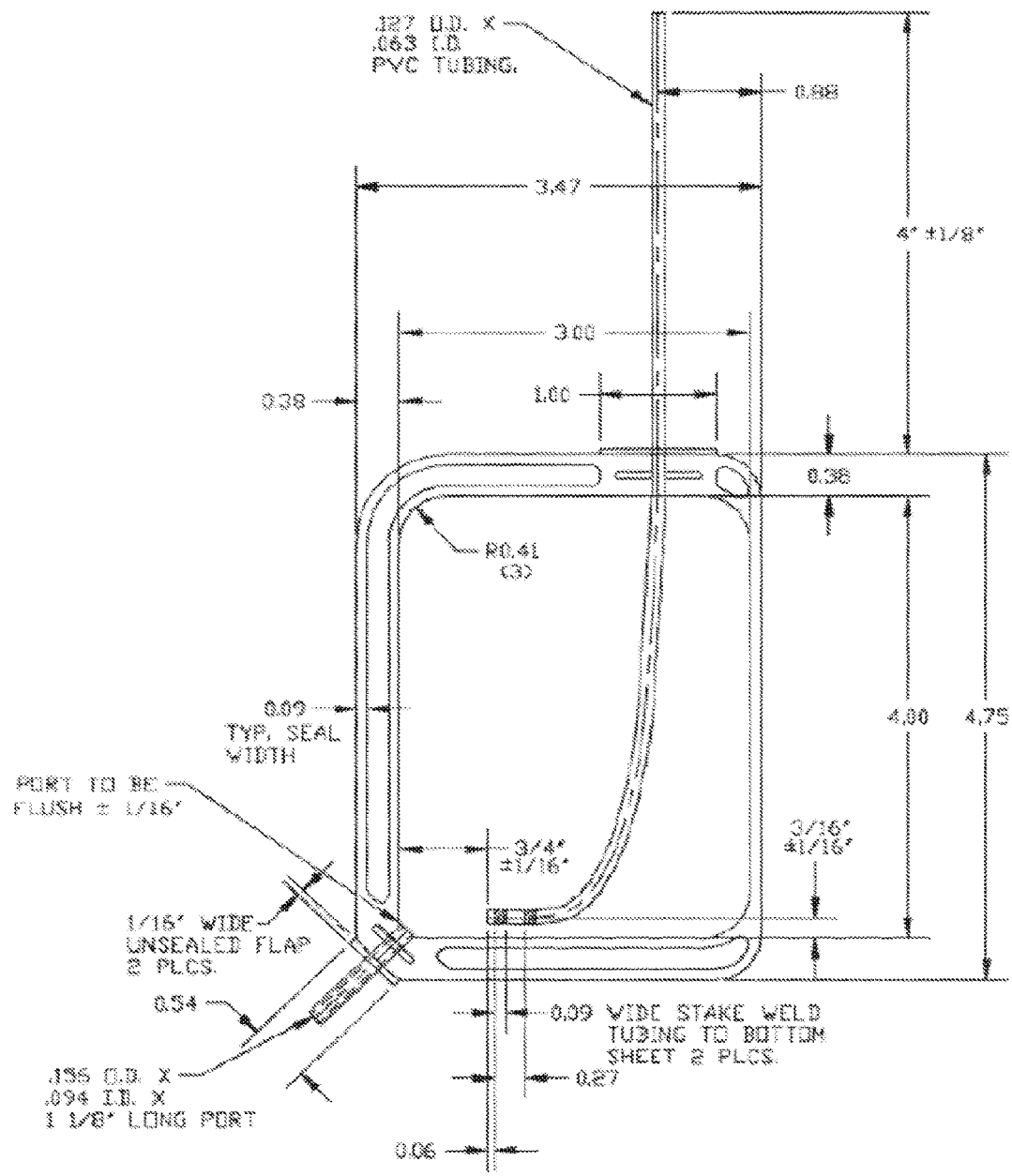
FIG. 30 depicts a schematic of the components of a concentration bag of a system described herein.
Figure 31:
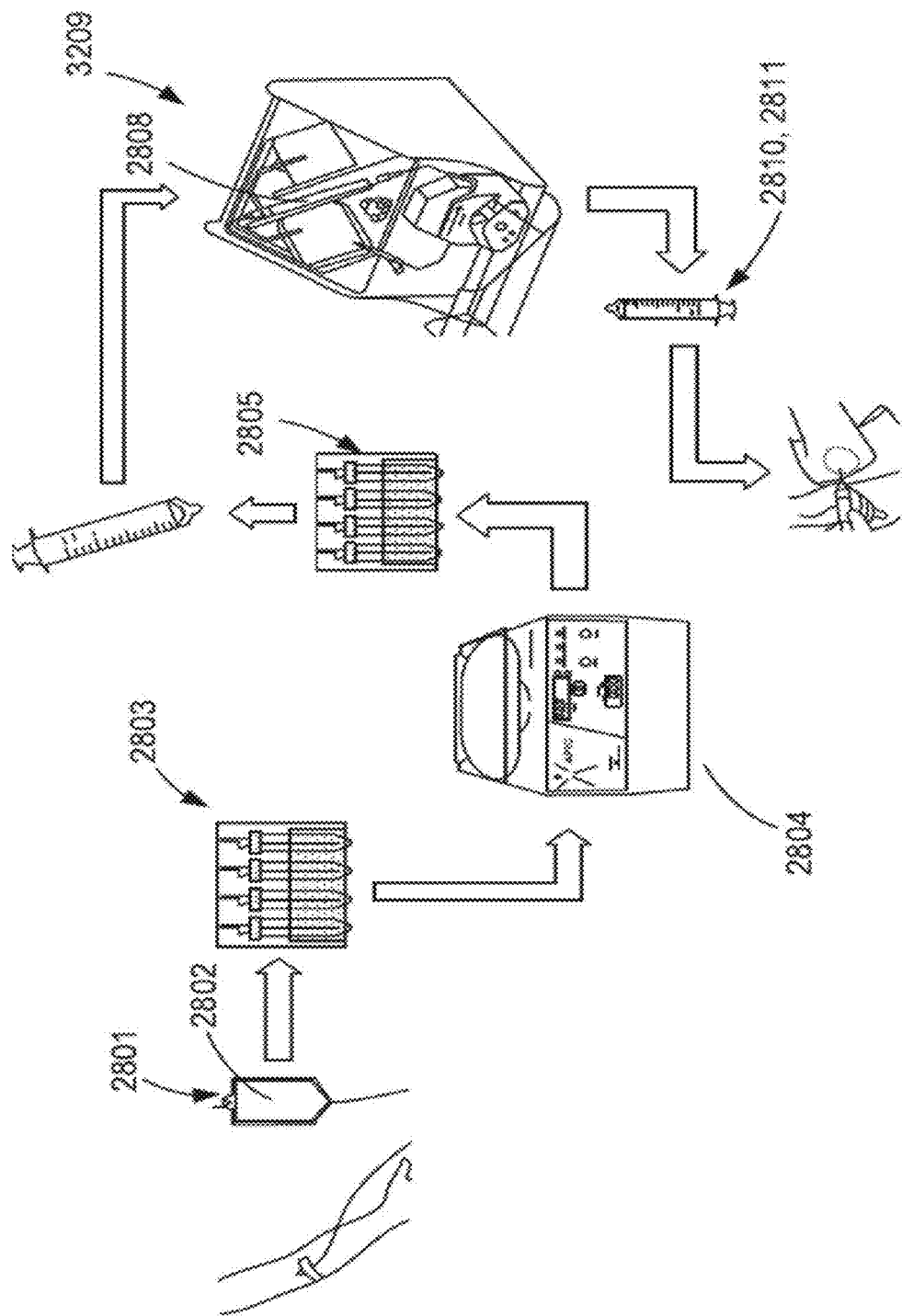
FIG. 31 depicts the components of a system described herein showing a centrifuge and a one filter system.
Figure 32B:
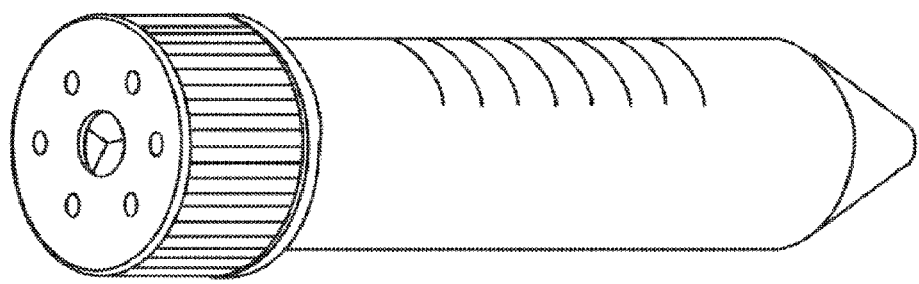
FIG. 32 depicts two different types of custom centrifuge tubes that can be used in the systems described herein.
Figure 32A:
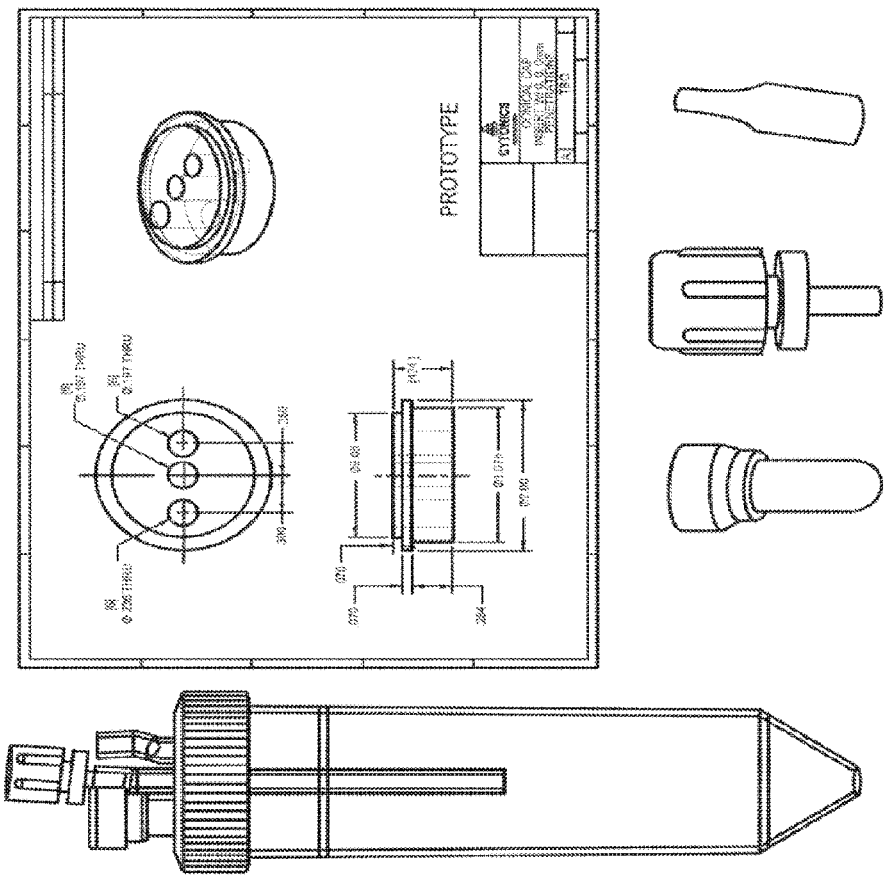
Figure 33:
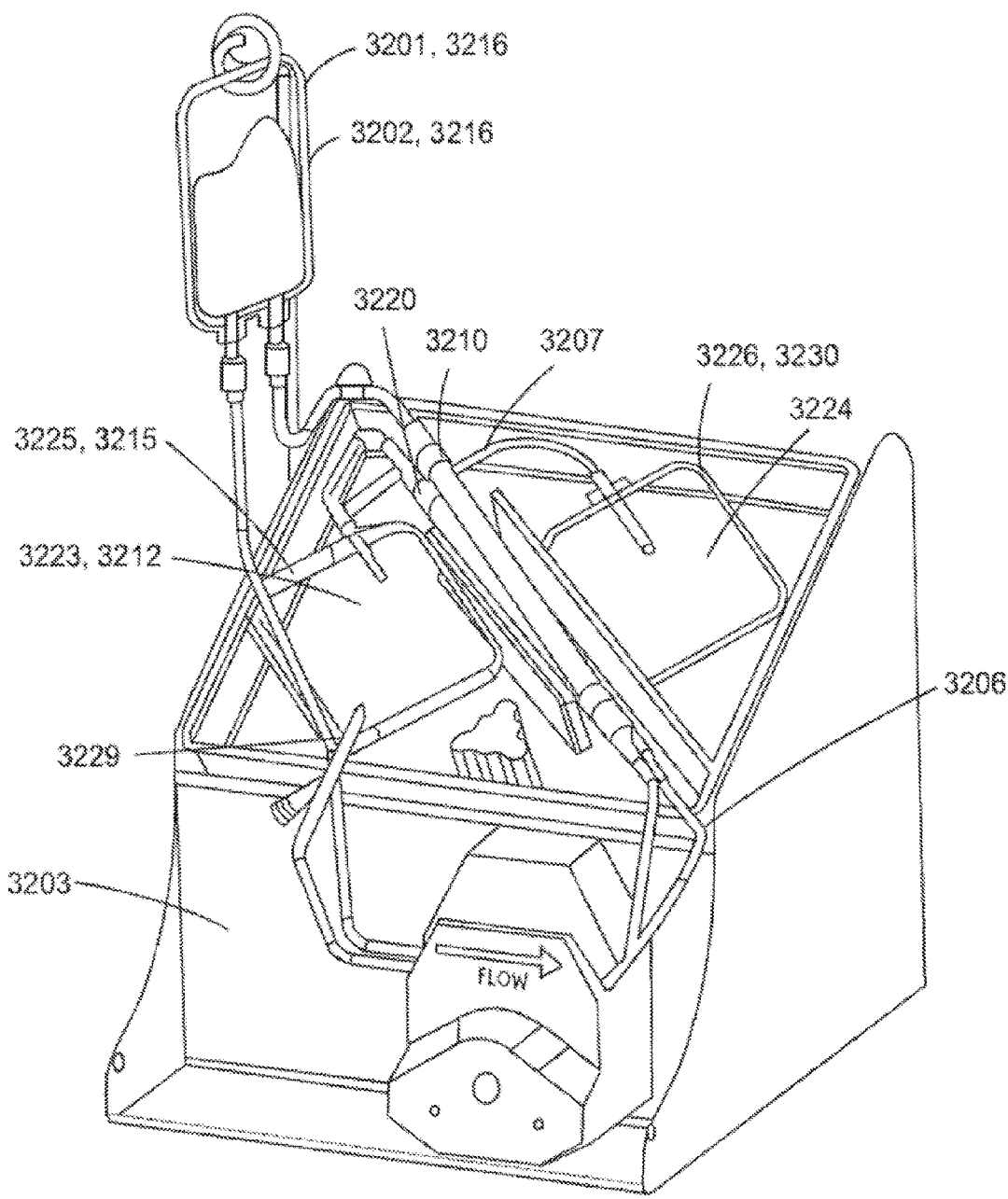
FIG. 33 depicts a schematic of a cell free concentration system as described herein with concentration component utilizing two filters.

1. Autologous Blood Harvest
 a. Prepare a 60 ml syringes containing 7.5 ml sterile ACDA.
 b. Perform venipuncture and autologous blood harvest into syringes.
 c. Draw blood until a total volume of 50 ml is achieved. (42.5 ml blood+7.5 ml ACDA=48 ml Vf, 15% ACDA)
   i. Transfer 5 ml of WB+ACDA to a 10 ml falcon tube using a blunt-ended canula for later analysis.
2. Production of Plasma
 a. Transfer the 45 ml whole blood+ACDA to a centrifuge tube using a blunt-ended canula. Careful that the centrifuge is balanced before spinning—you will need another centrifuge tube full of 47.7 ml water. The specific density of blood is ~1.06.
 b. Centrifuge blood with the "PRP" setting (4 minutes, 1280×g, brake 3).
 c. Carefully remove the centrifuge tubes and place vertically in the tube holder.
 d. Attach a spinal needle to a 20 ml syringe and slowly draw 17.5 ml of plasma from about 1 cm above the buffy coat. Be careful not to draw up any of the buffy coat into the syringe. This will be Syringe #1 in FIGS. 4-6.
   i. Transfer 2.5 ml of plasma to a 10 ml falcon tube for later analysis.
3. Prime the APIC-PRP System
 a. Adjust stopcock #1 so that the off position blocks access to the unused port.
 b. Adjust stopcock #2 to prevent access to Syringe #2.
 c. All syringes should be in the completely compressed state to prevent additional unwanted air in the system.
 d. Tap Syringe #1 with Plasma to get all air bubbles to the top. Remove the cap.
 e. Holding the APIC-filter setup at an angle with Syringe #3 at the top, attach Syringe #1 with Plasma to the APIC-PRP filter.
 f. Slowly push the Plasma from Syringe #1 into the filter until the sterile air from the filter and a few milliliters of plasma are in Syringe #3. The filter should be devoid of air now. Compress Syringe #3 until the plasma has just returned to stopcock #2.
 g. Rotate stopcock #2 to block Syringe #3 (sterile air) and expose Syringe #2.
 h. Pull back the plunger of Syringe #4 slightly to create a slight space for filtrate to enter.
 i. Attach the APIC Kit to the Styrofoam block to allow easy pumping action.
4. Production of APIC-PRP
 j. Sequentially compress Syringes #1 and #2 to process Plasma over the filter. Filtrate will soon fill the inner filtrate chamber of the filter and migrate into Syringe #4.
   i. Monitor Syringe #4 for progress. If the plunger does not migrate during processing a slight pull outwards will help it get started.
 k. If air bubbles are still in the system during processing, tilt the system so they migrate into Syringe #2. During processing, do not compress Syringe #2 completely to avoid injecting air bubbles into the filter. It is much easier to remove large air bubbles later than micro-bubbles caused by processing bubbles through a filter.

l. As needed, unlock Syringe #4 and pull back slightly to create room for additional filtrate.
m. Continue processing plasma into APIC until the desired amount of concentration is achieved.
  i. System void-volume is ~2 ml.
  ii. For a 4x volume concentration, 15 ml Plasma-PRP can be processed until ~2 ml are in Syringe #1.
n. Once the appropriate amount of concentration has been achieved, compress Syringe #2 until the APIC has been transferred to Syringe #1.
o. To remove excess APIC-PRP from the filter, turn the stopcock to block Syringe #2 and allow access to Syringe #3 containing the sterile air. Slowly compress Syringe #3 to push the APIC-PRP in the filter into Syringe #1. Avoid adding air bubbles to Syringe #1.
p. Syringe #1 containing APIC-PRP can be removed. Tap the syringe to displace any air bubbles to the top for removal. If any micro air bubbles are observed, place the Syringe with APIC upright for 15 minutes until bubbles rise, remove air from syringe. APIC is ready to use.

Example 3

Blood Collection

Autologous blood harvest was performed by venipuncture according to present IRBs from healthy donors who were at least 18 years of age or older, healthy, over 110 lbs, and not pregnant. Three Patients donated 216 ml of whole blood mixed with 24 ml of Acid Citrate Dextrose Solution A (ACDA) anticoagulant (10%) for the preparation of APIC-2 PRP and PPP in conditions #1 and #2, and 76 ml of whole blood mixed with 14 ml of ACDA (15%) for #3, for a total blood donation of 292 ml anticoagulated blood. The anticoagulated blood was used as needed for the following examples.

Example 4

Preparation of APIC-2 PRP

Briefly, 60 ml of anticoagulated whole blood mixed with 10% ACDA was added to a first port in a vessel. Two ml of ACDA was further added to a second port. The vessel was tapped to disperse blood to the bottom of the vessel. The vessel was then placed into a centrifuge and the centrifuge started and allowed to complete the full cycle (14 min) A 30 ml syringe with spacers was used to pull off the PPP contained in a smaller extension vessel by way of the white port. The PPP was saved for later concentration. The PRP was mixed and collected by the 20 ml syringe without spacers. The final ACDA concentration in the PRP and PPP was approximately 15%, depending on the total volume of blood tipped. The amount of analytes in this sample were measured and compared to the measurements of the same analytes in whole blood, plasma, and APIC-PRP; the concentration of cells platelets, WBC, and RBC (% of WB); the concentration of A2M; and the concentration of PDGF $\beta\beta$, PDGF $\alpha\beta/\beta\beta$, bFGF, VEGF, and TGF-$\beta$1.

Example 5

Red Blood Cell-Reduced PRP (RBC-R)

The PRP from Example 3 was further processed to reduce the amount of red and white blood cells by centrifugation in a 10 ml tube using the adapter to the current Harvest centrifuge rotor. The PRP was placed in this tube and centrifuged through the first part of the centrifugation cycle. The centrifuge was stopped manually as it completed braking, but before continuing to the second part of the cycle. The RBCR-PRP was removed by syringe to ~1 cm above the buffy coat, leaving the packed RBC and WBC in the tube.

Example 6

50 ml Conical Spin 90 ml of whole blood mixed with 14 ml of ACDA was added to the 45 ml mark on two 50 ml tubes. The tubes were centrifuged in the Harvest centrifuge using a separate rotor with buckets for 50 ml tubes. The buckets were taped to their swinging out positions to allow for the lid to close and brake without disturbing the tubes. The tubes were centrifuged for 1.5 cycles (the 14 min complete cycle, then restarted for the first part of another cycle) and manually stopped as the first part of the cycle came to a stop but before the second part of the cycle resumed. 15 ml of PRP was taken 1 cm from the buffy coat on each tube and mixed together.

Example 7

Concentration of Plasma by APIC-HL (HPH-Jr) or APIC-HH Filters

The APIC-HL manual concentration was assembled and the void volume of the filter was measured by how much material went into the filter before coming out the other side (12 ml). The APIC-HH Filter was assembled, with a void volume of 2 ml.

Plasma was concentrated using the following method:

Holding the filters vertically, plasma was slowly injected from the bottom syringe (30 ml syringe) into the filter. Sterile air from the filter was directed into the side 10 ml syringe. Once the filters had been primed with plasma, stop-cocks were adjusted to permit plasma from between the 20 ml and 30 ml side syringes. Sequential compressions of the side syringes caused flow of plasma through the hollow fiber membranes. Filtrate accumulated in the 20 ml syringe attached to the filter, whereas retentate remained in the side syringes. Once compressions were finished, the filters were held vertically and the stopcock adjusted to allow the sterile air back into the filter. The 10 ml syringe was then compressed to void more of the product into the bottom syringe. Plasma was concentrated by the APIC-HL until there was nothing left in the syringes to pump. The final amount of concentrated product was returned to the starting syringe by voiding the air from the 10 ml syringe. Plasma was concentrated by the APIC-HH filter until there was between 3-5 ml left in the syringe. The final amount of concentrated product was returned to the starting syringe by voiding the air from the 10 ml syringe.

Example 8

Generation of Concentrated Products

For each patient, 4 preparations and 2 50 ml spin conical were made according to the flow charts shown in the Figures. This allows for 6 concentrated products for each patient. For preparation 1, an activated product was made by mixing the RBCR portion with the PPP, then concentrating on either A) APIC-HL, or B) APIC-HH filter. In preparation 2, the PPP was concentrated on either A) APIC-HL, or B) APIC-HH filter first, then mixed with the RBCR portion to generate an un-activated product. Finally, preparation 3 the closest method to APIC preparation was made by concentrating the plasma containing most of the platelets pulled from the 50 ml spin on either A) APIC-HL, or B) APIC-HH filter.

Cell Counting.

Red and white blood cells, and PPP samples were counted by hemacytometer. Platelets in all samples, except PPP, were counted by coulter counter.

Volume.

The void volume for each filter in a large part determined how much product was available for use after concentration in procedure 1. In the APIC-HL, the void volume is 12 ml, however only an average of 3.5 ml is recovered when the air is voided from the filter. The large void volume prevents further concentration of the plasma and lowers the amount of available product. The APIC-HH filter has a void volume of only 2 ml, where ~1 ml is recovered in addition to what is concentrated in the syringe. The average recovered from process 1B is 5 ml. Much more product is available during process 2 because the RBCR is mixed after the fact, on average 9.6 ml and 10.5 ml for A and B respectively. Process 3 produces the approximately same volumes as process A given only the centrifugation is different (3.8 ml and 4 ml for A and B respectively). A summary of the average volumes obtained at each step are summarized in Table 2.

tions. However, only 3-4 ml of product could be recovered from the APIC-HL, leading to a much smaller dilution factor. It should also be noted that in all processes, the RBCR intermediate is higher in platelets than their corresponding concentrated products. This is due to the removal of the RBC and WBC volumes, leaving more platelets in a smaller volume. The cell counts for platelets, RBC and WBC for each product and intermediate are summarized in Table 3.

A2M Concentration.

A2M concentration was measured by ELISA for each PPP, whole blood, and concentrated product. In all cases, the APIC filter concentrated A2M better than the APIC-HL in each respective procedure. Pre-mixing with the APIC-HH filter (1B) gave the most concentrated A2M products (3.44× compared to PPP), followed by premixing with the APIC-HL (1A) (2.67× compared to PPP). Both of these processes result in activated platelets. Processes 3B and 2B, both using the APIC filter, gave the next highest A2M concentrations (2.5× and 2.02×). Process 2A was the lowest A2M concentration, very close to plasma levels at 0.93×. This is the result of the lower A2M concentration and lower volume recovery from the APIC-HL where 3-4 ml of concentrated PPP is being mixed with the RBCR at 6-7 ml. Therefore, use of an un-activated product would require the APIC-HH filter to concentrate A2M above plasma levels.

TABLE 2

Avg Volume (mL) of Each Component for Each Process

|  | 1A Avg ± SD | 1B Avg ± SD | 2A Avg ± SD | 2B Avg ± SD | 3A Avg ± SD | 3B Avg ± SD |
| --- | --- | --- | --- | --- | --- | --- |
| ml PPP | 21.0 ± 4.6 | 19.3 ± 4.5 | 19.7 ± 4.5 | 19.7 ± 3.8 | n/a | n/a |
| ml PRP | 10.2 ± 0.6 | 10.7 ± 0.3 | 1.05 ± 0.0 | 10.5 ± 0.0 | 15.0 ± 0.0 | 15.0 ± 0.0 |
| ml RBCR | 6.6 ± 0.6 | 6.5 ± 0.7 | 5.8 ± 0.5 | 6.5 ± 1.6 | n/a | n/a |
| total vol concentrated | 27.6 ± 4.8 | 25.8 ± 4.2 | 19.5 ± 6.4 | 19.7 ± 3.8 | n/a | n/a |
| ml in syringe | 0.0 ± 0.0 | 4.0 ± 1.0 | 0.0 ± 0.0 | 3.0 ± 0.0 | 0.0 ± 0.0 | 3.0 ± 0.0 |
| ml added to RBCR | n/a | n/a | 3.3 ± 0.4 | 3.3 ± 0.3 | n/a | n/a |
| $V_f$ produced concentrate | 12.0 ± 0.0 | 6.0 ± 1.0 | 12.0 ± 0.0 | 5.0 ± 0.0 | 12.0 ± 0.0 | 5.0 ± 0.0 |
| $V_f$ recovered concentrate | 3.5 ± 0.9 | 5.0 ± 1.0 | 3.5 ± 0.0 | 4.0 ± 0.0 | 3.8 ± 1.3 | 4.0 ± 0.0 |
| $V_f$ total product recovered | 3.5 ± 0.9 | 5.0 ± 1.0 | 9.6 ± 0.1 | 10.5 ± 1.6 | 3.8 ± 1.3 | 4.0 ± 0.0 |
| $V_f$ total product produced | 12.0 ± 0.0 | 6.0 ± 1.0 | 15.1 ± 0.1 | 11.5 ± 1.6 | 12.0 ± 0.0 | 12.0 ± 0.0 | produced = total amount estimated including void volumes,
recovered = actual amount available
Table 2 legend -
[ml PPP = amount of PPP taken off from Harvest centrifugation, ml PRP = ml of platelet rich fraction harvested after centrifugation, ml RBCR = ml taken off of RBCR centrifugation, total vol concentrated = the total volume added to the filter for concentration, ml in syringe = amount of concentrate remaining in syringe when the concentrate process is stopped, ml added to RBCR = ml of concentrate added to the RBCR fraction, $V_f$ produced concentrate = volume of concentrate produced, including what is not recoverable from the filter, $V_f$ recovered concentrate = volume of concentrate that is recovered, and available after the air has been voided from the filter, $V_f$ total product recovered = the total amount of product recovered and available, including any RBCR added during the process, $V_f$ total product produced = amount of product produced including any amount not recovered from the filter.]

Cell Counts.

RBC and WBC were negligible for all products that went through the RBCR process. Those that did not (3A and 3B), had small amounts of RBC but elevated WBC (1-1.6 fold over whole blood). The highest concentration of platelets was seen in process 1 using the APIC filter (1A) for a 4.69× concentration over whole blood. Processes 1A, 2A and 2B had similar platelet concentrations (3.14-3.97×). This was unexpected in processes 1A and 2A. For process 1A, given the total volume concentrated only ~2×, the platelets concentrated ~3×. This may be an artifact of the low patient number. The platelet fold concentration and A2M fold concentration is expected follow the volume concentrated to. In process 2A where the high void volume in the APIC-HL (12 ml) would have diluted the RBCR (6-7 ml) and should have resulted in much lower platelet concentra- Table 2 legend—[ml PPP=amount of PPP taken off from Harvest centrifugation, ml PRP=ml of platelet rich fraction harvested after centrifugation, ml RBCR=ml taken off of RBCR centrifugation, total vol concentrated=the total volume added to the filter for concentration, ml in syringe=amount of concentrate remaining in syringe when the concentrate process is stopped, ml added to RBCR=ml of concentrate added to the RBCR fraction, $V_f$ produced concentrate=volume of concentrate produced, including what is not recoverable from the filter, $V_f$ recovered concentrate=volume of concentrate that is recovered and available after the air has been voided from the filter, $V_f$ total product recovered=the total amount of product recovered and available, including any RBCR added during the process, $V_f$ total product produced=amount of product produced including any amount not recovered from the filter.]

TABLE 3

Cell Counts in Fold Change Over Whole Blood

|  |  | 1A | | 1B | | 2A | | 2B | | 3A | | 3B | |
| --- | --- | --- | --- | --- | --- | --- | --- | --- | --- | --- | --- | --- | --- |
|  | sample | AVE | SD | AVE | SD | AVE | SD | AVE | SD | AVE | SD | AVE | SD |
| Platelet | WB | 1.00 | 0.000 | 1.00 | 0.000 | 1.00 | 0.000 | 1.00 | 0.000 | 1.00 | 0.000 | 1.00 | 0.000 |
|  | PPP | 0.48 | 0.050 | 0.58 | 0.017 | 0.48 | 0.010 | 0.47 | 0.014 |  |  |  |  |
|  | PRP | 4.75 | 0.066 | 4.69 | 0.040 | 4.38 | 0.018 | 4.57 | 0.023 | 1.70 | 0.024 | 1.70 | 0.024 |
|  | RBCR | 5.12 | 0.099 | 5.27 | 0.026 | 4.65 | 0.058 | 4.75 | 0.024 |  |  |  |  |
|  | CP | 3.14 | 0.020 | 4.69 | 0.012 | 3.23 | 0.138 | 3.97 | 0.009 | 3.25 | 0.039 | 4.54 | 0.025 |
| RBC | WB | 1.00 | 0.000 | 1.00 | 0.000 | 1.00 | 0.000 | 1.00 | 0.000 | 1.00 | 0.000 | 1.00 | 0.000 |
|  | PPP | 0.00 | 0.000 | 0.00 | 0.000 | 0.00 | 0.000 | 0.00 | 0.000 |  |  |  |  |
|  | PRP | 1.13 | 0.705 | 1.00 | 0.661 | 0.50 | 0.343 | 0.55 | 0.278 | 0.01 | 0.002 | 0.01 | 0.002 |
|  | RBCR | 0.00 | 0.000 | 0.00 | 0.001 | 0.00 | 0.000 | 0.00 | 0.000 |  |  |  |  |
|  | CP | 0.00 | 0.000 | 0.00 | 0.000 | 0.00 | 0.000 | 0.00 | 0.000 | 0.02 | 0.006 | 0.02 | 0.010 |
| WBC | WB | 1.00 | 0.000 | 1.00 | 0.000 | 1.00 | 0.000 | 1.00 | 0.000 | 1.00 | 0.000 | 1.00 | 0.000 |
|  | PPP | 0.00 | 0.000 | 0.00 | 0.006 | 0.00 | 0.000 | 0.00 | 0.000 |  |  |  |  |
|  | PRP | 2.59 | 0.415 | 2.70 | 0.239 | 2.46 | 0.395 | 2.75 | 0.092 | 0.51 | 0.037 | 0.51 | 0.037 |
|  | RBCR | 0.01 | 0.005 | 0.14 | 0.224 | 0.02 | 0.017 | 0.02 | 0.023 |  |  |  |  |
|  | CP | 0.01 | 0.007 | 0.00 | 0.000 | 0.02 | 0.030 | 0.00 | 0.000 | 1.06 | 0.184 | 1.65 | 0.019 |

*whole blood (WB), platelet poor plasma (PPP), platelet rich plasma (PRP), red blood cell reduced (RBCR), concentrated product (CP)

Platelet Recovery.

Process 2B resulted in recoverable platelets at 60%, and process 2A resulted in 51% platelet recovery. Both of these processes result in un-activated platelets and are due to the lower recovered concentrate volumes which are added to the RBCR intermediate to make the final product. The APIC-HH filter had a greater percent platelet recovery for activated products (processes 1 and 2) at 39% for process 1B and 30% for process 3B. In process 1B, there is ~20% platelet loss at each intermediate step. Moving closer to the buffy coat in the RBCR intermediate would increase the recovery in that step some. For process 3B, the largest loss of platelets is due to the inefficiency of the centrifugation step. The APIC-HL had lower platelet recovery of the activated processes (1A and 3A), potentially due to the large amount of volume remaining on the filter.

Example 9

System Overview

The APIC PRP System (FIGS. 24-30) can contain three components for producing APIC PRP; High Speed Bench Top Centrifuge; Peristaltic Pump w/ Custom Housing; and Disposables Kit for Collection, Separation, and Administration of APIC PRP. The APIC System can separate and concentrate a patient's own blood for therapeutic use by a physician. 60 cc to 120 cc of a patient's blood can be drawn in to a collection bag, then transferred to centrifuge tubes. The tubes can be centrifuged and the recovered plasma is then drawn off and transferred to a concentration bag. The pump can circulate the blood through a Tangential Flow Filter concentrating the APIC PRP down to a 5 cc to 10 cc of APIC. The APIC can then be used by Physicians as they deem necessary and appropriate. The system can include: Industry Standard Centrifuge and Peristaltic Pump, Private Labeled and Customized for APIC, Low Cost Disposable with Filtration, Majority of Disposable Components are PPS, Minimal number of steps. The system can include: Integrated Centrifuge and Pump Separation, Custom Ergonomic Design, Lower Cost Equipment w/Smaller Footprint, Lower Cost and Less Disposables, Ease Of Use=Set It And Forget It APIC Cell Free Concentration Kit: No Centrifugation; Direct Connection of Blood Collection Bag to Concentration Bag; Two Filters Example 10

Preparation of Blood for Autologous Therapy 120 mL of whole human blood was obtained from a subject by venipuncture. 38 mL aliquots of the blood were collected into two or more hematologic collection bottles with a suitable volume of citrate dextrose solution A ("ACD-A") in each collection bottle. The collection bottles with blood/ACD-A were placed into a fixed angle rotor centrifuge, and centrifuged at predetermined velocities and times under ambient temperature conditions. Approximately 15 mL of plasma was aliquoted from each tube with a serological pipette, leaving approximately 1 mL, of plasma above the level of the buffy coat so as not to disturb the precipitated cells. This process was repeated for the collection bottles in one or more centrifuge spin cycles to yield a volume 45 mL of total plasma from a total blood draw of 120 mL. The plasma was pooled into a separate sterile hematologic collection bag. The compositions described herein can be mixed with pharmaceutical acceptable excipients, before administration to a subject.

Example 11

Inhibition of ADAMTS-5- and ADAMTS-4- with A2M

Bovine Cartilage Explants (BCEs) were treated with 500 ng/ml ADAMTS-5 or ADAMTS-4 for 2 days, with a 3-fold serial dilution of purified A2M. Concentration of A2M tested were 100, 33.3, 11.1, 3.7, 1.2, 0.4 μg/mL. The A2M inhibited the proteases in a concentration dependent manner. The $IC_{50}$ for inhibiting 500 ng/ml of ADAMTS-5 was calculated to be ~7 μg/ml A2M (a 1:1 molar ratio). Maximum inhibition was observed in ~90% with 100 μg/ml A2M (a 14:1 molar ratio). The A2M was shown to block formation of Aggrecan G3 fragments and FAC formation.

Example 12

Comparison of APIC Retentate and Filtrate

Wounds are treated with the A2M compositions containing ~7 mg/ml A2M. Wound healing is efficiently promoted by 1% v/v of the Retentate of the A2M compositions (concentration of proteins >500 kDa in size), but not by the filtrate (contains proteins <500 kDa), even at 5% v/v. The enhanced wound healing effects are dose dependent. The inability of filtrate to protect cartilage from catabolism by ADAMTS-5 demonstrates that the APIC system concentrates >99% of the protective factors of autologous blood.

Example 13

Cytokine Profile of Wound Cells Treated with APIC

Wound cells are treated with or without APIC or recombinant A2M for 2 days and the activation of the wound cells is monitored by secretion of cytokines and growth factors into the wound. Wound cells do not show a change in the cytokine profile of the test.

Example 14

Wound Healing Effect in Rabbit Model

The ability of the Autologous Protease Inhibitor Concentrate (APIC-Cell Free), which contains concentrated A2M from the blood, or recombinant A2M, is tested to promote wound healing, in a rabbit model. The rabbit model represents a functional load-bearing in vivo anatomical model for the evaluation of wound healing, which exhibits mechanical properties, morphological structures, and healing capacity similar to human tissues. Female 8-12 months old New Zealand white rabbits are used. Group 1: 6 rabbits receive a wound on the right knee and a wound on the left knee. Applications of recombinant A2M or Autologous Protease Inhibitor Concentrate (APIC-Cell Free) are prepared from the rabbit blood, and administered to the wound on the right knee one or more days following the wound and saline solution (sham) is administered to the wound on the left knee one or more days following the wound.
Autologous A2M Concentrate Preparation Prior to the wound, 20 mL of blood is removed from each animal in group 1 and is used to prepare the APIC Cell Free concentrate using a series of filters. Every rabbit receives the protease inhibitor concentrate from its own blood. After treating the wound, the animal is sacrificed for macroscopic and microscopic wound healing evaluation to determine healing advancement and enhancement.
Macroscopic and Histological Analyses For macroscopic evaluation, the wound surfaces are analyzed. After macroscopic examination, wound samples were analyzed for histological (microscopic) evaluation. Macroscopic evaluation of the wound demonstrates features consistent with enhanced wound healing. Treatment with APIC Cell Free or recombinant A2M considerably improves wound appearance. Application of APIC enhances wound healing by 53+/−20% compared to untreated controls (mean±SEM. p=0.0086). The concentration of A2M in the APIC Cell Free varies front 5-65 mg/ml. There is a dose-dependent correlation between higher concentrations of A2M in the API Cell Free and enhancement of wound healing on the macroscopic evaluation. The data suggests that the Autologous Protease Inhibitor Concentrate (APIC-Cell Free), which contains 9-10 times the A2M concentration in blood, has an enhanced wound healing effect on a rabbit model.

Example 15

In Vitro Effect of A2M on Wound Healing

To test the hypothesis that the addition of proinflammatory cytokines or cartilage-degrading metalloproteinases (ADAMTS and MMP) slow wound healing that will be inhibited by recombinant or autologous A2M, a controlled in vitro wound healing assay is performed. Cells from animal wounds are treated with or without proinflammatory cytokines (TNF-α or IL-1β) or cartilage-degrading metalloproteinases (ADAMTS-5, ADAMTS-4, MMP-7, or MMP-12) in the presence or absence of recombinant or autologous A2M compositions. Wound cells are incubated 2 days in Serum-Free Media (SFM) with or without 500 ng/mL ADAMTS-4 or ADAMTS-5 and 3-5 µg/mL of MMP-3, MMP-7, MMP-12, or MMP-13. MMP-3 is activated with chymotrypsin before application on wound cells. For cytokine-induced retardation of wound healing, wound cells are incubated 3 days in SFM with or without 80 ng/ml human TNF-α and 8 ng/mL human 1L-1β. Wound healing is enhanced with the addition of 100 µg/mL of purified human recombinant or autologous A2M for protease digestion or 5 mg/mL recombinant or autologous A2M for cytokine-induced degradation.

Example 16

Determination of Collagenase Activity and Inhibition by A2M Compositions

Reagents/Materials
140731NL Wound Fluid (15.34 µg/ml collagenase)
FITC-collagen, Type I (Life Technologies, D12060)
Purified plasma A2M (Molecular Innovations, HA2MG)
1×TN buffer (50 mM Tris pH 7.5, 150 mM NaCl)
10×TNCB (500 mM Tris pH7.5, 1.5M NaCl, 100 mM CaCl2, 0.2% NaN3, 0.5% Brijj35)
A2M (Molecular Innovations)
Sample Preparation
The wound fluid sample was diluted to prepare the 10×Cf Dil (1:40) by mixing 6.5 ul with 254 ul TN on ice (Vf 260 ul). A 1/400 dilution was the working concentration. Serially diluted A2M samples were prepared by mixing 76.8 ul of the purified plasma A2M (4.163 mg/ml) with 3.1 ul of TN (Vf 80 ul, Cf 4000 µg/ml) to create sample 1. As shown in the table below, 30 ul of this sample (1) was then added to 60 ul of TN (Vf 90 ul, Cf 1333 µg/ml) to create sample 2. 30 ul of this sample (2) was then added to 60 ul of TN (Vf 90 ul, Cf 444 µg/ml) to create sample 3. 30 ul of this sample (3) was then added to 60 ul of TN (Vf 90 ul, Cf 148 µg/ml) to create sample 4. 30 of this sample (4) was then added to 60 ul of TN (Vf 90 ul, Cf 49.4 µg/ml) to create sample 5. 30 ul of this sample (5) was then added to 60 ul of TN (Vf 16.5 ul, Cf 1333 µg/ml) to create sample 6.

|              | 1    | 2    | 3    | 4    | 5    | 6    |
|--------------|------|------|------|------|------|------|
| Transfer (µL)| 30   | 30   | 30   | 30   | 30   | 30   |
| 1x TN (µl)   | 80   | 60   | 60   | 60   | 60   | 60   |
| 10x Cf dil   | 4000 | 1333 | 444  | 148  | 49.4 | 16.5 |
| Work Cf Dil  | 400  | 133  | 44.4 | 14.8 | 49   | 17   |

Digestion 160 ul FITC-collagen was diluted 1:1 with 160 ul TN (Vf 350 μl) and kept in the dark. The following were combined in a 96-well black plate.

|  | Col - Only | WF | WF + A2M | Vf (μl) |
|---|---|---|---|---|
| WF (μl) | 0 | 20 | 20 | 200 |
| 10x A2M (μl) | 0 | 0 | 20 | 200 |
| 10x TNCB (μl) | 20 | 20 | 20 | 200 |
| WFI H$_2$O (μl) | 160 | 140 | 120 | 200 |
| FITC-Col (μl) | 20 | 20 | 20 | 200 |

The microplate was then read using a spectrophotometer at the excitation wavelength of 495 nm and emission wavelength of 515 nm every 20 second interval for 30 mins.

Example 17

Wound Fluid Collection Technique

There are several techniques that were utilized to collect wound fluid. One technique involved aspirating wound fluid from wet wounds utilizing a syringe. Another technique involved use of a filter paper to absorb the wound fluid, followed by extraction of the absorbed wound fluid from the filter paper, such as by washing with a buffer. Another technique involved running a straight edge tongue blade across the wound and collecting the fluid that gathered in front of the straight edge, such as with a filter paper.

For example, human chronic wound fluid is extracted from primary wound fluid dressing by soaking a single dressing overnight in 5 ml phosphate buffered saline pH 4.0-6.0 50 mM sodium acetate adjusted to relevant pH with glacial acetic buffer acid pH 7.0-8.0 0.2M Tris(hydroxymethyl)aminomethane (Tris) corrected to buffer relevant pH using 0.2M hydrochloric acid.

Example 18

Effects of A2M Compositions on Wound Healing in Diabetic Rats

Summary

Healing of chronic wounds such as diabetic ulcers is a significant clinical problem. This study examines the in vivo response to the therapeutic recombinant or autologous compositions according to the present invention. The preliminary animal study on a diabetic rat model with impaired wound healing is conducted comparing the recombinant or autologous A2M compositions described herein with distilled water. As a result, the time to complete closure of wounds is lower in the A2M treated group. The difference in wound healing since day $9^{th}$ of the treatment is apparent. The A2M treated animals have lower scar tissues and the fur growth is complete. In water-treated animals a scar with impaired fur growth is apparent. The results of this study suggest that dermal use of these A2M compositions have a potential to modulate wound healing and stimulate fur growth.

Methods

The animal model for in vivo testing of the recombinant or autologous A2M compositions is a full-thickness wound in the dorsal skin of diabetic rats. Wistar rats weighing 200-250 g are used. Animals are caged in separate cages. Diabetes is induced by administration of streptozotocin (Sigma-Aldrich, UK). Streptozotocin is administered at dose of 55 mg/kg intraperitoneally. Before the administration of streptozotocin, a baseline blood glucose of rats is determined. After 48 hours, the blood glucose is again measured to ensure rats are diabetic. The induction of diabetes is confirmed if the blood glucose level is doubled. Glucose is determined by a Glucometer (Infopia Co., Korea). Determination of blood glucose continues every 5 days to ensure the subsistence of diabetes. Regarding the entity of streptozotocin-induced diabetes, the animals which lose much weight and become week, and those with uncertain blood glucose levels are excluded from the study. A total of 14 rats are used with equal numbers in control and test groups. The test group has a volume of a solution comprising the recombinant or autologous A2M composition applied and the control group is dressed with distilled water. At time=0 days, a full-thickness, circular 15 mm diameter wound is created (e.g., according to Wound Rep. Reg. 2002; 10: 286-294). Rats are anaesthetized by intraperitoneal pentobarbital (55 mg/kg) and the dorsal skin is prepared for surgery using Betadine. The wound is created using surgical scissors. At time=0 days dressings are placed, as prepared, directly on the wounds. The wounds are covered by sterile gases and wrapped carefully. Every 2-3 days following surgery, wounds were redressed with fresh control or test dressings while the rats were under anesthesia. The wounds are flushed with sterile saline to remove debris and to clean the wound area. A digital camera is used to take the pictures of the wound. The pictures are examined for wound healing in terms of wound size and appearance of new fresh epithelium. Once photographed, fresh dressings are placed on the wounds, and the wounds are covered again. Control of bias is achieved by assigning a code to each of the experimental groups. Investigators are blinded to the identity of each of the groups and the test and control have a similar appearance. The code is broken following completion of the final 4-week analysis.

In the test group on the $15^{th}$ day of therapy the wound is completely closed and the new, short fur covers the scar area. On the $22^{nd}$ day of therapy the wound is completely healed and the new, long fur covers the entire scar area. No signs of the previous wound can be seen. In the control group on the $15^{th}$ day of therapy the wound is not closed. On the $22^{nd}$ day of testing the wound is closed but the scar is still sever and completely naked.

Wound areas and perimeters are similar in test and control groups; however, there is a tendency for more rapid closure in the test group, particularly at day 15 where the difference in wound areas and perimeters is most pronounced. The time to complete closure of wounds is lower in A2M treated animals. In both control and test groups, wound area begins to decrease at day $9^{th}$ and approximately complete wound closure first occurs by day $15^{th}$ (one out of seven rats). By day $22^{nd}$, are essentially closed in both groups but growth of fur in the A2M treated group is especially complete as compared to the water-treated group.

The results of this study suggest that dermal preparation comprising the recombinant or autologous A2M compositions according to the present invention has potential to enhance wound healing. In addition to accelerating wound closure, A2M treatment in this study appears to improve the quality of the tissue in the healing wound since the fur grew more efficiently than in the control group. Chronic wounds are not only characterized by untimely healing and the inability to remain closed following healing. Thus, time to closure may not be the only relevant end point or sole basis for efficacy of the treatment. Obtaining the healthier scar tissue in the test group animals treated with the recombinant or autologous A2M compositions allows anticipating a lowered recurrence rate.

Example 19

Wound Debridement

Recombinant or autologous A2M compositions are applied to necrotic tissues on pigs for an in vivo debridement efficacy study. Recombinant or autologous A2111 compositions, together with a debrider, are used to each of the wounds generated (about 2 cm in diameter). After 24 hours, significant wound debridement is observed on the wounds treated with the A2M compositions. After 5 days, those with recombinant or autologous A2M compositions show clean surfaces without any necrotic tissue and complete healing. Debrider treated wounds also show significant debridement after 48 hours. However, the wounds are not as clean as those treated with recombinant or autologous A2M compositions, and did not show complete healing after five days.

Example 20

Sequences of Modified Recombinant A2M Bait Regions

Sequences:
SEQ ID NO 1: Wild-Type A2M Precursor Protein—Complete Vector DNA Sequence Including Tag Sequences for Easier Purification.

```
1    CTCATGACCA AAATCCCTTA ACGTGAGTTA
     CGCGCGCGTC GTTCCACTGA GCGTCAGACC
61   CCGTAGAAAA GATCAAAGGA TCTTCTTGAG
     ATCCTTTTTT TCTGCGCGTA ATCTGCTGCT
121  TGCAAACAAA AAAACCACCG CTACCAGCGG
     TGGTTTGTTT GCCGGATCAA GAGCTACCAA
181  CTCTTTTTCC GAAGGTAACT GGCTTCAGCA
     GAGCGCAGAT ACCAAATACT GTTCTTCTAG
241  TGTAGCCGTA GTTAGCCCAC CACTTCAAGA
     ACTCTGTAGC ACCGCCTACA TACCTCGCTC
301  TGCTAATCCT GTTACCAGTG GCTGCTGCCA
     GTGGCGATAA GTCGTGTCTT ACCGGGTTGG
361  ACTCAAGACG ATAGTTACCG GATAAGGCGC
     AGCGGTCGGG CTGAACGGGG GGTTCGTGCA
421  CACAGCCCAG CTTGGAGCGA ACGACCTACA
     CCGAACTGAG ATACCTACAG CGTGAGCTAT
481  GAGAAAGCGC CACGCTTCCC GAAGGGAGAA
     AGGCGGACAG GTATCCGGTA AGCGGCAGGG
541  TCGGAACAGG AGAGCGCACG AGGGAGCTTC
     CAGGGGGAAA CGCCTGGTAT CTTTATAGTC
601  CTGTCGGGTT TCGCCACCTC TGACTTGAGC
     GTCGATTTTT GTGATGCTCG TCAGGGGGGC
661  GGAGCCTATG GAAAAACGCC AGCAACGCGG
     CCTTTTTACG GTTCCTGGCC TTTTGCTGGC
721  CTTTTGCTCA CATGTTCTTT CCTGCGTTAT
     CCCCTGATTC TGTGGATAAC CGTATTACCG
781  CCTTTGAGTG AGCTGATACC GCTCGCCGCA
     GCCGAACGAC CGAGCGCAGC GAGTCAGTGA
841  GCGAGGAAGC GGAAGGCGAG AGTAGGGAAC
     TGCCAGGCAT CAAACTAAGC AGAAGGCCCC
901  TGACGGATGG CCTTTTTGCG TTTCTACAAA
     CTCTTTCTGT GTTGTAAAAC GACGGCCAGT
961  CTTAAGCTCG GGCCCCCTGG GCGGTTCTGA
     TAACGAGTAA TCGTTAATCC GCAAATAACG
1021 TAAAAACCCG CTTCGGCGGG TTTTTTTATG
     GGGGGAGTTT AGGGAAAGAG CATTTGTCAG
1081 AATATTTAAG GGCGCCTGTC ACTTTGCTTG
     ATATATGAGA ATTATTTAAC CTTATAAATG
1141 AGAAAAAAGC AACGCACTTT AAATAAGATA
     CGTTGCTTTT TCGATTGATG AACACCTATA
1201 ATTAAACTAT TCATCTATTA TTTATGATTT TTT-
     GTATATA CAATATTTCT AGTTTGTTAA
1261 AGAGAATTAA GAAAATAAAT CTCGAAAATA
     ATAAAGGGAA AATCAGTTTT TGATATCAAA
1321 ATTATACATG TCAACGATAA TACAAAATAT
     AATACAAACT ATAAGATGTT ATCAGTATTT
1381 ATTATCATTT AGAATAAATT TTGTGTCGCC
     CTTAATTGTG AGCGGATAAC AATTACGAGC
1441 TTCATGCACA GTGGCGTTGA CATTGATTAT
     TGACTAGTTA TTAATAGTAA TCAATTACGG
1501 GGTCATTAGT TCATAGCCCA TATATGGAGT
     TCCGCGTTAC ATAACTTACG GTAAATGGCC
1561 CGCCTGGCTG ACCGCCCAAC GACCCCCGCC
     CATTGACGTC AATAATGACG TATGTTCCCA
1621 TAGTAACGCC AATAGGGACT TTCCATTGAC
     GTCAATGGGT GGAGTATTTA CGGTAAACTG
1681 CCCACTTGGC AGTACATCAA GTGTATCATA
     TGCCAAGTAC GCCCCCTATT GACGTCAATG
1741 ACGGTAAATG GCCCGCCTGG CATTATGCCC
     AGTACATGAC CTTATGGGAC TTTCCTACTT
1801 GGCAGTACAT CTACGTATTA GTCATCGCTA
     TTACCATGGT GATGCGGTTT TGGCAGTACA
1861 TCAATGGGCG TGGATAGCGG TTTGACTCAC
     GGGGATTTCC AAGTCTCCAC CCCATTGACG
1921 TCAATGGGAG TTTGTTTTGG CACCAAAATC
     AACGGGACTT TCCAAAATGT CGTAACAACT
1981 CCGCCCCATT GACGCAAATG GGCGGTAGGC
     GTGTACGGTG GGAGGTCTAT ATAAGCAGAG
2041 CTCTCTGGCT AACTAGAGAA CCCACTGCTT
     ACTGGCTTAT CGAAATTAAT ACGACTCACT
2101 ATAGGGGTAC CTGCCACCAT GGGGAAAAAC
     AAACTGCTGC ATCCAAGCCT GGTCCTGCTG
2161 CTGCTGGTTC TGCTGCCTAC TGACGCCTCT
     GTGAGCGGAA AGCCCCAGTA TATGGTTCTG
2221 GTCCCGTCCC TGCTGCACAC CGAGACCACA
     GAAAAAGGGT GCGTGCTGCT GTCTTACCTG
2281 AATGAAACAG TGACTGTTAG TGCCTCACTG
     GAGAGTGTGC GCGGAAATCG TTCACTGTTC
2341 ACCGATCTGG AGGCGGAAAA CGATGTGCTG
     CATTGCGTCG CATTTGCTGT GCCAAAAAGC
2401 TCCTCTAATG AAGAAGTGAT GTTCCTGACC
     GTCCAGGTGA AGGGCCCTAC ACAGGAATTC
2461 AAAAAACGCA CTACCGTTAT GGTCAAAAAC
     GAGGATAGCC TGGTGTTTGT TCAGACAGAC
2521 AAATCCATCT ATAAGCCTGG TCAGACTGTG
     AAGTTCCGGG TGGTTAGCAT GGATGAAAAT
2581 TTTCACCCCC TGAACGAGCT GATTCCACTG
     GTGTACATCC AGGACCCTAA AGGCAACCGC
2641 ATCGCCCAGT GGCAGTCTTT CCAGCTGGAA
     GGCGGTCTGA AGCAGTTTAG TTTCCCTCTG
2701 AGTTCAGAGC CGTTTCAGGG TTCTTATAAA
     GTCGTGGTTC AGAAAAAGAG TGGGGGACGT
2761 ACTGAACATC CTTTTACCGT TGAAGAGTTC
     GTCCTGCCGA AATTTGAGGT CCAGGTGACC
2821 GTTCCCAAGA TTATCACAAT TCTGGAAGAG
     GAAATGAACG TGAGCGTGTG CGGACTGTAT
2881 ACCTACGGCA AACCAGTGCC TGGTCACGTT
     ACAGTCAGTA TCTGCCGTAA GTACTCAGAT
2941 GCAAGCGACT GTCATGGCGA AGATTCACAG
     GCTTTTTGCG AGAAGTTCAG CGGCCAGCTG
3001 AACTCCCACG GTTGCTTCTA TCAGCAGGTG
     AAAACCAAGG TTTTTCAGCT GAAACGGAAG
```

3061 GAGTACGAAA TGAAACTGCA TACAGAAGCC CAGATTCAGG AAGAAGGCAC CGTCGTGGAA
3121 CTGACTGGTC GTCAGAGCTC CGAGATTACC CGGACAATCA CTAAACTGAG CTTCGTGAAG
3181 GTTGATTCCC ACTTTCGGCA GGGGATTCCC TTTTTCGGAC AGGTGCGCCT GGTTGACGGG
3241 AAAGGAGTTC CGATCCCCAA CAAAGTGATC TTTATTCGCG GCAATGAAGC CAACTATTAC
3301 AGCAACGCGA CAACTGATGA GCATGGGCTG GTGCAGTTCA GTATCAATAC CACAAACGTG
3361 ATGGGAACCT CACTGACAGT CCGCGTGAAT TATAAAGACC GTTCACCGTG TTATGGCTAC
3421 CAGTGGGTGA GCGAGGAACA CGAGGAAGCC CACCATACCG CGTACCTGGT TTTCAGCCCC
3481 TCCAAATCTT TTGTCCATCT GGAACCTATG TCTCACGAGC TGCCGTGCGG CCATACCCAG
3541 ACAGTGCAGG CACATTATAT TCTGAACGGC GGCACCCTGC TGGGTCTGAA AAAGCTGAGC
3601 TTTTATTACC TGATTATGGC TAAGGGGGGA ATCGTCCGCA CTGGCACCCA CGGTCTGCTG
3661 GTTAAACAGG AAGATATGAA GGGCCATTTC AGTATTTCAA TCCCTGTTAA AAGCGACATT
3721 GCTCCGGTCG CCCGTCTGCT GATCTATGCC GTGCTGCCAA CCGGCGATGT TATCGGTGAC
3781 TCCGCCAAAT ACGATGTGGA GAATTGTCTG GCGAACAAGG TTGACCTGAG CTTTTCCCCC
3841 TCTCAGAGTC TGCCAGCGTC TCATGCACAT CTGCGTGTGA CCGCAGCCCC TCAGAGCGTT
3901 TGCGCTCTGC GTGCAGTGGA TCAGTCCGTG CTGCTGATGA AGCCAGACGC AGAACTGTCT
3961 GCTAGCAGCG TGTATAATCT GCTGCCTGAG AAAGATCTGA CCGGGTTCCC AGGACCTCTG
4021 AACGATCAGG ATGACGAAGA CTGTATTAAT CGCCACAACG TGTATATTAA TGGGATCACA
4081 TACACTCCGG TTTCAAGCAC CAACGAAAAA GATATGTACA GCTTCCTGGA GGACATGGGT
4141 CTGAAAGCGT TACCAATTC CAAGATCCGG AAACCCAAGA TGTGCCCACA GCTGCAGCAG
4201 TATGAAATGC ACGGACCTGA GGGTCTGCGT GTGGGCTTTT ACGAATCTGA TGTGATGGGA
4261 CGTGGTCATG CACGTCTGGT TCATGTCGAG GAACCACACA CCGAAACAGT GCGTAAATAC
4321 TTCCCTGAGA CCTGGATTTG GGACCTGGTT GTGGTGAACT CCGCGGGTGT GGCAGAAGTG
4381 GGTGTTACCG TCCCGGATAC TATTACCGAA TGGAAAGCAG GTGCCTTCTG TCTGTCTGAG
4441 GATGCAGGGC TGGGAATCTC CTCTACAGCC TCTCTGCGCG CGTTTCAGCC CTTTTTCGTC
4501 GAACTGACTA TGCCATATAG CGTGATTCGT GGCGAGGCAT TCACTCTGAA AGCTACCGTG
4561 CTGAATTACC TGCCCAAGTG CATCCGCGTG AGCGTGCAGC TGGAAGCTAG TCCCGCCTTT
4621 CTGGCGGTCC CAGTGGAGAA GGAACAGGCA CCGCACTGCA TTTGTGCTAA CGGCCGGCAG
4681 ACTGTTTCCT GGGCCGTCAC CCCCAAATCT CTGGGTAATG TGAACTTCAC CGTTTCAGCA
4741 GAGGCTCTGG AAAGCCAGGA GCTGTGCGGC ACCGAAGTCC CATCCGTGCC TGAGCATGGT
4801 CGCAAAGATA CAGTCATCAA GCCTCTGCTG GTTGAACCGG AAGGCCTGGA GAAGGAAACT
4861 ACCTTTAATT CTCTGCTGTG CCCAGTGGG GGTGAAGTGT CCGAGGAACT GTCTCTGAAA
4921 CTGCCGCCCA ACGTGGTCGA GGAATCTGCC CGTGCGTCAG TTAGCGTCCT GGGGGATATT
4981 CTGGGAAGTG CCATGCAGAA TACCCAGAAC CTGCTGCAGA TGCCGTATGG CTGTGGCGAG

5041 CAGAATATGG TTCTGTTTGC GCCCAACATC TATGTCCTGG ATTACCTGAA TGAAACACAG
5101 CAGCTGACTC CTGAAATCAA AAGCAAGGCA ATCGGGTATC TGAATACCGG ATACCAGCGG
5161 CAGCTGAACT ATAAGCACTA CGACGGCTCC TATTCTACCT TCGGCGAACG GTACGGTCGC
5221 AATCAGGGGA ACACTTGGCT GACCGCCTTT GTGCTGAAAA CCTTTGCCCA GGCTCGCGCC
5281 TATATCTTTA TTGATGAGGC CCATATTACA CAGGCGCTGA TCTGGCTGTC ACAGCGCCAG
5341 AAGGACAACG GGTGTTTCCG TAGTTCAGGA AGCCTGCTGA ACAATGCCAT CAAAGGCGGC
5401 GTCGAGGATG AAGTGACACT GAGCGCATAC ATTACTATCG CTCTGCTGGA AATCCCTCTG
5461 ACAGTGACTC ACCCGGTGGT TCGCAATGCT CTGTTTTGCC TGGAAAGTGC ATGGAAAACA
5521 GCTCAGGAAG GCGATCACGG ATCACACGTG TATACTAAGG CACTGCTGGC GTACGCATTC
5581 GCTCTGGCCG GCAACCAGGA TAAACGTAAA GAAGTGCTGA AATCACTGAA TGAGGAAGCA
5641 GTTAAAAAGG ACAACAGCGT CCACTGGGAA CGGCCGCAGA AACCCAAGGC TCCAGTGGGT
5701 CACTTTTATG AGCCTCAGGC ACCGAGTGCT GAGGTGGAAA TGACCTCATA TGTTCTGCTG
5761 GCATACCTGA CCGCACAGCC TGCCCCCACA TCAGAAGATC TGACAAGCGC CACTAATATT
5821 GTGAAATGGA TCACCAAGCA GCAGAACGCG CAGGGCGGTT TTAGCTCCAC CCAGGACACA
5881 GTCGTGGCAC TGCACGCTCT GTCTAAATAT GGGGCAGCTA CCTTCACACG CACTGGAAAG
5941 GCCGCGCAAG TGACTATTCA GTCTAGTGGC ACCTTTTCAA GCAAGTTCCA GGTGGATAAC
6001 AATAACCGTC TGCTGCTGCA GCAGGTGTCC CTGCCCGAAC TGCCAGGCGA GTACTCTATG
6061 AAAGTCACTG GGGAAGGATG CGTGTATCTG CAGACCTCCC TGAAATACAA TATTCTGCCC
6121 GAGAAAGAAG AATTTCCATT CGCACTGGGC GTGCAGACCC TGCCTCAGAC ATGCGATGAA
6181 CCGAAGGCTC ATACTTCTTT TCAGATCAGT CTGTCAGTGA GCTATACCGG GTCCCGCTCT
6241 GCCAGTAACA TGGCGATTGT GGATGTGAAA ATGGTGAGTG GATTCATCCC TCTGAAACCG
6301 ACTGTGAAGA TGCTGGAACG GAGTAATCAC GTTTCACGCA CCGAGGTCTC CTCTAACCAT
6361 GTGCTGATCT ACCTGGATAA AGTGTCCAAT CAGACACTGT CTCTGTTTTT CACTGTGCTG
6421 CAGGATGTCC CCGTGCGTGA CCTGAAACCA GCCATTGTTA AGGTCTATGA TTATTACGAA
6481 ACCGACGAGT TCGCGATCGC AGAATACAAC GCGCCGTGCA GCAAAGACCT GGGGAATGCT
6541 GACTACAAGG ACGACGACGA CAAGGGGGCA AGCCACCACC ATCACCATCA CTAAGGATCC
6601 AAAATCAGCC TCGACTGTGC CTTCTAGTTG CCAGCCATCT GTTGTTTGCC CCTCCCCCGT
6661 GCCTTCCTTG ACCCTGGAAG GTGCCACTCC CACTGTCCTT TCCTAATAAA ATGAGGAAAT
6721 TGCATCACAA CACTCAACCC TATCTCGGTC TATTCTTTTG ATTTATAAGG GATTTTGCCG
6781 ATTTCGGCCT ATTGGTTAAA AAATGAGCTG ATTTAACAAA AATTTAACGC GAATTAATTC
6841 TGTGGAATGT GTGTCAGTTA GGGTGTGGAA AGTCCCCAGG CTCCCCAGCA GGCAGAAGTA
6901 TGCAAAGCAT GCATCTCAAT TAGTCAGCAA CCAGGTGTGG AAAGTCCCCA GGCTCCCCAG
6961 CAGGCAGAAG TATGCAAAGC ATGCATCTCA ATTAGTCAGC AACCATAGTC CCGCCCCTAA

7021 CTCCGCCCAT CCCGCCCCTA ACTCCGCCCA GTTCCGCCCA TTCTCCGCCC CATGGCTGAC
7081 TAATTTTTTT TATTTATGCA GAGGCCGAGG CCGCCTCTGC CTCTGAGCTA TTCCAGAAGT
7141 AGTGAGGAGG CTTTTTTGGA GGCCTAGGCT TTTGCAAAAA GCTCCCGGGA GCTTGTATAT
7201 CCATTTTCGG ATCTGATCAG CACGTGTTGA CAATTAATCA TCGGCATAGT ATATCGGCAT
7261 AGTATAATAC GACAAGGTGA GGAACTAAAC CATGGCCAAG CCTTTGTCTC AAGAAGAATC
7321 CACCCTCATT GAAAGAGCAA CGGCTACAAT CAACAGCATC CCCATCTCTG AAGACTACAG
7381 CGTCGCCAGC GCAGCTCTCT CTAGCGACGG CCGCATCTTC ACTGGTGTCA ATGTATATCA
7441 TTTTACTGGG GGACCTTGTG CAGAACTCGT GGTGCTGGGC ACTGCTGCTG CTGCGGCAGC
7501 TGGCAACCTG ACTTGTATCG TCGCGATCGG AAATGAGAAC AGGGGCATCT TGAGCCCCTG
7561 CGGACGGTGC CGACAGGTGC TTCTCGATCT GCATCCTGGG ATCAAAGCCA TAGTGAAGGA
7621 CAGTGATGGA CAGCCGACGG CAGTTGGGAT TCGTGAATTG CTGCCCTCTG GTTATGTGTG
7681 GGAGGGCTAA CACGTGCTAC GAGATTTCGA TTCCACCGCC GCCTTCTATG AAAGGTTGGG
7741 CTTCGGAATC GTTTTCCGGG ACGCCGGCTG GATGATCCTC CAGCGCGGGG ATCTCATGCT
7801 GGAGTTCTTC GCCCACCCCA ACTTGTTTAT TGCAGCTTAT AATGGTTACA AATAAAGCAA
7861 TAGCATCACA AATTTCACAA ATAAAGCATT TTTTTCACTG CATTCTAGTT GTGGTTTGTC
7921 CAAACTCATC AATGTATCTT ATCATGTCTG TATACCGTCG ACCTCTAGCT AGAGCTTGGC
7981 GTAATCATGG TCATTACCAA TGCTTAATCA GTGAGGCACC TATCTCAGCG ATCTGTCTAT
8041 TTCGTTCATC CATAGTTGCC TGACTCCCCG TCGTGTAGAT AACTACGATA CGGGAGGGCT
8101 TACCATCTGG CCCCAGCGCT GCGATGATAC CGCGAGAACC ACGCTCACCG GCTCCGGATT
8161 TATCAGCAAT AAACCAGCCA GCCGGAAGGG CCGAGCGCAG AAGTGGTCCT GCAACTTTAT
8221 CCGCCTCCAT CCAGTCTATT AATTGTTGCC GGGAAGCTAG AGTAAGTAGT TCGCCAGTTA
8281 ATAGTTTGCG CAACGTTGTT GCCATCGCTA CAGGCATCGT GGTGTCACGC TCGTCGTTTG
8341 GTATGGCTTC ATTCAGCTCC GGTTCCCAAC GATCAAGGCG AGTTACATGA TCCCCCATGT
8401 TGTGCAAAAA AGCGGTTAGC TCCTTCGGTC CTCCGATCGT TGTCAGAAGT AAGTTGGCCG
8461 CAGTGTTATC ACTCATGGTT ATGGCAGCAC TGCATAATTC TCTTACTGTC ATGCCATCCG
8521 TAAGATGCTT TTCTGTGACT GGTGAGTACT CAACCAAGTC ATTCTGAGAA TAGTGTATGC
8581 GGCGACCGAG TTGCTCTTGC CCGGCGTCAA TACGGGATAA TACCGCGCCA CATAGCAGAA
8641 CTTTAAAAGT GCTCATCATT GGAAAACGTT CTTCGGGGCG AAAACTCTCA AGGATCTTAC
8701 CGCTGTTGAG ATCCAGTTCG ATGTAACCCA CTCGTGCACC CAACTGATCT TCAGCATCTT
8761 TTACTTTCAC CAGCGTTTCT GGGTGAGCAA AAACAGGAAG GCAAAATGCC GCAAAAAAGG
8821 GAATAAGGGC GACACGGAAA TGTTGAATAC TCATATTCTT CCTTTTTCAA TATTATTGAA
8881 GCATTTATCA GGGTTATTGT CTCATGAGCG GATACATATT TGAATGTATT TAGAAAAATA
8941 AACAAATAGG GGTCAGTGTT ACAACCAATT AACCAATTCT GAACATTATC GCG

SEQ ID NO 2: Complete Vector DNA Sequence of the of the Acceptor Mutant.
1 CTCATGACCA AAATCCCTTA ACGTGAGTTA CGCGCGCGTC GTTCCACTGA GCGTCAGACC
61 CCGTAGAAAA GATCAAAGGA TCTTCTTGAG ATCCTTTTTT TCTGCGCGTA ATCTGCTGCT
121 TGCAAACAAA AAAACCACCG CTACCAGCGG TGGTTTGTTT GCCGGATCAA GAGCTACCAA
181 CTCTTTTTCC GAAGGTAACT GGCTTCAGCA GAGCGCAGAT ACCAAATACT GTTCTTCTAG
241 TGTAGCCGTA GTTAGCCCAC CACTTCAAGA ACTCTGTAGC ACCGCCTACA TACCTCGCTC
301 TGCTAATCCT GTTACCAGTG GCTGCTGCCA GTGGCGATAA GTCGTGTCTT ACCGGGTTGG
361 ACTCAAGACG ATAGTTACCG GATAAGGCGC AGCGGTCGGG CTGAACGGGG GGTTCGTGCA
421 CACAGCCCAG CTTGGAGCGA ACGACCTACA CCGAACTGAG ATACCTACAG CGTGAGCTAT
481 GAGAAAGCGC CACGCTTCCC GAAGGGAGAA AGGCGGACAG GTATCCGGTA AGCGGCAGGG
541 TCGGAACAGG AGAGCGCACG AGGGAGCTTC CAGGGGGAAA CGCCTGGTAT CTTTATAGTC
601 CTGTCGGGTT TCGCCACCTC TGACTTGAGC GTCGATTTTT GTGATGCTCG TCAGGGGGGC
661 GGAGCCTATG GAAAAACGCC AGCAACGCGG CCTTTTTACG GTTCCTGGCC TTTTGCTGGC
721 CTTTTGCTCA CATGTTCTTT CCTGCGTTAT CCCCTGATTC TGTGGATAAC CGTATTACCG
781 CCTTTGAGTG AGCTGATACC GCTCGCCGCA GCCGAACGAC CGAGCGCAGC GAGTCAGTGA
841 GCGAGGAAGC GGAAGGCGAG AGTAGGGAAC TGCCAGGCAT CAAACTAAGC AGAAGGCCCC
901 TGACGGATGG CCTTTTTGCG TTTCTACAAA CTCTTTCTGT GTTGTAAAAC GACGGCCAGT
961 CTTAAGCTCG GCCCCCTGG GCGGTTCTGA TAACGAGTAA TCGTTAATCC GCAAATAACG
1021 TAAAAACCCG CTTCGGCGGG TTTTTTATG GGGGGAGTTT AGGGAAAGAG CATTTGTCAG
1081 AATATTTAAG GCGCCTGTC ACTTTGCTTG ATATATGAGA ATTATTTAAC CTTATAAATG
1141 AGAAAAAAGC AACGCACTTT AAATAAGATA CGTTGCTTTT TCGATTGATG AACACCTATA
1201 ATTAAACTAT TCATCTATTA TTTATGATTT TTT-GTATATA CAATATTTCT AGTTTGTTAA
1261 AGAGAATTAA GAAAATAAAT CTCGAAAATA ATAAAGGGAA AATCAGTTTT TGATATCAAA
1321 ATTATACATG TCAACGATAA TACAAAATAT AATACAAACT ATAAGATGTT ATCAGTATTT
1381 ATTATCATTT AGAATAAATT TTGTGTCGCC CTTAATTGTG AGCGGATAAC AATTACGAGC
1441 TTCATGCACA GTGGCGTTGA CATTGATTAT TGACTAGTTA TTAATAGTAA TCAATTACGG
1501 GGTCATTAGT TCATAGCCCA TATATGGAGT TCCGCGTTAC ATAACTTACG GTAAATGGCC
1561 CGCCTGGCTG ACCGCCCAAC GACCCCCGCC CATTGACGTC AATAATGACG TATGTTCCCA
1621 TAGTAACGCC AATAGGGACT TTCCATTGAC GTCAATGGGT GGAGTATTTA CGGTAAACTG
1681 CCCACTTGGC AGTACATCAA GTGTATCATA TGCCAAGTAC GCCCCCTATT GACGTCAATG
1741 ACGGTAAATG GCCCGCCTGG CATTATGCCC AGTACATGAC CTTATGGGAC TTTCCTACTT
1801 GGCAGTACAT CTACGTATTA GTCATCGCTA TTACCATGGT GATGCGGTTT TGGCAGTACA
1861 TCAATGGGCG TGGATAGCGG TTTGACTCAC GGGGATTTCC AAGTCTCCAC CCCATTGACG 1921 TCAATGGGAG TTTGTTTTGG CACCAAAATC
AACGGGACTT TCCAAAATGT CGTAACAACT
1981 CCGCCCCATT GACGCAAATG GGCGGTAGGC
GTGTACGGTG GGAGGTCTAT ATAAGCAGAG
2041 CTCTCTGGCT AACTAGAGAA CCCACTGCTT
ACTGGCTTAT CGAAATTAAT ACGACTCACT
2101 ATAGGGGTAC CTGCCACCAT GGGGAAAAAC
AAACTGCTGC ATCCAAGCCT GGTCCTGCTG
2161 CTGCTGGTTC TGCTGCCTAC TGACGCCTCT
GTGAGCGGAA AGCCCCAGTA TATGGTTCTG
2221 GTCCCGTCCC TGCTGCACAC CGAGACCACA
GAAAAAGGGT GCGTGCTGCT GTCTTACCTG
2281 AATGAAACAG TGACTGTTAG TGCCTCACTG
GAGAGTGTGC GCGGAAATCG TTCACTGTTC
2341 ACCGATCTGG AGGCGGAAAA CGATGTGCTG
CATTGCGTCG CATTTGCTGT GCCAAAAAGC
2401 TCCTCTAATG AAGAAGTGAT GTTCCTGACC
GTCCAGGTGA AGGGCCCTAC ACAGGAATTC
2461 AAAAAACGCA CTACCGTTAT GGTCAAAAAC
GAGGATAGCC TGGTGTTTGT TCAGACAGAC
2521 AAATCCATCT ATAAGCCTGG TCAGACTGTG
AAGTTCCGGG TGGTTAGCAT GGATGAAAAT
2581 TTTCACCCCC TGAACGAGCT GATTCCACTG
GTGTACATCC AGGACCCTAA AGGCAACCGC
2641 ATCGCCCAGT GGCAGTCTTT CCAGCTGGAA
GGCGGTCTGA AGCAGTTTAG TTTCCCTCTG
2701 AGTTCAGAGC CGTTTCAGGG TTCTTATAAA
GTCGTGGTTC AGAAAAAGAG TGGGGGACGT
2761 ACTGAACATC CTTTTACCGT TGAAGAGTTC
GTCCTGCCGA AATTTGAGGT CCAGGTGACC
2821 GTTCCCAAGA TTATCACAAT TCTGGAAGAG
GAAATGAACG TGAGCGTGTG CGGACTGTAT
2881 ACCTACGGCA AACCAGTGCC TGGTCACGTT
ACAGTCAGTA TCTGCCGTAA GTACTCAGAT
2941 GCAAGCGACT GTCATGGCGA AGATTCACAG
GCTTTTTGCG AGAAGTTCAG CGGCCAGCTG
3001 AACTCCCACG GTTGCTTCTA TCAGCAGGTG
AAAACCAAGG TTTTTCAGCT GAAACGGAAG
3061 GAGTACGAAA TGAAACTGCA TACAGAAGCC
CAGATTCAGG AAGAAGGCAC CGTCGTGGAA
3121 CTGACTGGTC GTCAGAGCTC CGAGATTACC
CGGACAATCA CTAAACTGAG CTTCGTGAAG
3181 GTTGATTCCC ACTTTCGGCA GGGGATTCCC
TTTTTCGGAC AGGTGCGCCT GGTTGACGGG
3241 AAAGGAGTTC CGATCCCCAA CAAAGTGATC
TTTATTCGCG GCAATGAAGC CAACTATTAC
3301 AGCAACGCGA CAACTGATGA GCATGGGCTG
GTGCAGTTCA GTATCAATAC CACAAACGTG
3361 ATGGGAACCT CACTGACAGT CCGCGTGAAT
TATAAAGACC GTTCACCGTG TTATGGCTAC
3421 CAGTGGGTGA GCGAGGAACA CGAGGAAGCC
CACCATACCG CGTACCTGGT TTTCAGCCCC
3481 TCCAAATCTT TTGTCCATCT GGAACCTATG
TCTCACGAGC TGCCGTGCGG CCATACCCAG
3541 ACAGTGCAGG CACATTATAT TCTGAACGGC
GGCACCCTGC TGGGTCTGAA AAAGCTGAGC
3601 TTTTATTACC TGATTATGGC TAAGGGGGGA
ATCGTCCGCA CTGGCACCCA CGGTCTGCTG
3661 GTTAAACAGG AAGATATGAA GGGCCATTTC
AGTATTTCAA TCCCTGTTAA AAGCGACATT
3721 GCTCCGGTCG CCCGTCTGCT GATCTATGCC
GTGCTGCCAA CCGGCGATGT TATCGGTGAC
3781 TCCGCCAAAT ACGATGTGGA GAATTGTCTG
GCGAACAAGG TTGACCTGAG CTTTTCCCCC
3841 TCTCAGAGTC TGCCAGCGTC TCATGCACAT
CTGCGTGTGA CCGCAGCCCC TCAGAGCGTT 3901 TGCGCTCTGC GTGCAGTGGA TCAGTCCGTG
CTGCTGATGA AGCCAGACGC AGAACTGTCT
3961 GCTAGCAGCG TGTATAATCT GCTGCCTGAG
AAAGATCTGA CCGGGTTCCC AGGACCTCTG
4021 AACGATCAGG ATGACGAAGA CTGTATTAAT
CGCCACAACG TGTATATTAA TGGGATCACA
4081 TACACTCCGG TTTCAAGCAC CAACGAAAAA
GATATGTACA GCTTCCTGGA GGACATGGGT
4141 CTGAAAGCGT TTACCAATTC CAAGATCCGG
AAACCCCAAG ATGTGCCCAC AGCTCGAGCA
4201 GTATGAAATG CACGGACCTG AGGGTCTGCG
TGTGGGCTTT TACGAATCTG ATGTGATGGG
4261 ACGTGGTCAT GCACGTCTGG TTCATGTCGA
GGAACCACAC ACCGAAAAGC TTCGTAAATA
4321 CTTCCCTGAG ACCTGGATTT GGGACCTGGT
TGTGGTGAAC TCCGCGGGTG TGGCAGAAGT
4381 GGGTGTTACC GTCCCGGATA CTATTACCGA
ATGGAAAGCA GGTGCCTTCT GTCTGTCTGA
4441 GGATGCAGGG CTGGGAATCT CCTCTACAGC
CTCTCTGCGC GCGTTTCAGC CCTTTTTCGT
4501 CGAACTGACT ATGCCATATA GCGTGATTCG
TGGCGAGGCA TTCACTCTGA AAGCTACCGT
4561 GCTGAATTAC CTGCCCAAGT GCATCCGCGT
GAGCGTGCAG CTGGAAGCTA GTCCCGCCTT
4621 TCTGGCGGTC CCAGTGGAGA AGGAACAGGC
ACCGCACTGC ATTTGTGCTA ACGGCCGGCA
4681 GACTGTTTCC TGGGCCGTCA CCCCCAAATC
TCTGGGTAAT GTGAACTTCA CCGTTTCAGC
4741 AGAGGCTCTG GAAAGCCAGG AGCTGTGCGG
CACCGAAGTC CCATCCGTGC TGAGCATGG
4801 TCGCAAAGAT ACAGTCATCA AGCCTCTGCT
GGTTGAACCG GAAGGCCTGG AGAAGGAAAC
4861 TACCTTTAAT TCTCTGCTGT GCCCAAGTGG
CGGTGAAGTG TCCGAGGAAC TGTCTCTGAA
4921 ACTGCCGCCC AACGTGGTCG AGGAATCTGC
CCGTGCGTCA GTTAGCGTCC TGGGGGATAT
4981 TCTGGGAAGT GCCATGCAGA ATACCCAGAA
CCTGCTGCAG ATGCCGTATG CTGTGGCGA
5041 GCAGAATATG GTTCTGTTTG CGCCCAACAT
CTATGTCCTG GATTACCTGA ATGAAACACA
5101 GCAGCTGACT CCTGAAATCA AAAGCAAGGC
AATCGGTGTAT CTGAATACCG GATACCAGCG
5161 GCAGCTGAAC TATAAGCACT ACGACGGCTC
CTATTCTACC TTCGGCGAAC GGTACGGTCG
5221 CAATCAGGGG AACACTTGGC TGACCGCCTT
TGTGCTGAAA ACCTTTGCCC AGGCTCGCGC
5281 CTATATCTTT ATTGATGAGG CCCATATTAC
ACAGGCGCTG ATCTGGCTGT CACAGCGCCA
5341 GAAGGACAAC GGGTGTTTCC GTAGTTCAGG
AAGCCTGCTG AACAATGCCA TCAAAGGCGG
5401 CGTCGAGGAT GAAGTGACAC TGAGCGCATA
CATTACTATC GCTCTGCTGG AAATCCCTCT
5461 GACAGTGACT CACCCGGTGG TTCGCAATGC
TCTGTTTTGC CTGGAAAGTG CATGGAAAAC
5521 AGCTCAGGAA GGCGATCACG GATCACACGT
GTATACTAAG GCACTGCTGG CGTACGCATT
5581 CGCTCTGGCC GGCAACCAGG ATAAACGTAA
AGAAGTGCTG AAATCACTGA ATGAGGAAGC
5641 AGTTAAAAAG GACAACAGCG TCCACTGGGA
ACGGCCGCAG AAACCCAAGG CTCCAGTGGG
5701 TCACTTTTAT GAGCCTCAGG CACCGGAGTGC
TGAGGTGGAA ATGACCTCAT ATGTTCTGCT
5761 GGCATACCTG ACCGCACAGC CTGCCCCCAC
ATCAGAAGAT CTGACAAGCG CCACTAATAT
5821 TGTGAAATGG ATCACCAAGC AGCAGAACGC
GCAGGGCGGT TTTAGCTCCA CCCAGGACAC 5881 AGTCGTGGCA CTGCACGCTC TGTCTAAATA TGGGGCAGCT ACCTTCACAC GCACTGGAAA
5941 GGCCGCGCAA GTGACTATTC AGTCTAGTGG CACCTTTTCA AGCAAGTTCC AGGTGGATAA
6001 CAATAACCGT CTGCTGCTGC AGCAGGTGTC CCTGCCCGAA CTGCCAGGCG AGTACTCTAT
6061 GAAAGTCACT GGGGAAGGAT GCGTGTATCT GCAGACCTCC CTGAAATACA ATATTCTGCC
6121 CGAGAAAGAA GAATTTCCAT TCGCACTGGG CGTGCAGACC CTGCCTCAGA CATGCGATGA
6181 ACCGAAGGCT CATACTTCTT TTCAGATCAG TCTGTCAGTG AGCTATACCG GGTCCCGCTC
6241 TGCCAGTAAC ATGGCGATTG TGGATGTGAA AATGGTGAGT GGATTCATCC CTCTGAAACC
6301 GACTGTGAAG ATGCTGGAAC GGAGTAATCA CGTTTCACGC ACCGAGGTCT CCTCTAACCA
6361 TGTGCTGATC TACCTGGATA AAGTGTCCAA TCAGACACTG TCTCTGTTTT TCACTGTGCT
6421 GCAGGATGTC CCCGTGCGTG ACCTGAAACC AGCCATTGTT AAGGTCTATG ATTATTACGA
6481 AACCGACGAG TTCGCGTCG CAGAATACAA CGCGCCGTGC AGCAAAGACC TGGGGAATGC
6541 TGACTACAAG GACGACGACG ACAAGGGGGC AAGCCACCAC CATCACCATC ACTAAGGATC
6601 CAAAATCAGC CTCGACTGTG CCTTCTAGTT GCCAGCCATC TGTTGTTTGC CCCTCCCCCG
6661 TGCCTTCCTT GACCCTGGAA GGTGCCACTC CCACTGTCCT TTCCTAATAA AATGAGGAAA
6721 TTGCATCACA ACACTCAACC CTATCTCGGT CTATTCTTTT GATTTATAAG GGATTTTGCC
6781 GATTTCGGCC TATTGGTTAA AAAATGAGCT GATTTAACAA AAATTTAACG CGAATTAATT
6841 CTGTGGAATG TGTGTCAGTT AGGGTGTGGA AAGTCCCCAG GCTCCCCAGC AGGCAGAAGT
6901 ATGCAAAGCA TGCATCTCAA TTAGTCAGCA ACCAGGTGTG GAAAGTCCCC AGGCTCCCCA
6961 GCAGGCAGAA GTATGCAAAG CATGCATCTC AATTAGTCAG CAACCATAGT CCCGCCCCTA
7021 ACTCCGCCCA TCCCGCCCCT AACTCCGCCC AGTTCCGCCC ATTCTCCGCC CCATGGCTGA
7081 CTAATTTTTT TTATTTATGC AGAGGCCGAG GCCGCCTCTG CCTCTGAGCT ATTCCAGAAG
7141 TAGTGAGGAG GCTTTTTTGG AGGCCTAGGC TTTTGCAAAA AGCTCCCGGG AGCTTGTATA
7201 TCCATTTTCG GATCTGATCA GCACGTGTTG ACAATTAATC ATCGGCATAG TATATCGGCA
7261 TAGTATAATA CGACAAGGTG AGGAACTAAA CCATGGCCAA GCCTTTGTCT CAAGAAGAAT
7321 CCACCCTCAT TGAAAGAGCA ACGGCTACAA TCAACAGCAT CCCCATCTCT GAAGACTACA
7381 GCGTCGCCAG CGCAGCTCTC TCTAGCGACG GCCGCATCTT CACTGGTGTC AATGTATATC
7441 ATTTTACTGG GGGACCTTGT GCAGAACTCG TGGTGCTGGG CACTGCTGCT GCTGCGGCAG
7501 CTGGCAACCT GACTTGTATC GTCGCGATCG GAAATGAGAA CAGGGGCATC TTGAGCCCCT
7561 GCGGACGGTG CCGACAGGTG CTTCTCGATC TGCATCCTGG GATCAAAGCC ATAGTGAAGG
7621 ACAGTGATGG ACAGCCGACG GCAGTTGGGA TTCGTGAATT GCTGCCCTCT GGTTATGTGT
7681 GGGAGGGCTA ACACGTGCTA CGAGATTTCG ATTCCACCGC CGCCTTCTAT GAAAGGTTGG
7741 GCTTCGGAAT CGTTTTCCGG GACGCCGGCT GGATGATCCT CCAGCGCGGG GATCTCATGC
7801 TGGAGTTCTT CGCCCACCCC AACTTGTTTA TTGCAGCTTA TAATGGTTAC AAATAAAGCA 7861 ATAGCATCAC AAATTTCACA AATAAAGCAT TTTTTTCACT GCATTCTAGT TGTGGTTTGT
7921 CCAAACTCAT CAATGTATCT TATCATGTCT GTATACCGTC GACCTCTAGC TAGAGCTTGG
7981 CGTAATCATG GTCATTACCA ATGCTTAATC AGTGAGGCAC CTATCTCAGC GATCTGTCTA
8041 TTTCGTTCAT CCATAGTTGC CTGACTCCCC GTCGTGTAGA TAACTACGAT ACGGGAGGGC
8101 TTACCATCTG GCCCCAGCGC TGCGATGATA CCGCGAGAAC CACGCTCACC GGCTCCGGAT
8161 TTATCAGCAA TAAACCAGCC AGCCGGAAGG GCCGAGCGCA GAAGTGGTCC TGCAACTTTA
8221 TCCGCCTCCA TCCAGTCTAT TAATTGTTGC CGGGAAGCTA GAGTAAGTAG TTCGCCAGTT
8281 AATAGTTTGC GCAACGTTGT TGCCATCGCT ACAGGCATCG TGGTGTCACG CTCGTCGTTT
8341 GGTATGGCTT CATTCAGCTC CGGTTCCCAA CGATCAAGGC GAGTTACATG ATCCCCCATG
8401 TTGTGCAAAA AAGCGGTTAG CTCCTTCGGT CCTCCGATCG TTGTCAGAAG TAAGTTGGCC
8461 GCAGTGTTAT CACTCATGGT TATGGCAGCA CTGCATAATT CTCTTACTGT CATGCCATCC
8521 GTAAGATGCT TTTCTGTGAC TGGTGAGTAC TCAACCAAGT CATTCTGAGA ATAGTGTATG
8581 CGGCGACCGA GTTGCTCTTG CCCGGCGTCA ATACGGGATA ATACCGCGCC ACATAGCAGA
8641 ACTTTAAAAG TGCTCATCAT TGGAAAACGT TCTTCGGGGC GAAAACTCTC AAGGATCTTA
8701 CCGCTGTTGA GATCCAGTTC GATGTAACCC ACTCGTGCAC CCAACTGATC TTCAGCATCT
8761 TTTACTTTCA CCAGCGTTTC TGGGTGAGCA AAAACAGGAA GGCAAAATGC CGCAAAAAAG
8821 GGAATAAGGG CGACACGGAA ATGTTGAATA CTCATATTCT TCCTTTTTCA ATATTATTGA
8881 AGCATTTATC AGGGTTATTG TCTCATGAGC GGATACATAT TTGAATGTAT TTAGAAAAAT
8941 AAACAAATAG GGGTCAGTGT TACAACCAAT TAACCAATTC TGAACATTAT CGCG SEQ ID NO 3: Amino Acid Sequence of Tagged Wild-Type Human A2M
1 MGKNKLLHPS LVLLLLVLLP TDASVSGKPQ YMVLVPSLLH TETTEKGCVL LSYLNETVTV
61 SASLESVRGN RSLFTDLEAE NDVLHCVAFA VPKSSSNEEV MFLTVQVKGP TQEFKKRTTV
121 MVKNEDSLVF VQTDKSIYKP GQTVKFRVVS MDENFHPLNE LIPLVYIQDP KGNRIAQWQS
181 FQLEGGLKQF SFPLSSEPFQ GSYKVVVQKK SGGRTEHPFT VEEFVLPKFE VQVTVPKIIT
241 ILEEEMNVSV CGLYTYGKPV PGHVTVSICR KYSDASDCHG EDSQAFCEKF SGQLNSHGCF
301 YQQVKTKVFQ LKRKEYEMKL HTEAQIQEEG TVVELTGRQS SEITRTITKL SFVKVDSHFR
361 QGIPFFGQVR LVDGKGVPIP NKVIFIRGNE ANYYSNATTD EHGLVQFSIN TTNVMGTSLT
421 VRVNYKDRSP CYGYQWVSEE HEEAHHTAYL VFSPSKSFVH LEPMSHELPC GHTQTVQAHY
481 ILNGGTLLGL KKLSFYYLIM AKGGIVRTGT HGLLVKQEDM KGHFSISIPV KSDIAPVARL
541 LIYAVLPTGD VIGDSAKYDV ENCLANKVDL SFSPSQSLPA SHAHLRVTAA PQSVCALRAV
601 DQSVLLMKPD AELSASSVYN LLPEKDLTGF PGPLNDQDDE DCINRHNVYI NGITYTPVSS
661 TNEKDMYSFL EDMGLKAFTN SKIRKPKMCP QLQQYEMHGP EGLRVGFYES DVMGRGHARL
721 VHVEEPHTET VRKYFPETWI WDLVVVNSAG VAEVGVTVPD TITEWKAGAF CLSEDAGLGI 781 SSTASLRAFQ PFFVELTMPY SVIRGEAFTL KATVLNYLPK CIRVSVQLEA SPAFLAVPVE
841 KEQAPHCICA NGRQTVSWAV TPKSLGNVNF TVSAEALESQ ELCGTEVPSV PEHGRKDTVI
901 KPLLVEPEGL EKETTFNSLL CPSGGEVSEE LSLKLPPNVV EESARASVSV LGDILGSAMQ
961 NTQNLLQMPY GCGEQNMVLF APNIYVLDYL NETQQLTPEI KSKAIGYLNT GYQRQLNYKH
1021 YDGSYSTFGE RYGRNQGNTW LTAFVLKTFA QARAYIFIDE AHITQALIWL SQRQKDNGCF
1081 RSSGSLLNNA IKGGVEDEVT LSAYITIALL EIPLTVTHPV VRNALFCLES AWKTAQEGDH
1141 GSHVYTKALL AYAFALAGNQ DKRKEVLKSL NEEAVKKDNS VHWERPQKPK APVGHFYEPQ
1201 APSAEVEMTS YVLLAYLTAQ PAPTSEDLTS ATNIVKWITK QQNAQGGFSS TQDTVVALHA
1261 LSKYGAATFT RTGKAAQVTI QSSGTFSSKF QVDNNNRLLL QQVSLPELPG EYSMKVTGEG
1321 CVYLQTSLKY NILPEKEEFP FALGVQTLPQ TCDEPKAHTS FQISLSVSYT GSRSASNMAI
1381 VDVKMVSGFI PLKPTVKMLE RSNHVSRTEV SSNHVLIYLD KVSNQTLSLF FTVLQDVPVR
1441 DLKPAIVKVY DYYETDEFAI AEYNAPCSKD LGNADYKDDD DKGASHHHHHH SEQ ID NO 4: Amino Acid Sequence of the Acceptor Mutant.
1 MGKNKLLHPS LVLLLLVLLP TDASVSGKPQ YMVLVPSLLH TETTEKGCVL LSYLNETVTV
61 SASLESVRGN RSLFTDLEAE NDVLHCVAFA VPKSSSNEEV MFLTVQVKGP TQEFKKRTTV
121 MVKNEDSLVF VQTDKSIYKP GQTVKFRVVS MDENFHPLNE LIPLVYIQDP KGNRIAQWQS
181 FQLEGGLKQF SFPLSSEPFQ GSYKVVVQKK SGGRTEHPFT VEEFVLPKFE VQVTVPKIIT
241 ILEEEMNVSV CGLYTYGKPV PGHVTVSICR KYSDASDCHG EDSQAFCEKF SGQLNSHGCF
301 YQQVKTKVFQ LKRKEYEMKL HTEAQIQEEG TVVELTGRQS SEITRTITKL SFVKVDSHFR
361 QGIPFFGQVR LVDGKGVPIP NKVIFIRGNE ANYYSNATTD EHGLVQFSIN TTNVMGTSLT
421 VRVNYKDRSP CYGYQWVSEE HEEAHHTAYL VFSPSKSFVH LEPMSHELPC GHTQTVQAHY
481 ILNGGTLLGL KKLSFYYLIM AKGGIVRTGT HGLLVKQEDM KGHFSISIPV KSDIAPVARL
541 LIYAVLPTGD VIGDSAKYDV ENCLANKVDL SFSPSQSLPA SHAHLRVTAA PQSVCALRAV
601 DQSVLLMKPD AELSASSVYN LLPEKDLTGF PGPLNDQDDE DCINRHNVYI NGITYTPVSS
661 TNEKDMYSFL EDMGLKAFTN SKIRKPKMCP QLEQYEMHGP EGLRVGFYES DVMGRGHARL
721 VHVEEPHTEK LRKYFPETWI WDLVVVNSAG VAEVGVTVPD TITEWKAGAF CLSEDAGLGI
781 SSTASLRAFQ PFFVELTMPY SVIRGEAFTL KATVLNYLPK CIRVSVQLEA SPAFLAVPVE
841 KEQAPHCICA NGRQTVSWAV TPKSLGNVNF TVSAEALESQ ELCGTEVPSV PEHGRKDTVI
901 KPLLVEPEGL EKETTFNSLL CPSGGEVSEE LSLKLPPNVV EESARASVSV LGDILGSAMQ
961 NTQNLLQMPY GCGEQNMVLF APNIYVLDYL NETQQLTPEI KSKAIGYLNT GYQRQLNYKH
1021 YDGSYSTFGE RYGRNQGNTW LTAFVLKTFA QARAYIFIDE AHITQALIWL SQRQKDNGCF
1081 RSSGSLLNNA IKGGVEDEVT LSAYITIALL EIPLTVTHPV VRNALFCLES AWKTAQEGDH
1141 GSHVYTKALL AYAFALAGNQ DKRKEVLKSL NEEAVKKDNS VHWERPQKPK APVGHFYEPQ
1201 APSAEVEMTS YVLLAYLTAQ PAPTSEDLTS ATNIVKWITK QQNAQGGFSS TQDTVVALHA
1261 LSKYGAATFT RTGKAAQVTI QSSGTFSSKF QVDNNNRLLL QQVSLPELPG EYSMKVTGEG
1321 CVYLQTSLKY NILPEKEEFP FALGVQTLPQ TCDEPKAHTS FQISLSVSYT GSRSASNMAI
1381 VDVKMVSGFI PLKPTVKMLE RSNHVSRTEV SSNHVLIYLD KVSNQTLSLF FTVLQDVPVR
1441 DLKPAIVKVY DYYETDEFAI AEYNAPCSKD LGNADYKDDD DKGASHHHHH H SEQ ID NOs 5-66: Amino Acid Sequences of Variant Bait Regions.
SEQ ID NO 5: LEQYEMHGPE GLRVGKEEEG LGSIPENFFG VSELEGRGSK L
SEQ ID NO 6: LEQYEMHGPE GLRVGIPENF FGVSELEGRG SKEEEGLGSK L
SEQ ID NO 7: LEQYEMHGPE GLRVGSELEG RGSKEEEGLG SIPENFFGVK L
SEQ ID NO 8: LEQYEMHGPE GLRVGKEEEG LGSSELEGRG STAQEAGEGK L
SEQ ID NO 9: LEQYEMHGPE GLRVGIPENF FGVFYESDVM GRGHARLVHV EEPHTKLL
SEQ ID NO 10: LEQYEMHGPE GLRVGKEEEG LGSFYESDVM GRGHARLVHV EEPHTKLL
SEQ ID NO 11: LEQYEMHGPE GLRVGSELEG RGSFYESDVM GRGHARLVHV EEPHTKLL
SEQ ID NO 12: LEQYEMHGPE GLRVGEAIPM SIPFYESDVM GRGHARLVHV EEPHTKLL
SEQ ID NO 13: LEQYEMHGPE GLRVGTAQEA GEGFYESDVM GRGHARLVHV EEPHTKLL
SEQ ID NO 14: LEQYEMHGPE GLRVGVSQEL GQRFYESDVM GRGHARLVHV EEPHTKLL
SEQ ID NO 15: LEQYEMHGPE GLRVGTEGEA RGSFYESDVM GRGHARLVHV EEPHTKLL
SEQ ID NO 16: LEQYEMHGPE GLRVGTSEDL VVQFYESDVM GRGHARLVHV EEPHTKLL
SEQ ID NO 17: LEQYEMHGPE GLRVGEGEGE GEGFYESDVM GRGHARLVHV EEPHTKLL
SEQ ID NO 18: LEQYEMHGPE GLRVGGEEGV EEGFYESDVM GRGHARLVHV EEPHTKLL
SEQ ID NO 19: LEQYEMHGPE GLRVGGARGL EGFYESDVMG RGHARLVHVE EPHTKL
SEQ ID NO 20: LEQYEMHGPE GLRVGGPPGL APGFYESDVM GRGHARLVHV EEPHTKLL
SEQ ID NO 21: LEQYEMHGPE GLRVGGEPEG AKGFYESDVM GRGHARLVHV EEPHTKLL
SEQ ID NO 22: LEQYEMHGPE GLRVGEEEGG GFYESDVMGR GHARLVHVEE PHTKL
SEQ ID NO 23: LEQYEMHGPE GLRVGGYPGS SRGFYESDVM GRGHARLVHV EEPHTKLL
SEQ ID NO 24: LEQYEMHGPE GLRVGGARGL EGGFAGLPNG GEEGVEEGKL
SEQ ID NO 25: LEQYEMHGPE GLRVGESESE GGGGGSLLGE FEVEGGFAGL PNGKL
SEQ ID NO 26: LEQYEMHGPE GLRVGGFKEG VEGEIEEGGG FKEGVEGKL
SEQ ID NO 27: LEQYEMHGPE GLRVGESESE GGFAGLPNGK EEEGLGSIPE NFFGVKL
SEQ ID NO 28: LEQYEMHGPE GLRVGIPENF FGVTSEDLVV QEAIPMSIPK L
SEQ ID NO 29: LEQYEMHGPE GLRVGEAIPM SIPTSEDLVV QIPENFFGVK L
SEQ ID NO 30: LEPAGAARGE SESEGGFFGF PIGERESTGG DRGLPIGENE AGGKL
SEQ ID NO 31: LETEGRGERE AQGEFPEVEG EEEGGGPEKE TGGEREAQGK L SEQ ID NO 32: LEARGLEGGG GGSLLGGYPG SSRG-GFKEGV EGG PAG A ARC KL
SEQ ID NO 33: LEPGLAPGGE EGVEEGGPEE GVEEG-GFKEG VEGEPESSGK L
SEQ ID NO 34: LEEGEARGST AQEAGEGPKE QEL-GQRSELE GRGSPVSQEL GQRKL
SEQ ID NO 35: LEAQEAGEGK EEEGLGSPVS QEL-GQRSELE GRGSPTEGEA RGSKL
SEQ ID NO 36: LEEEEGLGSK EEEGLGSPKE EEGLG-SKEEE GLGSPKEEEG LGSKL
SEQ ID NO 37: LEELEGRGSK EEEGLGSIPE NFFGV-FYESD VMGRGHARLV HVEEPHTKL
SEQ ID NO 38: LEENFFGVTE GEARGSPTSE DLVVQ-KEEEG LGSEAIPMSI PKL
SEQ ID NO 39: LEIPMSIPKE EEGLGSIPEN FFGVTEGEAR GSPTSEDLVV QKL
SEQ ID NO 40: LELQQYEMHG PEGLRVGEAI PMSIP-IPENF FGVKEEEGLG SKL
SEQ ID NO 41: LEEEGVEEGK EEEGLGSGPA GAARG-SELEG RGSPTEGEAR GSKL
SEQ ID NO 42: LEPESSGEAI PMSIPTSEDL VVQ-IPENFFG VEAEGTGGER GVLGKL
SEQ ID NO 43: LEGGGSLLGE PEPEGEREAQ GGVEG-VELGG FKEGVEGEQE GRGKL
SEQ ID NO 44: LESQELGQRE SESEGSELEG RGS-GFKEGVE GKEEEGLSG FFGFPIGKL
SEQ ID NO 45: LEQYEMHGPK EEEGLGSSEL EGRG-SEAIPM SIPTIPENFF GVVEEPHTKL
SEQ ID NO 46: LEQYEMHGPS ELEGRGSIPE NFF-GVEAIPM SIPTSEDLVV QIVEEPHTKL
SEQ ID NO 47: LEQYEMHGPE GEGEGEGIPE NFF-GVSEDLV VQISELEGRG SVEEPHTKL
SEQ ID NO 50: LEQYEMHGPI PENFFGVSEL EGRG-SEAIPM SIPTEGEGEG EGVEEPHTKL
SEQ ID NO 51: LEQYEMHGPS ELEGRGSEAI PMSIPT-KEEE GLGSIPENFF GVVEEPHTKL
SEQ ID NO 52: LEQYEMHGPE AIPMSIPTEG EGEGE-GIPEN FFGVSEDLVV QIVEEPHTKL
SEQ ID NO 53: LEQYEMHGPS EDLVVQIEGE GEGE-GIPENF FGVEAIPMSI PTVEEPHTKL
SEQ ID NO 54: LEQYEMHGPE GEGEGEGISE DLVVQ-IPENF FGVKEEEGLG SVEEPHTKL
SEQ ID NO 55: LEQYEMHGPE GEGEGEGIPE NFF-GVSELEG RGSSEDLVVQ IVEEPHTKL
SEQ ID NO 56: LEQYEMHGPI PENFFGVEGE GEGE-SELEGR GSSEDLVVQI VEEPHTKL
SEQ ID NO 57: LEQYEMHGPS ELEGRGSIPE NFFGV-KEEEG LGSSEDLVVQ IVEEPHTKL
SEQ ID NO 58: LEQYEMHGPI PENFFGVSEL EGRGSSEDLV VQIKEEEGLG SVEEPHTKL
SEQ ID NO 59: LEQYEMHGPK EEEGLGSIPE NFF-GVSELEG RGSEGEGEGE GVEEPHTKL
SEQ ID NO 60: LEQYEMHGPS EDLVVQIKEE EGLG-SIPENF FGVSELEGRG SVEEPHTKL
SEQ ID NO 61: LEQYEMHGPS EDLVVQIEGE GEGE-GIPENF FGVKEEEGLG SVEEPHTKL
SEQ ID NO 62: LEQYEMHGPS EDLVVQIEGE GEGE-GIPENF FGVEAIPMSI PTEPHTKL
SEQ ID NO 63: LEQYEMHGPE GEGEGEGIPE NFF-GVEAIPM SIPTSELEGR GSEPHTKL
SEQ ID NO 64: LEQYEMHGPE AIPMSIPTSE LEGRG-SIPEN FFGVEGEGEG EGEPHTKL
SEQ ID NO 65: LEQYEMHGPS ELEGRGSIPE NFF-GVEGEGE GEGKEEEGLG SVEEPHTKL
SEQ ID NO 66: LEQYEMHGPI PENFFGVSED LVVQ-IEGEGE GEGEAIPMSI PTEPHTKL

---

What is claimed is:

1. A method for the treatment or prophylaxis of a chronic wound in a mammalian subject, comprising topically applying to the chronic wound an effective amount of a composition comprising a recombinant alpha-2-macroglobulin polypeptide (A2M) comprising a non-natural bait region that replaces a wild-type A2M bait region.

2. The method of claim 1, wherein activity of a protease of the mammalian subject is reduced by at least 10% at a site of topical application.

3. The method of claim 1, wherein activity of a protease of the mammalian subject is reduced at a site of topical application within an hour of the topically applying.

4. The method of claim 1, wherein proinflammatory activity of the mammalian subject is reduced by at least 10% at a site of topical application.

5. The method of claim 1, wherein the mammalian subject is a human.

6. The method of claim 1, wherein the chronic wound results from a cosmetic procedure.

7. The method of claim 1, wherein the composition is on a wound dressing.

8. The method of claim 1, wherein severity of the chronic wound is reduced, size of the chronic wound is reduced, infection of the chronic wound is reduced, bleeding of the chronic wound is reduced, or healing rate of the chronic wound is increased in the mammalian subject.

9. The method of claim 1, wherein the chronic wound is a sore or an ulcer.

10. The method of claim 9, wherein the chronic wound is an ulcer selected from the group consisting of a venous ulcer, a diabetic pressure ulcer, a stasis ulcer, a venous stasis ulcer, a diabetic foot ulcer, an arterial insufficiency ulcers, a burn ulcer, a traumatic ulcer, and combinations thereof.

11. The method of claim 9, wherein the chronic wound is a pressure sore.

12. The method of claim 1, wherein the composition is a liquid.

13. The method of claim 1, wherein the A2M is a recombinant A2M characterized by at least a 10% enhanced inhibition of a protease compared an inhibition of the protease by an equivalent amount of a wild-type A2M, wherein the non-natural bait region comprises a recognition site for a protease that is not present in a wild-type A2M.

14. The method of claim 13, wherein the non-natural bait region comprises a plurality of recognition sites for one or more proteases.

15. The method of claim 13, wherein the recombinant A2M is characterized by at least a 10% enhanced inhibition of two or more different proteases compared to an inhibition of the two or more different proteases by an equivalent amount of a wild-type A2M.

16. The method of claim 13, wherein the protease is selected from the group consisting of a serine protease, a threonine protease, a cysteine protease, an aspartate protease, a glutamic acid protease, a metalloprotease, and combinations thereof.

17. The method of claim 13, wherein the protease is selected from the group consisting of matrix metalloprotease 1 (MMP1), MMP2, MMP3, MMP7, MMP8, MMP9, MMP10, MMP11, MMP12, MMP13, MMP14, MMP15, MMP16, MMP17, MMP18, MMP19, MMP20, MMP21, MMP23A, MMP23B, MMP24, MMP25, MMP26, MMP27, MMP28; A Disintegrin and Metalloproteinase with Thrombospondin Motifs protease 1 (ADAMTS1), ADAMTS2, ADAMTS3, ADAMTS4, ADAMTS5, ADAMTS6, ADAMTS7, ADAMTS8, ADAMTS9, ADAMTS10, ADAMTS12, ADAMTS13, ADAMTS14, ADAMTS15, ADAMTS16, ADAMTS17, ADAMTS18, ADAMTS19, ADAMTS20, chymotrypsin, trypsin, elastase, a compliment factor; a clotting factor, thrombin, plasmin, subtilisin, neprilysin, thermolysin, Pregnancy-associated plasma protein A; Bone morphogenetic protein 1, lysostaphin, insulin degrading enzyme, ZMPSTE24, acetylcholinesterase, and combinations thereof.

18. The method of claim 1, wherein the composition does not elicit an immune response by the mammalian subject when topically applied to the chronic wound.

19. A wound dressing comprising an effective amount of a composition for the treatment or prophylaxis of a chronic wound in a mammalian subject, wherein the composition comprises a recombinant alpha-2-macroglobulin polypeptide (A2M) comprising a non-natural bait region that replaces a wild-type A2M bait region.

* * * * *

SEQUENCE LISTING

```
<160> NUMBER OF SEQ ID NOS: 76

<210> SEQ ID NO 1
<211> LENGTH: 8993
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
ctcatgacca aaatccctta acgtgagtta cgcgcgcgtc gttccactga gcgtcagacc        60
ccgtagaaaa gatcaaagga tcttcttgag atccttttttt tctgcgcgta atctgctgct      120
tgcaaacaaa aaaaccaccg ctaccagcgg tggtttgttt gccggatcaa gagctaccaa      180 ctcttttttcc gaaggtaact ggcttcagca gagcgcagat accaaatact gttcttctag      240
tgtagccgta gttagcccac cacttcaaga actctgtagc accgcctaca tacctcgctc      300
tgctaatcct gttaccagtg ctgctgcca gtggcgataa gtcgtgtctt accgggttgg        360
actcaagacg atagttaccg gataaggcgc agcggtcggg ctgaacgggg ggttcgtgca      420
cacagcccag cttggagcga acgacctaca ccgaactgag atacctacag cgtgagctat      480
gagaaagcgc cacgcttccc gaaggagaa aggcggacag gtatccggta agcggcaggg        540
tcggaacagg agagcgcacg agggagcttc caggggggaaa cgcctggtat ctttatagtc    600
ctgtcgggtt tcgccacctc tgacttgagc gtcgatttttt gtgatgctcg tcagggggc      660 ggagcctatg gaaaaacgcc agcaacgcgg cctttttacg gttcctggcc ttttgctggc      720
```

```
cttttgctca catgttctttt cctgcgttat ccctgattc tgtggataac cgtattaccg    780
cctttgagtg agctgatacc gctcgccgca gccgaacgac cgagcgcagc gagtcagtga    840
gcgaggaagc ggaaggcgag agtagggaac tgccaggcat caaactaagc agaaggcccc    900
tgacggatgg ccttttttgcg tttctacaaa ctctttctgt gttgtaaaac gacgccagt    960
cttaagctcg ggcccctgg gcggttctga taacgagtaa tcgttaatcc gcaaataacg   1020
taaaaacccg cttcggcggg ttttttttatg ggggagttt agggaaagag catttgtcag   1080
aatatttaag ggcgcctgtc actttgcttg atatatgaga attatttaac cttataaatg   1140
agaaaaaagc aacgcacttt aaataagata cgttgctttt tcgattgatg aacacctata   1200
attaaactat tcatctatta tttatgattt tttgtatata caatatttct agtttgttaa   1260
agagaattaa gaaataaat ctcgaaaata taaagggaa aatcagtttt tgatatcaaa   1320
attatacatg tcaacgataa tacaaaatat aatacaaact ataagatgtt atcagtattt   1380
attatcattt agaataaatt ttgtgtcgcc cttaattgtg agcggataac aattacgagc   1440
ttcatgcaca gtggcgttga cattgattat tgactagtta ttaatagtaa tcaattacgg   1500
ggtcattagt tcatagccca tatatggagt tccgcgttac ataacttacg gtaaatggcc   1560
cgcctggctg accgcccaac gacccccgcc cattgacgtc aataatgacg tatgttccca   1620
tagtaacgcc aatagggact ttccattgac gtcaatgggt ggagtattta cggtaaactg   1680
cccacttggc agtacatcaa gtgtatcata tgccaagtac gccccctatt gacgtcaatg   1740
acggtaaatg gcccgcctgg cattatgccc agtacatgac cttatgggac tttcctactt   1800
ggcagtacat ctacgtatta gtcatcgcta ttaccatggt gatgcggttt tggcagtaca   1860
tcaatgggcg tggatagcgg tttgactcac ggggatttcc aagtctccac cccattgacg   1920
tcaatgggag tttgttttgg caccaaaatc aacgggactt tccaaaatgt cgtaacaact   1980
ccgccccatt gacgcaaatg ggcggtaggc gtgtacggtg ggaggtctat ataagcagag   2040
ctctctggct aactagagaa cccactgctt actggcttat cgaaattaat acgactcact   2100
atagggtac ctgccaccat ggggaaaaac aaactgctgc atccaagcct ggtcctgctg   2160
ctgctggttc tgctgcctac tgacgcctct gtgagcggaa agccccagta tatggttctg   2220
gtcccgtccc tgctgcacac cgagaccaca gaaaagggt gcgtgctgct gtcttacctg   2280
aatgaaacag tgactgttag tgcctcactg gagagtgtgc gcggaaatcg ttcactgttc   2340
accgatctgg aggcggaaaa cgatgtgctg cattgcgtcg catttgctgt gccaaaaagc   2400
tcctctaatg aagaagtgat gttcctgacc gtccaggtga agggccctac acaggaattc   2460
aaaaaacgca ctaccgttat ggtcaaaaac gaggatagcc tggtgtttgt tcagacagac   2520
aaatccatct ataagcctgg tcagactgtg aagttccggg tggttagcat ggatgaaaat   2580
tttcacccccc tgaacgagct gattccactg gtgtacatcc aggaccctaa aggcaaccgc   2640
atcgcccagt ggcagtcttt ccagctggaa ggcggtctga agcagtttag tttccctctg   2700
agttcagagc cgtttcaggg ttcttataaa gtcgtggttc agaaaaagag tgggggacgt   2760
actgaacatc cttttaccgt tgaagagttc gtcctgccga aatttgaggt ccaggtgacc   2820
gttcccaaga ttatcacaat tctggaagag gaaatgaacg tgagcgtgtg cggactgtat   2880
acctacggca aaccagtgcc tggtcacgtt acagtcagta tctgccgtaa gtactcagat   2940
gcaagcgact gtcatggcga agattcacag gcttttttgcg agaagttcag cggccagctg   3000
aactcccacg gttgcttcta tcagcaggtg aaaaccaagg ttttttcagct gaaacgaag   3060
gagtacgaaa tgaaactgca tacagaagcc cagattcagg aagaaggcac cgtcgtggaa   3120
```

```
ctgactggtc gtcagagctc cgagattacc cggacaatca ctaaactgag cttcgtgaag    3180
gttgattccc actttcggca ggggattccc tttttcggac aggtgcgcct ggttgacggg    3240
aaaggagttc cgatcccaa  caaagtgatc tttattcgcg gcaatgaagc caactattac    3300
agcaacgcga caactgatga gcatgggctg gtgcagttca gtatcaatac acaaacgtg    3360
atgggaacct cactgacagt ccgcgtgaat tataaagacc gttcaccgtg ttatggctac    3420
cagtgggtga gcgaggaaca cgaggaagcc caccataccg cgtacctggt tttcagcccc    3480
tccaaatctt ttgtccatct ggaacctatg tctcacgagc tgccgtgcgg ccatacccag    3540
acagtgcagg cacattatat tctgaacggc ggcaccctgc tgggtctgaa aaagctgagc    3600
ttttattacc tgattatggc taagggggga atcgtccgca ctggcaccca cggtctgctg    3660
gttaaacagg aagatatgaa gggccatttc agtatttcaa tccctgttaa aagcgacatt    3720
gctccggtcg cccgtctgct gatctatgcc gtgctgccaa ccggcgatgt tatcggtgac    3780
tccgccaaat acgatgtgga gaattgtctg gcgaacaagg ttgacctgag cttttccccc    3840
tctcagagtc tgccagcgtc tcatgcacat ctgcgtgtga ccgcagcccc tcagagcgtt    3900
tgcgctctgc gtgcagtgga tcagtccgtg ctgctgatga agccagacgc agaactgtct    3960
gctagcagcg tgtataatct gctgcctgag aaagatctga ccgggttccc aggacctctg    4020
aacgatcagg atgacgaaga ctgtattaat cgccacaacg tgtatattaa tgggatcaca    4080
tacactccgg tttcaagcac caacgaaaaa gatatgtaca gcttcctgga ggacatgggt    4140
ctgaaagcgt ttaccaattc caagatccgg aaacccaaga tgtgcccaca gctgcagcag    4200
tatgaaatgc acggacctga gggtctgcgt gtgggctttt acgaatctga tgtgatggga    4260
cgtggtcatg cacgtctggt tcatgtcgag gaaccacaca ccgaaacagt gcgtaaatac    4320
ttccctgaga cctggatttg gaacctggtt gtggtgaact ccgcgggtgt ggcagaagtg    4380
ggtgttaccg tcccggatac tattaccgaa tggaaagcag gtgccttctg tctgtctgag    4440
gatgcagggc tgggaatctc ctctacagcc tctctgcgcg cgtttcagcc cttttccgtc    4500
gaactgacta tgccatatag cgtgattcgt ggcgaggcat tcactctgaa agctaccgtg    4560
ctgaattacc tgcccaagtg catccgcgtg agcgtgcagc tggaagctag tcccgccttt    4620
ctggcggtcc cagtggagaa ggaacaggca ccgcactgca tttgtgctaa cggccggcag    4680
actgttttcct gggccgtcac ccccaaatct ctgggtaatg tgaacttcac cgtttcagca    4740
gaggctctgg aaagccagga gctgtgcggc accgaagtcc catccgtgcc tgagcatggt    4800
cgcaaagata cagtcatcaa gcctctgctg gttgaaccgg aaggcctgga gaaggaaact    4860
acctttaatt ctctgctgtg cccaagtggc ggtgaagtgt ccgaggaact gtctctgaaa    4920
ctgccgccca acgtggtcga ggaatctgcc cgtgcgtcag ttagcgtcct gggggatatt    4980
ctgggaagtg ccatgcagaa tacccagaac ctgctgcaga tgccgtatgg ctgtggcgag    5040
cagaatatgt tctgtttgc  gcccaacatc tatgtcctgg attacctgaa tgaaacacag    5100
cagctgactc ctgaaatcaa aagcaaggca atcgggtatc tgaataccgg ataccagcgg    5160
cagctgaact ataagcacta cgacggctcc tattctacct tcggcgaacg gtacggtcgc    5220
aatcagggga cacttggct  gaccgccttt gtgctgaaaa cctttgccca ggctcgcgcc    5280
tatatcttta ttgatgaggc ccatattaca caggcgctga tctggctgtc acagcgccag    5340
aaggacaacg ggtgtttccg tagttcagga agcctgctga caatgccat  caaaggcggc    5400
gtcgaggatg aagtgacact gagcgcatac attactatcg ctctgctgga aatccctctg    5460
```

```
acagtgactc acccggtggt tcgcaatgct ctgttttgcc tggaaagtgc atggaaaaca    5520
gctcaggaag gcgatcacgg atcacacgtg tatactaagg cactgctggc gtacgcattc    5580
gctctggccg gcaaccagga taaacgtaaa gaagtgctga atcactgaa tgaggaagca     5640
gttaaaaagg acaacagcgt ccactgggaa cggccgcaga acccaaggc tccagtgggt     5700
cacttttatg agcctcaggc accgagtgct gaggtggaaa tgacctcata tgttctgctg    5760
gcatacctga ccgcacagcc tgccccaca tcagaagatc tgacaagcgc cactaatatt     5820
gtgaaatgga tcaccaagca gcagaacgcg cagggcggtt ttagctccac ccaggacaca    5880
gtcgtggcac tgcacgctct gtctaaatat ggggcagcta ccttcacacg cactggaaag   5940
gccgcgcaag tgactattca gtctagtggc accttttcaa gcaagttcca ggtggataac    6000
aataaccgtc tgctgctgca gcaggtgtcc ctgcccgaac tgccaggcga gtactctatg    6060
aaagtcactg gggaaggatg cgtgtatctg cagacctccc tgaaatacaa tattctgccc    6120
gagaaagaag aatttccatt cgcactgggc gtgcagaccc tgcctcagac atgcgatgaa    6180
ccgaaggctc atacttcttt tcagatcagt ctgtcagtga gctataccgg gtcccgctct    6240
gccagtaaca tggcgattgt ggatgtgaaa atggtgagtg gattcatccc tctgaaaccg    6300
actgtgaaga tgctggaacg gagtaatcac gtttcacgca ccgaggtctc ctctaaccat    6360
gtgctgatct acctggataa agtgtccaat cagacactgt ctctgttttt cactgtgctg    6420
caggatgtcc ccgtgcgtga cctgaaacca gccattgtta aggtctatga ttattacgaa    6480
accgacgagt tcgcgatcgc agaatacaac gcgccgtgca gcaaagacct ggggaatgct    6540
gactacaagg acgacgacga caagggggca agccaccacc atcaccatca ctaaggatcc    6600
aaaatcagcc tcgactgtgc cttctagttg ccagccatct gttgtttgcc cctccccgt     6660
gccttccttg accctggaag gtgccactcc cactgtcctt tcctaataaa atgaggaaat   6720
tgcatcacaa cactcaaccc tatctcggtc tattcttttg atttataagg gattttgccg    6780
atttcggcct attggttaaa aaatgagctg atttaacaaa aatttaacgc gaattaattc    6840
tgtggaatgt gtgtcagtta gggtgtggaa agtccccagg ctccccagca ggcagaagta    6900
tgcaaagcat gcatctcaat tagtcagcaa ccaggtgtgg aaagtcccca ggctccccag    6960
caggcagaag tatgcaaagc atgcatctca attagtcagc aaccatagtc ccgcccctaa    7020
ctccgcccat cccgccccta actccgccca gttccgccca ttctccgccc catggctgac    7080
taatttttt tatttatgca gaggccgagg ccgcctctgc ctctgagcta ttccagaagt      7140
agtgaggagg cttttttgga ggcctaggct tttgcaaaaa gctcccggga gcttgtatat    7200
ccatttcgg atctgatcag cacgtgttga caattaatca tcggcatagt atatcggcat     7260
agtataatac gacaaggtga ggaactaaac catggccaag cctttgtctc aagaagaatc    7320
caccctcatt gaaagagcaa cggctacaat caacagcatc cccatctctg aagactacag    7380
cgtcgccagc gcagctctct ctagcgacgg ccgcatcttc actggtgtca atgtatatca    7440
ttttactggg ggaccttgtg cagaactcgt ggtgctgggc actgctgctg ctgcggcagc    7500
tggcaacctg acttgtatcg tcgcgatcgg aaatgagaac aggggcatct tgagcccctg    7560
cggacggtgc cgacaggtgc ttctcgatct gcatcctggg atcaaagcca tagtgaagga    7620
cagtgatgga cagccgacgg cagttgggat tcgtgaattg ctgccctctg gttatgtgtg    7680
ggagggctaa cacgtgctac gagatttcga ttccaccgcc gccttctatg aaaggttggg    7740
cttcggaatc gttttccggg acgccggctg gatgatcctc cagcgcgggg atctcatgct    7800
ggagttcttc gcccaccccca acttgtttat tgcagcttat aatggttaca aataaagcaa    7860
```

```
tagcatcaca aatttcacaa ataaagcatt tttttcactg cattctagtt gtggtttgtc    7920
caaactcatc aatgtatctt atcatgtctg tataccgtcg acctctagct agagcttggc    7980
gtaatcatgg tcattaccaa tgcttaatca gtgaggcacc tatctcagcg atctgtctat    8040
ttcgttcatc catagttgcc tgactccccg tcgtgtagat aactacgata cgggagggct    8100
taccatctgg ccccagcgct gcgatgatac cgcgagaacc acgctcaccg gctccggatt    8160
tatcagcaat aaaccagcca gccggaaggg ccgagcgcag aagtggtcct gcaactttat    8220
ccgcctccat ccagtctatt aattgttgcc gggaagctag agtaagtagt tcgccagtta    8280
atagtttgcg caacgttgtt gccatcgcta caggcatcgt ggtgtcacgc tcgtcgtttg    8340
gtatggcttc attcagctcc ggttcccaac gatcaaggcg agttacatga tcccccatgt    8400
tgtgcaaaaa agcggttagc tccttcggtc ctccgatcgt tgtcagaagt aagttggccg    8460
cagtgttatc actcatggtt atggcagcac tgcataattc tcttactgtc atgccatccg    8520
taagatgctt ttctgtgact ggtgagtact caaccaagtc attctgagaa tagtgtatgc    8580
ggcgaccgag ttgctcttgc ccggcgtcaa tacgggataa taccgcgcca catagcagaa    8640
ctttaaaagt gctcatcatt ggaaaacgtt cttcggggcg aaaactctca aggatcttac    8700
cgctgttgag atccagttcg atgtaaccca ctcgtgcacc caactgatct tcagcatctt    8760
ttactttcac cagcgtttct gggtgagcaa aaacaggaag gcaaaatgcc gcaaaaaagg    8820
gaataagggc gacacggaaa tgttgaatac tcatattctt cctttttcaa tattattgaa    8880
gcatttatca gggttattgt ctcatgagcg gatacatatt tgaatgtatt tagaaaaata    8940
aacaaatagg ggtcagtgtt acaaccaatt aaccaattct gaacattatc gcg           8993

<210> SEQ ID NO 2
<211> LENGTH: 8994
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
ctcatgacca aaatccctta acgtgagtta cgcgcgcgtc gttccactga gcgtcagacc      60
ccgtagaaaa gatcaaagga tcttcttgag atccttttt tctgcgcgta atctgctgct     120
tgcaaacaaa aaaaccaccg ctaccagcgg tggtttgttt gccggatcaa gagctaccaa     180
ctctttttcc gaaggtaact ggcttcagca gagcgcagat accaaatact gttcttctag     240
tgtagccgta gttagcccac cacttcaaga actctgtagc accgcctaca tacctcgctc     300
tgctaatcct gttaccagtg gctgctgcca gtggcgataa gtcgtgtctt accgggttgg     360
actcaagacg atagttaccg gataaggcgc agcggtcggg ctgaacgggg ggttcgtgca     420
cacagcccag cttggagcga acgacctaca ccgaactgag atacctacag cgtgagctat     480
gagaaagcgc cacgcttccc gaagggagaa aggcggacag gtatccggta agcggcaggg     540
tcggaacagg agagcgcacg agggagcttc caggggggaa acgcctggtat ctttatagtc     600 ctgtcgggtt tcgccacctc tgacttgagc gtcgatttt tgtgatgctcg tcagggggggc     660 ggagcctatg gaaaaacgcc agcaacgcgg ccttttttacg gttcctggcc ttttgctggc     720
cttttgctca catgttcttt cctgcgttat cccctgattc tgtggataac cgtattaccg     780
cctttgagtg agctgatacc gctcgccgca gccgaacgac cgagcgcagc gagtcagtga     840
gcgaggaagc ggaaggcgag agtagggaac tgccaggcat caaactaagc agaaggcccc     900
```

```
tgacggatgg cctttttgcg tttctacaaa ctctttctgt gttgtaaaac gacggccagt    960
cttaagctcg ggcccctgg gcggttctga taacgagtaa tcgttaatcc gcaaataacg   1020
taaaaacccg cttcggcggg ttttttatg ggggagttt agggaaagag catttgtcag   1080
aatatttaag ggcgcctgtc actttgcttg atatatgaga attatttaac cttataaatg   1140 agaaaaagc aacgcacttt aaataagata cgttgctttt tcgattgatg aacacctata   1200
attaaactat tcatctatta tttatgattt tttgtatata caatatttct agtttgttaa   1260
agagaattaa gaaataaat ctcgaaaata ataaagggaa aatcagtttt tgatatcaaa   1320
attatacatg tcaacgataa tacaaaatat aatacaaact ataagatgtt atcagtattt   1380
attatcattt agaataaatt ttgtgtcgcc cttaattgtg agcggataac aattacgagc   1440
ttcatgcaca gtggcgttga cattgattat tgactagtta ttaatagtaa tcaattacgg   1500
ggtcattagt tcatagccca tatatggagt tccgcgttac ataacttacg gtaaatggcc   1560
cgcctggctg accgcccaac gaccccgcc cattgacgtc aataatgacg tatgttccca   1620
tagtaacgcc aatagggact ttccattgac gtcaatgggt ggagtattta cggtaaactg   1680
cccacttggc agtacatcaa gtgtatcata tgccaagtac gccccctatt gacgtcaatg   1740
acggtaaatg gcccgcctgg cattatgccc agtacatgac cttatgggac tttcctactt   1800
ggcagtacat ctacgtatta gtcatcgcta ttaccatggt gatgcggttt tggcagtaca   1860
tcaatgggcg tggatagcgg tttgactcac ggggatttcc aagtctccac cccattgacg   1920
tcaatgggag tttgttttgg caccaaaatc aacgggactt tccaaaatgt cgtaacaact   1980 ccgcccatt gacgcaaatg gcggtaggc gtgtacggtg ggaggtctat ataagcagag   2040
ctctctggct aactagagaa cccactgctt actggcttat cgaaattaat acgactcact   2100 atagggtac ctgccaccat ggggaaaaac aaactgctgc atccaagcct ggtcctgctg   2160
ctgctggttc tgctgcctac tgacgcctct gtgagcggaa agccccagta tatggttctg   2220
gtcccgtccc tgctgcacac cgagaccaca gaaaagggt gcgtgctgct gtcttacctg   2280
aatgaaacag tgactgttag tgcctcactg gagagtgtgc gcggaaatcg ttcactgttc   2340
accgatctgg aggcggaaaa cgatgtgctg cattgcgtcg catttgctgt gccaaaaagc   2400
tcctctaatg aagaagtgat gttcctgacc gtccaggtga agggccctac acaggaattc   2460
aaaaaacgca ctaccgttat ggtcaaaaac gaggatagcc tggtgtttgt tcagacagac   2520
aaatccatct ataagcctgg tcagactgtg aagttccggg tggttagcat ggatgaaaat   2580
tttcaccccc tgaacgagct gattccactg gtgtacatcc aggaccctaa aggcaaccgc   2640
atcgcccagt ggcagtcttt ccagctggaa ggcggtctga agcagtttag ttccctctg   2700 agttcagagc cgtttcaggg ttcttataaa gtcgtggttc agaaaaagag tggggacgt   2760 actgaacatc ctttttaccgt tgaagagttc gtcctgccga aatttgaggt ccaggtgacc   2820
gttcccaaga ttatcacaat tctggaagag gaaatgaacg tgagcgtgtg cggactgtat   2880
acctacggca aaccagtgcc tggtcacgtt acagtcagta tctgccgtaa gtactcagat   2940
gcaagcgact gtcatggcga agattccacag gctttttgcg agaagttcag cggccagctg   3000
aactcccacg gttgcttcta tcagcaggtg aaaaccaagg tttttcagct gaaacggaag   3060
gagtacgaaa tgaaactgca tacagaagcc cagattcagg aagaggcac cgtcgtggaa   3120 ctgactggtc gtcagagctc cgagattacc cggacaatca ctaaactgag cttcgtgaag   3180
gttgattccc actttcggca ggggattccc tttttcggac aggtgcgcct ggttgacggg   3240
```

-continued

```
aaaggagttc cgatccccaa caaagtgatc tttattcgcg gcaatgaagc caactattac    3300
agcaacgcga caactgatga gcatgggctg gtgcagttca gtatcaatac cacaaacgtg    3360
atgggaacct cactgacagt ccgcgtgaat tataaagacc gttcaccgtg ttatggctac    3420
cagtgggtga gcgaggaaca cgaggaagcc caccataccg cgtacctggt tttcagcccc    3480
tccaaatctt ttgtccatct ggaacctatg tctcacgagc tgccgtgcgg ccatacccag    3540
acagtgcagg cacattatat tctgaacggc ggcaccctgc tgggtctgaa aaagctgagc    3600
ttttattacc tgattatggc taagggggga atcgtccgca ctggcaccca cggtctgctg    3660
gttaaacagg aagatatgaa gggccatttc agtatttcaa tccctgttaa aagcgacatt    3720
gctccggtcg cccgtctgct gatctatgcc gtgctgccaa ccggcgatgt tatcggtgac    3780
tccgccaaat acgatgtgga gaattgtctg gcgaacaagg ttgacctgag cttttccccc    3840
tctcagagtc tgccagcgtc tcatgcacat ctgcgtgtga ccgcagcccc tcagagcgtt    3900
tgcgctctgc gtgcagtgga tcagtccgtc ctgctgatga agccagacgc agaactgtct    3960
gctagcagcg tgtataatct gctgcctgag aaagatctga ccgggttccc aggacctctg    4020
aacgatcagg atgacgaaga ctgtattaat cgccacaacg tgtatattaa tgggatcaca    4080
tacactccgg tttcaagcac caacgaaaaa gatatgtaca gcttcctgga ggacatgggt    4140
ctgaaagcgt ttaccaattc caagatccgg aaaccccaag atgtgcccac agctcgagca    4200
gtatgaaatg cacggacctg agggtctgcg tgtgggcttt tacgaatctg atgtgatggg    4260
acgtggtcat gcacgtctgg ttcatgtcga ggaaccacac accgaaaagc ttcgtaaata    4320
cttccctgag acctggattt gggacctggt tgtggtgaac ccgcgggtg tggcagaagt    4380 gggtgttacc gtcccggata ctattaccga atggaaagca ggtgccttct gtctgtctga    4440
ggatgcaggc ctgggaatct cctctacagc ctctctgcgc gcgtttcagc ccttttttcgt    4500 cgaactgact atgccatata gcgtgattcg tggcgaggca ttcactctga aagctaccgt    4560
gctgaattac ctgcccaagt gcatccgcgt gagcgtgcag ctggaagcta gtcccgcctt    4620
tctggcggtc ccagtggaga aggaacaggc accgcactgc atttgtgcta acggccggca    4680 gactgttttcc tgggccgtca cccccaaatc tctgggtaat gtgaacttca ccgtttcagc    4740
agaggctctg gaaagccagg agctgtgcgg caccgaagtc ccatccgtgc ctgagcatgg    4800
tcgcaaagat acagtcatca agcctctgct ggttgaaccg gaaggcctgg agaaggaaac    4860
tacctttaat tctctgctgt gcccaagtgg cggtgaagtg tccgaggaac tgtctctgaa    4920
actgccgccc aacgtggtcg aggaatctgc ccgtgcgtca gttagcgtcc tgggggatat    4980
tctgggaagt gccatgcaga ataccccagaa cctgctgcag atgccgtatg ctgtggcga    5040 gcagaatatg gttctgtttg cgcccaacat ctatgtcctg gattacctga atgaaacaca    5100
gcagctgact cctgaaatca aaagcaaggc aatcgggtat ctgaataccg gataccagcg    5160
gcagctgaac tataagcact acgacggctc ctattctacc ttcggcgaac ggtacggtcg    5220
caatcagggg aacacttggc tgaccgcctt tgtgctgaaa acctttgccc aggctcgcgc    5280
ctatatcttt attgatgagg cccatattac acaggcgctg atctggctgt cacagcgcca    5340
gaaggacaac gggtgtttcc gtagttcagg aagcctgctg aacaatgcca tcaaaggcgg    5400
cgtcgaggat gaagtgacac tgagcgcata cattactatc gctctgctgg aaatccctct    5460
gacagtgact cacccggtgg ttcgcaatgc tctgttttgc ctggaaagtg catggaaaac    5520
agctcaggaa ggcgatcacg gatcacacgt gtatactaag gcactgctgg cgtacgcatt    5580
cgctctggcc ggcaaccagg ataaacgtaa agaagtgctg aaatcactga atgaggaagc    5640
```

```
agttaaaaag gacaacagcg tccactggga acggccgcag aaacccaagg ctccagtggg    5700
tcacttttat gagcctcagg caccgagtgc tgaggtggaa atgacctcat atgttctgct    5760
ggcatacctg accgcacagc ctgccccac atcagaagat ctgacaagcg ccactaatat     5820
tgtgaaatgg atcaccaagc agcagaacgc gcagggcggt tttagctcca cccaggacac    5880
agtcgtggca ctgcacgctc tgtctaaata tggggcagct accttcacac gcactggaaa    5940
ggccgcgcaa gtgactattc agtctagtgg caccttttca gcaagttcc aggtggataa     6000 caataaccgt ctgctgctgc agcaggtgtc cctgcccgaa ctgccaggcg agtactctat    6060
gaaagtcact ggggaaggat gcgtgtatct gcagacctcc ctgaaataca atattctgcc    6120
cgagaaagaa gaatttccat tcgcactggg cgtgcagacc ctgcctcaga catgcgatga    6180
accgaaggct catacttctt ttcagatcag tctgtcagtg agctataccg ggtcccgctc    6240
tgccagtaac atggcgattg tggatgtgaa aatggtgagt ggattcatcc ctctgaaacc    6300
gactgtgaag atgctggaac ggagtaatca cgtttcacgc accgaggtct cctctaacca    6360
tgtgctgatc tacctggata agtgtccaa tcagacactg tctctgtttt tcactgtgct     6420
gcaggatgtc cccgtgcgtg acctgaaacc agccattgtt aaggtctatg attattacga    6480
aaccgacgag ttcgcgatcg cagaatacaa cgcgccgtgc agcaaagacc tggggaatgc    6540
tgactacaag gacgacgacg acaagggggc aagccaccac catcaccatc actaaggatc    6600
caaaatcagc ctcgactgtg ccttctagtt gccagccatc tgttgtttgc cctcccccg     6660 tgccttcctt gaccctggaa ggtgccactc ccactgtcct ttcctaataa aatgaggaaa    6720
ttgcatcaca acactcaacc ctatctcggt ctattctttt gatttataag ggattttgcc    6780
gatttcggcc tattggttaa aaaatgagct gatttaacaa aaatttaacg cgaattaatt    6840
ctgtggaatg tgtgtcagtt agggtgtgga agtcccccag gctccccagc aggcagaagt    6900
atgcaaagca tgcatctcaa ttagtcagca accaggtgtg gaaagtcccc aggctcccca    6960
gcaggcagaa gtatgcaaag catgcatctc aattagtcag caaccatagt cccgccccta    7020
actccgccca tcccgcccct aactccgccc agttccgccc attctccgcc ccatggctga    7080
ctaatttttt ttatttatgc agaggccgag gccgcctctg cctctgagct attccagaag    7140
tagtgaggag gcttttttgg aggcctaggc ttttgcaaaa agctcccggg agcttgtata    7200
tccattttcg gatctgatca gcacgtgttg acaattaatc atcggcatag tatatcggca    7260
tagtataata cgacaaggtg aggaactaaa ccatggccaa gcctttgtct caagaagaat    7320
ccaccctcat tgaaagagca acggctacaa tcaacagcat ccccatctct gaagactaca    7380
gcgtcgccag cgcagctctc tctagcgacg ccgcatctt cactggtgtc aatgtatatc     7440
attttactgg gggaccttgt gcagaactcg tggtgctggg cactgctgct gctgcggcag    7500
ctggcaacct gacttgtatc gtcgcgatcg gaaatgagaa caggggcatc ttgagcccct    7560
gcggacggtg ccgacaggtg cttctcgatc tgcatcctgg gatcaaagcc atagtgaagg    7620
acagtgatgg acagccgacg gcagttggga ttcgtgaatt gctgccctct ggttatgtgt    7680
gggagggcta acacgtgcta cgagatttcg attccaccgc cgccttctat gaaaggttgg    7740
gcttcggaat cgttttccgg gacgccggct ggatgatcct ccagcgcggg gatctcatgc    7800
tggagttctt cgcccacccc aacttgttta ttgcagctta taatggttac aaataaagca    7860
atagcatcac aaatttcaca aataaagcat ttttttcact gcattctagt tgtggtttgt    7920
ccaaactcat caatgtatct tatcatgtct gtataccgtc gacctctagc tagagcttgg    7980
```

-continued

| | |
|---|---|
| cgtaatcatg gtcattacca atgcttaatc agtgaggcac ctatctcagc gatctgtcta | 8040 |
| tttcgttcat ccatagttgc ctgactcccc gtcgtgtaga taactacgat acgggagggc | 8100 |
| ttaccatctg gccccagcgc tgcgatgata ccgcgagaac cacgctcacc ggctccggat | 8160 |
| ttatcagcaa taaccagcc agccggaagg gccgagcgca gaagtggtcc tgcaacttta | 8220 |
| tccgcctcca tccagtctat taattgttgc cgggaagcta gagtaagtag ttcgccagtt | 8280 |
| aatagtttgc gcaacgttgt tgccatcgct acaggcatcg tggtgtcacg ctcgtcgttt | 8340 |
| ggtatggctt cattcagctc cggttcccaa cgatcaaggc gagttacatg atcccccatg | 8400 |
| ttgtgcaaaa aagcggttag ctccttcggt cctccgatcg ttgtcagaag taagttggcc | 8460 |
| gcagtgttat cactcatggt tatggcagca ctgcataatt ctcttactgt catgccatcc | 8520 |
| gtaagatgct tttctgtgac tggtgagtac tcaaccaagt cattctgaga atagtgtatg | 8580 |
| cggcgaccga gttgctcttg cccggcgtca atacgggata taccgcgcc acatagcaga | 8640 |
| actttaaaag tgctcatcat tggaaaacgt tcttcggggc gaaaactctc aaggatctta | 8700 |
| ccgctgttga gatccagttc gatgtaaccc actcgtgcac ccaactgatc ttcagcatct | 8760 |
| tttactttca ccagcgtttc tgggtgagca aaaacaggaa ggcaaaatgc cgcaaaaaag | 8820 |
| ggaataaggg cgacacggaa atgttgaata ctcatattct cctttttca atattattga | 8880 |
| agcatttatc agggttattg tctcatgagc ggatacatat ttgaatgtat ttagaaaaat | 8940 |
| aaacaaatag gggtcagtgt tacaaccaat taaccaattc tgaacattat cgcg | 8994 |

<210> SEQ ID NO 3
<211> LENGTH: 1491
<212> TYPE: PRT
<213> ORGANISM: Homo sapiens
<220> FEATURE:
<223> OTHER INFORMATION: Tagged wild-type human A2M polypeptide

<400> SEQUENCE: 3

Met Gly Lys Asn Lys Leu Leu His Pro Ser Leu Val Leu Leu Leu
1               5                   10                  15

Val Leu Leu Pro Thr Asp Ala Ser Val Ser Gly Lys Pro Gln Tyr Met
            20                  25                  30

Val Leu Val Pro Ser Leu Leu His Thr Glu Thr Thr Glu Lys Gly Cys
        35                  40                  45

Val Leu Leu Ser Tyr Leu Asn Glu Thr Val Thr Val Ser Ala Ser Leu
    50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu
        115                 120                 125

Val Phe Val Gln Thr Asp Lys Ser Ile Tyr Lys Pro Gly Gln Thr Val
    130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

```
Pro Leu Ser Ser Glu Pro Phe Gln Gly Ser Tyr Lys Val Val Gln
        195                 200                 205

Lys Lys Ser Gly Gly Arg Thr Glu His Pro Phe Thr Val Glu Glu Phe
210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                245                 250                 255

Gly Lys Pro Val Pro Gly His Val Thr Val Ser Ile Cys Arg Lys Tyr
                260                 265                 270

Ser Asp Ala Ser Asp Cys His Gly Glu Asp Ser Gln Ala Phe Cys Glu
                275                 280                 285

Lys Phe Ser Gly Gln Leu Asn Ser His Gly Cys Phe Tyr Gln Gln Val
        290                 295                 300

Lys Thr Lys Val Phe Gln Leu Lys Arg Lys Glu Tyr Glu Met Lys Leu
305                 310                 315                 320

His Thr Glu Ala Gln Ile Gln Glu Gly Thr Val Val Glu Leu Thr
                325                 330                 335

Gly Arg Gln Ser Ser Glu Ile Thr Arg Thr Ile Thr Lys Leu Ser Phe
                340                 345                 350

Val Lys Val Asp Ser His Phe Arg Gln Gly Ile Pro Phe Phe Gly Gln
        355                 360                 365

Val Arg Leu Val Asp Gly Lys Gly Val Pro Ile Pro Asn Lys Val Ile
        370                 375                 380

Phe Ile Arg Gly Asn Glu Ala Asn Tyr Tyr Ser Asn Ala Thr Thr Asp
385                 390                 395                 400

Glu His Gly Leu Val Gln Phe Ser Ile Asn Thr Thr Asn Val Met Gly
                405                 410                 415

Thr Ser Leu Thr Val Arg Val Asn Tyr Lys Asp Arg Ser Pro Cys Tyr
                420                 425                 430

Gly Tyr Gln Trp Val Ser Glu Glu His Glu Glu Ala His His Thr Ala
        435                 440                 445

Tyr Leu Val Phe Ser Pro Ser Lys Ser Phe Val His Leu Glu Pro Met
450                 455                 460

Ser His Glu Leu Pro Cys Gly His Thr Gln Thr Val Gln Ala His Tyr
465                 470                 475                 480

Ile Leu Asn Gly Gly Thr Leu Leu Gly Leu Lys Lys Leu Ser Phe Tyr
                485                 490                 495

Tyr Leu Ile Met Ala Lys Gly Gly Ile Val Arg Thr Gly Thr His Gly
                500                 505                 510

Leu Leu Val Lys Gln Glu Asp Met Lys Gly His Phe Ser Ile Ser Ile
        515                 520                 525

Pro Val Lys Ser Asp Ile Ala Pro Val Ala Arg Leu Leu Ile Tyr Ala
        530                 535                 540

Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
                565                 570                 575

Ser Leu Pro Ala Ser His Ala His Leu Arg Val Thr Ala Ala Pro Gln
                580                 585                 590

Ser Val Cys Ala Leu Arg Ala Val Asp Gln Ser Val Leu Leu Met Lys
                595                 600                 605
```

```
Pro Asp Ala Glu Leu Ser Ala Ser Val Tyr Asn Leu Leu Pro Glu
    610                 615                 620

Lys Asp Leu Thr Gly Phe Pro Gly Pro Leu Asn Asp Gln Asp Glu
625                 630                 635                 640

Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
                660                 665                 670

Met Gly Leu Lys Ala Phe Thr Asn Ser Lys Ile Arg Lys Pro Lys Met
        675                 680                 685

Cys Pro Gln Leu Gln Gln Tyr Glu Met His Gly Pro Glu Gly Leu Arg
    690                 695                 700

Val Gly Phe Tyr Glu Ser Asp Val Met Gly Arg Gly His Ala Arg Leu
705                 710                 715                 720

Val His Val Glu Glu Pro His Thr Glu Thr Val Arg Lys Tyr Phe Pro
                725                 730                 735

Glu Thr Trp Ile Trp Asp Leu Val Val Asn Ser Ala Gly Val Ala
            740                 745                 750

Glu Val Gly Val Thr Val Pro Asp Thr Ile Thr Glu Trp Lys Ala Gly
        755                 760                 765

Ala Phe Cys Leu Ser Glu Asp Ala Gly Leu Gly Ile Ser Ser Thr Ala
    770                 775                 780

Ser Leu Arg Ala Phe Gln Pro Phe Phe Val Glu Leu Thr Met Pro Tyr
785                 790                 795                 800

Ser Val Ile Arg Gly Glu Ala Phe Thr Leu Lys Ala Thr Val Leu Asn
                805                 810                 815

Tyr Leu Pro Lys Cys Ile Arg Val Ser Val Gln Leu Glu Ala Ser Pro
                820                 825                 830

Ala Phe Leu Ala Val Pro Val Glu Lys Glu Gln Ala Pro His Cys Ile
        835                 840                 845

Cys Ala Asn Gly Arg Gln Thr Val Ser Trp Ala Val Thr Pro Lys Ser
    850                 855                 860

Leu Gly Asn Val Asn Phe Thr Val Ser Ala Glu Ala Leu Glu Ser Gln
865                 870                 875                 880

Glu Leu Cys Gly Thr Glu Val Pro Ser Val Pro Glu His Gly Arg Lys
                885                 890                 895

Asp Thr Val Ile Lys Pro Leu Leu Val Glu Pro Glu Gly Leu Glu Lys
            900                 905                 910

Glu Thr Thr Phe Asn Ser Leu Leu Cys Pro Ser Gly Gly Glu Val Ser
        915                 920                 925

Glu Glu Leu Ser Leu Lys Leu Pro Pro Asn Val Val Glu Glu Ser Ala
    930                 935                 940

Arg Ala Ser Val Ser Val Leu Gly Asp Ile Leu Gly Ser Ala Met Gln
945                 950                 955                 960

Asn Thr Gln Asn Leu Leu Gln Met Pro Tyr Gly Cys Gly Glu Gln Asn
                965                 970                 975

Met Val Leu Phe Ala Pro Asn Ile Tyr Val Leu Asp Tyr Leu Asn Glu
            980                 985                 990

Thr Gln Gln Leu Thr Pro Glu Ile Lys Ser Lys Ala Ile Gly Tyr Leu
        995                 1000                1005

Asn Thr Gly Tyr Gln Arg Gln Leu Asn Tyr Lys His Tyr Asp Gly
            1010                1015                1020

Ser Tyr Ser Thr Phe Gly Glu Arg Tyr Gly Arg Asn Gln Gly Asn
```

```
             1025                1030                1035
Thr Trp Leu Thr Ala Phe Val Leu Lys Thr Phe Ala Gln Ala Arg
    1040                1045                1050

Ala Tyr Ile Phe Ile Asp Glu Ala His Ile Thr Gln Ala Leu Ile
    1055                1060                1065

Trp Leu Ser Gln Arg Gln Lys Asp Asn Gly Cys Phe Arg Ser Ser
    1070                1075                1080

Gly Ser Leu Leu Asn Asn Ala Ile Lys Gly Gly Val Glu Asp Glu
    1085                1090                1095

Val Thr Leu Ser Ala Tyr Ile Thr Ile Ala Leu Leu Glu Ile Pro
    1100                1105                1110

Leu Thr Val Thr His Pro Val Val Arg Asn Ala Leu Phe Cys Leu
    1115                1120                1125

Glu Ser Ala Trp Lys Thr Ala Gln Glu Gly Asp His Gly Ser His
    1130                1135                1140

Val Tyr Thr Lys Ala Leu Leu Ala Tyr Ala Phe Ala Leu Ala Gly
    1145                1150                1155

Asn Gln Asp Lys Arg Lys Glu Val Leu Lys Ser Leu Asn Glu Glu
    1160                1165                1170

Ala Val Lys Lys Asp Asn Ser Val His Trp Glu Arg Pro Gln Lys
    1175                1180                1185

Pro Lys Ala Pro Val Gly His Phe Tyr Glu Pro Gln Ala Pro Ser
    1190                1195                1200

Ala Glu Val Glu Met Thr Ser Tyr Val Leu Leu Ala Tyr Leu Thr
    1205                1210                1215

Ala Gln Pro Ala Pro Thr Ser Glu Asp Leu Thr Ser Ala Thr Asn
    1220                1225                1230

Ile Val Lys Trp Ile Thr Lys Gln Gln Asn Ala Gln Gly Gly Phe
    1235                1240                1245

Ser Ser Thr Gln Asp Thr Val Val Ala Leu His Ala Leu Ser Lys
    1250                1255                1260

Tyr Gly Ala Ala Thr Phe Thr Arg Thr Gly Lys Ala Ala Gln Val
    1265                1270                1275

Thr Ile Gln Ser Ser Gly Thr Phe Ser Ser Lys Phe Gln Val Asp
    1280                1285                1290

Asn Asn Asn Arg Leu Leu Leu Gln Gln Val Ser Leu Pro Glu Leu
    1295                1300                1305

Pro Gly Glu Tyr Ser Met Lys Val Thr Gly Glu Gly Cys Val Tyr
    1310                1315                1320

Leu Gln Thr Ser Leu Lys Tyr Asn Ile Leu Pro Glu Lys Glu Glu
    1325                1330                1335

Phe Pro Phe Ala Leu Gly Val Gln Thr Leu Pro Gln Thr Cys Asp
    1340                1345                1350

Glu Pro Lys Ala His Thr Ser Phe Gln Ile Ser Leu Ser Val Ser
    1355                1360                1365

Tyr Thr Gly Ser Arg Ser Ala Ser Asn Met Ala Ile Val Asp Val
    1370                1375                1380

Lys Met Val Ser Gly Phe Ile Pro Leu Lys Pro Thr Val Lys Met
    1385                1390                1395

Leu Glu Arg Ser Asn His Val Ser Arg Thr Glu Val Ser Ser Asn
    1400                1405                1410

His Val Leu Ile Tyr Leu Asp Lys Val Ser Asn Gln Thr Leu Ser
    1415                1420                1425
```

```
Leu Phe Phe Thr Val Leu Gln Asp Val Pro Val Arg Asp Leu Lys
    1430                1435                1440

Pro Ala Ile Val Lys Val Tyr Asp Tyr Tyr Glu Thr Asp Glu Phe
    1445                1450                1455

Ala Ile Ala Glu Tyr Asn Ala Pro Cys Ser Lys Asp Leu Gly Asn
    1460                1465                1470

Ala Asp Tyr Lys Asp Asp Asp Lys Gly Ala Ser His His His
    1475                1480                1485

His His His
    1490

<210> SEQ ID NO 4
<211> LENGTH: 1491
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Lys Asn Lys Leu Leu His Pro Ser Leu Val Leu Leu Leu
1               5                   10                  15

Val Leu Leu Pro Thr Asp Ala Ser Val Ser Gly Lys Pro Gln Tyr Met
            20                  25                  30

Val Leu Val Pro Ser Leu Leu His Thr Glu Thr Thr Glu Lys Gly Cys
        35                  40                  45

Val Leu Leu Ser Tyr Leu Asn Glu Thr Val Thr Val Ser Ala Ser Leu
    50                  55                  60

Glu Ser Val Arg Gly Asn Arg Ser Leu Phe Thr Asp Leu Glu Ala Glu
65                  70                  75                  80

Asn Asp Val Leu His Cys Val Ala Phe Ala Val Pro Lys Ser Ser Ser
                85                  90                  95

Asn Glu Glu Val Met Phe Leu Thr Val Gln Val Lys Gly Pro Thr Gln
            100                 105                 110

Glu Phe Lys Lys Arg Thr Thr Val Met Val Lys Asn Glu Asp Ser Leu
        115                 120                 125

Val Phe Val Gln Thr Asp Lys Ser Ile Tyr Lys Pro Gly Gln Thr Val
    130                 135                 140

Lys Phe Arg Val Val Ser Met Asp Glu Asn Phe His Pro Leu Asn Glu
145                 150                 155                 160

Leu Ile Pro Leu Val Tyr Ile Gln Asp Pro Lys Gly Asn Arg Ile Ala
                165                 170                 175

Gln Trp Gln Ser Phe Gln Leu Glu Gly Gly Leu Lys Gln Phe Ser Phe
            180                 185                 190

Pro Leu Ser Ser Glu Pro Phe Gln Gly Ser Tyr Lys Val Val Val Gln
        195                 200                 205

Lys Lys Ser Gly Gly Arg Thr Glu His Pro Phe Thr Val Glu Glu Phe
    210                 215                 220

Val Leu Pro Lys Phe Glu Val Gln Val Thr Val Pro Lys Ile Ile Thr
225                 230                 235                 240

Ile Leu Glu Glu Glu Met Asn Val Ser Val Cys Gly Leu Tyr Thr Tyr
                245                 250                 255

Gly Lys Pro Val Pro Gly His Val Thr Val Ser Ile Cys Arg Lys Tyr
            260                 265                 270

Ser Asp Ala Ser Asp Cys His Gly Glu Asp Ser Gln Ala Phe Cys Glu
```

```
            275                 280                 285
Lys Phe Ser Gly Gln Leu Asn Ser His Gly Cys Phe Tyr Gln Gln Val
290                 295                 300

Lys Thr Lys Val Phe Gln Leu Lys Arg Lys Glu Tyr Glu Met Lys Leu
305                 310                 315                 320

His Thr Glu Ala Gln Ile Gln Glu Gly Thr Val Val Glu Leu Thr
                325                 330                 335

Gly Arg Gln Ser Ser Glu Ile Thr Arg Thr Ile Thr Lys Leu Ser Phe
                340                 345                 350

Val Lys Val Asp Ser His Phe Arg Gln Gly Ile Pro Phe Phe Gly Gln
                355                 360                 365

Val Arg Leu Val Asp Gly Lys Gly Val Pro Ile Pro Asn Lys Val Ile
370                 375                 380

Phe Ile Arg Gly Asn Glu Ala Asn Tyr Tyr Ser Asn Ala Thr Thr Asp
385                 390                 395                 400

Glu His Gly Leu Val Gln Phe Ser Ile Asn Thr Thr Asn Val Met Gly
                405                 410                 415

Thr Ser Leu Thr Val Arg Val Asn Tyr Lys Asp Arg Ser Pro Cys Tyr
                420                 425                 430

Gly Tyr Gln Trp Val Ser Glu Glu His Glu Glu Ala His His Thr Ala
                435                 440                 445

Tyr Leu Val Phe Ser Pro Ser Lys Ser Phe Val His Leu Glu Pro Met
450                 455                 460

Ser His Glu Leu Pro Cys Gly His Thr Gln Thr Val Gln Ala His Tyr
465                 470                 475                 480

Ile Leu Asn Gly Gly Thr Leu Leu Gly Leu Lys Lys Leu Ser Phe Tyr
                485                 490                 495

Tyr Leu Ile Met Ala Lys Gly Gly Ile Val Arg Thr Gly Thr His Gly
                500                 505                 510

Leu Leu Val Lys Gln Glu Asp Met Lys Gly His Phe Ser Ile Ser Ile
                515                 520                 525

Pro Val Lys Ser Asp Ile Ala Pro Val Ala Arg Leu Leu Ile Tyr Ala
530                 535                 540

Val Leu Pro Thr Gly Asp Val Ile Gly Asp Ser Ala Lys Tyr Asp Val
545                 550                 555                 560

Glu Asn Cys Leu Ala Asn Lys Val Asp Leu Ser Phe Ser Pro Ser Gln
                565                 570                 575

Ser Leu Pro Ala Ser His Ala His Leu Arg Val Thr Ala Ala Pro Gln
                580                 585                 590

Ser Val Cys Ala Leu Arg Ala Val Asp Gln Ser Val Leu Leu Met Lys
                595                 600                 605

Pro Asp Ala Glu Leu Ser Ala Ser Ser Val Tyr Asn Leu Leu Pro Glu
                610                 615                 620

Lys Asp Leu Thr Gly Phe Pro Gly Pro Leu Asn Asp Gln Asp Asp Glu
625                 630                 635                 640

Asp Cys Ile Asn Arg His Asn Val Tyr Ile Asn Gly Ile Thr Tyr Thr
                645                 650                 655

Pro Val Ser Ser Thr Asn Glu Lys Asp Met Tyr Ser Phe Leu Glu Asp
                660                 665                 670

Met Gly Leu Lys Ala Phe Thr Asn Ser Lys Ile Arg Lys Pro Lys Met
                675                 680                 685

Cys Pro Gln Leu Glu Gln Tyr Glu Met His Gly Pro Glu Gly Leu Arg
690                 695                 700
```

```
Val Gly Phe Tyr Glu Ser Asp Val Met Gly Arg Gly His Ala Arg Leu
705                 710                 715                 720

Val His Val Glu Glu Pro His Thr Glu Lys Leu Arg Lys Tyr Phe Pro
            725                 730                 735

Glu Thr Trp Ile Trp Asp Leu Val Val Asn Ser Ala Gly Val Ala
            740                 745                 750

Glu Val Gly Val Thr Val Pro Asp Thr Ile Thr Glu Trp Lys Ala Gly
            755                 760                 765

Ala Phe Cys Leu Ser Glu Asp Ala Gly Leu Gly Ile Ser Ser Thr Ala
770                 775                 780

Ser Leu Arg Ala Phe Gln Pro Phe Phe Val Glu Leu Thr Met Pro Tyr
785                 790                 795                 800

Ser Val Ile Arg Gly Glu Ala Phe Thr Leu Lys Ala Thr Val Leu Asn
                805                 810                 815

Tyr Leu Pro Lys Cys Ile Arg Val Ser Val Gln Leu Glu Ala Ser Pro
                820                 825                 830

Ala Phe Leu Ala Val Pro Val Glu Lys Glu Gln Ala Pro His Cys Ile
            835                 840                 845

Cys Ala Asn Gly Arg Gln Thr Val Ser Trp Ala Val Thr Pro Lys Ser
850                 855                 860

Leu Gly Asn Val Asn Phe Thr Val Ser Ala Glu Ala Leu Glu Ser Gln
865                 870                 875                 880

Glu Leu Cys Gly Thr Glu Val Pro Ser Val Pro Glu His Gly Arg Lys
                885                 890                 895

Asp Thr Val Ile Lys Pro Leu Leu Val Glu Pro Glu Gly Leu Glu Lys
                900                 905                 910

Glu Thr Thr Phe Asn Ser Leu Leu Cys Pro Ser Gly Gly Glu Val Ser
                915                 920                 925

Glu Glu Leu Ser Leu Lys Leu Pro Pro Asn Val Val Glu Glu Ser Ala
930                 935                 940

Arg Ala Ser Val Ser Val Leu Gly Asp Ile Leu Gly Ser Ala Met Gln
945                 950                 955                 960

Asn Thr Gln Asn Leu Leu Gln Met Pro Tyr Gly Cys Gly Glu Gln Asn
                965                 970                 975

Met Val Leu Phe Ala Pro Asn Ile Tyr Val Leu Asp Tyr Leu Asn Glu
            980                 985                 990

Thr Gln Gln Leu Thr Pro Glu Ile Lys Ser Lys Ala Ile Gly Tyr Leu
                995                 1000                1005

Asn Thr Gly Tyr Gln Arg Gln Leu Asn Tyr Lys His Tyr Asp Gly
        1010                1015                1020

Ser Tyr Ser Thr Phe Gly Glu Arg Tyr Gly Arg Asn Gln Gly Asn
        1025                1030                1035

Thr Trp Leu Thr Ala Phe Val Leu Lys Thr Phe Ala Gln Ala Arg
        1040                1045                1050

Ala Tyr Ile Phe Ile Asp Glu Ala His Ile Thr Gln Ala Leu Ile
        1055                1060                1065

Trp Leu Ser Gln Arg Gln Lys Asp Asn Gly Cys Phe Arg Ser Ser
        1070                1075                1080

Gly Ser Leu Leu Asn Asn Ala Ile Lys Gly Gly Val Glu Asp Glu
        1085                1090                1095

Val Thr Leu Ser Ala Tyr Ile Thr Ile Ala Leu Leu Glu Ile Pro
        1100                1105                1110
```

| | | | | | | | | | | | |
|---|---|---|---|---|---|---|---|---|---|---|---|
| Leu | Thr | Val | Thr | His | Pro | Val | Val | Arg | Asn | Ala | Leu | Phe | Cys | Leu |
| | 1115 | | | | 1120 | | | | | 1125 | |
| Glu | Ser | Ala | Trp | Lys | Thr | Ala | Gln | Glu | Gly | Asp | His | Gly | Ser | His |
| 1130 | | | | | 1135 | | | | | 1140 |
| Val | Tyr | Thr | Lys | Ala | Leu | Leu | Ala | Tyr | Ala | Phe | Ala | Leu | Ala | Gly |
| 1145 | | | | | 1150 | | | | | 1155 |
| Asn | Gln | Asp | Lys | Arg | Lys | Glu | Val | Leu | Lys | Ser | Leu | Asn | Glu | Glu |
| 1160 | | | | | 1165 | | | | | 1170 |
| Ala | Val | Lys | Lys | Asp | Asn | Ser | Val | His | Trp | Glu | Arg | Pro | Gln | Lys |
| 1175 | | | | | 1180 | | | | | 1185 |
| Pro | Lys | Ala | Pro | Val | Gly | His | Phe | Tyr | Glu | Pro | Gln | Ala | Pro | Ser |
| 1190 | | | | | 1195 | | | | | 1200 |
| Ala | Glu | Val | Glu | Met | Thr | Ser | Tyr | Val | Leu | Leu | Ala | Tyr | Leu | Thr |
| 1205 | | | | | 1210 | | | | | 1215 |
| Ala | Gln | Pro | Ala | Pro | Thr | Ser | Glu | Asp | Leu | Thr | Ser | Ala | Thr | Asn |
| 1220 | | | | | 1225 | | | | | 1230 |
| Ile | Val | Lys | Trp | Ile | Thr | Lys | Gln | Gln | Asn | Ala | Gln | Gly | Gly | Phe |
| 1235 | | | | | 1240 | | | | | 1245 |
| Ser | Ser | Thr | Gln | Asp | Thr | Val | Val | Ala | Leu | His | Ala | Leu | Ser | Lys |
| 1250 | | | | | 1255 | | | | | 1260 |
| Tyr | Gly | Ala | Ala | Thr | Phe | Thr | Arg | Thr | Gly | Lys | Ala | Ala | Gln | Val |
| 1265 | | | | | 1270 | | | | | 1275 |
| Thr | Ile | Gln | Ser | Ser | Gly | Thr | Phe | Ser | Ser | Lys | Phe | Gln | Val | Asp |
| 1280 | | | | | 1285 | | | | | 1290 |
| Asn | Asn | Asn | Arg | Leu | Leu | Leu | Gln | Gln | Val | Ser | Leu | Pro | Glu | Leu |
| 1295 | | | | | 1300 | | | | | 1305 |
| Pro | Gly | Glu | Tyr | Ser | Met | Lys | Val | Thr | Gly | Glu | Gly | Cys | Val | Tyr |
| 1310 | | | | | 1315 | | | | | 1320 |
| Leu | Gln | Thr | Ser | Leu | Lys | Tyr | Asn | Ile | Leu | Pro | Glu | Lys | Glu | Glu |
| 1325 | | | | | 1330 | | | | | 1335 |
| Phe | Pro | Phe | Ala | Leu | Gly | Val | Gln | Thr | Leu | Pro | Gln | Thr | Cys | Asp |
| 1340 | | | | | 1345 | | | | | 1350 |
| Glu | Pro | Lys | Ala | His | Thr | Ser | Phe | Gln | Ile | Ser | Leu | Ser | Val | Ser |
| 1355 | | | | | 1360 | | | | | 1365 |
| Tyr | Thr | Gly | Ser | Arg | Ser | Ala | Ser | Asn | Met | Ala | Ile | Val | Asp | Val |
| 1370 | | | | | 1375 | | | | | 1380 |
| Lys | Met | Val | Ser | Gly | Phe | Ile | Pro | Leu | Lys | Pro | Thr | Val | Lys | Met |
| 1385 | | | | | 1390 | | | | | 1395 |
| Leu | Glu | Arg | Ser | Asn | His | Val | Ser | Arg | Thr | Glu | Val | Ser | Ser | Asn |
| 1400 | | | | | 1405 | | | | | 1410 |
| His | Val | Leu | Ile | Tyr | Leu | Asp | Lys | Val | Ser | Asn | Gln | Thr | Leu | Ser |
| 1415 | | | | | 1420 | | | | | 1425 |
| Leu | Phe | Phe | Thr | Val | Leu | Gln | Asp | Val | Pro | Val | Arg | Asp | Leu | Lys |
| 1430 | | | | | 1435 | | | | | 1440 |
| Pro | Ala | Ile | Val | Lys | Val | Tyr | Asp | Tyr | Tyr | Glu | Thr | Asp | Glu | Phe |
| 1445 | | | | | 1450 | | | | | 1455 |
| Ala | Ile | Ala | Glu | Tyr | Asn | Ala | Pro | Cys | Ser | Lys | Asp | Leu | Gly | Asn |
| 1460 | | | | | 1465 | | | | | 1470 |
| Ala | Asp | Tyr | Lys | Asp | Asp | Asp | Lys | Gly | Ala | Ser | His | His | His |
| 1475 | | | | | 1480 | | | | | 1485 |
| His | His | His |
| 1490 |

```
<210> SEQ ID NO 5
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Leu Glu Gln Tyr Glu Met His Gly Pro Glu Gly Leu Arg Val Gly Lys
1               5                   10                  15

Glu Glu Glu Gly Leu Gly Ser Ile Pro Glu Asn Phe Phe Gly Val Ser
            20                  25                  30

Glu Leu Glu Gly Arg Gly Ser Lys Leu
        35                  40

<210> SEQ ID NO 6
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Leu Glu Gln Tyr Glu Met His Gly Pro Glu Gly Leu Arg Val Gly Ile
1               5                   10                  15

Pro Glu Asn Phe Phe Gly Val Ser Glu Leu Glu Gly Arg Gly Ser Lys
            20                  25                  30

Glu Glu Glu Gly Leu Gly Ser Lys Leu
        35                  40

<210> SEQ ID NO 7
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Leu Glu Gln Tyr Glu Met His Gly Pro Glu Gly Leu Arg Val Gly Ser
1               5                   10                  15

Glu Leu Glu Gly Arg Gly Ser Lys Glu Glu Glu Gly Leu Gly Ser Ile
            20                  25                  30

Pro Glu Asn Phe Phe Gly Val Lys Leu
        35                  40

<210> SEQ ID NO 8
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Leu Glu Gln Tyr Glu Met His Gly Pro Glu Gly Leu Arg Val Gly Lys
1               5                   10                  15

Glu Glu Glu Gly Leu Gly Ser Ser Glu Leu Glu Gly Arg Gly Ser Thr
            20                  25                  30

Ala Gln Glu Ala Gly Glu Gly Lys Leu
        35                  40
```

```
<210> SEQ ID NO 9
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Leu Glu Gln Tyr Glu Met His Gly Pro Glu Gly Leu Arg Val Gly Ile
1               5                   10                  15

Pro Glu Asn Phe Phe Gly Val Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 10
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Leu Glu Gln Tyr Glu Met His Gly Pro Glu Gly Leu Arg Val Gly Lys
1               5                   10                  15

Glu Glu Glu Gly Leu Gly Ser Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 11
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Leu Glu Gln Tyr Glu Met His Gly Pro Glu Gly Leu Arg Val Gly Ser
1               5                   10                  15

Glu Leu Glu Gly Arg Gly Ser Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 12
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Leu Glu Gln Tyr Glu Met His Gly Pro Glu Gly Leu Arg Val Gly Glu
1               5                   10                  15

Ala Ile Pro Met Ser Ile Pro Phe Tyr Glu Ser Asp Val Met Gly Arg
            20                  25                  30

Gly His Ala Arg Leu Val His Val Glu Glu Pro His Thr Lys Leu Leu
        35                  40                  45
```

```
<210> SEQ ID NO 13
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Leu Glu Gln Tyr Glu Met His Gly Pro Glu Gly Leu Arg Val Gly Thr
1               5                   10                  15

Ala Gln Glu Ala Gly Glu Gly Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 14
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Leu Glu Gln Tyr Glu Met His Gly Pro Glu Gly Leu Arg Val Gly Val
1               5                   10                  15

Ser Gln Glu Leu Gly Gln Arg Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 15
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Leu Glu Gln Tyr Glu Met His Gly Pro Glu Gly Leu Arg Val Gly Thr
1               5                   10                  15

Glu Gly Glu Ala Arg Gly Ser Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 16
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Leu Glu Gln Tyr Glu Met His Gly Pro Glu Gly Leu Arg Val Gly Thr
1               5                   10                  15

Ser Glu Asp Leu Val Val Gln Phe Tyr Glu Ser Asp Val Met Gly Arg
            20                  25                  30

Gly His Ala Arg Leu Val His Val Glu Glu Pro His Thr Lys Leu Leu
```

```
            35                  40                  45

<210> SEQ ID NO 17
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Leu Glu Gln Tyr Glu Met His Gly Pro Glu Gly Leu Arg Val Gly Glu
1               5                   10                  15

Gly Glu Gly Glu Gly Glu Gly Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 18
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Leu Glu Gln Tyr Glu Met His Gly Pro Glu Gly Leu Arg Val Gly Gly
1               5                   10                  15

Glu Glu Gly Val Glu Glu Gly Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 19
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Leu Glu Gln Tyr Glu Met His Gly Pro Glu Gly Leu Arg Val Gly Gly
1               5                   10                  15

Ala Arg Gly Leu Glu Gly Phe Tyr Glu Ser Asp Val Met Gly Arg Gly
            20                  25                  30

His Ala Arg Leu Val His Val Glu Glu Pro His Thr Lys Leu
        35                  40                  45

<210> SEQ ID NO 20
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Leu Glu Gln Tyr Glu Met His Gly Pro Glu Gly Leu Arg Val Gly Gly
1               5                   10                  15

Pro Pro Gly Leu Ala Pro Gly Phe Tyr Glu Ser Asp Val Met Gly Arg
            20                  25                  30
```

```
Gly His Ala Arg Leu Val His Val Glu Glu Pro His Thr Lys Leu Leu
        35                  40                  45

<210> SEQ ID NO 21
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Leu Glu Gln Tyr Glu Met His Gly Pro Glu Gly Leu Arg Val Gly Gly
1               5                   10                  15

Glu Pro Glu Gly Ala Lys Gly Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 22
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Leu Glu Gln Tyr Glu Met His Gly Pro Glu Gly Leu Arg Val Gly Glu
1               5                   10                  15

Glu Glu Gly Gly Gly Phe Tyr Glu Ser Asp Val Met Gly Arg Gly His
            20                  25                  30

Ala Arg Leu Val His Val Glu Glu Pro His Thr Lys Leu
        35                  40                  45

<210> SEQ ID NO 23
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Leu Glu Gln Tyr Glu Met His Gly Pro Glu Gly Leu Arg Val Gly Gly
1               5                   10                  15

Tyr Pro Gly Ser Ser Arg Gly Phe Tyr Glu Ser Asp Val Met Gly Arg
            20                  25                  30

Gly His Ala Arg Leu Val His Val Glu Glu Pro His Thr Lys Leu Leu
        35                  40                  45

<210> SEQ ID NO 24
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Leu Glu Gln Tyr Glu Met His Gly Pro Glu Gly Leu Arg Val Gly Gly
1               5                   10                  15

Ala Arg Gly Leu Glu Gly Gly Phe Ala Gly Leu Pro Asn Gly Gly Glu
            20                  25                  30
```

```
Glu Gly Val Glu Glu Gly Lys Leu
        35                  40

<210> SEQ ID NO 25
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Leu Glu Gln Tyr Glu Met His Gly Pro Glu Gly Leu Arg Val Gly Glu
1               5                   10                  15

Ser Glu Ser Glu Gly Gly Gly Gly Ser Leu Leu Gly Glu Phe Glu
            20                  25                  30

Val Glu Gly Gly Phe Ala Gly Leu Pro Asn Gly Lys Leu
        35                  40                  45

<210> SEQ ID NO 26
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Leu Glu Gln Tyr Glu Met His Gly Pro Glu Gly Leu Arg Val Gly Gly
1               5                   10                  15

Phe Lys Glu Gly Val Glu Gly Glu Ile Glu Glu Gly Gly Phe Lys
            20                  25                  30

Glu Gly Val Glu Gly Lys Leu
        35

<210> SEQ ID NO 27
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Leu Glu Gln Tyr Glu Met His Gly Pro Glu Gly Leu Arg Val Gly Glu
1               5                   10                  15

Ser Glu Ser Glu Gly Gly Phe Ala Gly Leu Pro Asn Gly Lys Glu Glu
            20                  25                  30

Glu Gly Leu Gly Ser Ile Pro Glu Asn Phe Phe Gly Val Lys Leu
        35                  40                  45

<210> SEQ ID NO 28
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Leu Glu Gln Tyr Glu Met His Gly Pro Glu Gly Leu Arg Val Gly Ile
1               5                   10                  15

Pro Glu Asn Phe Phe Gly Val Thr Ser Glu Asp Leu Val Val Gln Glu
```

```
                    20                  25                  30

Ala Ile Pro Met Ser Ile Pro Lys Leu
            35                  40

<210> SEQ ID NO 29
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Leu Glu Gln Tyr Glu Met His Gly Pro Glu Gly Leu Arg Val Gly Glu
1               5                   10                  15

Ala Ile Pro Met Ser Ile Pro Thr Ser Glu Asp Leu Val Val Gln Ile
            20                  25                  30

Pro Glu Asn Phe Phe Gly Val Lys Leu
            35                  40

<210> SEQ ID NO 30
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Leu Glu Pro Ala Gly Ala Ala Arg Gly Glu Ser Glu Ser Glu Gly Gly
1               5                   10                  15

Phe Phe Gly Phe Pro Ile Gly Glu Arg Glu Ser Thr Gly Gly Asp Arg
            20                  25                  30

Gly Leu Pro Ile Gly Glu Asn Glu Ala Gly Gly Lys Leu
            35                  40                  45

<210> SEQ ID NO 31
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Leu Glu Thr Glu Gly Arg Gly Glu Arg Glu Ala Gln Gly Glu Phe Pro
1               5                   10                  15

Glu Val Glu Gly Glu Glu Gly Gly Gly Pro Glu Lys Glu Thr Gly
            20                  25                  30

Gly Glu Arg Glu Ala Gln Gly Lys Leu
            35                  40

<210> SEQ ID NO 32
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Leu Glu Ala Arg Gly Leu Glu Gly Gly Gly Gly Ser Leu Leu Gly
1               5                   10                  15
```

```
Gly Tyr Pro Gly Ser Ser Arg Gly Gly Phe Lys Glu Gly Val Glu Gly
            20                  25                  30

Gly Pro Ala Gly Ala Ala Arg Gly Lys Leu
        35                  40
```

<210> SEQ ID NO 33
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Leu Glu Pro Gly Leu Ala Pro Gly Gly Glu Glu Gly Val Glu Glu Gly
1               5                   10                  15

Gly Pro Glu Glu Gly Val Glu Glu Gly Gly Phe Lys Glu Gly Val Glu
            20                  25                  30

Gly Glu Pro Glu Ser Ser Gly Lys Leu
        35                  40
```

<210> SEQ ID NO 34
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

```
Leu Glu Glu Gly Glu Ala Arg Gly Ser Thr Ala Gln Glu Ala Gly Glu
1               5                   10                  15

Gly Pro Lys Glu Glu Gly Leu Gly Ser Ser Glu Leu Glu Gly Arg
            20                  25                  30

Gly Ser Pro Val Ser Gln Glu Leu Gly Gln Arg Lys Leu
        35                  40                  45
```

<210> SEQ ID NO 35
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Leu Glu Ala Gln Glu Ala Gly Glu Gly Lys Glu Glu Gly Leu Gly
1               5                   10                  15

Ser Pro Val Ser Gln Glu Leu Gly Gln Arg Ser Glu Leu Glu Gly Arg
            20                  25                  30

Gly Ser Pro Thr Glu Gly Glu Ala Arg Gly Ser Lys Leu
        35                  40                  45
```

<210> SEQ ID NO 36
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Leu Glu Glu Glu Glu Gly Leu Gly Ser Lys Glu Glu Gly Leu Gly
1               5                   10                  15
```

-continued

Ser Pro Lys Glu Glu Gly Leu Gly Ser Lys Glu Glu Gly Leu
                20                  25                  30

Gly Ser Pro Lys Glu Glu Gly Leu Gly Ser Lys Leu
            35                  40                  45

<210> SEQ ID NO 37
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Leu Glu Glu Leu Glu Gly Arg Gly Ser Lys Glu Glu Gly Leu Gly
1               5                   10                  15

Ser Ile Pro Glu Asn Phe Phe Gly Val Phe Tyr Glu Ser Asp Val Met
                20                  25                  30

Gly Arg Gly His Ala Arg Leu Val His Val Glu Glu Pro His Thr Lys
            35                  40                  45

Leu

<210> SEQ ID NO 38
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Leu Glu Glu Asn Phe Phe Gly Val Thr Glu Gly Glu Ala Arg Gly Ser
1               5                   10                  15

Pro Thr Ser Glu Asp Leu Val Val Gln Lys Glu Glu Gly Leu Gly
                20                  25                  30

Ser Glu Ala Ile Pro Met Ser Ile Pro Lys Leu
            35                  40

<210> SEQ ID NO 39
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Leu Glu Ile Pro Met Ser Ile Pro Lys Glu Glu Gly Leu Gly Ser
1               5                   10                  15

Ile Pro Glu Asn Phe Phe Gly Val Thr Glu Gly Glu Ala Arg Gly Ser
                20                  25                  30

Pro Thr Ser Glu Asp Leu Val Val Gln Lys Leu
            35                  40

<210> SEQ ID NO 40
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Leu Glu Leu Gln Gln Tyr Glu Met His Gly Pro Glu Gly Leu Arg Val
1               5                   10                  15

Gly Glu Ala Ile Pro Met Ser Ile Pro Ile Pro Glu Asn Phe Phe Gly
            20                  25                  30

Val Lys Glu Glu Glu Gly Leu Gly Ser Lys Leu
        35                  40

<210> SEQ ID NO 41
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Leu Glu Glu Glu Gly Val Glu Glu Gly Lys Glu Glu Gly Leu Gly
1               5                   10                  15

Ser Gly Pro Ala Gly Ala Ala Arg Gly Ser Glu Leu Gly Arg Gly
            20                  25                  30

Ser Pro Thr Glu Gly Glu Ala Arg Gly Ser Lys Leu
        35                  40

<210> SEQ ID NO 42
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Leu Glu Pro Glu Ser Ser Gly Glu Ala Ile Pro Met Ser Ile Pro Thr
1               5                   10                  15

Ser Glu Asp Leu Val Val Gln Ile Pro Glu Asn Phe Phe Gly Val Glu
            20                  25                  30

Ala Glu Gly Thr Gly Gly Glu Arg Gly Val Leu Gly Lys Leu
        35                  40                  45

<210> SEQ ID NO 43
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Leu Glu Gly Gly Gly Ser Leu Leu Gly Glu Pro Glu Pro Glu Gly Glu
1               5                   10                  15

Arg Glu Ala Gln Gly Gly Val Glu Gly Val Glu Leu Gly Gly Phe Lys
            20                  25                  30

Glu Gly Val Glu Gly Glu Gln Gly Gly Arg Gly Lys Leu
        35                  40                  45

<210> SEQ ID NO 44
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 44

Leu Glu Ser Gln Glu Leu Gly Gln Arg Glu Ser Glu Ser Glu Gly Ser
1               5                   10                  15

Glu Leu Glu Gly Arg Gly Ser Gly Phe Lys Glu Gly Val Glu Gly Lys
            20                  25                  30

Glu Glu Glu Gly Leu Gly Ser Gly Phe Phe Gly Phe Pro Ile Gly Lys
        35                  40                  45

Leu

<210> SEQ ID NO 45
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Leu Glu Gln Tyr Glu Met His Gly Pro Lys Glu Glu Gly Leu Gly
1               5                   10                  15

Ser Ser Glu Leu Glu Gly Arg Gly Ser Glu Ala Ile Pro Met Ser Ile
            20                  25                  30

Pro Thr Ile Pro Glu Asn Phe Phe Gly Val Val Glu Glu Pro His Thr
        35                  40                  45

Lys Leu
    50

<210> SEQ ID NO 46
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Leu Glu Gln Tyr Glu Met His Gly Pro Ser Glu Leu Glu Gly Arg Gly
1               5                   10                  15

Ser Ile Pro Glu Asn Phe Phe Gly Val Glu Ala Ile Pro Met Ser Ile
            20                  25                  30

Pro Thr Ser Glu Asp Leu Val Val Gln Ile Val Glu Glu Pro His Thr
        35                  40                  45

Lys Leu
    50

<210> SEQ ID NO 47
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Leu Glu Gln Tyr Glu Met His Gly Pro Glu Gly Glu Gly Glu Gly Glu
1               5                   10                  15

Gly Ile Pro Glu Asn Phe Phe Gly Val Ser Glu Asp Leu Val Val Gln
            20                  25                  30

Ile Ser Glu Leu Glu Gly Arg Gly Ser Val Glu Glu Pro His Thr Lys
        35                  40                  45
```

Leu

<210> SEQ ID NO 48

<400> SEQUENCE: 48

000

<210> SEQ ID NO 49

<400> SEQUENCE: 49

000

<210> SEQ ID NO 50
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

```
Leu Glu Gln Tyr Glu Met His Gly Pro Ile Pro Glu Asn Phe Phe Gly
1               5                   10                  15

Val Ser Glu Leu Glu Gly Arg Gly Ser Glu Ala Ile Pro Met Ser Ile
            20                  25                  30

Pro Thr Glu Gly Glu Gly Glu Gly Val Glu Pro His Thr
        35                  40                  45

Lys Leu
    50
```

<210> SEQ ID NO 51
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Leu Glu Gln Tyr Glu Met His Gly Pro Ser Glu Leu Glu Gly Arg Gly
1               5                   10                  15

Ser Glu Ala Ile Pro Met Ser Ile Pro Thr Lys Glu Glu Gly Leu
            20                  25                  30

Gly Ser Ile Pro Glu Asn Phe Phe Gly Val Val Glu Glu Pro His Thr
        35                  40                  45

Lys Leu
    50
```

<210> SEQ ID NO 52
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

```
Leu Glu Gln Tyr Glu Met His Gly Pro Glu Ala Ile Pro Met Ser Ile
1               5                   10                  15

Pro Thr Glu Gly Glu Gly Glu Gly Glu Gly Ile Pro Glu Asn Phe Phe
            20                  25                  30
```

```
Gly Val Ser Glu Asp Leu Val Val Gln Ile Val Glu Glu Pro His Thr
            35                  40                  45

Lys Leu
    50

<210> SEQ ID NO 53
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Leu Glu Gln Tyr Glu Met His Gly Pro Ser Glu Asp Leu Val Val Gln
1               5                   10                  15

Ile Glu Gly Glu Gly Glu Gly Glu Gly Ile Pro Glu Asn Phe Phe Gly
            20                  25                  30

Val Glu Ala Ile Pro Met Ser Ile Pro Thr Val Glu Glu Pro His Thr
            35                  40                  45

Lys Leu
    50

<210> SEQ ID NO 54
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Leu Glu Gln Tyr Glu Met His Gly Pro Glu Gly Glu Gly Glu Gly Glu
1               5                   10                  15

Gly Ile Ser Glu Asp Leu Val Val Gln Ile Pro Glu Asn Phe Phe Gly
            20                  25                  30

Val Lys Glu Glu Glu Gly Leu Gly Ser Val Glu Glu Pro His Thr Lys
            35                  40                  45

Leu

<210> SEQ ID NO 55
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Leu Glu Gln Tyr Glu Met His Gly Pro Glu Gly Glu Gly Glu Gly Glu
1               5                   10                  15

Gly Ile Pro Glu Asn Phe Phe Gly Val Ser Glu Leu Glu Gly Arg Gly
            20                  25                  30

Ser Ser Glu Asp Leu Val Val Gln Ile Val Glu Glu Pro His Thr Lys
            35                  40                  45

Leu

<210> SEQ ID NO 56
<211> LENGTH: 48
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 56

Leu Glu Gln Tyr Glu Met His Gly Pro Ile Pro Glu Asn Phe Phe Gly
1               5                   10                  15

Val Glu Gly Glu Gly Glu Gly Ser Glu Leu Glu Gly Arg Gly Ser
            20                  25                  30

Ser Glu Asp Leu Val Val Gln Ile Val Glu Glu Pro His Thr Lys Leu
        35                  40                  45

<210> SEQ ID NO 57
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Leu Glu Gln Tyr Glu Met His Gly Pro Ser Glu Leu Glu Gly Arg Gly
1               5                   10                  15

Ser Ile Pro Glu Asn Phe Phe Gly Val Lys Glu Glu Gly Leu Gly
            20                  25                  30

Ser Ser Glu Asp Leu Val Val Gln Ile Val Glu Glu Pro His Thr Lys
        35                  40                  45

Leu

<210> SEQ ID NO 58
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Leu Glu Gln Tyr Glu Met His Gly Pro Ile Pro Glu Asn Phe Phe Gly
1               5                   10                  15

Val Ser Glu Leu Glu Gly Arg Gly Ser Ser Glu Asp Leu Val Val Gln
            20                  25                  30

Ile Lys Glu Glu Glu Gly Leu Gly Ser Val Glu Glu Pro His Thr Lys
        35                  40                  45

Leu

<210> SEQ ID NO 59
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Leu Glu Gln Tyr Glu Met His Gly Pro Lys Glu Glu Glu Gly Leu Gly
1               5                   10                  15

Ser Ile Pro Glu Asn Phe Phe Gly Val Ser Glu Leu Glu Gly Arg Gly
            20                  25                  30

Ser Glu Gly Glu Gly Glu Gly Glu Gly Val Glu Glu Pro His Thr Lys
        35                  40                  45

Leu

<210> SEQ ID NO 60
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Leu Glu Gln Tyr Glu Met His Gly Pro Ser Glu Asp Leu Val Val Gln
1               5                   10                  15

Ile Lys Glu Glu Glu Gly Leu Gly Ser Ile Pro Glu Asn Phe Phe Gly
            20                  25                  30

Val Ser Glu Leu Glu Gly Arg Gly Ser Val Glu Glu Pro His Thr Lys
        35                  40                  45

Leu

<210> SEQ ID NO 61
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Leu Glu Gln Tyr Glu Met His Gly Pro Ser Glu Asp Leu Val Val Gln
1               5                   10                  15

Ile Glu Gly Glu Gly Glu Gly Glu Gly Ile Pro Glu Asn Phe Phe Gly
            20                  25                  30

Val Lys Glu Glu Glu Gly Leu Gly Ser Val Glu Glu Pro His Thr Lys
        35                  40                  45

Leu

<210> SEQ ID NO 62
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Leu Glu Gln Tyr Glu Met His Gly Pro Ser Glu Asp Leu Val Val Gln
1               5                   10                  15

Ile Glu Gly Glu Gly Glu Gly Glu Gly Ile Pro Glu Asn Phe Phe Gly
            20                  25                  30

Val Glu Ala Ile Pro Met Ser Ile Pro Thr Glu Pro His Thr Lys Leu
        35                  40                  45

<210> SEQ ID NO 63
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Leu Glu Gln Tyr Glu Met His Gly Pro Glu Gly Glu Gly Glu Gly Glu
1               5                   10                  15

```
Gly Ile Pro Glu Asn Phe Phe Gly Val Glu Ala Ile Pro Met Ser Ile
            20                  25                  30

Pro Thr Ser Glu Leu Glu Gly Arg Gly Ser Pro His Thr Lys Leu
        35                  40                  45
```

<210> SEQ ID NO 64
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Leu Glu Gln Tyr Glu Met His Gly Pro Glu Ala Ile Pro Met Ser Ile
1               5                   10                  15

Pro Thr Ser Glu Leu Glu Gly Arg Gly Ser Ile Pro Glu Asn Phe Phe
            20                  25                  30

Gly Val Glu Gly Glu Gly Glu Gly Gly Glu Pro His Thr Lys Leu
        35                  40                  45
```

<210> SEQ ID NO 65
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

```
Leu Glu Gln Tyr Glu Met His Gly Pro Ser Leu Glu Gly Arg Gly
1               5                   10                  15

Ser Ile Pro Glu Asn Phe Phe Gly Val Glu Gly Glu Gly Glu Gly Glu
            20                  25                  30

Gly Lys Glu Glu Glu Gly Leu Gly Ser Val Glu Pro His Thr Lys
        35                  40                  45

Leu
```

<210> SEQ ID NO 66
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Leu Glu Gln Tyr Glu Met His Gly Pro Ile Pro Glu Asn Phe Phe Gly
1               5                   10                  15

Val Ser Glu Asp Leu Val Val Gln Ile Glu Gly Glu Gly Glu Gly Glu
            20                  25                  30

Gly Glu Ala Ile Pro Met Ser Ile Pro Thr Glu Pro His Thr Lys Leu
        35                  40                  45
```

<210> SEQ ID NO 67
<211> LENGTH: 10
<212> TYPE: PRT
<213> ORGANISM: Homo sapiens

<400> SEQUENCE: 67

```
Asn Ile Thr Glu Gly Glu Ala Arg Gly Ser
1               5                   10
```

<210> SEQ ID NO 68
<211> LENGTH: 11
<212> TYPE: PRT
<213> ORGANISM: Homo sapiens

<400> SEQUENCE: 68

Thr Ala Ser Glu Leu Glu Gly Arg Gly Thr Ile
1               5                   10

<210> SEQ ID NO 69
<211> LENGTH: 11
<212> TYPE: PRT
<213> ORGANISM: Homo sapiens

<400> SEQUENCE: 69

Thr Phe Lys Glu Glu Glu Gly Leu Gly Ser Val
1               5                   10

<210> SEQ ID NO 70
<211> LENGTH: 9
<212> TYPE: PRT
<213> ORGANISM: Homo sapiens

<400> SEQUENCE: 70

Val Asp Ile Pro Glu Asn Phe Phe Gly
1               5

<210> SEQ ID NO 71
<211> LENGTH: 5
<212> TYPE: PRT
<213> ORGANISM: Homo sapiens

<400> SEQUENCE: 71

Ala Arg Gly Ser Val
1               5

<210> SEQ ID NO 72
<211> LENGTH: 10
<212> TYPE: PRT
<213> ORGANISM: Homo sapiens

<400> SEQUENCE: 72

Ile Leu Thr Val Lys Pro Ile Phe Glu Val
1               5                   10

<210> SEQ ID NO 73
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Asp Tyr Lys Asp Asp Asp Lys Gly Ala Ser His His His His His
1               5                   10                  15

His

<210> SEQ ID NO 74
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

```
<400> SEQUENCE: 74

His His His His His His
1               5

<210> SEQ ID NO 75
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Leu Glu Gln Tyr Glu Met His Gly Pro Glu Gly Leu Arg Val Gly Glu
1               5                   10                  15

Gly Glu Gly Glu Gly Glu Gly Phe Tyr Glu Ser Asp Val Met Gly Arg
            20                  25                  30

Gly His Ala Arg Leu Val His Val Glu Glu Pro His Thr Lys Leu
        35                  40                  45

<210> SEQ ID NO 76
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Leu Glu Gln Tyr Glu Met His Gly Pro Glu Gly Leu Arg Val Gly Ser
1               5                   10                  15

Glu Leu Glu Gly Arg Gly Ser Phe Tyr Glu Ser Asp Val Met Gly Arg
            20                  25                  30

Gly His Ala Arg Leu Val His Val Glu Glu Pro His Thr Lys Leu
        35                  40                  45
```